US012606602B2

(12) United States Patent (10) Patent No.: US 12,606,602 B2

Attramadal et al. (45) Date of Patent: Apr. 21, 2026

(54) RECOMBINANT CCN DOMAIN PROTEINS AND FUSION PROTEINS

(71) Applicant: OSLO UNIVERSITETSSYKEHUS HF, Nydalen (NO)

(72) Inventors: Håvard Attramadal, Hobol (NO); Ole Jørgen Kaasbøll, Oslo (NO)

(73) Assignee: OSLO UNIVERSITETSSYKEHUS HF, Nydalen (NO)

( * ) Notice: Subject to any disclaimer, the term of this patent is extended or adjusted under 35 U.S.C. 154(b) by 1150 days.

(21) Appl. No.: 17/440,576

(22) PCT Filed: Mar. 20, 2020

(86) PCT No.: PCT/EP2020/057773

§ 371 (c)(1),
(2) Date: Sep. 17, 2021

(87) PCT Pub. No.: WO2020/188081

PCT Pub. Date: Sep. 24, 2020

(65) Prior Publication Data

US 2022/0144903 A1 May 12, 2022

(30) Foreign Application Priority Data

Mar. 20, 2019 (EP) .................................... 19163970

(51) Int. Cl.
C07K 14/47 (2006.01)
A61K 38/00 (2006.01)

(52) U.S. Cl.
CPC .......... *C07K 14/4702* (2013.01); *A61K 38/00* (2013.01); *C07K 2319/30* (2013.01); *C07K 2319/31* (2013.01)

(58) Field of Classification Search
CPC ..... A61K 38/00; C07K 2319/31; A61P 35/00; C12N 15/62
See application file for complete search history.

(56) References Cited

U.S. PATENT DOCUMENTS

| 7,507,712 | B2 * | 3/2009 | Plou ......................... | A61P 29/00 |
| | | | | 530/399 |
| 7,943,733 | B2 | 5/2011 | Shen et al. | |
| 8,378,076 | B2 | 2/2013 | Shen et al. | |
| 9,200,060 | B2 | 12/2015 | Kannan et al. | |
| 9,855,315 | B2 | 1/2018 | Park et al. | |
| 10,028,906 | B2 | 7/2018 | Riser | |
| 10,125,185 | B2 | 11/2018 | Lawler et al. | |
| 2005/0054563 | A1 * | 3/2005 | Desnoyer ................ | A61P 29/00 |
| | | | | 514/8.9 |
| 2007/0059314 | A1 | 3/2007 | Plouet et al. | |
| 2008/0207489 | A1 | 8/2008 | Castellot et al. | |
| 2012/0058928 | A1 | 3/2012 | Tohata et al. | |
| 2013/0216504 | A1 | 8/2013 | Riser | |
| 2015/0273019 | A1 | 10/2015 | Hamilton et al. | |
| 2018/0127478 | A1 | 5/2018 | Shen et al. | |
| 2018/0273603 | A1 | 9/2018 | Westbrook | |
| 2019/0105340 | A1 | 4/2019 | Hannon et al. | |
| 2020/0017564 | A1 | 1/2020 | Griffioen et al. | |

FOREIGN PATENT DOCUMENTS

| CN | 101146826 A | 3/2008 | |
| CN | 105396136 A | 3/2016 | |
| CN | 105396139 A | 3/2016 | |
| EP | 0413622 A1 | 2/1991 | |
| EP | 1648494 A2 | 4/2006 | |
| EP | 2556839 A2 | 2/2013 | |
| EP | 2654780 B1 | 2/2017 | |
| FR | 2858234 A1 | 2/2005 | |
| JP | 2012-528812 A | 11/2012 | |
| KR | 10-2018-0099537 A | 9/2018 | |
| KR | 10-2019-0026426 A | 3/2019 | |
| WO | 89/02922 A1 | 4/1989 | |
| WO | 90/13653 A1 | 11/1990 | |
| WO | 93/15199 A1 | 8/1993 | |
| WO | WO-9947556 A2 * | 9/1999 | .......... C07K 14/475 |
| WO | 2005/011725 A2 | 2/2005 | |
| WO | WO-2005/040191 A2 | 5/2005 | |
| WO | 2006/010891 A2 | 2/2006 | |
| WO | 2006/074452 A2 | 7/2006 | |
| WO | WO-2006/079120 A2 | 7/2006 | |

(Continued)

OTHER PUBLICATIONS

Halbourn et al. Proteins on the catwalk: modelling the structural domains of the CCN family of proteins. J Cell Commun Signal, 2009; 3:25-41. (Year: 2009).*

Eustache et al. Progress with peptide scanning to study structure activity relationships: the implications for drug discovery. Expert Opin Drug Discov, 2016; 11(8):771-784. (Year: 2016).*

Kaasboll et al. Connective tissue growth factor (CCN2) is a matricellular preproprotein controlled by proteolytic activation. J Biol Chem, 2018; 293(46):17953-17970. (Year: 2018).*

Tyndall et al., Causes and risk factors for death in systemic sclerosis: a study from the EULAR Scleroderma Trials and Research (EUSTAR) database, Ann. Rheum. Dis., 69(10):1809-15 (2010).

(Continued)

*Primary Examiner* — Daniel E Kolker
*Assistant Examiner* — Maureen Varina Driscoll
(74) *Attorney, Agent, or Firm* — MARSHALL, GERSTEIN & BORUN LLP

(57) ABSTRACT

The present invention relates to recombinant proteins having an amino acid sequence corresponding to or related to the thrombospondin type 1 repeat homology domain of a member of the CCN family proteins and the use thereof. Furthermore, the present invention relates to fusion proteins comprising an amino acid sequence corresponding to or related to the thrombospondin type 1 repeat homology domain of a member of the CCN family proteins combined with a fusion partner and optionally a linker region. Also, novel protease resistant Fc-fragments are disclosed herein.

18 Claims, 16 Drawing Sheets

Specification includes a Sequence Listing.

(56) References Cited

FOREIGN PATENT DOCUMENTS

| WO | WO-2007/033215 A2 | 3/2007 | |
| WO | 2007/066823 A1 | 6/2007 | |
| WO | 2009/086132 A2 | 7/2009 | |
| WO | WO-2010/139469 A2 | 12/2010 | |
| WO | WO-2011/031771 A1 | 3/2011 | |
| WO | 2011/118928 A2 | 9/2011 | |
| WO | 2011/123858 A2 | 10/2011 | |
| WO | WO-2012050930 A2 * | 4/2012 | ............... A61P 1/16 |
| WO | WO-2016145307 A1 | 9/2016 | |
| WO | WO-2016/197071 A1 | 12/2016 | |
| WO | WO-2017/013188 A1 | 1/2017 | |
| WO | WO-2017/121842 A1 | 7/2017 | |
| WO | 2017/158426 A1 | 9/2017 | |
| WO | 2018/026283 A1 | 2/2018 | |
| WO | 2019/071007 A1 | 4/2019 | |

OTHER PUBLICATIONS

Uniprot Consortium, Uniprot: a worldwide hub of protein knowledge, Nucleic Acids Res., 47(D1):D506-D515 (2019).

Valeria et al., A New Approach to Drug Therapy: Fc-Fusion Technology, Prim. Health Care: Open Access, 7(1):255 (2017).

Wang et al., Connective tissue growth factor confers drug resistance in breast cancer through concomitant up-regulation of Bcl-XL and cIAP1, Cancer Res., 69(8):3482-3491 (2009).

Wu et al., Conditional overexpression of connective tissue growth factor disrupts postnatal lung development, Am. J. Respir Cell Mol. Biol., 42(5):552-563 (2010).

Xiao et al., A novel peptide binding to the C-terminal domain of connective tissue growth factor for the treatment of bleomycin-induced pulmonary fibrosis, Int. J. Biol. Macromol., 156:1464-1473 (2020).

Yoon et al., The opposing effects of CCN2 and CCN5 on the development of cardiac hypertrophy and fibrosis, J. Mol. Cell. Cardiol., 49(2):294-303 (2010).

Zheng et al., Epithelial-to-mesenchymal transition is dispensable for metastasis but induces chemoresistance in pancreatic cancer, Nature, 527:525-530 (2015).

Zhu et al., Epithelial derived CTGF promotes breast tumor progression via inducing EMT and collagen I fibers deposition, Oncotarget, 6(28):25320-25338 (2015).

Feng Meiqing, Biotechnological Pharmaceutics, China Medical Science Press, p. 130, published on Jan. 1, 2016.

Ying et al., Monomeric IgG1 Fc molecules displaying unique Fc receptor interactions that are exploitable to treat inflammation-mediated diseases, mAbs, 6(5): 1201-1210, (2014).

Zolfaghari et al., The carboxyl-terminal TSP1-homology domain is the biologically active effector peptide of matricellular protein CCN5 that counteracts profibrotic CCN2, J. Biol. Chem., 299(1): 102803, (2023).

Andersen et al., Extending serum half-life of albumin by engineering neonatal Fc receptor (FcRn) binding, J. Biol. Chem., 289(19):13492-13502 (2014).

Arai et al., Design of the linkers which effectively separate domains of a bifunctional fusion protein, Protein engineering, 14(8):529-532 (2001).

Bickelhaupt et al., Effects of CTGF Blockade on Attenuation and Reversal of Radiation-Induced Pulmonary Fibrosis, J. Natl. Cancer Inst., 109(8):djw339 (2017).

Bonniaud et al., Adenoviral gene transfer of connective tissue growth factor in the lung induces transient fibrosis, Am. J. Respir Crit Care Med., 168(7):770-778 (2003).

Bonniaud et al., Connective tissue growth factor is crucial to inducing a profibrotic environment in "fibrosis-resistant" BALB/c mouse lungs, Am. J. Respir Cell Mol. Biol., 31(5):510-516 (2004).

Borrok et al., An "Fc-Silenced" IgG1 Format With Extended Half-Life Designed for Improved Stability, J. Pham. Sci., 106(4):1008-1017 (2017).

Butler et al., Degradomic and yeast 2-hybrid inactive catalytic domain substrate trapping identifies new membrane-type 1 matrix metalloproteinase (MMP14) substrates: CCN3 (Nov) and CCN5 (WISP2), Matrix Biol., 5923-38 (2017).

Chen et al., CTGF disrupts alveolarization and induces pulmonary hypertension in neonatal mice: implication in the pathogenesis of severe bronchopulmonary dysplasia, Am. J. Physiol. Lung Cell Mol. Physiol., 300(3): L330-340 (2011).

Chen et al., CTGF enhances the motility of breast cancer cells via an integrin-alphavbeta3-ERK1/2-dependent S100A4-upregulated pathway, J. Cell Sci., 120:2053-2065 (2007).

Chien et al., Expression of connective tissue growth factor (CTGF/CCN2) in breast cancer cells is associated with increased migration and angiogenesis, Int. J. Oncol., 38(6):1741-1747 (2011).

Dozie et al., Site-Specific PEGylation of Therapeutic Proteins, Int. J. Mol. Sci., 16(10):25831-25864 (2015).

Edelman et al., The covalent structure of an entire gammaG immunoglobulin molecule, Proc. Natl. Acad. Sci. USA, 63(1):78-85 (1969).

Esposito et al., Gateway cloning for protein expression, Methods in Molecular Biology, 498:31-54 (2009).

European Application No. 19163970.7, European Search Report and Opinion, mailed Sep. 10, 2019.

Fischer et al., Epithelial-to-mesenchymal transition is not required for lung metastasis but contributes to chemoresistance, Nature, 527:472-476 (2015).

Gao et al., Connective tissue growth factor (CCN2) induces adhesion of rat activated hepatic stellate cells by binding of its C-terminal domain to integrin alpha(v)beta(3) and heparan sulfate proteoglycan, J. Biol. Chem., 279(10):8848-55 (2004).

Guillon-Munos et al., Kallikrein-related peptidase 12 hydrolyzes matricellular proteins of the CCN family and modifies interactions of CCN1 and CCN5 with growth factors, J. Biol. Chem., 286(29):25505-25518 (2011).

Holbourn et al., Proteins on the catwalk: modelling the structural domains of the CCN family of proteins, J. Cell Commun. Signal, 3(1):25-41 (2009).

International Application No. PCT/EP2020/057773, International Preliminary Report on Patentability, mailed Sep. 30, 2021.

International Application No. PCT/EP2020/057773, International Search Report and Written Opinion, mailed Jun. 8, 2020.

Jacobsen et al., Engineering an IgG Scaffold Lacking Effector Function with Optimized Developability, J. Biol. Chem., 292(5):1865-1875 (2017).

Jang et al., Connective Tissue Growth Factor Promotes Pulmonary Epithelial Cell Senescence and Is Associated with COPD Severity, COPD, 14(2):228-237 (2017).

Jeong et al., Matricellular Protein CCN5 Reverses Established Cardiac Fibrosis, J. American College of Cardiology, 67(13):1557-1568 (2016).

Jun et al., Taking aim at the extracellular matrix: CCN proteins as emerging therapeutic targets, Nat. Rev. Drug. Discovery, 10(12):945-963 (2011).

Kaasboll et al., Connective tissue growth factor (CCN2) is a matricellular preproprotein controlled by proteolytic activation, J. Biol. Chem., 293(46):17953-17970 (2018).

Kang et al., A multigenic program mediating breast cancer metastasis to bone, Cancer Cell, 3(6):537-549 (2003).

Karagiannis et al., Peptides derived from type I thrombospondin repeat-containing proteins of the CCN family inhibit proliferation and migration of endothelial cells, The International Journal of Biochemistry & Cell Biology, 39(12):2314-2323 (2007).

Kinder et al., Engineered protease-resistant antibodies with selectable cell-killing functions, J. Biol. Chem., 288(43):30843-54 (2013).

Konigshoff et al., WNT1-inducible signaling protein-1 mediates pulmonary fibrosis in mice and is upregulated in humans with idiopathic pulmonary fibrosis, J. Clin. Invest., 119(4):772-787 (2009).

Lai et al., Taxol resistance in breast cancer cells is mediated by the hippo pathway component TAZ and its downstream transcriptional targets Cyr61 and CTGF, Cancer Res., 71(7):2728-2738 (2011).

Leask, Yin and yang revisited: CCN3 as an anti-fibrotic therapeutic?, J. Cell Commun. Signal, 9:97-98 (2015).

(56)        References Cited

OTHER PUBLICATIONS

Lefranc, Immunoglobulins: 25 years of immunoinformatics and IMGT-Ontology, Biomolecules, 4(4):1102-1139 (2014).
Leu et al., Identification of a novel integrin alpha 6 beta 1 binding site in the angiogenic inducer CCN1 (CYR61), J. Biol. Chem., 278(36):33801-33808 (2003).
Liu et al., Role of CCN5 (WNT1 inducible signaling pathway protein 2) in pancreatic islets, Journal of Diabetes, 9(5):462-474 (2017).
Lu et al., Mapping native disulfide bonds at a proteome scale, Nat methods, 12(4):329-331 (2015).
Macwilliam et al., Analysis Tool Web Services from the EMBL-EBI, Nucleic Acids Res., 41(Web Server issue):W597-W600 (2013).
Moe et al., CCN2 exerts direct cytoprotective actions in adult cardiac myocytes by activation of the PI3-kinase/Akt/GSK-38 signaling pathway, J. Cell Commun. Signal, 7(1):31-47 (2013).
Mueller et al., Humanized porcine VCAM-specific monoclonal antibodies with chimeric IgG2/G4 constant regions block human leukocyte binding to porcine endothelial cells, Mol. Immunol., 34(6):441-452 (1997).
Parapuram et al., Loss of PTEN expression by mouse fibroblasts results in lung fibrosis through a CCN2-dependent mechanism, Matrix Biol., 43:35-41 (2015).
Perbal et al., Correction to: The official unified nomenclature adopted by the HGNC calls for the use of the acronyms, CCN1-6, and discontinuation in the use of CYR61, CTGF, NOV and WISP 1-3 respectively, J. Cell. Commun. Signal., 13(3):435 (2019).
Riser et al., CCN3/CCN2 regulation and the fibrosis of diabetic renal disease, J. Cell Commun. Signal, 4:39-50 (2010).
Riser et al., Treatment with the matricellular protein CCN3 Blocks and/or Reverses fibrosis development in obesity with diabetic nephropathy, The American J. Pathol., 184(11):2908-2921 (2014).
Rother et al., Discovery and development of the complement inhibitor eculizumab for the treatment of paroxysmal nocturnal hemoglobinuria, Nat. Biotechnol., 25(11):1256-1264 (2007).
Sambrook et al., Molecular Cloning: A laboratory Manual (third edition), CSHL Press, (2001).
Schutze et al., CYR61/CCN1 and WISP3/CCN6 are chemoattractive ligands for human multipotent mesenchymal stroma cells, BMC Cell Biol., 8:45 (2007).
Schutze et al., Expression, purification, and functional testing of recombinant CYR61/CCN1, Protein Expr. Purif., 42(1):219-225 (2005).
Sievers et al., Clustal Omega for making accurate alignments of many protein sequences, Protein Sci., 27(1):135-145 (2018).

Sonnylal et al., Connective tissue growth factor causes EMT-like cell fate changes in vivo and in vitro, J. Cell Sci., 126:2164-2175 (2013).
Sonnylal et al., Selective expression of connective tissue growth factor in fibroblasts in vivo promotes systemic tissue fibrosis, Arthritis Rheum, 62(5):1523-1532 (2010).
Strohl, Fusion Proteins for Half-Life Extension of Biologics as a Strategy to Make Biobetters, BioDrugs, 29(4):215-239 (2015).
Berry et al., Substitution of Cystein for Selenocysteine in Type I Iodothyronine Deiodinase Reduces the Catalytic Efficiency of the Protein but Enhances its Translation, Endocrinology, 131(4):1848-1852 (1992).
Chen et al., Fusion protein linkers: Property, design and functionality, Advances Drug Delivery Reviews, 65(10):1357-1369 (2013).
Gasser et al., Antibody production with yeasts and filamentous fungi on the road to large scale?, Biotechnology letters, 29(2):201-212 (2007).
Glaesner et al., Engineering and characterization of the long-acting glucagon-like peptide-analogue LY2189265, an Fc fusion protein, Diabetes/Metabolism Research and Reviews, 26(4):287-296 (2010).
Keskin et al., A new, structurally nonredundant, diverse data set of protein-protein interfaces and its implications, Protein Sci., 13(4):1043-1055 (2004).
Kontermann et al., Bispecific antibodies, Drug Discovery Today, 7(20):838-847 (2015).
Kuznetsova et al., Immunoregulatory Properties of Thrombospondin-1, a Component of Extracellular Matrix and an Angiogenesis Inhibitor, Medical Immunology, 10(6):499-506 (2008).
Maeda et al., Engineering of Functional Chimeric Protein G-Vargula Luciferase, Analytical biochemistry, 249(2):147-152 (1997).
Muller et al., Spliceosomal Peptide P140 for Immunotherapy of Systemic Lupus Erythematosus, Arthritis & Rheumatism, 58(12):3874 (2008).
Pakula et al., Genetic Analysis of Protein Stability and Function, Annu. Rev. Genet., 23:289-310 (1989).
Shen et al., Single Variable Domain-IgG Fusion, a Novel Recombinant Approach to Fc Domain-Containing Bispecific Antibodies, Journal of Biological Chemistry, 281(16):10706-10714 (2006).
Tokuriki et al., Stability effects of mutations and protein evolvability, Current Opinion in Structural Biology, 19(5):596-604 (2009).
Yampolsky et al., The Exchangeability of Amino Acids in Proteins, Genetics, 170(4):1459-1472 (2005).
GenBank Accession No. AAA51688.1, albumin, partial [*Homo sapiens*], dated Jul. 25, 2016.
GenBank Accession No. CAG33713.1, NOV [*Homo sapiens*], dated Oct. 16, 2008.

* cited by examiner

A

B

C

D

Conditioned media from ExpiCHO suspension cultures
transiently transfected with CCN5(domain III)-Fc-fusion hinge variants
with Constant Heavy domains 2-3 from IgG4

WB: anti-human IgG4          Stain-Free protein visualization

Conditioned media from ExpiCHO suspension cultures
transiently transfected with CCN5(domain III)-Fc-fusion variants
with different peptide linkers WB: anti-human IgG4

Stain-Free™ gel of eluted protein
corresponding to SEQ ID No. 58
(CCN5(dIII)-SL-Fcv0)
purified by protein A capture chromatography Stain-Free™ gel of eluted protein
corresponding to SEQ ID No. 27
purified by protein A capture chromatography Stain-Free™ gel of eluted protein
corresponding to SEQ ID No.   73
purified by protein A capture chromatography ▲ EGF
■ Protein corresponding to SEQ ID No. 102
θ Protein corresponding to SEQ ID No. 97

▲ EGF
◆ Protein corresponding to SEQ ID No. 110

A

B

C

D

E

F

RECOMBINANT CCN DOMAIN PROTEINS AND FUSION PROTEINS

CROSS REFERENCE TO RELATED APPLICATIONS

This application is a 35 U.S.C. § 371 national phase entry of International Application No. PCT/EP2020/057773, filed Mar. 20, 2020, which claims priority to European Patent Application No. 19163970.7, filed Mar. 20, 2019, and the disclosures of which are hereby incorporated by reference in their entireties.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "56868_Seqlisting.txt." The Sequence Listing was created on Aug. 30, 2021, and is 228,387 Bytes in size. The subject matter of the Sequence Listing is incorporated by reference herein in its entirety.

FIELD OF INVENTION

The present invention relates to recombinant proteins having an amino acid sequence corresponding to or related to the thrombospondin type 1 repeat homology domain (domain III) of a member of the CCN family proteins and the use thereof, including particularly such proteins which are truncated and/or comprise certain amino acid modifications. Furthermore, the present invention relates to fusion proteins comprising an amino acid sequence corresponding to or related to the thrombospondin type 1 repeat homology domain of a member of the CCN family proteins combined with a fusion partner optionally via a linker peptide. In particular, the fusion partner is a monomeric protein, and the fusion proteins are monomeric.

Also, novel protease resistant Fc-fragments are disclosed herein.

BACKGROUND OF THE INVENTION

CCN proteins are a family of secreted glycoproteins. CCN was originally coined as an acronym derived from the first three identified members of the gene family; Cyr61, CTGF and NOV. However the acronym has recently been adapted to be short for Cellular Communication Network factors and ratified by the HUGO Gene Nomenclature Committee (Perbal B, Tweedie S and Bruford E, J Cell Commun Signal. 2019 September; 13(3):435). The proteins are often classified as matricellular proteins, associated with the extracellular matrix (ECM). The CCN proteins are not part of the scaffold function, organizing the cells into tissues, but are rather considered signaling proteins and can function as independent autocrine or paracrine signaling factors, or as modifiers of other extracellular signaling proteins. Together with a set of three Wnt-inducible signaling pathway proteins (WISP1/CCN4, WISP2/CCN5, and WISP3/CCN6), they comprise a family of six homologous cysteine-rich proteins in mammals that have been renamed CCN1-6.

The initial members of the CCN family share a modular structure, with an N-terminal peptide signal for secretion followed by four conserved domains. The first domain shows sequence homologies to insulin-like growth factor binding proteins (IGFBP) and is thus known as IGF-binding protein homology domain, although only having neglible affinity for IGF. The second domain is known as the von Willebrand factor type C repeat (VWC) homology domain often seen in extracellular matrix (ECM) proteins. The third domain is known as the thrombospondin type I repeat homology domain (TSP-1) which may be involved in the attachment of CCN proteins to integrins. The forth domain is a cysteine-rich, C-terminal repeat or cystine knot homology domain, a domain reported to bind heparin. The $5^{th}$ member of the CCN protein family, the WISP2 (Wnt1-inducible signaling pathway protein 2), also known as CCN5, is atypical in lacking the carboxyl-terminal cystine knot domain (domain 4). The TSP-1 homology domains of the CCN protein family share 34% amino acid sequence identity and 25% sequence similarity (as analyzed by ClustalOmega, see below for reference). Four-domain CCN proteins contain 38 conserved cysteines throughout the primary sequence except for CCN6 in which 4 cysteines of the VWC homology domain are not conserved among the other family members. Also, for CCN5 which lacks the carboxyl-terminal cystine knot homology domain, all cysteines of the IGFBP, VWC and TSP-1 homology domains are conserved compared with the other CCN family members.

A non-conserved, protease-sensitive central region, often referred to as the hinge region, bisects the proteins into two halves. The expression of CCN proteins is regulated at transcriptional, post-transcriptional and translational levels in response to changes in environmental stimuli.

Information on the domain organization of the CCN-protein family is found in e.g. Liu et al, 2017, Journal of Diabetes, 9, pp. 462-474.

At the cellular level, CCN proteins may have diverse regulatory roles at the interface of the extracellular matrix and the cell surface. CCN proteins can regulate cell adhesion, migration, proliferation, differentiation, apoptosis, survival, senescence and gene expression. By modulating one or more aspects of these cellular functions, in a cell type-specific manner, CCNs coordinate complex biological processes, including cardiovascular and skeletal development during embryogenesis, as well as inflammation, wound healing, and tissue injury and repair in the adult. Generally speaking, the 4-domain CCN 1-4 and CCN6 (particularly CCN1, CCN2 and CCN4) may exert pro-fibrotic activity, whereas CCN5, which comprises only the 3 domains I-III, has anti-fibrotic activity.

CCN proteins are also involved in a broad diversity of pathological conditions, such as organ failure due to progressive fibrosis, for example hepatic fibrosis and idiopathic pulmonary fibrosis, and in cancer invasion and metastasis. Reference is in this respect made to Jun and Lau, 2011, Nat. Rev. Drug. Discovery, 10(12), pp. 945-963. Again, generally speaking, the 4-domain CCN proteins, in particular CCN2 have been shown to be implicated in the mechanisms of various fibrotic diseases, whereas in preclinical disease models of such diseases it has conversely been shown that increased CCN5 levels may be beneficial.

In Kaasbøll et al., J. Biol. Chem, 293:46, pp. 17953-17970, it is reported that connective tissue growth factor (CTGF), also known as CCN2, is synthesized and secreted as an inactive preproprotein that requires proteolytic cleavage to release biologically active CCN2, and that a homodimer of the C-terminal fragment comprised of domains III-IV represents the biologically fully active form of CCN2, and finally, that all major reported activities of CCN2 could be recapitulated by the homodimer of the C-terminal domains III-IV fragment. Activity assays reported by Kaasbøll et al.

revealed that neither unprocessed, full-length CCN2 nor the N-terminal fragment comprised of domains I-II were biologically active. Furthermore, it was found that proteolytic processing of full-length CCN2 by matrix metalloproteinase (MMP)-activities released its latent activity. Collectively, the findings reported by Kaasbøll et al. imply that prepro-CCN2 is autoinhibited by N-terminal domains I and II. It was also found that the C-terminal domains III and IV fragment of CCN1 and CCN3 was sufficient for activation of rapid cell signaling and eliciting cell physiologic responses. However, to what extent endopeptidase cleavage of the hinge region of CCN1 and/or CCN3, or any other CCN protein family member, are required for release of biologic activity, is unknown.

It is known that CCN2 is highly expressed during development, in various pathological conditions that involves enhanced fibrogenesis and tissue fibrosis, and in several cancers (Jun and Lau, 2011, supra). The fact that CCN proteins are involved in a broad diversity of pathological conditions, are extracellular proteins mechanistically involved in the development of fibrosis, and display limited expression in healthy organisms, make them attractive therapeutic targets.

Jeong et al., 2016, J. American College of Cardiology, 67: 13, pp. 1557-1568, reports on a study examining the role of adeno-associated virus-mediated gene transfer of CCN5 to murine hearts after experimentally-induced pressure overload of the heart. The study concludes that CCN5 may reverse established cardiac fibrosis by inhibiting generation of and enhancing apoptosis of myofibroblasts in the myocardium, suggesting that CCN5 may provide a platform for developing anti-cardiac fibrosis therapies.

In US2008/0207489, a method for treating a smooth muscle proliferation-based disorder is disclosed, involving expression of CCN5 or administering the CCN5 protein to smooth muscle cells.

In EP 2 556 839, a composition is provided comprising a genetic carrier comprising a nucleotide sequence encoding full-length CCN5 or CCN2ΔCT, and its role in treatment of heart failure is suggested. CCN2ΔCT in EP 2 556 839 is defined as the amino acid sequence of CCN2 truncated after K251 (uniprot numbering).

Although overexpression of CCN5 has been reported in some experimental systems to result in an opposite phenotype to that of CCN2 overexpression (Jeong et al. supra, Yoon et al., J Mol Cell Cardiol, 49 (2), 294-33 Aug. 2010), direct antagonization of the four-domain CCN proteins by CCN5 has to the authors' knowledge not been reported. In particular, the structural basis for CCN5/WISP2-mediated antagonism of the other CCN family members, was unknown prior to the work presented in this invention.

The inventors have at an earlier stage shown that full-length-CCN2 (FL-CCN2) is a preproprotein, an inactive precursor, and that a fragment comprising domains III and IV appears to convey all biologically relevant activities of CCN2. To what extent CCN proteins in general are secreted as inactive preproproteins that require proteolytic activation remains unknown. Yet, the susceptibility of full-length CCN-proteins to multiple proteases, as demonstrated by the inventors (Kaasbøll et al., J. Biol. Chem. (2018) 293(46) 17953-17970) and others (Butler, G. S. et al. *Matrix Biol* 59, 23-38 (2017) and Guillon-Munos, A. et al. *J Biol Chem* 286, 25505-25518 (2011)) implies that unmodified, full-length CCN proteins will be highly unsuitable as drugs for reasons of stability both during recombinant protein manufacturing and following in vivo administration. This unsuitability of using unmodified, full-length CCN proteins as therapeutic proteins also applies to fusion proteins of full-length CCN proteins, e.g. as described for full-length CCN1 (Schutze, N. et al. (2005) Protein Expr Purif 42, 219-225) and full-length CCN6 (Schutze, N et al. (2007) BMC Cell Biol 8, 45). It is well known in the field of CCN proteins that the susceptibility of these proteins to proteolysis is one of the reasons why it is very difficult to produce recombinant CCN proteins. Furthermore, based on the novel findings of Kaasbøll et al. (J Biol Chem 2018; 293(46):17953-17970) recombinant full-length CCN proteins may be far from ideal biologic drugs, as their activity may be dependent on prior proteolytic processing, making pharmacokinetics and pharmacodynamics unpredictable. Furthermore, in the case of Fc-fusion proteins, in addition to the proteolytic susceptibility of the components, e.g. peptide linker, CCN-fragment and Fc-fragment, the arrangement of the components has also been shown to be of importance for the efficacy and potency of the recombinant fusion proteins. One example of this is in the paper published by the inventors (Kaasbøll et al. (2018)), in which variants of Fc-fusion proteins containing domains III-IV of CCN2 are found to have widely varying activities in a manner not easily predictable beforehand.

The actions of CCN proteins has been reported to be susceptible to antagonizing effects by high concentrations of synthetic peptides derived from the primary sequences of the CCN proteins. One example is inhibition of AKT phosphorylation stimulated by recombinant CCN2 in Rat2 fibroblasts by peptides derived from domain I, the IGFBP homology domain, and to a lesser extent peptides derived from domain III, the TSP-1 repeat homology domain, of CCN2 (Moe et al., J. Cell Commun. Signal. (2013) 7:31-47). Another example is the inhibition of CCN2 (domain IV)-stimulated adhesion of hepatic stellate cells by a peptide derived from domain IV, the cystin knot homology domain, of CCN2 (Gao R and Brigstock D R., J Biol Chem. 2004 Mar. 5; 279(10):8848-55). Furthermore, peptides from domain III of CCN1 (Leu et al. J. Biol. Chem, 2003, Vol. 278, No. 36, Issue of September 5, pp. 33801-33808, 2003) and domain III of CCN1, CCN2, CCN3, CCN5 and CCN6 (Karagiannis E G and Popel The International Journal of Biochemistry & Cell Biology 39 (2007) 2314-2323) have been reported to have some anti-angiogenic effects in in vitro assays with HUVEC cells (Leu et al. J. Biol. Chem, 2003 and Karagiannis E G and Popel, Int J Biochem Cell Biol 39 (2007)) and anti-adhesion effects on 1064SK human foreskin fibroblasts (Leu et al. J. Biol. Chem, 2003), these peptides only contain one (Leu et al. J. Biol. Chem, 2003) or two (Karagiannis E G and Popel, Int J Biochem Cell Biol 39, 2007) of the conserved cysteines which are central to the invention described in this document. The cysteines in domain III of the CCN proteins are known to create disulfide bridges, as demonstrated in CCN2 endogenously expressed from HUVEC cells (Lu, S et al. (2015) Nat methods 12, 329-331) and from purified, recombinant CCN2 (Kaasbøll et al., J. Biol. Chem. 2018). The disulfide bridges demonstrated in CCN2 spanning C199-C228 (uniprot numbering) confers a complex 3D structure where the amino acid chain folds back upon itself. This implies that the complete domain III of a CCN protein cannot be expected to be replicated by short peptides that are not structurally constrained by disulfide-bridges between the cysteines as in the complete domain III of the CCN proteins produced in eucaryotic systems. Furthermore, the inhibition of CCN2 activities by peptides derived from the primary sequences of domains LIM and IV illustrates the lack of knowledge in the field regarding whether peptides derived from a specific domain of CCN2 can confer inhibition of four-domain CCN proteins.

The inventors have now, based on structure-activity analysis of CCN family proteins and the observation that CCN2 need to undergo proteolytic processing in order to become biologically active, found that the biologically active part of the CCN5 protein is domain III, the thrombospondin type I repeat homology domain. This new knowledge has resulted in the providing of bioactive structures based on domain III of CCN5 as well as domain III of other members of the CCN protein family.

SUMMARY OF INVENTION

The present inventors insights into the structure-activity relationship of CCN5, and other CCN-proteins has resulted in the providing of novel biologically active recombinant proteins that recapitulate the cell signaling and cell physiological functions ascribed to CCN5-signaling and, which may also counteract the other four-domain CCN proteins (Cyr61 (also known as CCN1), CTGF (also known as CCN2), NOV (also known as CCN3), WISP1 (also known as CCN4) and WISP3 (also known as CCN6)). In other words, proteins are provided, including in the form of fusion proteins, based on domain III, the TSP-1 homology domain, of a CCN protein, which recapitulate, or which have, the biological activity of CCN5, and which are able to antagonize, or inhibit, the effects of the 4-domain CCN proteins, CCN1-4 or CCN6. In particular the proteins herein have anti-fibrotic activity and may also have direct anti-cancer activity.

As noted above, domain III (the TSP-1 homology domain) of the other CCN proteins, namely the 4-domain CCN proteins, when provided as a separate domain in the absence of the other CCN domains, has surprisingly been found to be sufficient to recapitulate the reported activities of CCN5. Accordingly, in other words, domain III of the 4-domain CCN proteins, when provided as a separate domain in the absence of the other CCN domains (i.e. as an isolated domain), has the same activity as CCN5, or, alternatively expressed, as domain III/TSP-1 homology domain of CNN5, (that is an opposite activity to that of full-length 4-domain CCN proteins). Thus from the experiments disclosed in this document it is clear that the isolated TSP-1 homology domain of any CCN protein may exert the same activity as that of the TSP-1 homology domain of CCN5. Other than in the case of CCN5, this may not be the same as the activities exerted by the full-length CCN protein.

It has been found that monomeric fusion proteins, wherein the domain III of a CCN protein is fused to a monomeric fusion partner, are of particular benefit and utility according to the invention and disclosure herein.

According to a first aspect, the present invention provides a monomeric fusion protein comprising:

(i) a polypeptide corresponding to at least a portion of the thrombospondin type 1 repeat (TSP-1) homology domain of a CCN family protein;

(ii) a monomeric fusion partner N- or C-terminally fused to the amino acid sequence of (i); and (iii) optionally a peptide linker between the polypeptide of (i) and the monomeric fusion partner of (ii), wherein the polypeptide of (i) is 40 to 60 amino acids in length and comprises an amino acid sequence selected from SEQ ID NOs: 37 or 2 to 6, or a sequence having at least 80% sequence identity to a sequence selected from SEQ ID NOs: 37 or 2 to 6 wherein all of the cysteine residues in said sequence selected from SEQ ID NOs: 37 or 2 to 6 are conserved, and wherein the monomeric fusion partner of (ii) and the peptide linker of (iii) are not or do not comprise an IGF binding protein homology domain, a von Willebrand factor type C repeat homology domain, or a cysteine knot domain of a CCN family protein.

As will be described in more detail below, SEQ ID NOs. 37, and 2-6 represent 44 amino acid truncated fragments of domain III of CCN5, CCN3, CCN2, CCN1, CCN4 and CCN6, respectively, which comprise the 6 conserved cysteine residues of this domain. In particular the fragments are flanked by the first and last cysteine residues of the domain. It has been found that such fragments are particularly effective and resistant to proteolytic degradation.

In an embodiment, the polypeptide of (i) comprises or consists of:

(a) an amino acid sequence selected from SEQ ID NOs: 1 or 8 to 12; or (b) an amino acid sequence having at least 80% sequence identity to a sequence selected from SEQ ID NOs: 1 or 8 to 12; or (c) a part of an amino acid sequence of (a) or (b), wherein said part comprises at least the 44 amino acid sequence of SEQ ID NOs: 37, 6, 2, 3, 4 or 5 respectively or a sequence having at least 80% sequence identity to a sequence selected from SEQ ID NOs: 37, 6, 2, 3, 4 or 5 respectively.

SEQ ID NOs. 1, and 8-12 represent slightly longer N-terminally truncated fragments of domain III of CCN5, CCN6, CCN3, CCN2, CCN1, and CCN4 respectively. These fragments comprise the corresponding sequences of SEQ ID NOs. 37, 6, 2, 3, 4, and 5 respectively, with some additional C-terminal sequence from the respective domain III.

In a further embodiment, the polypeptide of (i) comprises an alanine residue at the position corresponding to position 2 of said sequence selected from SEQ ID NOs: 37 or 2 to 6, or SEQ ID NOs: 1 or 8 to 12. In some embodiments, the amino acid sequence of (i) comprises an amino acid sequence selected from SEQ ID NO: 38 or 42 to 46, or an amino acid sequence having at least 80% sequence identity thereto. In another embodiment, the amino acid sequence of (i) comprises an amino acid sequence selected from SEQ ID NO: 7, or 47 to 51, or an amino acid sequence having at least 80% sequence identity thereto. It has been found in this respect that substitution of this residue at position 2 is beneficial in promoting stability of the protein.

According to a further aspect of the invention, the monomeric fusion protein has an amino acid sequence selected from the group consisting of SEQ ID NOs: 84, 85, 88, 89, 97, 98, 102, 103, 106, 107, 110, 111, or an amino acid sequence having 80% sequence identity thereto.

In embodiments of these aspects the monomeric fusion partner is selected from serum albumin, transferrin and monomeric Fc fragments, particularly monomeric Fc fragments of IgG, more particularly human IgG.

As noted above, substitution of position 2 of the domain III fragments herein improves the stability of the fragment, in particular resistance to protease degradation. It is believed and proposed herein that such sequence-modified variants of the domain III fragments represent useful proteins in their own right, without being linked to a fusion partner.

Accordingly, another aspect of the invention also provides a protein 40 to 60 amino acids in length which comprises, or a protein which consists of, an amino acid sequence as set out in SEQ ID NO: 7, 38, 42 to 46, or 47 to 51 or a sequence with at least 80% sequence identity thereto, wherein the protein comprises an alanine residue at the position corresponding to position 2 of said sequence of SEQ ID NO: 7, 38, 42 to 46, 47 to 51, and wherein all of the cysteine residues in said sequence are conserved.

Other proteins and fusion proteins are also provided as further aspects of the inventions, as detailed below.

According to a further aspect of the invention, a recombinant protein is provided comprising a of formula (I)

Cys-A-Cys-B-Cys-C-Cys-D-Cys-E-Cys-F     (formula (I))

wherein

A is a peptide of formula II

A1-A2-A3-A5-A6-A7-A8-A9 wherein A1 is selected from the group consisting of P, A, V, I, and L; A2 is selected from the group consisting of E, D, A, I, L, and V; A3 is selected from the group consisting of G, Q, Y, S, N, W, F; A4 is selected from the group consisting of A, I, L, V, S, T; A5 is an amino acid selected from the group consisting of T, Y, N, G, Q and S; A6 is an amino acid selected from the group consisting of A, V, I, L, P, S, E, D, K, R, and H; A7 is W; A8 is selected from the group consisting of G, T, S, Q, Y, N, P, A, V, I, and L; A9 is an amino acid selected from the group consisting of A, P, L, I, V, Q; and B is a peptide of formula III

B1-B2-B3 wherein B1 is an amino acid selected from the group consisting of G, Q, N, S, Y, and T; B2 is an amino acid selected from the group consisting of, T, S, N, F, Q, H, R and K; B3 is an amino acid selected from the group consisting of G, Q, N, S, Y, T; wherein one of B1-B3 is absent; and C is a peptide of formula IV

C1-C2-C3-C4-05-C6-C7-C8-C9-C10-C11-C12-C13-C14

Wherein C1 is an amino acid selected from the group consisting of G, Q, N, S, Y, and T; C2 is an amino acid selected from the group consisting of K, R, H, M, T, S, A, L, I, and V; C3 is an amino acid selected from the group consisting of G, Q, N, S, Y, and T; C4 is an amino acid selected from the group consisting of M, F, A, I, L, V, and W; C5 is an amino acid selected from the group consisting of G, Q, N, S, T, Y, A, I, L, and V; C6 is an amino acid selected from the group consisting of G, Q, N, S, and T; C7 is an amino acid selected from the group consisting of H, R, and L; C8 is an amino acid selected from the group consisting of A, L, I, and V; C9 is an amino acid selected from the group consisting of G, Q, N, S, T and Y; C10 is an amino acid selected from the group consisting of G, Q, N, S, T, Y (preferably N); C11 is an amino acid selected from the group consisting of V, P, A, I, L, G, Q, N, S, T, Y, R, K, D, and E; C12 is an amino acid selected from the group consisting of G, Q, N, S, Y, and T; C13 is an amino acid selected from the group consisting of H, K, R, A, L, I, V, P, G, Q, N, S, Y, and T; C14 is an amino acid selected from the group consisting of F, P, W, G, Q, N, S, Y, T, E, and D; and D is a peptide of formula V

D1-D2-D3-D4-D5-D6-D7-D8 wherein D1 is an amino acid selected from the group consisting of R, K, H, D, E, W, P; D2 is an amino acid selected from the group consisting of P, A, L, I, V, M, W, D, and E; D3 is an amino acid selected from the group consisting of D, E, A, L, I, V, R, K, and H; D4 is an amino acid selected from the group consisting of G, Q, S, Y, T, R, L, K, and H; D5 is an amino acid selected from the group consisting of G, Q, N, S, Y, T, D, and E; D6 is an amino acid selected from the group consisting of H, R; K, G, Q, N, S, Y, and T; D7 is an amino acid selected from the group consisting of L, H, and R; D8 is an amino acid selected from the group consisting of A, L, I, and V; and E is a peptide of formula VI

E1-E2-E3-E4 wherein E1 is an amino acid selected from the group consisting of P, A, L, I, V, M, W, G, Q, N, S, T, Y, D, and E; E2 is an amino acid selected from the group consisting of; P, A, L, I, V, M, W, G, Q, N, S, T, Y; E3 is an amino acid selected from the group consisting of, R, K, H, G, Q, N, S, T and Y; E4 is an amino acid selected from the group consisting of P, A, L, I and V; F is absent or an amino acid sequence of up to about 13 amino acids, wherein the recombinant protein comprises from 40 to 60 amino acid.

According to one embodiment of the above aspect, a recombinant protein of formula (I) is provided, wherein A1 is selected from the group consisting of P, I, and L; A2 is selected from the group consisting of E, V, and A; A3 is selected from the group consisting of W, Q, and Y; A4 is selected from the group consisting of S, T, and A; A5 is an amino acid selected from the group consisting of T and S; A6 is an amino acid selected from the group consisting of A, E, P, S and K; A7 is W; A8 is selected from the group consisting of G, S and T; A9 is an amino acid selected from the group consisting of P, Q and A; and B1 is serine (S); B2 is an amino acid selected from the group consisting of T, K and R; B3 is an amino acid selected from the group consisting of T and S; and C1 is an amino acid G; C2 is an amino acid selected from the group consisting of T, L and M; C3 is G; C4 is an amino acid selected from the group consisting of M, F, I, and V; C5 is an amino acid selected from the group consisting of S and A; C6 is an amino acid selected from the group consisting of T and N; C7 is R; C8 is an amino acid selected from the group consisting of V, and I; C9 is an amino acid selected from the group consisting of S, and T; C10 is asparagine N; C11 is an amino acid selected from the group consisting of Q, R, D, V, and E; C12 is asparagine N; C13 is an amino acid selected from the group consisting of R, A, P, and S; C14 is an amino acid selected from the group consisting of F, Q, S, E, and N; and D1 is an amino acid selected from the group consisting of R, E, and W; D2 is an amino acid selected from the group consisting of L, M, and P; D3 is an amino acid selected from the group consisting of E, L, V and R; D4 is an amino acid selected from the group consisting of T, K, and Q; D5 is an amino acid selected from the group consisting of Q and E; D6 is an amino acid selected from the group consisting of R, T, S, and K; D7 is arginine (R); D8 is an amino acid selected from the group consisting of L, and I; and E1 is an amino acid selected from the group consisting of L, M, E, N, and Y; E2 is an amino acid selected from the group consisting of; S, V, L and I; E3 is an amino acid selected from the group consisting of, Q and R; E4 is P; F is absent or a peptide of up to 13 amino acids and comprising an amino acid sequence selected from the group consisting of PPSRGRSPQNSAF, GQPVYSSL, EADLEEN, EQEPEQPTD, DVDIHTLI, and DSNILKTIKIP, wherein the recombinant protein comprises in total from 44 to 57 amino acid.

According to yet an embodiment of the above aspect, a recombinant protein of formula I is provided wherein F is fully absent, partially absent, or a peptide of about 13 amino acids comprising the amino acid sequence of PPSRGR-SPQNSAF.

More particularly, a recombinant protein is provided, wherein the protein comprises an amino acid sequence selected from the group consisting of SEQ ID No. 1, SEQ ID No. 2, SEQ ID No. 3, SEQ ID No. 4, SEQ ID No. 5, SEQ ID No. 6, and SEQ ID No. 7, SEQ ID No. 8, SEQ ID No. 9, SEQ ID No. 10, SEQ ID No. 11, SEQ ID No. 12, SEQ ID No. 37, SEQ ID No. 38; and fragments or variants thereof having above 50% sequence identity with the amino acid sequences SEQ ID No. 1, SEQ ID No. 2, SEQ ID No. 3, SEQ ID No. 4, SEQ ID No. 5, SEQ ID No. 6, and SEQ ID No. 7, SEQ ID No. 8, SEQ ID No. 9, SEQ ID No. 10, SEQ ID No. 11, SEQ ID No. 12, SEQ ID No. 37, SEQ ID No. 38.

According to another aspect of the invention, recombinant proteins as defined above are provided, wherein said protein is pegylated.

According to another aspect, the present invention provides a fusion protein comprising (i) Thrombospondin type 1 repeat (TSP-1) homology domain of a CCN family protein;

(ii) fusion partner N- or C terminally fused to the TSP-1 repeat homology domain of (i) and wherein said fusion partner is selected from the group consisting of serum albumin, transferrin and Fc-fragment of human IgG;

(iii) optionally a peptide linker between the TSP-1 repeat homology domain and the Fc fragment (N- or C-terminally fused to the TSP-1 repeat homology domain of (i)).

According to an embodiment of the above aspect, fusion proteins are provided comprising a recombinant protein according to the present invention as described above as a further aspect of the invention.

The fusion partner of a fusion protein according to the invention is according to one embodiment selected from the group consisting of an Fc fragment of IgG1, IgG2 or IgG4, serum albumin and transferrin.

According to a further embodiment, a fusion protein is provided wherein the fusion partner (ii) is an Fc fragment of IgG1, IgG2 or IgG4 comprising a stabilizing disulfide bridge. Such mutations may increase thermal stability of the protein. Stabilising mutations are known and have been reported in the art.

According to yet a further embodiment, a fusion protein is provided wherein the fusion partner (ii) is an Fc fragment of IgG1, IgG2 or IgG4 comprising one or more mutations selected from the group consisting of S228P (refers to IgG4), E233P (refers to IgG1 and IgG4), F234A (refers to IgG4), L234A (refers to IgG1), L234V (refers to IgG1), F234V (refers to IgG4), L235A (refers to IgG1 and IgG4), ΔG236 (refers to IgG1 and IgG4) and ΔK447 (refers to IgG1, IgG2 and IgG4).

According to another embodiment, a fusion protein may comprise an Fc fragment selected from the group consisting of SEQ ID No. 15, SEQ ID No. 16, SEQ ID No. 17, SEQ ID No. 18, and SEQ ID No. 19.

According to another embodiment, a fusion protein comprises a linker selected from the group consisting of SEQ ID No. 20; SEQ ID No. 21; SEQ ID No. 22, SEQ ID No. 23, SEQ ID No. 24, SEQ ID No. 25, and SEQ ID No. 39.

According to one embodiment, the linker comprises the amino acid sequence (EAAAK)n, wherein n is at least 4, preferably n is 8.

According to another embodiment, the fusion protein comprises an amino acid sequence selected from the group consisting of SEQ ID No. 26, SEQ ID No. 27; SEQ ID No. 28, SEQ ID No. 29, SEQ ID No. 30, SEQ ID No. 31, SEQ ID No. 40 and SEQ ID No. 41.

According to another embodiment, the fusion partner of (ii) is serum albumin.

According to another embodiment of the second aspect of the invention, the fusion partner of (ii) is transferrin.

The present invention furthermore, according to a still further aspect, provides a nucleic acid molecule (e.g. DNA) encoding a recombinant protein, protein or fusion protein according to the present invention.

According to one embodiment of this aspect, a DNA sequence is provided comprising a nucleic acid sequence as depicted in SEQ ID No. 34, SEQ ID No. 35, SEQ ID No. 36 or SEQ ID NOs: 86, 87, 90, 91, 99, 100, 104, 105, 108, 109, 112 or 113 and nucleic acid sequences having about 80% sequence identity with SEQ ID NO. 34, SEQ ID No. 35, SEQ ID No. 36 or SEQ ID NOs: 86, 87, 90, 91, 99, 100, 104, 105, 108, 109, 112 or 113.

Furthermore, according to another aspect of the invention, an expression vector is provided comprising a DNA sequence according to the present invention. Also a host cell comprising an expression vector according to the invention is provided.

Finally, a thrombospondin type 1 repeat (TSP-1) homology domain of a CCN family protein, a protein and a fusion protein as defined above is provided for use as a medicament is provided for treatment or prevention of disorders by inhibiting or counteracting the cell signaling, and cell physiological functions ascribed to the four-domain CCN family proteins.

In one aspect, there is provided a fusion protein, or a protein, as defined herein for use in therapy.

The fusion protein or protein may be for use in the treatment of a condition associated with activity of a 4-domain CCN protein, particularly unwanted or abberant activity of a 4-domain CCN protein. The activity may be associated with a fibrotic effect. The activity may be pro-fibrotic activity.

In another aspect, there is provided a fusion protein, or a protein, as defined herein for use in the treatment or prevention of fibrosis, or any condition exhibiting fibrosis (i.e. a fibrotic condition or disease). In a further aspect, there is provided a fusion protein, or a protein, as defined herein for use in the treatment of cancer. Also provided is a fusion protein, or a protein, as defined herein for use in the treatment of inflammatory or autoimmune diseases, or metabolic diseases.

Also provided according to such aspects of the invention is the use of a protein or a fusion protein as defined herein for the manufacture of a medicament for treating or preventing a condition or disease as defined or described herein.

Such aspects also include a composition (e.g. a pharmaceutical composition) comprising a protein or a fusion protein as defined herein for use in treating or preventing a condition or disease as defined or described herein.

Such aspects also include a method of treating or preventing a condition or disease as defined or described herein, said method comprising administering to a subject in need thereof a protein or a fusion protein as defined herein, particularly an effective amount of a said protein or fusion protein.

FIGURES

FIG. 1 shows the cell physiological and cell signaling of CCN5(dIII)-Fcv2 (an embodiment of the invention as defined in sequence SEQ ID No. 28).

A) shows that CCN5(dIII)-Fcv2 fusion protein of SEQ ID No. 28 causes concentration-dependent inhibition of phosphorylation of Akt (Serine-473) in A549 lung cancer cells.

B) Shows that the CCN5(dIII)-Fcv2 fusion protein of SEQ ID. No. 28 inhibits proliferation in a human lung fibroblast cell line, IMR90.

C) Shows that the CCN5(dIII)-Fcv2 fusion protein of SEQ ID No. 28 inhibits the sphere-forming ability (anchorage-independent growth) of the estrogen receptor-positive breast cancer cell line MCF-7 and of the triple-negative breast cancer cell line MDA-MB-231.

D) Shows that the CCN5(dIII)-Fcv2 fusion protein of SEQ ID No. 28 dose-dependently inhibits TGF-β-induced SMAD reporter activity (SMAD proteins are canonical TGF-β-regulated transcription factors).

All error bars show SD. Statistical significance calculated by 1-way ANOVA with Dunnetts post hoc test (p<0.05 indicated by *).

Figure 6:
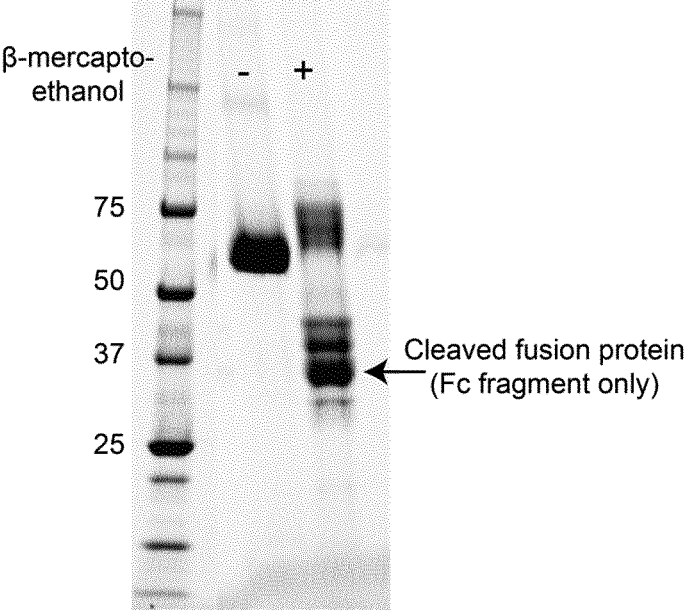

FIG. 6 shows the production of a protein corresponding to SEQ ID NO: 58, purified by protein A capture chromatography. It can be seen that a dimer is present in the absence of the reducing agent beta-mercaptoethanol (−lane). However, in the presence of beta-mercaptoethanol (+ lane), it can be seen that the primary product is a cleavage fragment comprised of the Fc fragment only, rather than the intact fusion protein containing all of the parts encoded by SEQ ID NO: 58 (the TSP-1 homology domain fragment, the peptide linker and the Fc fragment).

Figure 7:
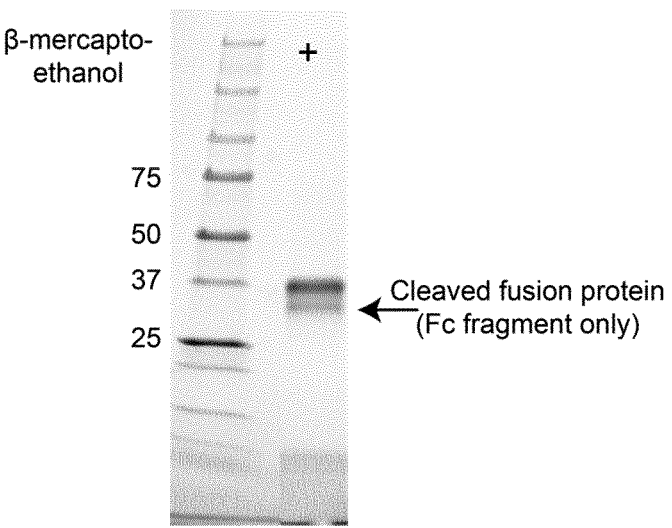

FIG. 7 shows the production of a protein corresponding to SEQ ID NO: 27, having a truncated C terminal tail, purified by protein A capture chromatography. It can be seen that the protein is significantly more resistant to protease degradation that the protein corresponding to SEQ ID NO: 58, which has the C terminal tail included.

Figure 8:
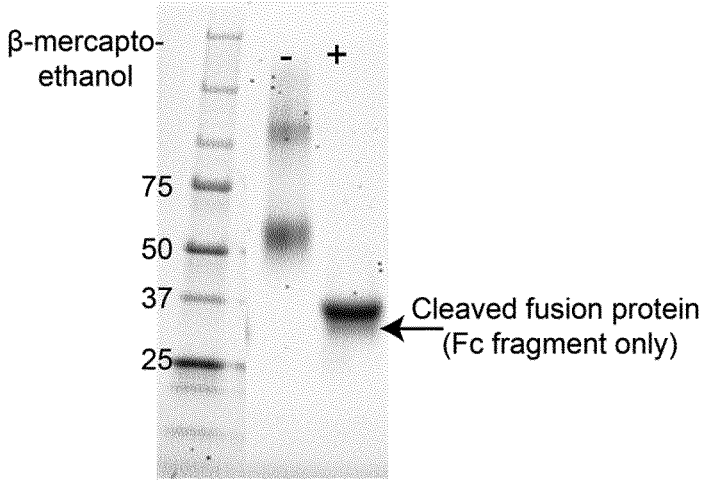

FIG. 8 shows the production of a protein corresponding to SEQ ID NO: 73, analogous to the protein corresponding to SEQ ID NO: 27, purified by protein A capture chromatography. Again, it can be seen in the presence of beta-mercaptoethanol (+ lane) that the protein is more resistant to protease degradation that the protein corresponding to SEQ ID NO: 58.

Figure 9:
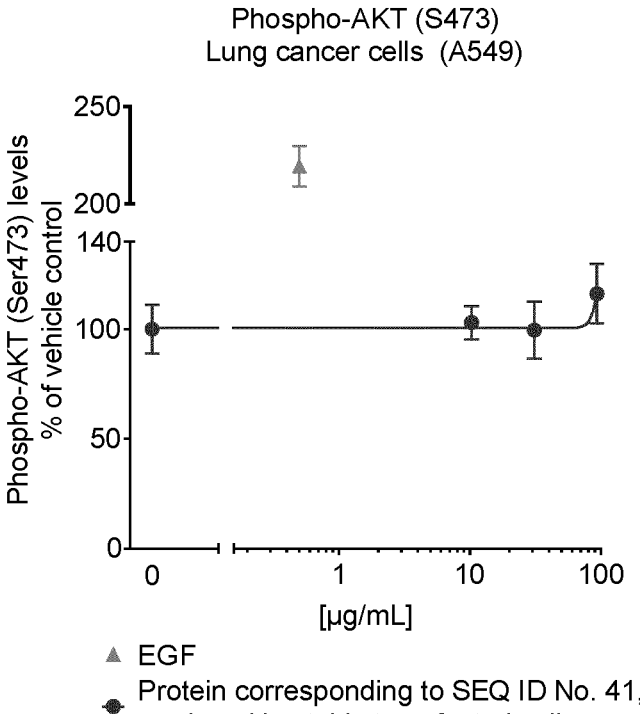

FIG. 9 shows the results of an assay measuring Phospho-AKT (Ser-473) levels in A549 lung cancer cells following administration of varying concentrations of a protein corresponding to SEQ ID NO: 41 produced in stably transfected cells. It can be seen that the protein shows no inhibition of the phosphorylation of AKT.

Figure 10:
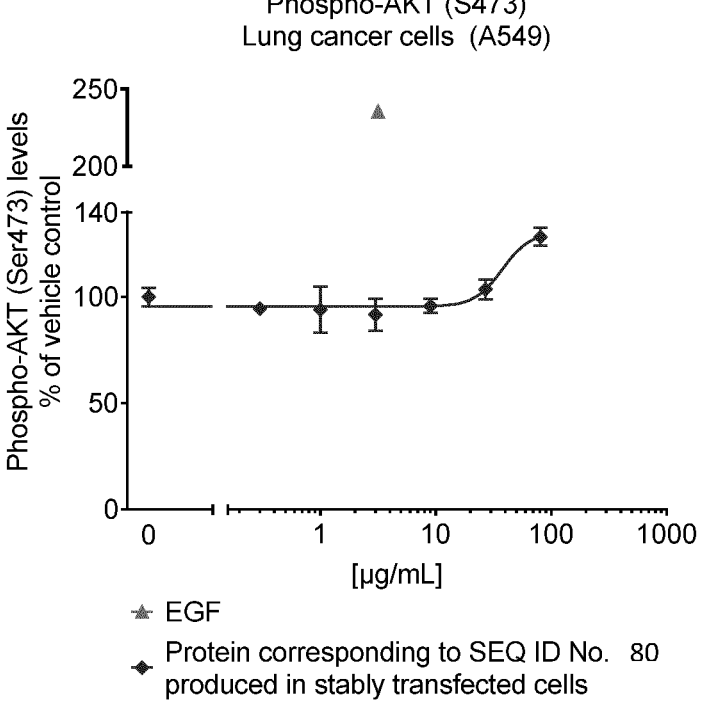

FIG. 10 shows the results of an assay measuring Phospho-AKT (Ser-473) levels in A549 lung cancer cells following administration of varying concentrations of a protein corresponding to SEQ ID NO: 80 produced in stably transfected cells. It can be seen that the protein shows no significant inhibition of the phosphorylation of AKT and indeed may even result in increased phospho-AKT at a higher concentration.

Figure 11:
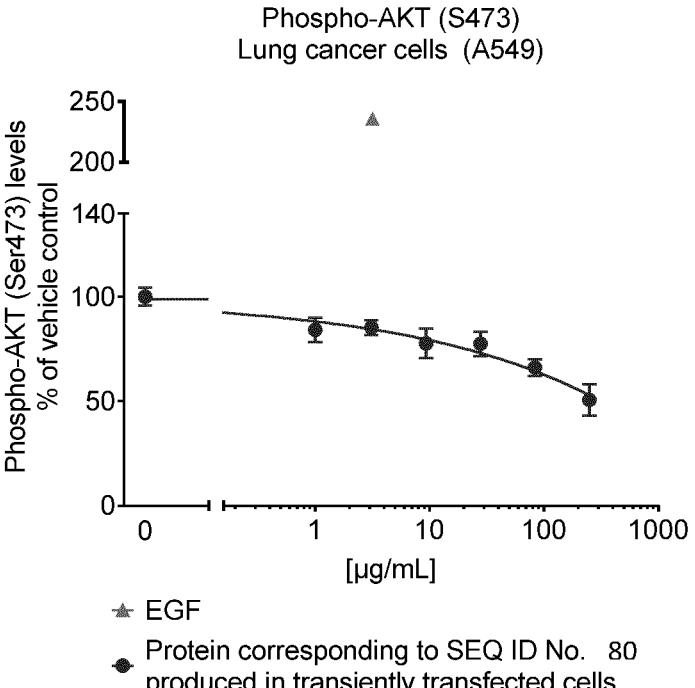

FIG. 11 shows the results of an assay measuring Phospho-AKT (Ser-473) levels in A549 lung cancer cells following administration of varying concentrations of a protein corresponding to SEQ ID NO: 80 produced in transiently transfected cells. It can be seen that, when produced in transiently transfected cells, the protein has a concentration dependent inhibitory activity on the phosphorylation of AKT.

Figure 12:
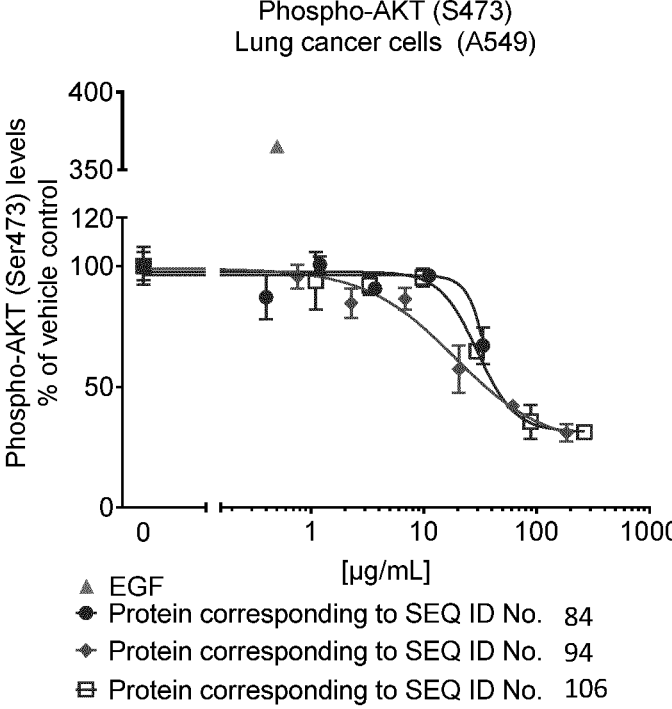

FIG. 12 shows the results of an assay measuring Phospho-AKT (Ser-473) levels in A549 lung cancer cells following administration of varying concentrations of proteins corresponding to SEQ ID NOs: 84, 94 and 106. It can be seen that each of these proteins has a concentration dependent inhibitory activity on the phosphorylation of AKT.

Figure 13:
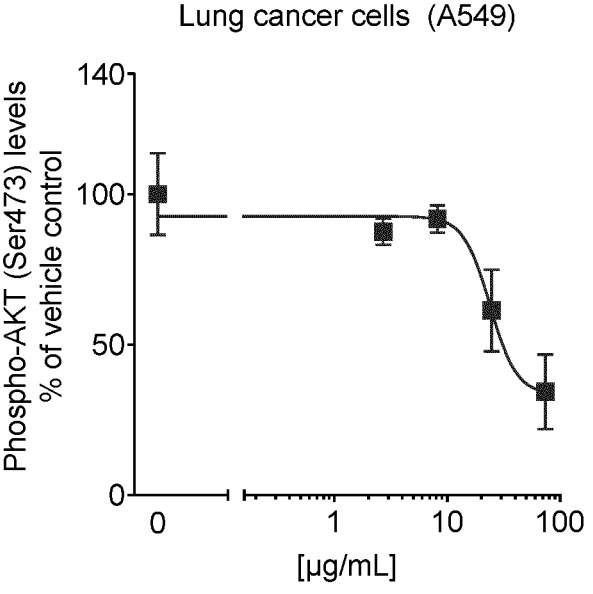

FIG. 13 shows the results of an assay measuring Phospho-AKT (Ser-473) levels in A549 lung cancer cells following administration of varying concentrations of a protein corresponding to SEQ ID NO: 88. It can be seen that the protein is able to inhibit the phosphorylation of AKT at concentrations above 10 ug/ml.

Figure 14:
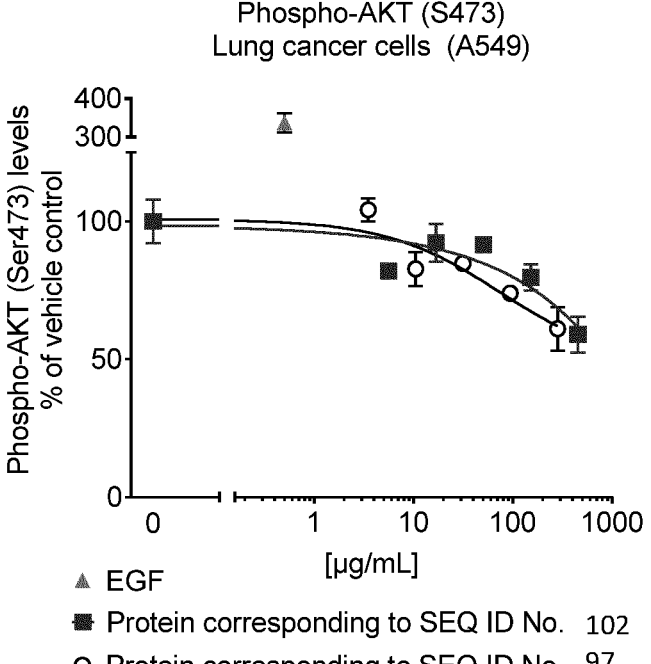

FIG. 14 shows the results of an assay measuring Phospho-AKT (Ser-473) levels in A549 lung cancer cells following administration of varying concentrations of proteins corresponding to SEQ ID NOs: 102 and 97. It can be seen that both proteins have a concentration dependent inhibitory activity on the phosphorylation of AKT.

Figure 15:
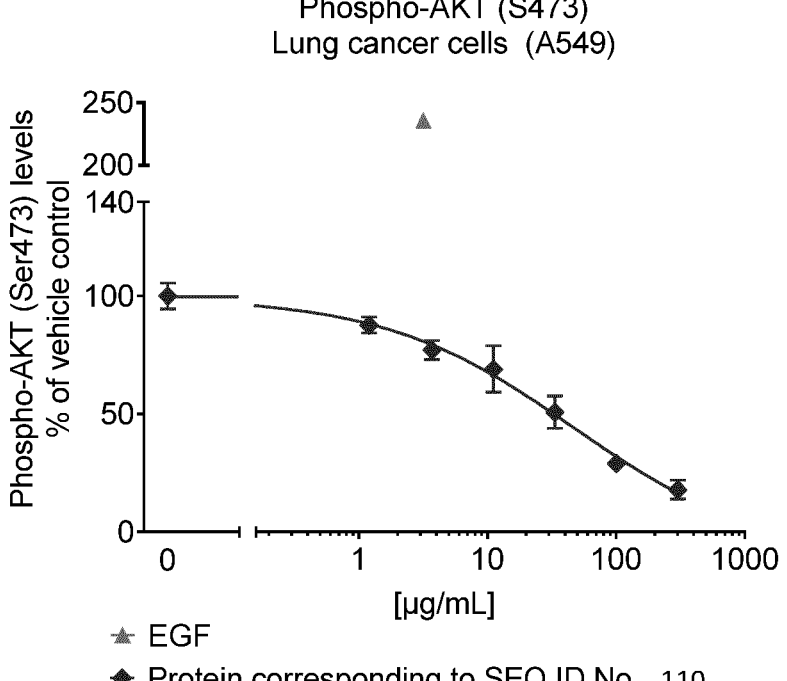

FIG. 15 shows the results of an assay measuring Phospho-AKT levels in A549 lung cancer cells following administration of varying concentrations of a protein corresponding to SEQ ID NO: 110. It can be seen that the protein has a concentration dependent inhibitory activity on the phosphorylation of AKT.

Figure 16:
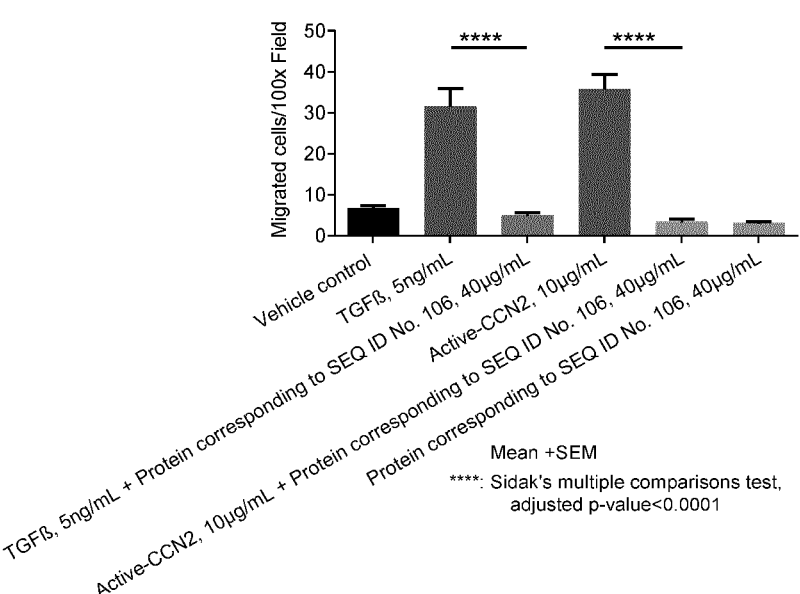
Figure 16:
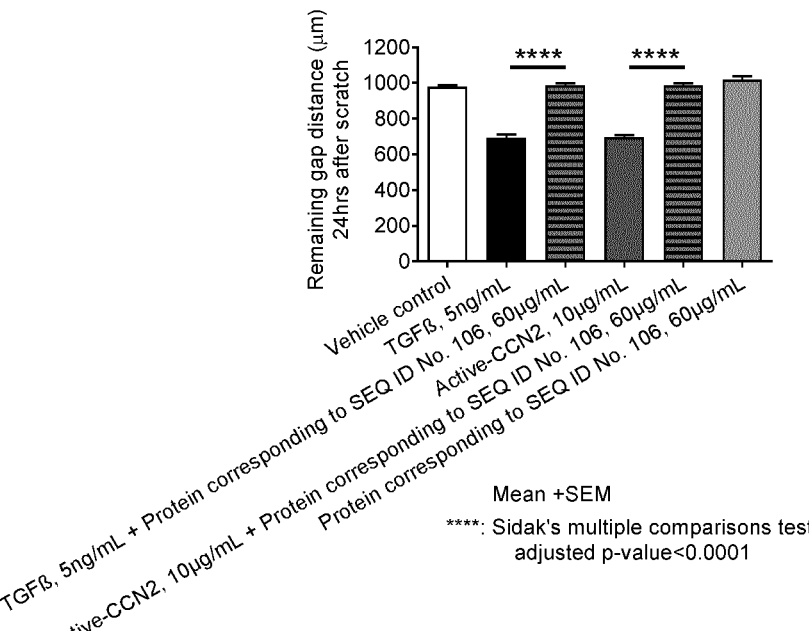
Figure 16:
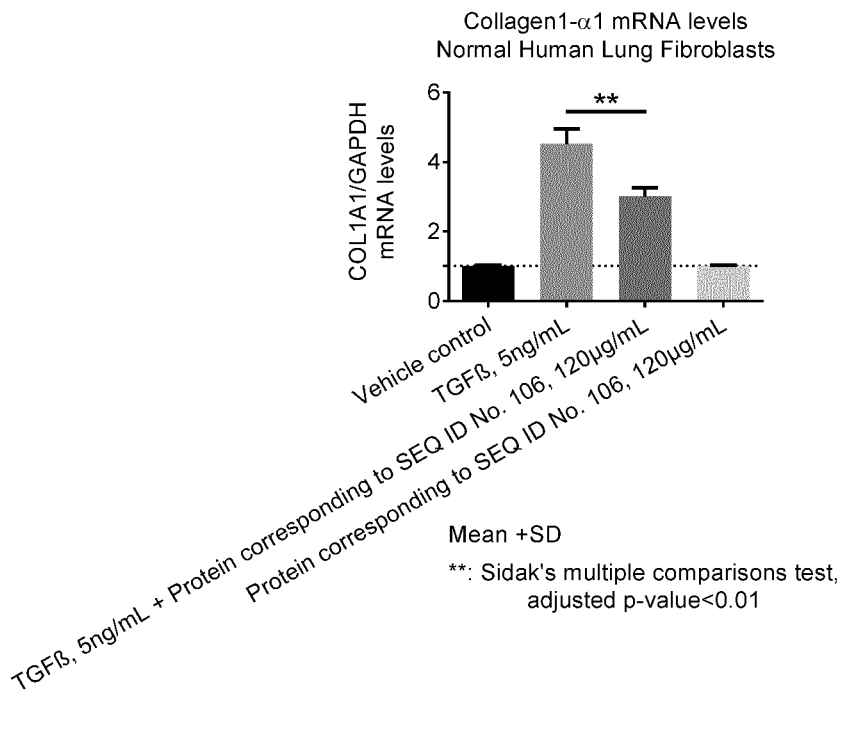
Figure 16:
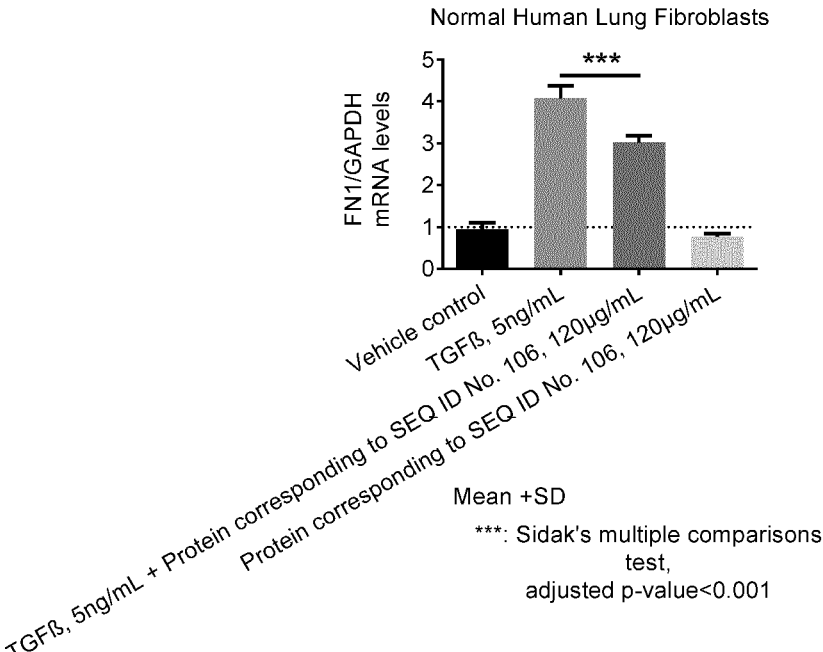
Figure 16:
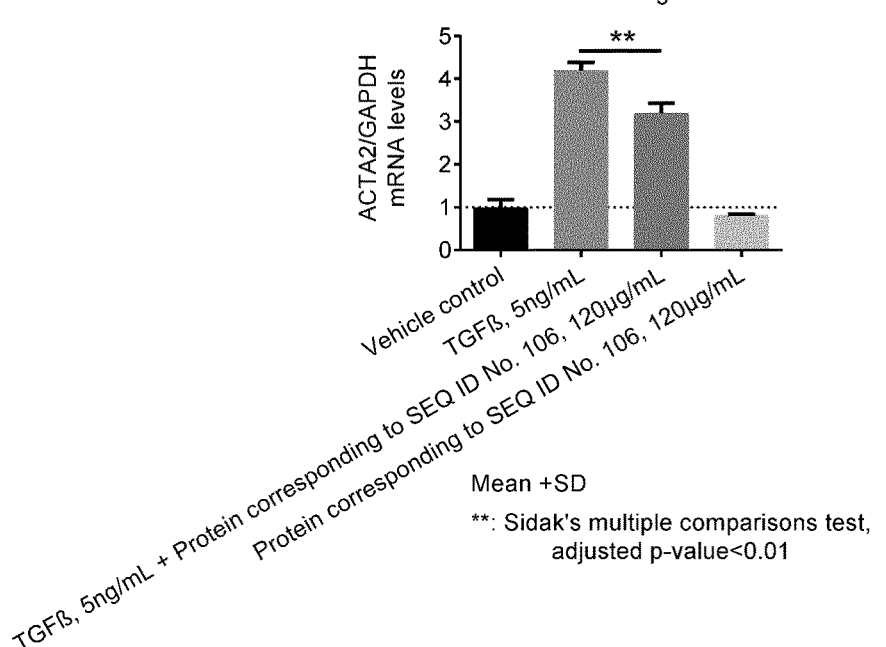
Figure 16:
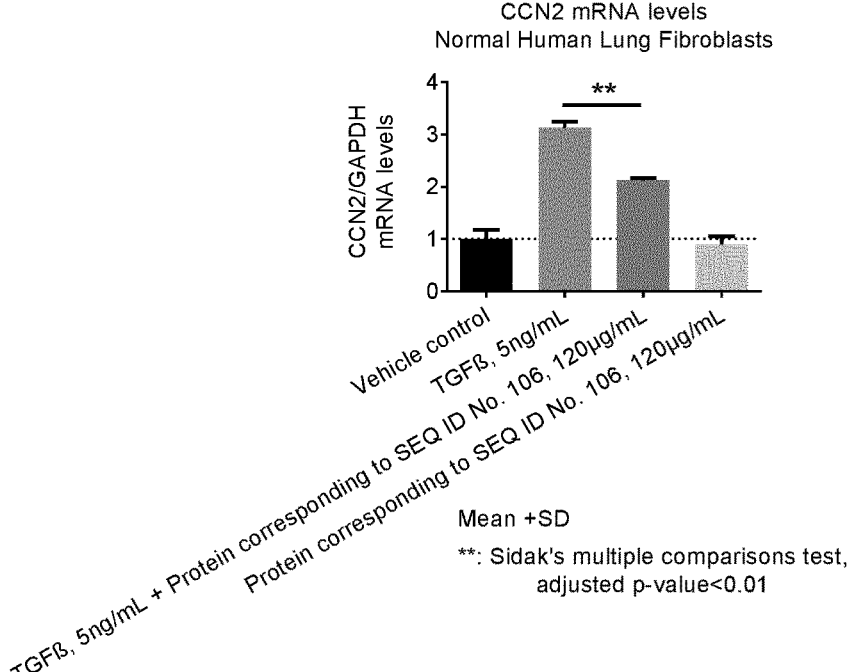

FIG. 16 shows the results of a number of experiments involving a protein corresponding to SEQ ID NO: 106.

A) shows that the protein inhibits the migration of human lung fibroblasts induced by both TGF-beta and CCN2.

B) shows that the protein inhibits the closure of a scratch wound induced by both TGF-beta and CCN2.

C) shows that the protein results in partial inhibition of TGF-beta induction of expression of the gene COL1A1, which is known to be pro-fibrotic.

D) shows that the protein results in partial inhibition of TGF-beta induction of expression of the gene FN1, which is known to be pro-fibrotic.

E) shows that the protein results in partial inhibition of TGF-beta induction of expression of the gene ACTA2, which is known to be pro-fibrotic.

F) shows that the protein results in partial inhibition of TGF-beta induction of expression of the gene CCN2, which is known to be pro-fibrotic.

DETAILED DESCRIPTION OF THE INVENTION

The present invention is as mentioned based upon the surprising findings that the thrombospondin type 1 repeat (TSP-1) homology domain of CCN5 is a fully active structure conferring the cell signaling functions of CCN5/WISP2. Based on this new insight on the activity of the TSP-1 repeat homology domain of CCN5, the inventors provide proteins, recombinant proteins and fusion proteins according to the present invention that may be used to inhibit or counteract the cell signaling and cell physiological functions ascribed to four-domain CCN proteins, i.e. CCN1, CCN2, CCN3, CCN4 and CCN6. This new insight is considered critical for allowing the formation of a stable, homogenous, drug-like molecule based on CCN5, as it previously has not been revealed which part of the full-length CCN5 that is necessary to recapitulate the activity of CCN5, and as full-length CCN molecules are highly susceptible to proteolysis and difficult to produce in active, homogenous forms. Furthermore, this connotation that a specific part of CCN5 can be sufficient to recapitulate the activity observed upon e.g. transient overexpression of a full-length protein is also in contrast to the prevailing opinion in the field that the CCN proteins works as matricellular proteins. The prevailing opinion for the mechanism of action of the CCN proteins, and matricellular proteins in general, is that the different segments of the CCN proteins interact with various other ECM proteins and cell surface receptors thereby modulating their activity rather than working as direct modulators of cell signaling. The new knowledge of the activity of the TSP-1 repeat homology domain of CCN5, and the knowledge of the structurally close relationship with other members of the CCN protein family suggest that also the TSP-1 repeat homology domains of other CCN family proteins may also be utilized to inhibit the cell signaling functions of the four-domain CCN family proteins. According to one aspect, the recombinant proteins and fusion proteins of the present invention inhibits the phosphorylation of AKT (Ser473) in A549 cells.

Inhibition of said cell signaling is of relevance in the treatment of various disorders. CCN2 is, for example, implicated in several diseases, in particular diseases in which enhanced fibrogenesis and tissue fibrosis are a characteristic pathophysiological feature.

For example, it has been shown that overexpression of CCN2 alone is sufficient to induce fibrosis in the lung (cf. Sonnylal et al., *Arthritis Rheum* 62, 1523-1532 (2010)). CCN2 has also been found to be necessary for bleomycin-induced pulmonary fibrosis (Bonniaud, P. et al. *Am J Respir Cell Mol Biol* 31, 510-516 (2004)), radiation-induced pulmonary fibrosis (Bickelhaupt, S. et al. *J Natl Cancer Inst* 109 (2017), and pulmonary fibrosis due to loss of PTEN (Phosphatase And Tensin Homolog) expression (Parapuram, S. K. et al. *Matrix Biol* 43, 35-41 (2015)). Furthermore, in the absence of other eliciting agents, CCN2 has been found to induce pulmonary fibrosis when it is expressed and secreted from pulmonary Clara cells (Wu, S. et al. *Am J Respir Cell Mol Biol* 42, 552-563 (2010)), alveolar type II epithelial cells (Chen, S. et al. *Am J Physiol Lung Cell Mol*

*Physiol* 300, L330-340), when expressed from a fibroblast specific promoter (Sonnylal et al (2010), supra, Sonnylal, S. et al., *J Cell Sci* 126, 2164-2175 (2013)) or delivered by adenovirus (Bonniaud, P. et al., *Am J Respir Crit Care Med* 168, 770-778 (2003)). Thus, multiple reports all support the conclusion that CCN2 is not only sufficient to elicit fibrosis in the skin or the lung, but also necessary for a full blown fibrotic phenotype in several disease models. Pulmonary fibrosis is the hallmark of the human disease idiopathic pulmonary fibrosis (IPF), however it also occurs in the setting of chronic obstructive pulmonary disease (COPD) (Jang, J. H. et al., *COPD* 14, 228-237 (2017)), and systemic sclerosis. In fact, pulmonary fibrosis has been reported to be the primary cause of death in up to 40% of systemic sclerosis patients (Tyndall A J et al., Ann Rheum Dis. 2010 October; 69(10):1809-15). CCN2, and other CCN proteins, such as WISP1, have also been implicated in the pathophysiology of both IPF (Konigshoff, M. et al., *J Clin Invest* 119, 772-787 (2009) and COPD (Jang et al, supra) in human patients.

Another example is neoplastic disorders. For example, in the setting of breast cancer CCN2 has been shown to contribute to bone metastasis in a triple negative breast cancer model (MDA-MB-231) (Kang, Y. et al., *Cancer Cell* 3, 537-549 (2003)). Furthermore, knockdown of CCN2 in triple negative breast cancer cells (MDA-MB-231), a cell line that expresses high levels of CCN2 (Chen, P. S. et al., *J Cell Sci* 120, 2053-2065 (2007)), reduced the migratory ability of these cells, while overexpression of CCN2 in the hormone receptor-positive MCF-7 breast cancer cell line, with low endogenous CCN2 expression (Chen et al, supra), increased the migratory ability of the latter cells (Chen et al, supra, Chien, W. et al., *Int J Oncol* 38, 1741-1747 (2011)). A later report also found that overexpression of CCN2 in MCF-7 cells increased chemoresistance, while knockdown of CCN2 in MDA-MB-231 cells decreased chemoresistance (Wang, M. Y. et al., *Cancer Res* 69, 3482-3491 (2009)). The increase in chemoresistance conferred by CCN2 has also been reported for other breast cancer cells (Lai, D et al., *Cancer Res* 71, 2728-2738 (2011)). Furthermore, through overexpression or knockdown studies it has also been shown that CCN2 contributes to epithelial-to-mesenchymal transition (EMT) and an increased ability of anchorage independent growth (mammosphere formation) of breast cancer cells (Chen et al, supra, Zhu, X. et al., *Oncotarget* 6, 25320-25338 (2015)). The finding of both increased chemoresistance and enhanced EMT induced by CCN2 is in line with the connection made between EMT and chemoresistance also in other cancer types (Fischer, K. R. et al., *Nature* 527, 472-476 (2015), Zheng, X. et al., *Nature* 527, 525-530 (2015)).

In a particular aspect, the present invention provides a monomeric fusion protein as defined above comprising a polypeptide corresponding to at least a portion of the thrombospondin type 1 repeat (TSP-1) homology domain of a CCN family protein, wherein the TSP-1 homology domain sequence may be truncated and/or modified, but wherein the cysteine residues of the domain are conserved. This polypeptide may for convenience be referred to herein as a "TSP-1 polypeptide", and this term is accordingly to be understood as not conveying or implying any limitation to a specific native TSP-1 homology domain sequence only. The term "TSP-1 polypeptide" may be used synonomously or interchangeably with "TSP-1 domain protein" or TSP-1 domain sequence".

As demonstrated in the examples below, it has surprisingly been found that monomeric fusion partners are advantageous in producing active and stable proteins as compared to dimeric fusion partners, such as Fc fragments derived from IgG proteins, which produce dimeric fusion proteins. Monomeric fusions retain the activity of the TSP-1 domain polypeptide that they comprise. Furthermore, the proteins are stable, including with respect to proteolytic degradation. As described further below, resistance to proteolytic degradation may be improved by making modifications to the amino acid sequence of the TSP-1 polypeptide, including in particular the Ala substitution referred to above.

Accordingly, the polypeptide of component (i) of the fusion protein may comprise insertions, deletions, substitutions, mutations or any combination thereof, relative to said sequence selected from SEQ ID NOs: 37 or 2 to 6, or to the sequence selected from SEQ ID NOs: 1 or 8 to 12, provided that the polypeptide retains at least 80% sequence identity with said sequence and that all of the cysteine residues in said sequence are conserved.

In another aspect, the invention provides a protein (e.g. a recombinant protein) which consists of or comprises a polypeptide corresponding to at least a portion of the thrombospondin type 1 repeat (TSP-1) homology domain of a CCN family protein but not in the context of a fusion protein, wherein the TSP-1 domain sequence may be truncated and/or modified and comprises an Ala substitution at the position corresponding to position 2 of SEQ ID NOs: 37 or 2 to 6, or SEQ ID NOs: 1 or 8 to 12, but wherein the cysteine residues of the domain are conserved. In other words the TSP-1-domain protein may be provided without, or independently of, another component such as a fusion partner. Thus, the TSP-1 domain protein is not fused to or linked to another protein domain or component or other functional or structural protein sequence. For convenience such proteins may be referred to as "Ala-substituted proteins".

As used herein, the term "conserved" means that a residue in a given sequence is not deleted or substituted. In other words the term "conserved" is being used synonymously (and interchangeably) with the term "retained". It simply means that the cysteine residues are not removed from the sequence. Accordingly, in the context above it means that the cysteine residues in the sequence selected from SEQ ID NOs: 37 or 2 to 6 or 1 or 8 to 12 are not deleted or substituted. It is noted that the insertion of additional residues between conserved residues (e.g. between conserved cysteines), or the deletion of non-conserved (e.g. non-cysteine) residues, may alter the position of the conserved residues in the polypeptide sequence relative to their position in the original reference sequence (e.g. the sequence selected from SEQ ID NOs: 37 or 2 to 6). However, such residues are still considered to be "conserved", as defined herein. Thus, the term "conserved" does not imply any restriction or limitation on the position (or more particularly, position number) of the cysteine residues.

In some embodiments, the polypeptide of (i) comprises or consists of:

(a) an amino acid sequence selected from SEQ ID NOs: 1 or 8 to 12; or (b) an amino acid sequence having at least 80% sequence identity to a sequence selected from SEQ ID NOs: 1 or 8 to 12; or (c) a part of an amino acid sequence of (a) or (b), wherein said part comprises at least the 44 amino acid sequence of SEQ ID NOs: 37, 6, 2, 3, 4 or 5 respectively or a sequence having at least 80% sequence identity to a sequence selected from SEQ ID NOs: 37, 6, 2, 3, 4 or 5 respectively.

As noted above, the monomeric fusion partner of (ii) and the peptide linker of (iii) are not or do not comprise an IGF binding protein homology domain, a von Willebrand factor type C repeat homology domain, or a cysteine knot domain of a CCN family protein. Alternatively put, the only domain of a CCN family protein that may be present in the fusion protein of the present invention is a TSP-1 homology domain.

Similarly and analagously, in the context of the Ala-substituted proteins which are not fusion proteins, the protein does not comprise any other CCN domain (beyond the TSP-1 domain protein).

In some embodiments, the polypeptide of (i), or the Ala-substituted protein, may comprise only part of a TSP-1 homology domain, as defined above. The present inventors have found that the minimum fragment of the TSP-1 domain required is the 44 amino acid sequence of SEQ ID NOs: 37, 6, 2, 3, 4 or 5. Accordingly, in some embodiments, the polypeptide of (i) is at least 44 amino acids in length. In some embodiments, the polypeptide of (i) is 44 to 57 amino acids in length. However, as noted above, there may be one or more deletions of amino acids in the 44 amino acid minimum fragment which lie between the cysteine residues. Thus, in some embodiments the length of the TSP-1 polypeptide may be less than 44 residues, i.e. 40-43 residues.

In some embodiments, the polypeptide of (i) consists of an amino acid sequence selected from SEQ ID NOs: 37 or 2 to 6, or a sequence having at least 80% sequence identity to a sequence selected from SEQ ID NOs: 37 or 2 to 6.

As described above, the proteins of the invention, including fusion proteins, exhibit (or in other words, demonstrate or have) the activity, more particularly the biological activity, of CCN5. In an embodiment, the proteins may retain or exhibit or have the activity of the TSP-1 homology domain of CCN5. Alternatively, the proteins may be defined as exhibiting (or demonstrating or having) the activity, particularly biological activity, of an isolated TSP-1 homology domain of a CCN protein. The foregoing may apply to any activity of the domain, and particular activities which reflect the anti-fibrotic effect of the TSP-1 homology domain. Such an activity may be assayed for (or tested or detected) using any convenient assay or method, based on any particular biological effect of the domain.

It is noted that the activity of a given protein may conveniently be assessed by analyzing the effect of the protein on the phosphorylation of AKT. In particular, a given protein may be assayed for its ability to inhibit the phosphorylation of AKT (Ser-473) in A549 human lung cancer cells, as described in Example 2. The skilled person will appreciate that other similar assays may be devised to assess the same activity, or to assess other related anti-fibrotic activities.

As noted above, in other aspects of the present invention, recombinant proteins that inhibit or counteract the cell signaling and cell physiological functions ascribed to four-domain CCN proteins are provided, comprising an amino acid sequence according to formula I above.

Cys-A-Cys-B-Cys-C-Cys-D-Cys-E-Cys-F wherein A, B, C, D, E and F is as defined above and in the appended claims. Formula I is a result of the alignment of TSP-1 repeat homology domain of the structurally related CCN family proteins (CCN 1-CCN6), all comprising 6 conserved cysteins, and taking account that amino acids may be substituted without affecting the activity of the protein (conservative substitutions as discussed further below). The position of the first conserved cysteine of the TSP1 repeat homology domain of the different CCN proteins is defined as position #1 of the recombinant protein of formula I.

The five segments between the conserved cysteines are A, B, C, D, and E, respectively.

The first segment A is defined by the formula A1-A2-A3-A5-A6-A7-A8-A9, wherein A1-A9 is as defined above. The amino acid in position #7 (A7) of segment A is tryptophan (W) in all the members of the CCN family proteins and is believed to be conserved.

The second segment B is defined by the formula B1-B2-B3, wherein B1-B3 is as defined above. According to one embodiment, B1 and B3 is either serine or Threonine.

The third segment C is defined by the formula C1-C2-C3-C4-05-C6-C7-C8-C9-C10-C11-C12-C13-C14, wherein the amino acids C1-C14 is as defined above. According to one embodiment, the amino acids C1 and C3 is glycine (G). According to another embodiment, C7 is Arginine (R), C10 and C12 is both asparagine (N).

The fourth segment D is defined by the formula D1-D2-D3-D4-D5-D6-D7-D8, wherein the amino acids D1-D8 is as defined above. According to one embodiment, D7 is Arginine (R).

The fifth segment E is defined by the formula E1-E2-E3-E4, wherein the amino acids E1-E4 is as defined above. According to one embodiment of the invention, E4 is proline.

Following the last cysteine is a carboxyl-terminal peptide segment of variable length (F) comprising from 0 to 13 amino acids.

F may be deleted or shortened compared with the amino acid sequences of the TSP-1 repeat homology domain of the CCN family proteins. According to one embodiment, F is absent. According to another embodiment, F consists of a peptide selected from the group consisting of PPSRGR-SPQNSAF, GQPVYSSL, EADLEEN, EQEPEQPTD, DVDIHTLI, and DSNILKTIKIP. According to one aspect of this embodiment, the recombinant proteins may take the form of an amino acid sequence as depicted in SEQ ID No. 8-12.

According to another aspect, the present invention provides recombinant proteins comprising an amino acid sequence selected from the group consisting of SEQ ID No. 1, SEQ ID No. 2, SEQ ID No. 3, SEQ ID No. 4, SEQ ID No. 5, SEQ ID No. 6, and SEQ ID No. 7, SEQ ID No. 8, SEQ ID No. 9, SEQ ID No. 10, SEQ ID No. 11, SEQ ID No. 12, SEQ ID No. 37, SEQ ID No. 38; and fragments or variants thereof having at least 50% sequence identity with the amino acid sequences SEQ ID No. 1, SEQ ID No. 2, SEQ ID No. 3, SEQ ID No. 4, SEQ ID No. 5, SEQ ID No. 6, and SEQ ID No. 7, SEQ ID No. 8, SEQ ID No. 9, SEQ ID No. 10, SEQ ID No. 11, SEQ ID No. 12, SEQ ID No. 37, SEQ ID No. 38.

According to one aspect, a recombinant protein is provided, consisting of an amino acid sequence selected from the group consisting of SEQ ID No. 1, SEQ ID No. 2, SEQ ID No. 3, SEQ ID No. 4, SEQ ID No. 5, SEQ ID No. 6, and SEQ ID No. 7, SEQ ID No. 8, SEQ ID No. 9, SEQ ID No. 10, SEQ ID No. 11, SEQ ID No. 12, SEQ ID No. 37, SEQ ID No. 38; and fragments or variants thereof having more than 50% sequence identity with the amino acid sequences SEQ ID No. 1, SEQ ID No. 2, SEQ ID No. 3, SEQ ID No. 4, SEQ ID No. 5, SEQ ID No. 6, and SEQ ID No. 7, SEQ ID No. 8, SEQ ID No. 9, SEQ ID No. 10, SEQ ID No. 11, SEQ ID No. 12, SEQ ID No. 37, SEQ ID No. 38.

"Recombinant proteins" as used herein are proteins encoded by recombinant nucleic acids. They are expressed from recombinant nucleic acids in a host cell as further disclosed below.

"Recombinant nucleic acid" is used herein to describe a nucleic acid molecule which, by virtue of its origin or manipulation is not associated with all or a portion of the polynucleotide with which it is associated in nature and/or is linked to a polynucleotide other than that to which it is linked in nature as further disclosed below.

The skilled person will acknowledge that modification of the amino acid sequence of the recombinant proteins and fusion proteins according to the present invention may be introduced without altering the activity of said protein. Amino acids are commonly classified as hydrophobic or hydrophilic and/or as having polar or non-polar side chain. Substitutions of one amino acid for another having the same biochemical characteristics are commonly known as conservative substitution.

Conservative substitutions of amino acids include substitutions made among amino acids within the following groups:

MILV
FYW
KRH
AG
ST
QN
ED

Generally, a conservative amino acid substitution refers to an amino acid substitution that does not alter the relative charge or size characteristics of the protein in which the amino acid substitution is made, and thus seldom alter the structure of the protein, which is why the biological activity are neither altered significantly.

The skilled person will acknowledge that the biological activity of a protein also may be retained if one or a few amino acids are deleted, inserted or added to an amino acid sequence, as long as structural and chemico-physical properties are conserved.

The symbol "Δ" when used herein in front of an amino acid refers to the deletion of the indicated amino acid, e.g. ΔK447 is to be understood as a protein in which K447 is not present. A deletion of a specific amino acid is also herein alternatively indicated with a "-", e.g. K447- is also to be understood as a protein in which K447 is not present.

It is thus to be understood that the present invention encompasses recombinant proteins and fusion proteins as disclosed in the appended claims, wherein such modifications as described above (substitutions, deletions, insertions and additions of amino acids) may be introduced without essentially altering their biological activity, i.e. ability to inhibit or counteract the cell signaling and cell physiological functions ascribed to the four-domain CCN-family proteins; CCN1, CCN2, CCN3, CCN4 and CCN6.

Throughout the present specification, references are made to amino acid sequences. When referring to amino acid sequences herein, reference is sometimes made to modification of the amino acid sequence or protein in question by reference to "uniprot numbering" or Eu numbering in the present specification. Uniprot numbering refers to the numbering utilized in the uniprot database (UniProt Consortium, Nucleic Acids Res. 2019 Jan. 8; 47(D1):D506-D515). Uniprot numbering is used when referring to amino acid numeration of the CCN proteins. Eu numbering refers to the numbering of the Eu antibody (Edelman et al., 1969, Proc Natl Acad Sci USA 63:78-85), and is used when referring to amino acids in the Fc-fragments of human IgG subclasses with or without mutations or chimeras different from the wild-type. The Eu numbering system is accessible e.g. from the international ImMunoGeneTics information system (IMGT) in the IMGT Scientific chart. The IMGT is described in Lefranc M-P, Biomolecules. 2014 December; 4(4): 1102-1139.

As used herein, when referring to "sequence identity", a sequence having at least x % identity to a second sequence means that x % represents the number of amino acids in the first sequence which are identical to their matched amino acids of the second sequence when both sequences are optimally aligned via a global alignment, relative to the total length of the second amino acid sequence. Both sequences are optimally aligned when x is maximum. The alignment and the determination of the percentage of identity may be carried out manually or automatically.

Alignment for purposes of determining percent amino acid sequence identity can be achieved in various ways that are within the skill in the art, for instance, using publicly available computer software such as ClustalOmega (Sievers F, Higgins D G (2018) *Protein Sci* 27:135-145), Protein BLAST (from National Center for Biotechnology Information (NCBI), USA) or commercially available software such as Megalign (DNASTAR) software. Those skilled in the art can determine appropriate parameters for measuring alignment, including any algorithms needed to achieve maximal alignment over the full length of the sequences being compared. NCBI BLAST is another example of software used to determine amino acid sequence identity (MacWilliam et al., *Nucleic Acids Res.* 2013 July; 41 (Web Server issue): W597-W600).

According to one aspect of the invention, a recombinant protein is provided comprising an amino acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 37 and SEQ ID No. 38; and fragments or variants thereof having at least 50% sequence identity with the amino acid sequences SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 37 and SEQ ID No. 38.

According to another aspect, a recombinant protein is provided comprising an amino acid sequence having at least 60%, 70%, 80%, 90%, or 95% sequence identity with an amino acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 37, and SEQ ID No. 38.

Biologically active proteins and peptides have an important place in clinical management of human disease. However, many proteins and peptides present challenges due to having less than ideal pharmacokinetic properties, either because they are eliminated by kidney filtration due to their small size and/or due to proteolytic metabolism. Such factors may impose limitations or challenges upon administration of the drug to a subject in need of treatment such as having to administer constant infusions or frequent subcutaneous administrations to keep the circulating concentrations of protein or peptide at an effective therapeutic level. The need for constant or very frequent administration of a drug is clinically undesirable due to the obvious challenges and inconvenience for both patient and physician.

One strategy for extending half-life of a biologically active peptide or protein is to link a polyethylene glycol (PEG) group to the peptide or protein of interest, by a process called PEGylation (cf. e.g. Dozie et al. (2015), *Int. J. Mol. Sci,* 16(10) 25831-25864). The general strategy for protein PEGylation is to react a functional group on a protein with a complementary group on a PEG molecule to form a protein-PEG conjugate. The PEG moiety offers several advantages for increasing a protein's stability and circulating half-life, due to its flexibility, hydrophilicity, variable size and low toxicity.

In one embodiment the present invention thus provides a recombinant protein as described above, wherein the said protein is pegylated. The fusion proteins according to the present invention may also be pegylated.

Fusion Proteins

Another way of obviating the challenges related to medical use of peptides and proteins is obtaining an extension in half-life for the bio-active protein or peptide by making fusion proteins (cf. e.g. Valeria et al. (2017), "A New Approach to Drug Therapy: Fc-Fusion Technology), *Prim Health Care,* 7:255, doi:10.4172/2167-1079.1000255). By covalently fusing the protein or peptide to a carrier protein via genetic recombination one can increase the molecular weight of the protein of interest to approximately 60 to 70 kDa, which is the threshold for renal filtration.

The present invention provides a fusion protein comprising (i) Thrombospondin type 1 repeat (TSP-1) homology domain of a CCN family protein;

(ii) fusion partner N- or C-terminally fused to the TSP-1 repeat homology domain of (i) and wherein said fusion partner is selected from the group consisting of serum albumin, transferrin and immunoglobulin Fc-fragment.

(iii) optionally a peptide linker between the TSP-1 repeat homology domain and the Fc fragment (being N- or C-terminally fused to the TSP-1 repeat homology domain) of (i).

Throughout this specification, the TSP-1 repeat homology domain may also be denoted and refer to domain III, referring to the third domain of the CCN family proteins.

In one preferred aspect, the fusion partner is a monomeric fusion partner, and results in a fusion protein which is monomeric. Such fusion proteins, and in particular the TSP-1 domains thereof, are defined above and described further below.

However, the present disclosure also includes other embodiments, both with respect to the TSP-1 domain protein component and the fusion partner component.

According to one such embodiment, the TSP-1 repeat homology domain is a recombinant protein of formula I as defined above.

The TSP-1-repeat-homology-domain is according to another embodiment a recombinant protein having an amino acid sequence as defined in any one of the sequences depicted in SEQ ID No. 1-12, 37, and 38, or a recombinant protein of formula I as defined above.

According to one embodiment, the TSP-1 repeat homology domain is a recombinant protein comprising an amino acid sequence having at least 50%, 60%, 70%, 80%, 90%, or 95% sequence identity with an amino acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 37, and SEQ ID No. 38.

Proteins are inherently susceptible to protease degradation. In order to prevent protease degradation of the recombinant proteins and fusion proteins according to the present invention, modifications to the amino acid sequence may be introduced, e.g. by site directed mutagenesis, in order to provide protease resistant recombinant proteins and fusion proteins. For example, a point mutation may be introduced in the thrombospondin type 1 repeat (TSP-1) homology domain of a CCN family protein as defined in SEQ ID No. 1-12, 37 or 38, or more particularly a protein as defined in any one of SEQ ID NO.s 1-6, 8-12 or 37, of the fusion protein or in the recombinant protein. According to one embodiment, a point mutation is introduced decreasing the susceptibility of proteolytic degradation. A non-limiting example of a point mutation resulting in less proteolysis of the recombinant proteins and fusion proteins of the present invention is by introducing a point mutation corresponding to the replacement of proline with alanine in position 195 (P195A) of domain III of CCN5, such as shown in SEQ ID No. 7. A similar mutation may also be introduced in the amino acid sequences originating from domain III of other CCN family members. SEQ ID NO. 38 represents the truncated 44 amino acid sequence of the TSP-1 domain of CCN5 comprising the Ala substitution. SEQ ID NOs. 42-46 represent the truncated 44 amino acid sequences of the TSP-1 homology domains of CCN1, 2, 3, 4 and 6 respectively comprising the Ala substitution. SEQ ID NOs. 47 to 51 represent the longer TSP-1 homology sequences of CCN1, 2, 3, 4 and 6 respectively comprising the Ala substitution. Any such sequence, or a sequence having at least 80% sequence identity therewith, may be used according to the present invention.

As noted above, in a preferred embodiment, the fusion partner (ii) of the fusion protein according to the present invention is monomeric. Any monomeric fusion partner may be used. Thus the fusion partner may be any protein, or part thereof (e.g. protein domain), which occurs and remains in monomeric form when fused to the TSP-1 homology domain protein component. Thus the fusion protein comprising the monomeric fusion partner and the TSP-1 homology domain protein remains as a monomer. That is, it does not dimerise or form higher multimers with itself.

Various proteins are known as possible fusion partners and may include native proteins, or fragments or amino acid sequence-modified variants thereof, as well as synthetic proteins or amino acid homopolymers. Such proteins include notably Fc fragments of IgG, serum albumin or transferrin.

A fusion partner is defined broadly herein as a second polypeptide (or second amino acid sequence) which is not present in combination with (e.g. adjacent to, or linked to, directly or indirectly) the first CCN TSP-1 homology polypeptide in nature, and which is linked to the first CCN TSP-1 homology polypeptide in a synthetic or artificial combination. Thus, a fusion protein comprises a non-native combination of at least two amino acid sequences or polypeptides linked, or fused together.

The fusion partner may be an amino acid sequence which is at least 6, 8, 9, 10, 15, 20, 25, 30, 40 or 50 or more amino acids long. Typically, the fusion partner is a functional polypeptide, or in other words it is a polypeptide which imparts a function or property to the fusion protein, e.g. to stabilise the fusion protein (to make the first polypeptide more stable), or to increase its serum half-life. Thus the fusion partner may be a structural protein or have a structural function, or it may impart an activity or property to the fusion protein, e.g. a binding activity (e.g. the fusion partner may be a member of a binding pair, or it may be an affinity binding partner etc.). In representative examples the fusion partner may be an albumin (in particular a serum albumin), a fibrinogen, a glutathione S-transferase, a transferrin, streptavidin or a streptavidin-like protein, or an immunoglobulin, or a part thereof, in particular the Fc portion of an immunoglobulin (e.g. IgG1, IgG2, IgG3 or IgG4), or a part or modification thereof. Suitable serum albumins include bovine serum albumin (BSA), mouse serum albumin (MSA) and in particular human serum albumin (HSA). Other possible fusion partners include polypeptides which may act to improve pharmacokinetic properties of the fusion protein, e.g. synthetic polypeptides, such as a homo amino acid polymer, a proline-alanine-serine polymer, or an elastin-like peptide, for example as described in Strohl, 2015, BioDrugs 29, 215-239. Any fusion partner known in the art for use with therapeutic proteins may be used.

In an embodiment, the fusion partner (ii) of a fusion protein according to the present invention may be either an Fc-fragment of IgG (any subclass or chimera of any subclasses), serum albumin or transferrin.

The fusion partner may be coupled N- or C-terminally to the TSP-1 homology domain protein component of the fusion protein, e.g. to the TSP-1 repeat homology domain of CCN5 or any of the other CCN proteins, as defined herein. It may be linked directly, or indirectly, via a linker, as described further below.

Fc fragments tend to form dimers, and when used in fusion proteins, the fusion protein construct tends to comprise two copies of the fusion protein. However, it is known in the art that monomeric Fc fragments and monomeric fusion proteins comprising them may be prepared.

Accordingly, where the fusion partner is an Fc-fragment, it is preferably a monomeric Fc-fragment, such as a monomeric Fc-fragment of human IgG, of any class. Chimeric Fc fragments comprising parts of Fc regions from different classes are encompassed, as are Fc fragments with modified sequences.

Fc-fusion proteins are a growing class of protein therapeutics based on chimeric proteins consisting of an effector domain coupled to the Fc-fragment of an IgG-isotype. A typical example of a biopharmaceutic product is etanercept (TNF-α receptor coupled to an Fc fragment) used in treatment of e.g. rheumatoid arthritis. Another example of an Fc fusion biopharmaceutical protein is aflibercept. Aflibercept, a VEGF receptor-Fc-fusion protein used in the treatment of wet macular degeneration and metastatic colorectal cancer. The principal rationale for making Fc fragment fusion proteins is to obtain extension of half-life due to increase of molecular mass sufficient to exclude renal excretion and to enhance renal proximal tubular reabsorption via the neonatal Fc-receptor. Also, pH-dependent binding of Fc-fusion proteins to the neonatal Fc receptor (FcRn) on endothelial cells allow Fc-based fusion proteins that would otherwise be destined for endocytosis and subsequent lysosomal degradation to be recycled and released back into circulation.

According to one embodiment, a fusion protein is provided wherein the fusion partner (ii) is an Fc-fragment from a human IgG (immunoglobulin G, also known as immunoglobulin γ), including all subclasses of human IgG. According to yet another embodiment of the present invention, a fusion protein is provided, wherein the fusion partner is the Fc fragment of IgG1, IgG2 or IgG4. Preferably, the Fc-fragment of human IgG is that of subclass IgG4 (SEQ ID. No 13) or IgG2 (SEQ ID. No 14).

IgG1, IgG2 and IgG4 are often preferred to IgG3 due to their longer half-lives of approximately 3 weeks. The skilled person will acknowledge that the choice of the IgG isotype of a particular subclass as an Fc fusion partner will depend on the desired half-life extension and cytotoxic level of activity for the final compound. Therapeutic antibodies that are indicated for the treatment of cancer or autoimmune diseases belong, for the most part, to the IgG1 subclass because of their high affinity to Fc receptors and potent ability to exert immune-effector functions. IgG2 and IgG4 are, on the other hand, preferred subclasses of IgG for use as the backbone of a therapeutic candidate when a lack of immune-effector functions is desired, as the immune-effector functions may cause adverse effects. The propensity of the Fc-fragment to activate immune effector functions is dependent upon the Ig isotype and subclass and varies for different immune effector functions. In addition to selecting an Fc-fragment of a suitable IgG subclass, the amino acid sequence of the IgG subclass may be modified, e.g. by site directed mutagenesis, in order to reduce the Fc-fragments capacity to activate immune-effector functions.

Fc fragments may be selected which form monomers, or more precisely which retain or have monomeric form, or may be modified to introduce mutations which allow, or facilitate a monomeric structure. Such mutations are termed herein "monomer-generating mutations" Examples of Fc fragments which comprise monomer generating mutations are SEQ ID NOs. 54 and 55. The person skilled in the art knows how to introduce such mutations and select monomeric Fc mutants.

Avoidance of Immune Effector Activation Functions of Fc Fragments

For instance, in the biopharmaceutic fusion protein dulaglutide (Trulicity™), a GLP-1 agonist-Fc-fragment fusion protein used in the once weekly treatment of type 2 diabetes, the well characterized mutations F234A and L235A are introduced in the hinge region of an IgG4 Fc-fragment to reduce the capacity of activating immune effector functions.

According to one embodiment of the invention, the Fc fusion partner is an Fc-fragment of IgG4, wherein the IgG4 Fc fragment is modified in order to avoid immune effector functions, e.g. comprising the above F234A and L235A mutations.

Protease Resistant Fc Fragments

Another factor that can reduce both yields in manufacturing and the biological half-life is endopeptidase cleavage of the fusion protein. To reduce or eliminate the risk of proteolytic degradation, modifications may be introduced in the amino acid sequence of the Fc fragment, in particularly by introducing mutation in the sites susceptible of proteolytic cleavage. In EP patent application EP2654780B1, the Fc domain of IgG1 constant region was modified by replacing E233-L234-L235-G236 with P233-V234-A235 (deleting G236) (EU numbering) to render the resulting modified Fc-containing protein resistant towards proteolytic degradation.

Incorporation of the amino acid modification disclosed in EP2654780B1 in an Fc fragment of IgG4 coupled to domain III of CCN5 were considered not to provide sufficient resistance to endopeptidases. Improved protease resistance was however achieved by further modifications of the IgG subtype used as a fusion partner according to the present invention.

More specifically, it has been found that fusion proteins comprising the entire hinge region of IgG2 and the constant heavy chains 2 and 3 of IgG4 displayed superior proteolytic resistance.

In Mueller J P et al., *Mol. Immunol.* (1997), 34(6), pp. 441-452, the use of IgG2/IG4 chimeras in IgG antibodies are disclosed. Another biopharmaceutical monoclonal antibody named eculizumab, which are used in the treatment of paroxysmal nocturnal hemoglobinuria and atypical hemolytic uremic syndrome, has been shown to be useful e.g. in avoiding the capacity of IgG4 to activate the FcγR dependent immune effector. Furthermore, the IgG4 constant domains 2 and 3 of such a chimeric Fc-fragment are also shown to avoid the capacity of IgG2 to activate complement dependent immune effector functions. Reference is in this respect made to the report of Rother et al., (2007), cf. *Nat. Biotechnol.*, 25(11), pp. 1256-1264 and Mueller J P et al., supra.

Also, Borrok et al. (2017), *J. Pharm. Sci.* 106; 1008-1017, disclose the introduction of modifications in an Fc-fragment to study its effect on immune effector functions of antibodies (FQQ-YTE mutations). In WO2017158426A1, modifications of antibodies by introducing mutations in the Fc fragment to improve the half-life of antibodies are disclosed. In particular, modifications in one or more of the positions 311, 434, 428, 438, and 435 in the Fc-region of an immunoglobulin are disclosed.

Furthermore, Kinder et al. *J Biol Chem.* 2013 Oct. 25; 288(43):30843-54 reports of mutations in the lower hinge of IgG1 (i.e. E233P, L234V, L235A, G236-, Eu numbering) resulted in protease resistant IgG1 antibodies.

According to one embodiment, the Fc-fragment of the fusion protein according to the present invention consists of an Fc fragment of the IgG4 subclass incorporating the following mutations; S228P, F234A, L235A, K447-, Eu-numbering, cf. SEQ ID No. 15.

Jacobsen et al. *J Biol Chem.* 2017 Feb. 3; 292(5):1865-1875 reported that mutation of Asn297 resulting in that the Fc fragment was aglycosylated, which further resulted in lack of IgG effector functions. Jacobsen also found that some variants (N297G) resulted in antibodies having better stability and developability compared with other variants (N297Q or N297A). Further modifications were also introduced (disulfide bridges) that resulted in better stability than the parental IgG1.

According to the present invention, when the fusion partner is an Fc-fragment, it may be aglycosylated without, or with a stabilizing disulfide bridge, such as e.g. in SEQ ID No. 16.

To the knowledge of the inventors, an Fc-fragment composed of the entire hinge region of IgG2 and constant heavy chains 2 and 3 of IgG4 has not previously been used to prepare fusions proteins by linking said Fc-fragment to an effector protein.

According to one embodiment, the fusion partner of the present fusion protein is a Fc fragment of IgG1 being aglycosylated and stabilized by a disulfide bridge, and wherein the lower hinge with the following mutations have been introduced: E233P, L234V, L235A, G236- (Eu numbering) (SEQ ID NO. 17).

According to one embodiment, the fusion partner of the fusion protein comprising the TSP-1 repeat homology domain of a CCN family protein is an Fc fragment of IgG4, and wherein the following mutations have been introduced to the lower hinge: E233P, L234V, L235A, G236- (Eu numbering) in addition to the S228P and K477-mutations (SEQ ID NO. 18).

In one preferred embodiment the Fc-fragment is a chimera of the hinge region of IgG2 (216 ERKCCVECPPCPAPPVA-GP 238, Eu numbering) and any of the other IgG subclasses. Most preferably the Fc-fragment is a chimera of the hinge region of IgG2 and the constant heavy domains 2 and 3 of IgG4 with a deletion of the carboxyl-terminal K477 (Eu numbering), as shown in SEQ ID. No. 19. This embodiment of the invention has been shown to have improved protease resistance characteristics (cf. example 6).

In one embodiment, the fusion partner of the monomeric fusion protein of the invention is an Fc-fragment of IgG1 being disulfide bridge stabilized (R292C, V302C), aglycosylated (N297G) and with monomer-generating mutations (C220Q, C226Q, C229Q, T366R, L368H, P395K, K409T, M428L), Eu numbering), as provided in SEQ ID NO: 54.

In a further embodiment, the fusion partner of the monomeric fusion protein of the invention is an Fc-fragment being a chimera of the hinge region of IgG2 and the constant heavy domains 2 and 3 of IgG4 with a deletion of the carboxyl-terminal K477- and with monomer-generating mutations (C219Q, C220Q, C226Q, C229Q, L351F, T366R, P395K, F405R, Y407E) and half-life extending mutations (M252Y, S254T, T256E) (Eu numbering), as provided in SEQ ID NO: 55.

Although a fusion protein according to the present invention is exemplified by using an Fc-fragment consisting of the entire hinge region of IgG2, the constant heavy chains 2 and 3 of IgG4, and domain III of a CCN protein family member, it is believed that the advantageous protease resistance is also achieved if such an Fc-fragment chimera is coupled to other effector molecules, e.g. such as VEGFR, FGF-21 or GLP1. The effector molecule is the part of the Fc fusion protein that affords the desired pharmacodynamics properties, while the Fc fragment contributes to the pharmacokinetic properties.

Serum Albumin as Fusion Partner

An alternative strategy for extending the half-life of peptides and proteins is using serum albumin (SA) as a fusion partner. IgG and SA share a prolonged half-life of about 19 days compared to a few days or less for most other circulating proteins. SA also has affinity for the neonatal Fc receptor (FcRn) and is rescued from intracellular degradation (cf. Andersen et al. (2014), *J Biol Chem,* 289(19); pp 13492-13502).

In one embodiment of the present invention, a fusion protein is provided as described above, wherein the fusion partner is serum albumin, preferably human serum albumin.

In one embodiment, a monomeric fusion protein is provided as described above, wherein the fusion protein comprises amino acids 25 to 606 of human serum albumin, as provided in SEQ ID NO: 101.

In a further embodiment of the invention the albumin, e.g. human serum albumin, is modified, for example in order to increase or decrease half-life by altering its FcRn affinity, with or without pH-dependence resulting in increased or decreased half-life.

Transferrin as Fusion Partner

Yet an alternative strategy for extending the half-life of peptides and proteins is using transferrin as a fusion partner, utilizing the naturally long half-life of transferrin. (Strohl W. BioDrugs. 2015; 29(4): 215-239). Transferrin may be used in its glycosylated or non-glycosylated form.

In one embodiment of the present invention, a fusion protein is provided as described above, wherein the fusion partner is transferrin, preferably human transferrin.

In one embodiment, a monomeric fusion protein is provided as described above, wherein the fusion protein comprises amino acids 20 to 698 of human transferrin, as provided in SEQ ID NO: 53.

Linker

According to another embodiment, the fusion proteins according to the present invention may optionally comprise a peptide linker between the fusion partner and the effector molecule, i.e. the linker is being N- or C-terminally fused to the TSP-1 repeat homology domain of the CCN protein (the TSP-1 domain protein/polypeptide).

Any peptide linker may be used (as long as it is not a CCN protein sequence), many of which are known and described in the art. The linker may be a flexible linker sequence (which may include repeats of a flexible linker sequence motif). Typical linkers known in the art are rich in small non-polar (e.g. glycine) or polar (e.g. serine or threonine) residues, and commonly consist of stretches of glycine and serine residues (GS) or other amino acid residues such alanine, lysine and/or glutamate (A, K, and/or E), or indeed any amino acids. A commonly used linker is the (GGGGS) linker (SEQ ID NO: 121), which may be provided as a repeating unit in a linker (as (GGGGS)n, where the copy number of n may be adjusted, e.g. from 1-10, 1-6, 1-4 etc.). The linker may be 1-50, 1-45, 1-40, 1-30, 1-25, 1-20, 1-15, 1-12, 1-10, e.g. 1-8, 1-6, 1-5, or 1-4, amino acids long. Various different linkers are described and used in the Examples below, and any of these may be used in any of the fusion proteins of the invention.

In some embodiments, the linker comprises no more than 50 amino acids.

The properties of the peptide linker may further improve the maintenance of the effector functions. However, peptide linkers may be susceptible to endopeptidase cleavage and elimination of the fusion protein. Peptide linkers with glycine with or without serine residues interspersed are commonly utilized, however this design does not always yield fusion proteins with desired activities and resistance to endopeptidases. In US20180273603, disclosing a neurotrophin binding protein-Fc-fusion protein, the use of a-helical linkers comprising repetitions of the sequence A(EAAAK)A (SEQ ID No. 14 therein) are suggested. Furthermore, US2018/0127478 discloses the use of an amino acid linker consisting of one to three repetitions of the sequence EAAAK is suggested in an Fc-fusion protein.

According to the present invention, a linker consisting of the peptide sequence EAAAK (SEQ ID No. 21 herein) may also be incorporated between the TSP-1 homology domain and the fusion partner (Fc fragment). More preferably, the linker is composed of a repetition of the amino acid sequence EAAAK.

If a linker is included in the fusion protein of the present invention, the linker is placed between the fusion partner and the effector molecule, i.e. the domain III of the CCN protein. The linker may be introduced either C-terminally or N-terminally of domain III of the CCN protein.

Furthermore, the helical linker was resistant to endopeptidase cleavage following expression of the recombinant protein in suspension CHO cells. This is important both for manufacturing purposes and for in vivo efficacy. Furthermore, the incorporation of an a-helical linker between the Fc-fragment and the effector domain in an Fc fusion protein is shown to reduce the aggregation tendency of the Fc fusion protein.

Although these findings are shown with a fusion protein comprising domain III of CCN family protein as an effector protein, it is believed that the advantageous reduced tendency to aggregation and the protease resistance effects are also obtained if combining other effector molecules to a Fc fragment an a-helical linker according to the present invention.

The present invention therefore provides an Fc fusion protein comprising an Fc-fragment that has a peptide linker sequence of the formula aa1-aa2-(EAAAK)n-aa3-aa4-aa5, wherein n≥4, between the Fc-fragment and an effector molecule, and wherein aa1, aa2, aa3, aa4, aa5 is independently absent or an amino acid. The linker may be placed N-terminally or C-terminally of the Fc-fragment. According to one embodiment, n is 8. According to another embodiment, aa1 is Threonine (T), aa1, aa2, aa3, aa4 and aa5 is Ala (A). According to one embodiment, the linker of the above Fc-fusion protein is selected from the group consisting of SEQ ID NO. 22, SEQ ID NO. 23, SEQ ID No. 24 and SEQ ID No. 25. In particular, it has been shown that the use of a fusion protein according to the present invention comprising a linker consisting of a (EAAAK)-repeat, i.e. such as (EAAAK)n wherein n is 8 advantageously results in less aggregation.

An alternative linker that may be used according to the present invention is a linker with an amino acid sequence as depicted in SEQ ID No. 20 (TEGRMD).

In one embodiment, the invention may thus include the incorporation of a linker peptide between the fusion partner, and domain III on CCN5 (e.g. SEQ ID. No 1-SEQ ID. No. 12, 37 or 38). Non-limiting examples of fusion proteins incorporating a linker of SEQ ID No. 20 is shown in SEQ ID No. 28, SEQ ID No. 29 and SEQ ID No. 30, respectively.

In the case when the invention takes the embodiment of domain III of CCN5 genetically fused N-terminal of a peptide linker (as in SEQ ID. No 20) and an Fc-fragment of IgG subtype IgG4 incorporating the following mutations (S228P, F234A, L235A, K447-, Eu-numbering) (as in SEQ ID No.: 15), the complete sequence will be as in SEQ ID. No 28, also denominated as CCN5(dIII)-Fcv2.

In the case when the invention takes the embodiment of domain III of CCN5 genetically fused N-terminal of a peptide linker (as in SEQ ID. No 20) and an Fc-fragment of IgG subtype IgG4 incorporating the following mutations (S228P, E233P, F234V, L235A, G236-, K447-, Eu-numbering) as shown in SEQ ID. No 18, the resulting sequence will be as shown in SEQ ID. No 29, also denominated as CCN5(dIII)-Fcv2.1.

In the case when the invention takes the embodiment of domain III of CCN5 genetically fused N-terminal of a peptide linker (as in SEQ ID. No 20) and a chimeric Fc-fragment of IgG subtype IgG2/4 subtype, as shown in SEQ ID. No 19, the resulting sequence will be as shown in SEQ ID. No 30, also denominated as CCN5(dIII)-Fcv2.3.

In the case when the invention takes the embodiment of domain III of CCN5 (as in SEQ ID. No 1) genetically fused N-terminal of a peptide linker (as in SEQ ID. No 25) and a chimeric Fc-fragment of IgG subtype IgG2/4 subtype, as shown in SEQ ID. No 19, the resulting sequence will be as shown in SEQ ID. No 31, also denominated as CCN5(dIII)-HLn8-Fcv2.3.

According to a preferred embodiment of the invention, a fusion protein according to the present invention are provided comprising:

1) a point mutation into domain III of a CCN family protein, in particular CCN5 (cf. SEQ ID No. 7, resulting in reduced proteolytic susceptibility of said domain III;

2) an engineered chimera of the Fc-fragment of human IgG4 and human IgG2 (SEQ ID No. 19, which decreases proteolytic susceptibility relative to previously described Fc-fragment backbones utilized in Fc-fusion proteins; and 3) comprising an optimized composition of the peptide linker (cf. SEQ ID No. 21-25), which decreases proteolytic susceptibility, enhances biologic activity of the fusion protein and reduces aggregation tendency of the fusion protein.

In some embodiments, the peptide linker between the amino acid sequence of (i) and the monomeric fusion partner has an amino acid sequence selected from the group consisting of SEQ ID NOs: 20 to 25 or 39, or an amino acid sequence having 80% sequence identity thereto.

Alternative linker sequences which may be used according to the present invention are provided in SEQ ID NOs: 57, 63, 65, 67 and 121.

Recombinant Expression

The recombinant proteins and fusion proteins according to the present invention may be manufactured by culturing a host cell enabling the expression of nucleotide sequences encoding said proteins. The skilled person is well familiar with the various available biotechnological techniques providing for the expression of isolated nucleic acid sequences for the preparation of recombinant proteins by heterologous expression in various host cell systems using commonly available genetic engineering techniques and recombinant DNA expression systems, cf. e.g. "Recombinant Gene Expression Protocols, in Methods in Molecular Biology, 1997, Ed. Rocky S Tuan, Human Press (ISSN 1064-3745) or Sambrook et al., Molecular Cloning: A laboratory Manual (third edition), 2001, CSHL Press, (ISBN 978-087969577-4). For example, the nucleic acid sequences encoding the recombinant proteins according to the present invention may be inserted in suitable expression vectors comprising all the necessary transcriptional and translational regulatory sequences specifically adapted for directing the expression of the desired protein coding nucleic acid sequence in a suitable host cell. Suitable expression vectors are e.g. plasmids, cosmids, viruses or artificial yeast chromosomes (YAC's).

DNA sequences encoding the recombinant proteins of the invention may be synthesized by methods well known to the skilled person or commercial suppliers well known to the skilled person, e.g. Genscript, Thermo Fisher Scientific etc.

According to one embodiment of this aspect, a DNA molecule is provided comprising a nucleic acid sequence as depicted in SEQ ID NO: 86, 87, 90, 91, 99, 100, 104, 105, 108, 109, 112, or 113, or a sequence having at least 80% sequence identity to any aforementioned sequence. Expression vectors comprising such DNA molecules are also provided. According to another embodiment of this aspect, host cells comprising such vectors are also provided.

DNA sequences to be expressed and used to prepare recombinant proteins may be inserted in vectors commonly known as entry vectors using the Gateway cloning system (Esposito et al, 2009, "Gateway Cloning for Protein Expression", in Methods in Molecular Biology, 498, pp. 31-54). Genes cloned into an entry vector may easily be introduced into a variety of expression vectors by recombination. As an example, the synthesized sequence encoding a recombinant protein or fusion protein according to the present invention may be recombined by BP Gateway recombinase cloning to generate an Entry vector which may be used to propagate the plasmids in a suitable host cell, such as *E. coli* cells. In a preferred embodiment, *E. coli* cells mutated to allow for efficient propagation of plasmids is used, such as e.g. One Shot Top10™ cells.

According to one embodiment of the present invention, an expression vector is prepared comprising a DNA sequence encoding a recombinant protein or a fusion protein according to the present invention operably linked to a promotor. The skilled person will acknowledge that a "promoter" as used herein refers to a region of DNA upstream (5'-prime) of a DNA coding sequence that controls and initiates transcription of the particular gene. The promoter controls recognition and binding of RNA polymerase and other proteins to initiate transcription. "Operably linked" refers to a functional linkage between a promoter and a second sequence, where the promoter sequence initiates and mediates transcription of the DNA sequence corresponding to the second sequence. In general, operably linked means that the nucleic acid sequences being linked are contiguous.

The entry vector as well as an expression vector, such as that generated from a destination vector mentioned below, may be isolated using standard plasmid isolation techniques well known to the skilled person, such as e.g. using a QIAprep™ Spin Miniprep kit from Qiagen™ or QIAGEN™ Plasmid Plus Maxi Kit.

If using an Entry vector containing a DNA sequence encoding a recombinant protein or fusion protein according to the present invention, said entry vector may be further recombined with a destination vector using LR gateway recombinase to generate an expression vector. The expression vector may then be used to express the protein coding DNA sequence in an appropriate host cell. Non-limiting examples of applicable destination vector is e.g. pUCOE-DHFR-DEST, as described in Kaasbøll et al., *J. Biol. Chem*, 293:46, pp. 17953-17970.

Also, the resulting expression vector may be verified by standard restriction enzyme digestion and DNA gel electrophoresis.

According to one aspect of the invention, an expression vector is provided comprising a nucleic acid sequence encoding a recombinant protein of formula (I). According to yet another aspect of the invention, an expression vector is provided comprising a nucleic acid sequence encoding a protein comprising an amino acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, and SEQ ID NOs: 8-12, 37, 38, 84, 85, 88, 89, 97, 98, 102, 103, 106, 107, 110 and 111; and fragments or variants thereof having at least 50% sequence identity with the amino acid sequences SEQ ID No. 1, SEQ ID No. 2, SEQ ID No. 3, SEQ ID No. 4, SEQ ID No. 5, SEQ ID No. 6, and SEQ ID No. 7, SEQ ID No. 8, SEQ ID No. 9, SEQ ID No. 10, SEQ ID No. 11, SEQ ID No. 12, SEQ ID No. 37 and SEQ ID No. 38, and, and SEQ ID NOs: 84, 85, 88, 89, 97, 98, 102, 103, 106, 107, 110 and 111.

According to another aspect, an expression vector is provided encoding a recombinant protein comprising an amino acid sequence having at least 60%, 70%, 80%, 90%, or 95% sequence identity with an amino acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 37, and SEQ ID No. 38, and SEQ ID NOs: 84, 85, 88, 89, 97, 98, 102, 103, 106, 107, 110 and 111.

According to yet an embodiment of the present invention, expressions vectors are provided encoding a fusion protein according to the present invention.

The skilled person is well aware of the degeneration of the genetic code, and the preference for specific codons in various organisms. Thus, dependent upon the selection of host cell, the nucleic acid sequence encoding the recombinant protein and fusion proteins of the invention may be adapted to the preferred codons of the host cell. Thus, the amino acids of the proteins of the invention may be encoded by any combination of the codons as shown in the table below:

| Amino Acid | Single Letter Amino Acid Code | DNA codons |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Stop codons | Stop | TAA, TAG, TGA |

Preferably the codons are furthermore optimized for high expression according to the selected host cell.

For expression of proteins by recombinant DNA technology, in addition to the particular embodiment of the invention, a DNA sequence encoding a signal peptide is preferably appended to the N-terminal end of the protein sequence. The signal peptide may serve to direct localization of the fusion protein during and/or after synthesis in a host cell. It may accordingly be a sequence directing secretion of the fusion protein. The use of such signal peptide sequences is well known in the art. The signal peptide may take any form, e.g. it may constitute the IgGk-chain signal peptide, or it may constitute the signal peptide from human serum albumin (SEQ ID. No 32).

In the case when the signal peptide from human serum albumin (SEQ ID. No 32) is appended to the N-terminal of SEQ ID. No 28, the protein sequence to be expressed may be as shown in SEQ ID. No 33, or SEQ ID NOs: 85, 89, 98, 103, 107, or 111.

Furthermore, for expression of the protein by recombinant DNA technology, in according to one particular embodiment of the invention, a protein having an amino acid sequence as depicted in SEQ ID NO. 33, a nucleotide sequence as depicted in SEQ ID. No 34 or SEQ ID NOs: 86, 90, 99, 104, 108, or 112 may be used, wherein a translational stop codon is appended to the 3' end of the coding sequence.

In the case when the invention is embodied by the nucleotide sequence in SEQ ID. No. 34, the nucleotide sequence is preferably appended to the immediate 5'-end of the coding sequence by a Kozak sequence, e.g. GCCACC, as in SEQ ID No. 35 or SEQ ID NOs: 86, 90, 99, 104, 108, or 112. The DNA sequence may further be flanked by DNA elements to enable subcloning, e.g. such as gateway recombinase attB sites. However, any cloning or synthesis strategy may be used to generate the DNA sequence and facilitate subcloning into an expression vector. In the case when the DNA sequence incorporates gateway recombinase sites to enable subcloning, the nucleotide sequence may be as shown in SEQ ID. No 36 or SEQ ID NOs: 87, 91, 100, 105, 109, or 113.

The obtained expression vector including a nucleic acid sequence encoding a recombinant protein of fusion protein of the invention may be introduced in suitable host cells for the production of the desired protein. Various commercially available or proprietary host cells may be used. For example, an expression vector may be transferred into eukaryote host cells, such as CHO cells, e.g. CHO DG44 DHFR (dihydrofolate reductase$^{-/-}$) suspension culture adapted CHO cells. Transfection of host cells with the expression vector may be performed by methods well known to the skilled person, e.g. using electroporation.

Upon culturing the host cells in a suitable culturing media, the recombinant proteins or fusion proteins according to the present invention encoded by the expression vector in the host cell will be produced, and the resulting protein may be collected and purified by methods well known to the skilled person.

The expression vector may include signal sequences, commonly known as "signal peptide", for secretion of the expressed protein or fusion protein into the culture media.

For isolation and purification of the secreted recombinant protein from the cell culture medium, one or more pre-treatments or clarification steps is commonly used first in order to remove large particles and biomass. Non-limiting examples of applicable pre-treatment steps are e.g. reverse osmosis, centrifugation, filtration methods and diafiltration, or a combination thereof. The obtained protein is then commonly purified by one or more of a variety of chromatographic methods well known to the skilled person, e.g. by affinity chromatography, ion-exchange chromatography, mixed-mode chromatography, hydrophobic interaction chromatography, size exclusion chromatography or other chromatography techniques, or a combination thereof.

For example, a recombinant protein or fusion protein expressed by a suitable host cell may be purified using an affinity chromatography method, such as using MabSelect™ SuRe™ media, e.g. such as a 5 ml HiTrap MabSelect™ SuRe™ column mounted on an FPLC chromatography system, e.g. the BioRad NGC Discover™ 10 Pro system fitted with a 5 mm UV flow cell. After loading of the sample comprising the protein to be purified, the column is commonly washed one or more times with one or more applicable wash buffers, whereafter the protein is eluted using an applicable elution buffer. The obtained protein may be further purified using one or more of the chromatography methods listed above.

It should be understood that various modification may be introduced in the nucleic sequences encoding the recombinant proteins of the present invention utilising techniques well known to the skilled person for example to facilitate expression. By the use of site directed mutagenesis, modification may be introduced to adapt the coding sequence to the desired host used to express the sequence and thus produce the recombinant protein. The skilled person is well aware of the fact of the presence of host specific codons, and that the adaption of a heterologous nucleic acid sequence to the host specific codons increase the expression efficiency as mentioned above. Other modifications may also be introduced, e.g. to facilitate isolation and purification, i.e. by adding a sequence coding for a peptide or protein useful for such purposes. Also, nucleic acid sequences coding signal peptide providing for secretion of the desired recombinant protein from the host cell may also be linked to the nucleic acid sequences of the present invention.

The present invention furthermore provides a host cell suitable for production of a recombinant protein or fusion protein according to the present invention. Various commercially available host cells specifically adapted for the production of recombinant proteins may be used, both prokaryotic host cells and eukaryotic host cells. Non-limiting examples of suitable host cells are e.g. CHO cells, HEK293 cells, *Pichia pastoris* cells, NS0 cells or e-coli cells.

Finally, the present invention also relates to thrombospondin type 1 repeat (TSP-1) homology domain of a CCN family protein and fusion protein comprising said TSP-1 repeat homology domain for use as a medicament for treatment or prevention of disorders by inhibiting or counteracting the cell signaling and cell physiological functions ascribed to CCN family proteins.

In one aspect, the present invention provides a protein, e.g. fusion protein, as defined herein for use in therapy.

In some aspects, the protein, e.g. fusion protein, may be for use in the treatment or prevention of fibrosis, or any condition exhibiting fibrosis (i.e. any fibrotic condition or disorder). The fibrosis may affect any tissue or organ, including for example, the lung, eye, heart, skeletal muscle, peritoneum, kidney, liver, pancreas, bile ducts, skin, blood vessels, or more systemic systems. In particular, the condition exhibiting fibrosis may be selected from pulmonary fibrosis, which may be of any etiology, including idiopathic pulmonary fibrosis, bronchopulmonary dysplasia, retinal fibrosis, diabetic retinopathy, age-related macular degeneration, retinal detachment, oxygen induced retinopathy, glaucoma, cardiac fibrosis, post-transplant graft fibrosis, cardiomyopathy associated fibrosis, muscular fibrosis, Duchenne muscular dystrophy, peritoneal fibrosis, diabetic nephropathy, chronic kidney disease (kidney fibrosis), acute kidney injury, tubulointerstitial fibrosis, chronic allograft nephropathy, liver fibrosis, non-alcoholic steatohepatitis, fatty liver disease, chronic pancreatitis, biliary fibrosis, keloids, scarring, systemic sclerosis, atherosclerosis, epidural fibrosis.

In the context of cardiac fibrosis, the conditions to be treated or prevented may include cardiac hypertrophy and heart failure with or without preserved ejection fraction.

In a further aspect, the present invention provides a protein, e.g. fusion protein, as defined herein for use in the treatment of an inflammatory or autoimmune disease. In some embodiments, the inflammatory disease is selected from rheumatoid arthritis, amyotrophic lateral sclerosis (ALS), inflammatory bowel disease, ulcerative colitis, Crohn's disease.

In a further aspect, the present invention provides a protein, e.g. fusion protein as defined herein for use in the treatment of cancer. It is known in this regard that 4-domain CCN proteins can both elicit oncogenic responses in isolated cancer cells as well as contribute to metastasis, chemoresistance and immunotherapy resistance by acting on cancer cells directly or the tumour stroma. The activity of the proteins herein in inhibiting the effect or activity of a 4-domain CCN protein accordingly provides a rationale for treating cancer. The cancer may be any malignant or pre-malignant neoplastic condition. It may be of any tissue or organ. In an embodiment the cancer may manifest as solid tumours. In another embodiment the cancer may be of or in the haemopoietic system. It may be a primary cancer or a secondary cancer, or metastasis. The cancer may thus be a cancer of the pancreas, breast, prostate, cervix, ovary, liver, bladder, brain, blood, bone, skin, lung or stomach. In some embodiments, the cancer is selected from pancreatic cancer, pancreatic ductal adenocarcinoma, breast cancer, prostate cancer, cervical cancer, ovarian carcinoma, liver cancer, hepatocellular carcinoma, urothelial bladder cancer, brain cancer, glioblastoma, acute lymphoblastic leukemia, osteo-sarcoma, melanoma, mesothelioma, gastric carcinoma, oral squamous cell carcinoma, oesophagal cancer, colorectal cancer, lung cancer.

In a further aspect, the present invention provides a protein, e.g. a fusion protein, as defined herein for use in the treatment of a metabolic disease. The metabolic disease may be, or may be associated with, insulin resistance or glucose intolerance. In some embodiments, the metabolic disease is selected from type 2 diabetes and metabolic syndrome.

The fusion protein of the present invention may also be use in methods of treatment of the conditions described above. Similarly, the fusion protein of the present invention may be used in methods of manufacture of a medicament for use in the treatment of the conditions described above.

EXAMPLES

Example 1

Expression of a Fusion Protein According to the Invention

In this example, the providing of a fusion protein comprising amino acid 194-246 of CCN5 (SEQ ID. No. 1), fused N-terminal of a peptide linker (SEQ ID No. 20) and Fc-fragment of IgG, IgG4 subclass of SEQ ID NO. 15 (S228P, F234A, L235A, K447-, Eu-numbering) (CCN5(dIII)-Fcv2) (i.e. a fusion protein according to SEQ ID. No. 28) is described. The fusion protein was further appended with an N-terminal signal sequence originating from albumin of SEQ ID No. 32 and was expressed in mammalian cells as disclosed below.

The DNA sequence shown in sequence SEQ ID No. 36 was synthesized and sequence verified by a commercial supplier. The synthesized sequence was recombined with pDonrZeo by BP Gateway recombinase cloning to generate an Entry vector. Following transfection of competent *E. coli* mutated to allow for efficient propagation of plasmids (One Shot Top10™ cells), the entry vector was isolated with standard plasmid isolation techniques through use of a QIAprep™ Spin Miniprep kit from Qiagen™. Following plasmid isolation, the entry vector was verified by restriction enzyme digestion followed by DNA gel electrophoresis according to standard techniques well known to the skilled person.

The Entry vector containing sequence SEQ ID NO. 35 was further recombined with a destination vector using LR gateway recombinase. The destination vector used was pUCOE-DHFR-DEST, as described by Kaasbøll et al., 2018, supra.

Following transfection of competent *E. coli*, mutated to allow for efficient propagation of plasmids (One Shot Top10™ cells), the expression vector was isolated with standard plasmid isolation techniques using a QIAGEN™

Plasmid Plus Maxi Kit. The resulting expression vector was verified by standard restriction enzyme digestion and DNA gel electrophoresis according to standard techniques well known to the skilled person. The resulting expression vector was then transferred into ExpiCHO suspension culture adapted CHO cells according to the "Max Titer" protocol supplied by the manufacturer of the Expifectamine™ CHO transfection kit (Gibco Cat. #: A29129) and as described briefly in Kaasbøll et al., 2018, supra. The cells were sedimented 6 days after transfection by centrifugation at 4750 g for 20 minutes at 4° C. and the supernatant cell culture medium harvested. 0.1M PMSF in 100% isopropanol was added to a concentration of 1 mM and 0.5M EDTA was added to a concentration of 2 mM. Then, 96% ethanol was added to a final concentration of about 3%. 1M TrisHCl pH 7.4 was added to a final concentration of 25 mM prior to chromatographic purification.

The capture step of the purification was performed by affinity chromatography with a protein A chromatography media. The media used in this experiment was rProtein A FF (GE Healthcare). A 5 mL HiTrap™ rProtein A FF column (GE Healthcare) was used for purification of the expressed recombinant protein from 60 mL of cell culture medium harvested and supplemented as described, supra. The HiTrap™ rProtein A FF column was mounted on an FPLC chromatography system (BioRad NGC Discover™ 10 Pro system) fitted with a 5 mm UV flow cell and equilibrated with a buffer containing 25 mM TrisHCl pH 7.4, 25 mM NaCl and 3% ethanol. The harvested cell culture medium containing the recombinant protein was loaded with a sample pump at a speed of 2.5 ml/min, followed by washing with 6 column volumes of wash buffer (25 mM TrisHCl pH 7.4, 25 mM NaCl and 3% ethanol)) prior to elution with 0.1M NaCitrate, pH 3.0, in 3% ethanol. Eluate with a UV 280 nm absorbance exceeding 100 mAU was collected in fractions of 3 mL in low-protein binding tubes pre-filled with 1 mL 1M TrisHCl pH 9.0. The fraction containing the UV absorbance peak was concentrated to 500 μL with the use of a Vivaspin® 20 mL, 30 kDA MWCO concentration device. Following concentration, the sample was loaded into a sample loading loop on the FPLC chromatography system (BioRad NGC Discover™ 10 Pro system). The FPLC chromatography system was fitted with a Superdex® 200 Increase 10/300 GL column (GE Healthcare) equilibrated with 50 mM NaCl, 20 mM HEPES pH 7.0. The sample was injected, and the column perfused with the pre-equilibration buffer (50 mM NaCl, 20 mM HEPES pH 7.0) at a flowrate of 0.25 mL/minute. The main UV 280 nm absorbance peak was found to contain the purified recombinant protein (CCN5(dIII)-Fcv2, SEQ ID No. 28). 104, samples of the collected fractions were subjected to SDS-PAGE utilizing Mini-PROTEAN® TGX Stain-Free™ precast gels and the isolated recombinant proteins were visualized utilizing a ChemiDoc™ imaging system (BioRad).

It is widely known to the skilled person that recombinant proteins may be produced in various expressions systems and purified by a variety of chromatographic methods with similar results.

Example 2

A DNA sequence encoding a fusion protein comprising amino acid 194-246 of CCN5 (SEQ ID. No. 1), fused N-terminal of a peptide linker (SEQ ID No. 20) and an Fc-fragment of IgG, subclass IgG4 of SEQ ID NO. 15 (S228P, F234A, L235A, K447-, Eu-numbering) (CCN5

(dIII)-Fcv2) was expressed in order to produce a recombinant protein according to SEQ ID NO. 28.

Figure 1:
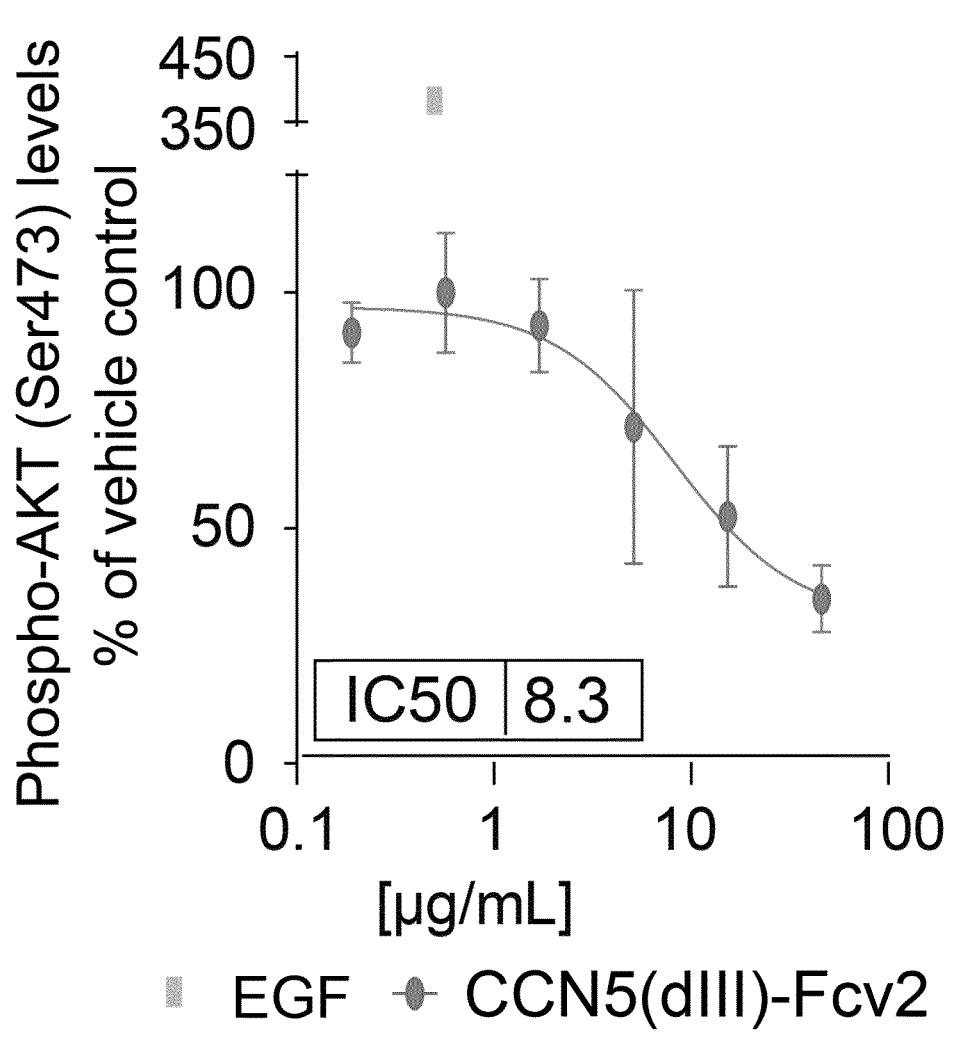
Figure 1:
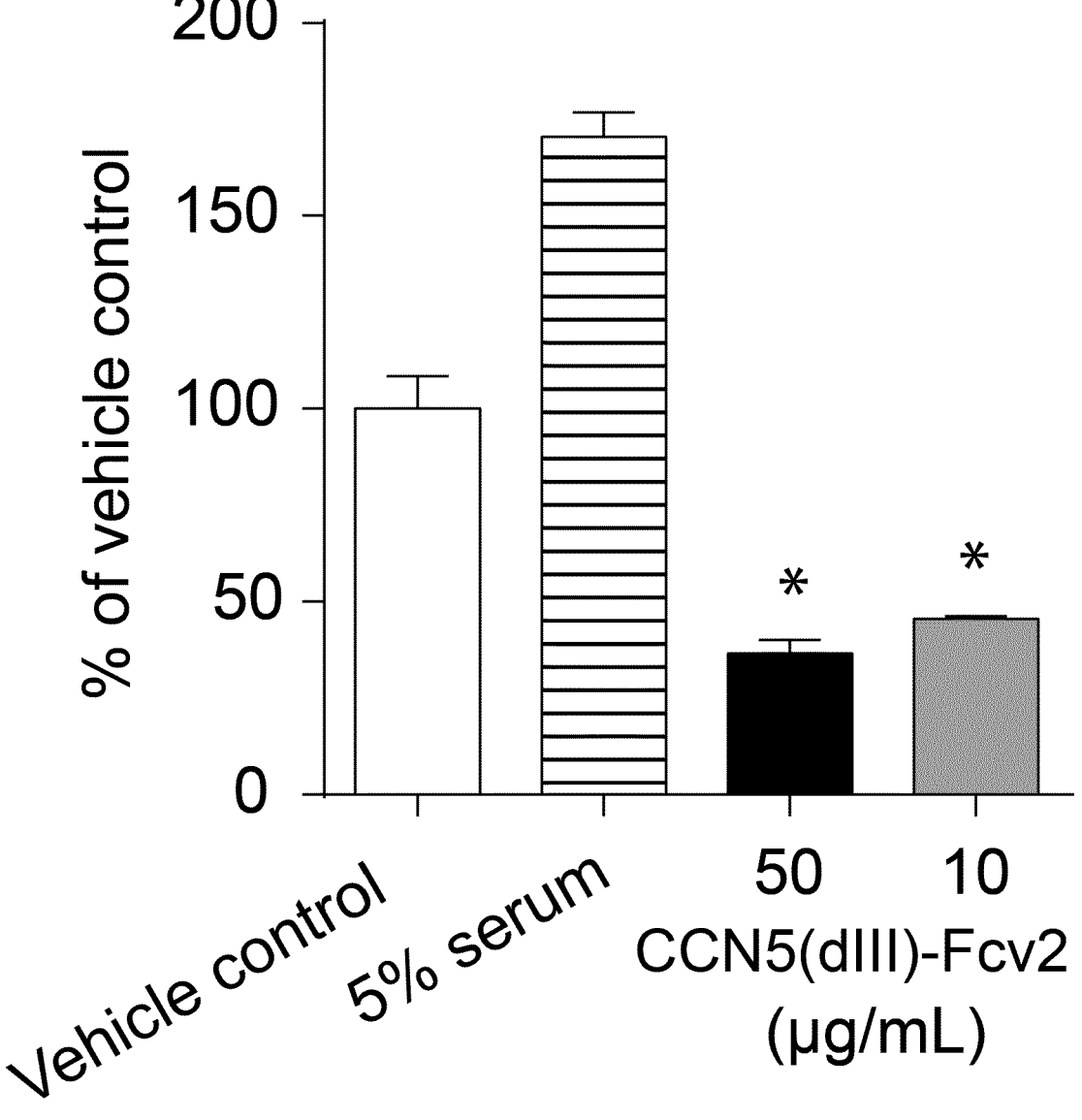
Figure 1:
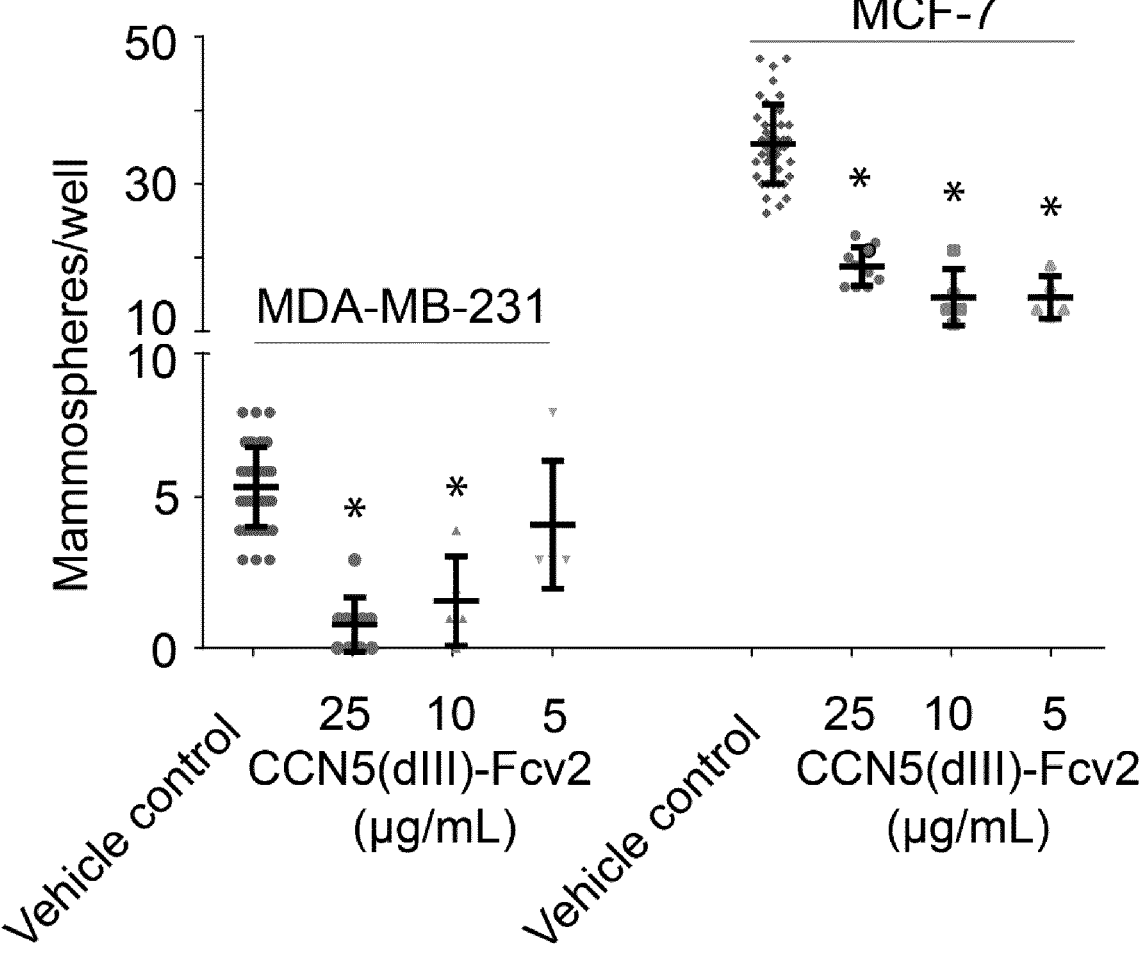
Figure 1:
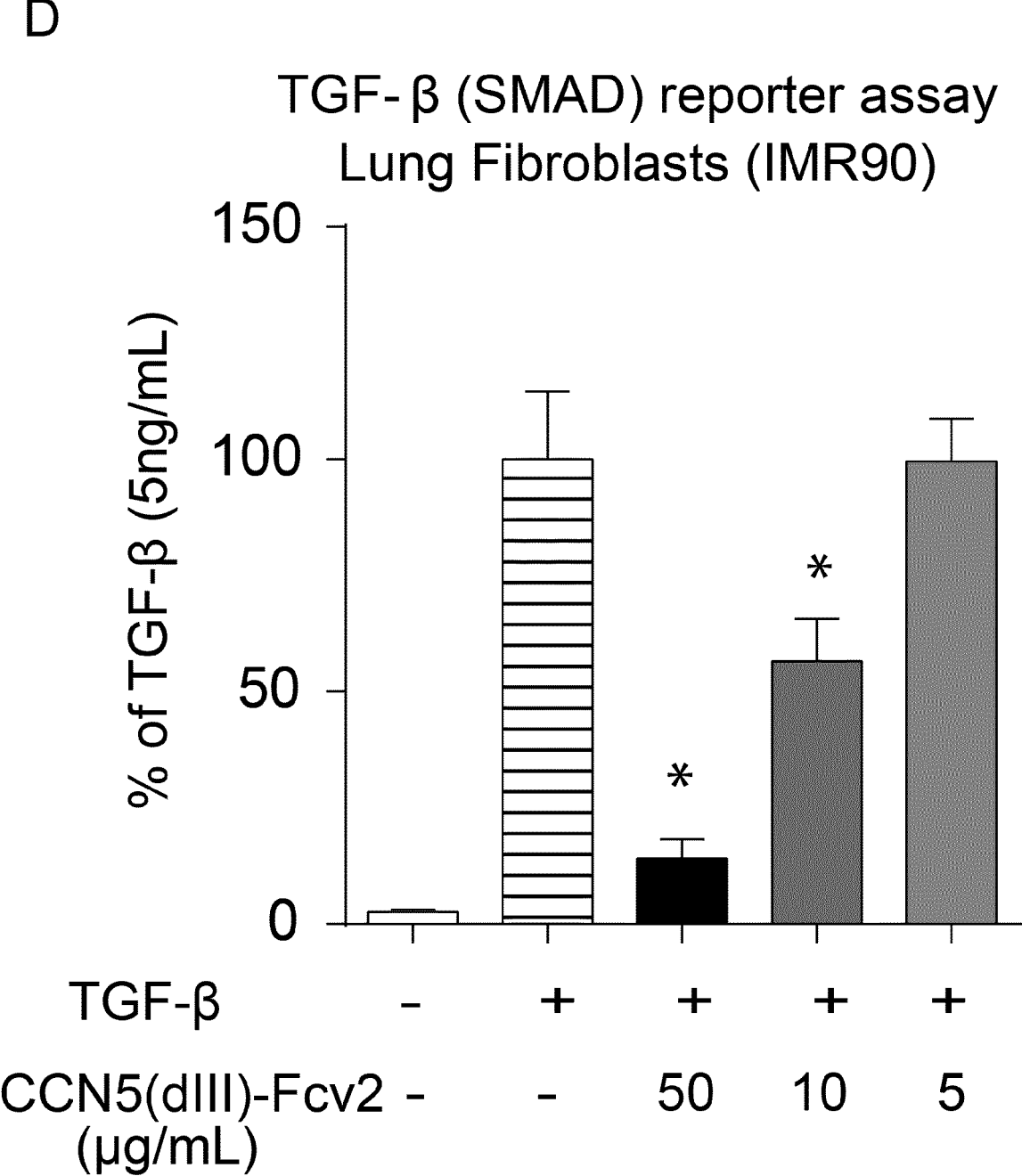

The obtained protein was tested for its ability to inhibit prosurvival signaling (Serine-473 phosphorylation of AKT) in A549 human lung cancer cells (FIG. 1A). Tissue cultured treated Corning Incorporated Costar® 96 well sterile polystyrene plates were coated with fibronectin (Sigma Cat #F1141 diluted to 10 µg/mL in BioWhittaker® Dulbecco's phosphate buffered saline (Lonza Cat. No. 17-512F, hereafter referred to as PBS)). The coating solution containing fibronectin was distributed to the wells at a volume of 100 µL/well, incubated for 1 hour at room-temperature followed by decantation of the coating solution, 100 µL of PBS was also distributed to the fibronectin coated wells, which was also decanted. A549 cells sub-cultured to maintain a density of maximum 80% confluency were detached by enzymatic treatment (Accutase®, Cat No. L0950-100 from Biowest®), diluted in Dulbecco's Modified Eagle Medium with high glucose (Gibco Cat. No.: 41965-039) supplemented with 10% heat-inactivated Fetal Bovine Serum (FBS) (500 mL flasks with FBS (Cat. No. 16000-044 from gibco) equilibrated to room-temperature were incubated in a water bath with a temperature of 60° C. with shaking for 30 minutes) and 50 µg/ml gensumycin (Sanofi)) to a concentration of 110000 cells/mL and 1004, of the cell solution was distributed to the fibronectin coated wells. All cell incubations were done in cell culture incubators maintaining a temperature of 37° C., a humid atmosphere of room-air and 5% $CO_2$. Following overnight incubation, the A549 cells were washed twice in PBS and 90 µL Dulbecco's Modified Eagle Medium with high glucose (DMEM, Gibco Cat. No.: 41965-039) and 50 µg/ml gensumycin (Sanofi) without FBS was distributed to the wells. Following 18 hours incubation in medium without FBS the cells were stimulated with 104, solution of the recombinant protein in question. After stimulation for 60 minutes the medium was decanted, and cells harvested by adding 50 µL lysis buffer with blocking reagent as per supplied by the Cisbio Phospho-AKT (Ser473) kit (Cisbio Inc, Cat. No.: 64AKSPEG). Following addition of the lysis buffer with blocking reagent the 96-well plate is incubated for 60 min on on a PST-60HL plus (ThermoFisher) plate shaker at 500 rpm. Following shaking, the lysed samples were triturated prior to the transfer of 16 µL from each well to white-walled HTRF 96 well low volume plates (Cisbio Inc., Cat. #: 66PL96025). To assay the amount of phosphorylated AKT (Ser473) 4 µL of a mix of labeled antibodies (50/50 vol/vol mix of phospho-AKT d2 and phospho-AKT Cryptate from the Cisbio Inc, Cat. No.: 64AKSPEG) was added to each well (to the negative control well only the cryptate antibody was used), the plates were sealed with adhesive plastic film and incubated at 4° C. overnight prior to reading at a PolarStar Omega plate reader (BMG Labtech, Germany) fitted with a TR-FRET recording head and 337 nm emission and 615 nm and 665 nm excitation filters. The ratio between the 665 nm and 615 nm excitation recordings were blank corrected and the values of the recombinant protein stimulated wells expressed as percentage of vehicle stimulated wells.

Example 3

A DNA sequence encoding a fusion protein comprising amino acid 194-246 of CCN5 (SEQ ID. No. 1), fused N-terminal of a peptide linker (SEQ ID No. 20) and an Fc-fragment of IgG, subclass IgG4 of SEQ ID NO. 15 (S228P, F234A, L235A, K447-, Eu-numbering) (CCN5

(dIII)-Fcv2) was expressed in order to produce a recombinant protein according to SEQ ID NO. 28.

The obtained protein was tested for its ability for inhibiting pro-fibrotic TGF-β-stimulated transcription (from SMAD2/3 binding cis-elements) in IMR90 human lung fibroblasts. (FIG. 1D). The assay was performed technically as described in Kaasbøll et al. (2018) supra, with the exception of the utilization of 2500 IMR90 lung fibroblasts/well in place of Rat2 cells. The proteins used for stimulation were as indicated in FIG. 1D. The IMR90 cells were sub-cultured as described for the A549 cells prior to use, supra. The IMR90 cells were used prior to passage 20, i.e. prior to reaching replicative senescence.

Example 4

A DNA sequence encoding a fusion protein comprising amino acid 194-246 of CCN5 (SEQ ID. No. 1), fused N-terminal of a peptide linker (SEQ ID No. 20) and an Fc-fragment of IgG, subclass IgG4 of SEQ ID NO. 15 (S228P, F234A, L235A, K447-, Eu-numbering) (CCN5 (dIII)-Fcv2) was expressed in order to produce a recombinant protein according to SEQ ID NO. 28.

The obtained protein was tested for its ability for inhibiting proliferation of the human lung fibroblast cell line IMR90 (FIG. 1B). The IMR90 cells were sub-cultured as described for the A549 cells prior to use, supra. The IMR90 cells were used prior to passage 20, i.e. prior to reaching replicative senescence. For the experiments the IMR90 cells were harvested as described for the A549 cells, supra, washed in PBS, diluted in DMEM with 1% FBS with gensumycin as described for Experiment 2, supra, and seeded in xCELLigence impedance plates at a density of 12000/well. After 2 hours the cells were stimulated with 104, solution of the recombinant protein in question or FBS and incubated for a further 72 hours before harvesting with CellTiter-Glo® (Promega Inc.) as described in Kaasbøll et al., (2018), supra.

Example 5

A DNA sequence encoding a fusion protein comprising amino acid 194-246 of CCN5 (SEQ ID. No. 1), fused N-terminal of a peptide linker (SEQ ID No. 20) and an Fc-fragment of IgG, subclass IgG4 of SEQ ID NO. 15 (S228P, F234A, L235A, K447-, Eu-numbering) (CCN5 (dIII)-Fcv2) was expressed in order to produce a recombinant protein according to SEQ ID NO. 28.

The obtained protein was tested for its ability for inhibiting the sphere-forming ability (anchorage-independent growth) of the estrogen receptor-positive breast cancer cell line MCF-7 and of the triple-negative breast cancer cell line MDA-MB-231 (FIG. 1C) as described in Kaasbøll et al., supra. The MDA-MB-231 cells were treated the same as described for the MCF-7 cell line in Kaasbøll et al., supra. The MCF-7 and MDA-MB-231 cell lines were sub-cultured as described for the A549 cell line, supra.

Example 6

DNA sequences encoding a fusion protein comprising amino acid 194-246 of CCN5 (SEQ ID. No. 1), fused N-terminal of a peptide linker (SEQ ID No. 20) and either the Fc-fragment of IgG, subclass IgG4 of SEQ ID NO. 15 (S228P, F234A, L235A, K447-, Eu-numbering) (CCN5 (dIII)-Fcv2), the Fc-fragment of IgG, subclass IgG4 of SEQ ID No. 18 (S228P, E233P, F234V, L235A, G236-, K447-, Eu-numbering) (CCN5(dIII)-Fcv2.1) or a chimeric Fc-fragment of IgG2/4 subclasses (SEQ ID No. 19) (CCN5(dIII)-Fcv2.3) were expressed in order to produce recombinant protein according to SEQ ID NO. 28 (CCN5(dIII)-Fcv2), SEQ ID NO. 29 (CCN5(dIII)-Fcv2.1) and SEQ ID NO. 30 (CCN5(dIII)-Fcv2.3).

Specifically, expression vectors coding for the expression of SEQ ID NO. 28 (CCN5(dIII)-Fcv2), SEQ ID NO. 29 (CCN5(dIII)-Fcv2.1) and SEQ ID NO. 30 (CCN5(dIII)-Fcv2.3) were transfected into ExpiCHO suspension culture adapted CHO cells according to the "Max Titer" protocol supplied by the manufacturer of the Expifectamine™ CHO transfection kit (Gibco Cat. #: A29129) and as described briefly in Kaasbøll et al., supra. The cells were sedimented 6 days after transfection by centrifugation at 13000 rpm in an Heraeus biofuge pico benchtop centrifuge for 5 minutes and the supernatant cell culture medium harvested. Samples of the harvested cell culture supernatants were separated by SDS-PAGE utilizing Mini-PROTEAN® TGX Stain-Free™ precast gels and the recombinant proteins were visualized utilizing a ChemiDoc™ imaging system (BioRad). The separated proteins were proteins were then transferred to PVDF-membranes using the Trans-Blot Turbo, semi-dry blotting system (Bio-Rad) for Western-blot analysis. The blot was probed with an anti-human IgG4 antibody conjugated to horseradish peroxidase (Invitrogen Cat. #: A10654) that was used in conjunction with SuperSignal™ West Femto Maximum Sensitivity Substrate (ThermoFisherScientific) and a ChemiDoc™ imaging system (BioRad) for visualization.

Figure 2:
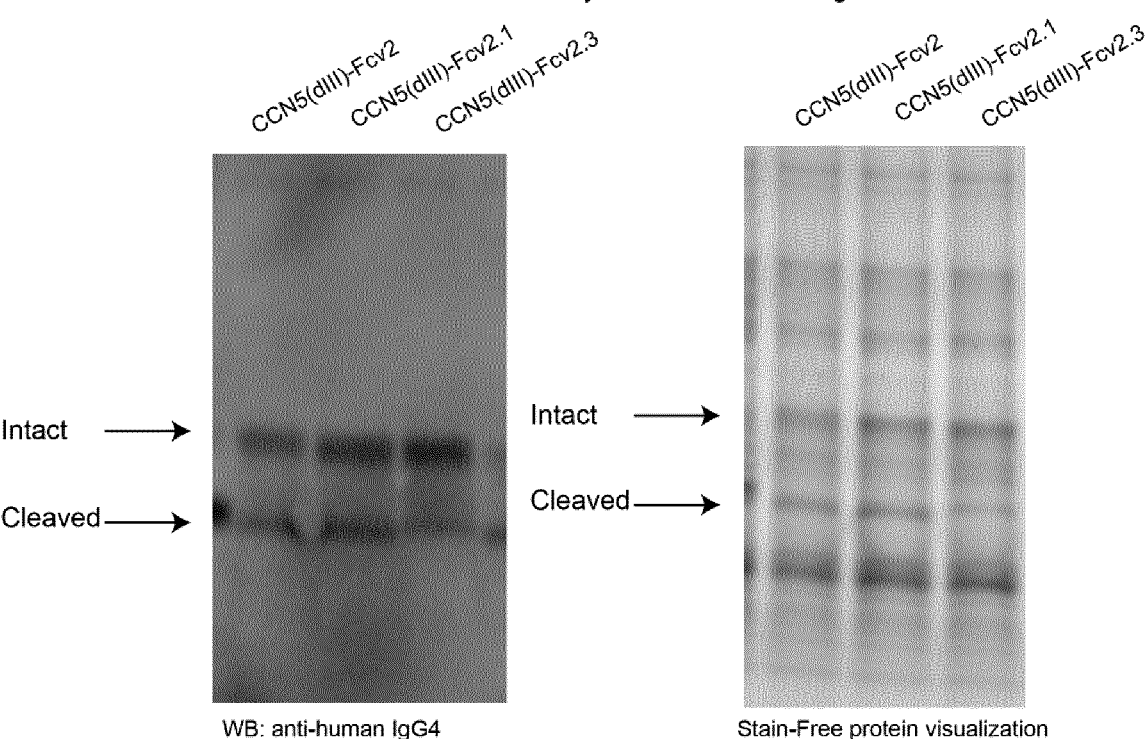
FIG. 2 shows the effect of different variants of the hinge region of the Fc fragment on the protease susceptibility of embodiments of the invention in which CCN5(dIII) is fused to the Fc fragment of IgG, wherein the tested fusion protein comprises a sequence as depicted in depicted in SEQ ID No. 28; SEQ ID No. 29, and SEQ ID No. 30, respectively, cf. example 6 below.

In FIG. 2, data demonstrating the improved protease resistance of the Fc-fragment backbone composed of the IgG2/4 chimera (shown in SEQ ID No. 19) are shown.

CCN5/WISP2(domain III) fused to IgG4 Fc-fragment with either an immune-effector silenced IgG4 hinge (as defined in SEQ ID No. 28); CCN5(domain III)-Fcv2, the same IgG4 backbone incorporating mutations based on IgG2 (as defined in SEQ ID No. 29); CCN5(domain III)-Fcv2.1, or the same IgG4 backbone with a complete hinge region from IgG2 (as defined in SEQ ID No. 30); CCN5(domain III)-Fcv2.3 were expressed in the ExpiCHO system and conditioned medium (CM) was harvested after 6 days. Western blotting and total protein staining of SDS-PAGE gels reveals that the CCN5(domain III)-Fcv2.3 variant is the least susceptible to the proteases present during cultivation. Notice that the immunoreactivity of the anti-IgG4 antibody towards the Fc-fragment is partially lost with the substitution of sequences from IgG2, and thus underestimates the protein levels relative to the general protein staining.

Example 7

DNA sequences encoding a fusion protein comprising amino acid 194-246 of CCN5 (SEQ ID. No. 1), fused N-terminal of either the peptide linker described in SEQ ID No. 20 and a chimeric Fc-fragment of IgG2/4 subclasses (SEQ ID No. 19). (CCN5(dIII)-Fcv2.3) or the peptide linker described in SEQ ID No. 25 and a chimeric Fc-fragment of IgG2/4 subclasses (SEQ ID No. 19) (CCN5(dIII)-HLn8-Fcv2.3) were expressed in order to produce recombinant protein according to SEQ ID NO. 30 (CCN5(dIII)-Fcv2.3) and SEQ ID No. 31 (CCN5(dIII)-HLn8-Fcv2.3). Specifically, expression vectors coding for the expression of SEQ ID NO. 30 (CCN5(dIII)-Fcv2.3) and SEQ ID No. 31 (CCN5 (dIII)-HLn8-Fcv2.3) were transfected into ExpiCHO suspension culture adapted CHO cells according to the "Max Titer" protocol supplied by the manufacturer of the Expifectamine™ CHO transfection kit (Gibco Cat. #: A29129) and as described briefly in Kaasbøll et al., supra. The cells were sedimented 4 days after transfection by centrifugation at 13000 rpm in an Heraeus biofuge pico benchtop centrifuge for 5 minutes and the supernatant cell culture medium harvested. Samples of the harvested cell culture supernatant were separated by SDS-PAGE utilizing Mini-PROTEAN® TGX Stain-Free™ precast gels. The separated proteins were proteins were transferred to PVDF-membranes using the Trans-Blot Turbo, semi-dry blotting system (Bio-Rad) for Western-blot analysis. The blot was probed with an anti-human IgG4 antibody conjugated to horseradish peroxidase (Invitrogen Cat. #: A10654) that was used in conjunction with SuperSignal™ West Femto Maximum Sensitivity Substrate (ThermoFisherScientific) and a ChemiDoc™ imaging system (BioRad) for visualization.

Figure 3:
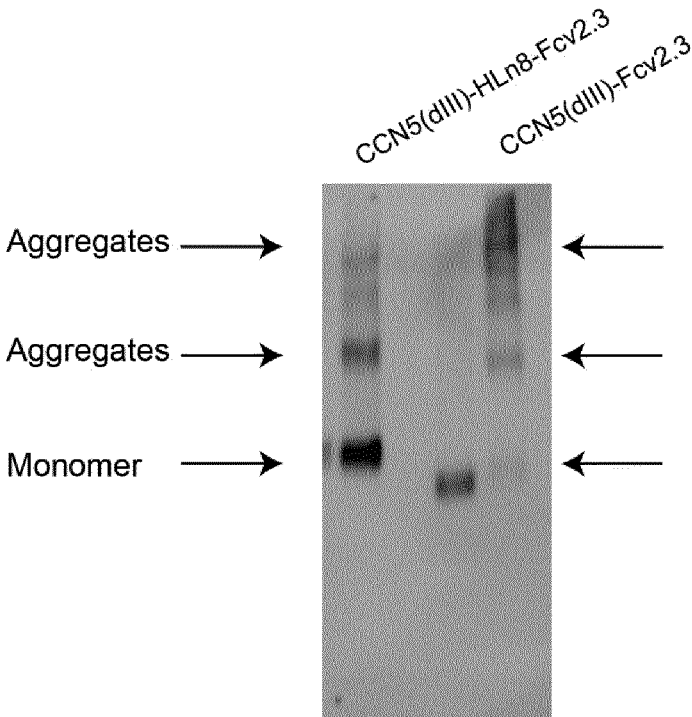
FIG. 3 shows the propensity of aggregation of an embodiment of the invention depending on the structure of the peptide linker connecting CCN5(dIII) with the Fc fragment of IgG, wherein the tested fusion protein comprises a sequence as depicted in depicted in SEQ ID No. 30 and SEQ ID No. 31.
Figure 4:
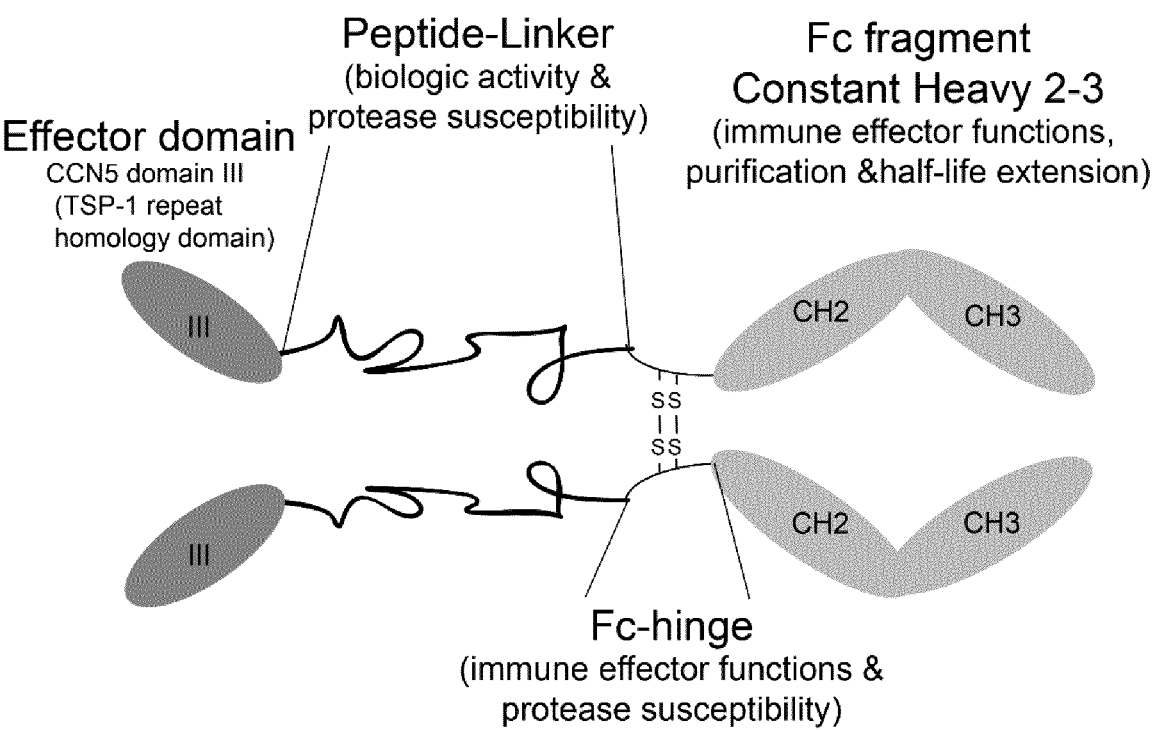
FIG. 4 illustrates a fusion protein according to the present invention, comprising the TSP-1 repeat homology domain C-terminally linked to a peptide linker, and via an Fc-hinge to an Fc-fragment.

In FIG. 3 data showing the reduced tendency to aggregation when the embodiment of the invention incorporates a peptide linker as depicted in SEQ ID NO. 25 is provided.

Non-reducing SDS-PAGE of CM from transiently transfected CHO suspension cells expressing CCN5(domain III) fused to the amino-terminal end of the chimeric IgG2/4 Fc-fragment through various peptide linkers. The Western blot reveals that fusion protein with an amino sequence as depicted SEQ ID No. 31; (dIII)-HLn8-Fcv2.3 has lower tendency to aggregate than a fusion protein of the invention having an amino acid sequence as depicted in SEQ ID No. 30; CCN5(domain III)-Fcv2.3. This finding demonstrates that the peptide linker defined in sequence SEQ ID No. 25 affords lower tendency of aggregation of the fusion protein compared with the fusion protein containing the peptide linker defined in sequence SEQ ID No. 20.

Example 8

DNA sequences encoding a fusion protein comprising either amino acid 194-246 of CCN5 (SEQ ID. No. 1) or amino acids 194-246 of CCN5 (SEQ ID. No. 7), where amino acid in position 195 (proline) is substituted with alanine, fused C-terminal of a peptide linker (SEQ ID No. 39) and an Fc-fragment of IgG subtype IgG4 of SEQ ID NO. 15 (S228P, F234A, L235A, K447-, Eu-numbering) were expressed in order to produce recombinant protein according to SEQ ID No.: 40 (Fc-HLn8-CCN5(dIII)) or SEQ ID No.: 41 (Fc-HLn8-CCN5(dIII)-P195A).

Specifically, expression vectors coding for the expression of SEQ ID NO. 40 (Fc-HLn8-CCN5(dIII)) and SEQ ID No.: 41 (Fc-HLn8-CCN5(dIII)-P195A) were transfected into ExpiCHO suspension culture adapted CHO cells according to the "Max Titer" protocol supplied by the manufacturer of the Expifectamine™ CHO transfection kit (Gibco Cat. #: A29129) and as described briefly in Kaasbøll et al., supra. The cells were sedimented 3 days after transfection by centrifugation at 13000 rpm in an Heraeus biofuge pico benchtop centrifuge for 5 minutes and the supernatant cell culture medium harvested. Samples of the harvested cell culture supernatant were separated by SDS-PAGE utilizing Mini-PROTEAN® TGX Stain-Free™ precast gels. The separated proteins were proteins were transferred to PVDF-membranes using the Trans-Blot Turbo, semi-dry blotting system (Bio-Rad) for Western-blot analysis. The blot was probed with an anti-human IgG4 antibody conjugated to horseradish peroxidase (Invitrogen Cat. #: A10654) that was used in conjunction with SuperSignal™ West Femto Maximum Sensitivity Substrate (ThermoFisherScientific) and a ChemiDoc™ imaging system (BioRad) for visualization.

Figure 5:
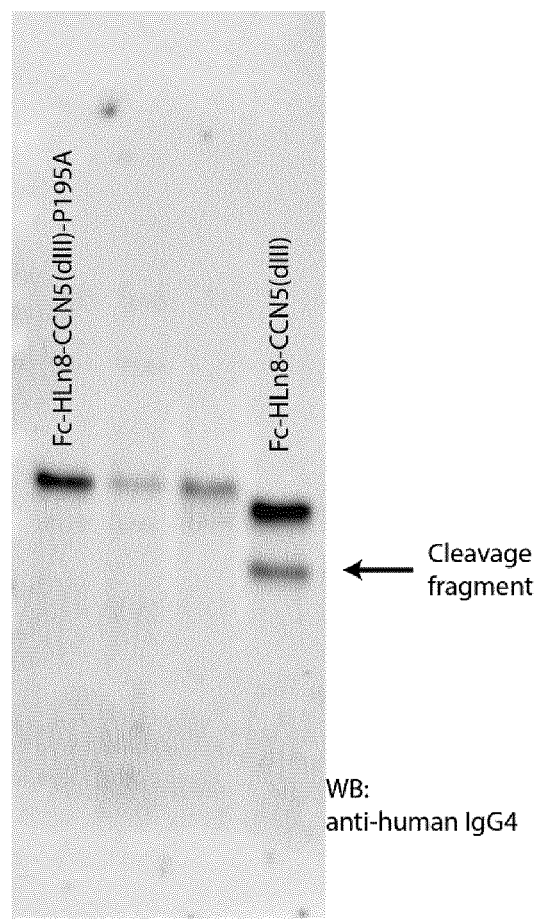
FIG. 5 shows the reduced susceptibility to endopeptidase cleavage when the embodiment of the invention incorporates a mutation of Proline195 of the CCN5 TSP-1 repeat homology domain, as depicted in SEQ ID No 7 (Fc-HLn8-CCN5(dIII)-P195A, SEQ ID No. 41) relative to the wild-type P195 variant of the CCN5 TSP-1 repeat homology domain (Fc-HLn8-CCN5(dIII), SEQ ID No. 40).

In FIG. 5, data is presented showing the reduced susceptibility to endopeptidase cleavage when the embodiment of the invention incorporates a mutation of Proline195 of the CCN5 TSP-1 repeat homology domain, as depicted in SEQ ID No 7.

Reducing SDS-PAGE of CM from transiently transfected CHO suspension cells expressing CCN5(domain III) fused to the carboxyl-terminal end of an IgG4 Fc-fragment as described in SEQ ID No. 15 either incorporating a P195A mutation (Fc-HLn8-CCN5(dIII)-P195A) or expressing the wild-type P195 variant of the CCN5 TSP-1 repeat homology domain (Fc-HLn8-CCN5(dIII)). This blot demonstrates that the P195A mutation affords the proteolytic resistance to the TSP-1 repeat homology domain of CCN5.

Example 9

A fusion protein comprising amino acids 194-250 of human CCN5 (SEQ ID No. 56), fused N-terminal of a peptide linker (SEQ ID No. 57) and Fc-fragment of human IgG, IgG4 subclass of SEQ ID NO. 15 (S228P, F234A, L235A, K447-, Eu-numbering) resulting in a protein sequence corresponding to SEQ ID No. 58 (CCN5(dIII)-SL-Fcv0) is disclosed. The fusion protein was further appended with an N-terminal signal sequence for secretion originating from albumin of SEQ ID No. 32 to generate a fusion protein corresponding to SEQ ID No. 59 and was expressed in mammalian cells as disclosed below.

A DNA sequence of encoding the fusion protein of SEQ ID No. 59 was codon optimized for protein expression in hamster cells (by the algorithm of the commercial supplier), and a KOZAK sequence for translation was appended at the 5' end and a STOP-codon was introduced at the 3' end resulting in a DNA sequence of SEQ ID. No. 60. The DNA sequence was further appended at both ends by Gateway attB sites resulting in a DNA sequence of SEQ ID No. 61. The sequence of SEQ ID No. 61 was synthesized and verified by a commercial supplier. The synthesized sequence was recombined with pDonrZeo by BP Gateway recombinase cloning to generate an Entry vector. Following transfection of competent *E. coli* mutated to allow for efficient propagation of plasmids (One Shot Top10™ cells), the entry vector was isolated with standard plasmid isolation techniques through use of a QIAprep™ Spin Miniprep kit from Qiagen™. Following plasmid isolation, the entry vector was verified by restriction enzyme digestion followed by DNA gel electrophoresis according to standard techniques well known to the skilled person.

The Entry vector containing sequence SEQ ID No. 60 was further recombined with a destination vector using LR gateway recombinase. The destination vector used was pUCOE-DHFR-DEST, as described by Kaasbøll et al., 2018, J. Biol. Chem, 293:46, pp. 17953-17970.

Following transfection of competent *E. coli*, mutated to allow for efficient propagation of plasmids (One Shot Top 10™ cells), the expression vector was isolated with standard plasmid isolation techniques using a QIAGEN™ Plasmid Plus Maxi Kit. The resulting expression vector was verified by standard restriction enzyme digestion and DNA gel electrophoresis according to standard techniques well known to the skilled person. The resulting expression vector was then transfected into ExpiCHO cells adapted for suspension culture according to the "Max Titer" protocol supplied by the manufacturer of the Expifectamine™ CHO transfection kit (Gibco Cat. #: A29129) and as described briefly in Kaasbøll et al., 2018, supra. The cells were sedimented 4 days after transfection by centrifugation at 4750×g for 20 minutes at 4° C. and the supernatant cell culture medium harvested. 0.1M PMSF in 100% isopropanol was added to a concentration of 1 mM and 0.5M EDTA was added to a concentration of 2 mM. Then, 96% ethanol was added to a final concentration of about 3%. 1M TrisHCl pH 7.4 was added to a final concentration of 25 mM prior to chromatographic purification.

The protein was purified by affinity chromatography utilizing protein A chromatography media. The chromatography media used in this experiment was rProtein A FF (GE Healthcare). A 5 mL HiTrap™ rProtein A FF column (GE Healthcare) was used for purification of the expressed recombinant protein from 120 mL of cell culture medium harvested and supplemented as described, supra. The HiTrap™ rProtein A FF column was mounted on an FPLC chromatography system (BioRad NGC Discover™ 10 Pro system) fitted with a 5 mm UV flow cell and equilibrated with a buffer containing 25 mM TrisHCl pH 7.4, 25 mM NaCl and 3% ethanol. The harvested cell culture medium containing the recombinant protein was loaded with a sample pump at a speed of 2.5 ml/min, followed by washing with 10 column volumes of wash buffer (25 mM TrisHCl pH 7.4, 25 mM NaCl and 3% ethanol)) prior to elution with 0.1M NaCitrate, pH 3.0, in 3% ethanol. Eluted fractions of 3 mL were collected in in low-protein binding tubes pre-filled with 1 mL 1M TrisHCl pH 9.0. Protein elution was monitored with 280 nm UV absorbance and 104, samples of the pooled fractions containing the UV 280 nm absorbance peak were subjected to SDS-PAGE utilizing Mini-PROTEAN® TGX Stain-Free™ precast gels in the presence or absence of the reducing agent β-mercaptoethanol and the isolated recombinant proteins were visualized utilizing a ChemiDoc™ imaging system (BioRad).

It is widely known to the skilled person that recombinant proteins may be produced in various expressions systems and purified by a variety of chromatographic methods with similar results.

In FIG. 6 it is shown that the expression and purification of a protein corresponding to SEQ ID No. 58 does result in a protein that migrates higher than expected in the absence of the reducing agent β-mercaptoethanol, thus indicating dimer formation. However, as can be seen from the lane which contains the purified protein in the presence of the reducing agent β-mercaptoethanol, the expression and purification of the protein corresponding to SEQ ID No. 58 results primarily in cleavage fragments and not intact protein.

Example 10

Multiple variants of the sequence of SEQ ID No. 58 were generated in attempt to increase the proteolytic resistance of the protein corresponding to SEQ ID No. 58. DNA sequences were synthesized and verified by a commercial supplier before being sub-cloned to generate plasmids as described in example 9 and the proteins expressed as described in example 9. The variants included proteins with modifications as listed below:

1) an N-terminal signal sequence originating from albumin of SEQ ID No. 32 amino-terminal to fragment of CCN5 comprised of amino acids 194 to 249 incorporating mutation (P245L) corresponding to SEQ ID No. 62 combined with truncation of the peptide linker corresponding to SEQ ID No. 63 and the Fc fragment of SEQ ID No. 15 resulting in a sequence corresponding to SEQ ID No. 64, 2) an N-terminal signal sequence originating from albumin of SEQ ID No. 32 amino-terminal to fragment of CCN5 comprised of amino acids 194 to 246 corresponding to SEQ ID No. 1 combined with a variation of the peptide linker corresponding to SEQ ID No. 65 and the Fc fragment of SEQ ID No. 15 resulting in a sequence corresponding to SEQ ID No. 66, 3) an N-terminal signal sequence originating from albumin of SEQ ID No. 32 amino-terminal to fragment of CCN5 comprised of amino acids 194 to 246 corresponding to SEQ ID No. 1 combined with a variation of the peptide linker corresponding to SEQ ID No. 67 and the Fc fragment of SEQ ID No. 15 resulting in a sequence corresponding to SEQ ID No. 68, 4) an N-terminal signal sequence originating from albumin of SEQ ID No. 32 amino-terminal to fragment of CCN5 comprised of amino acids 194 to 246 corresponding to SEQ ID No. 1 combined with a variation of the peptide linker corresponding to SEQ ID No. 65 and the Fc fragment of SEQ ID No. 19 resulting in a sequence corresponding to SEQ ID No. 69.

These iterations (1-4, supra) of the protein disclosed in Example 12 did show some improvement in their resistance to proteolytic cleavage during expression in the ExpiCHO system, performed as described in Example 9. However, expression of proteins corresponding to SEQ ID No. 64, SEQ ID. No 66, SEQ ID No. 68 and SEQ ID 69 revealed that the degree of proteolytic resistance was still insufficient to allow for the production of intact purified proteins.

Example 11

A fusion protein was generated comprising amino acids 194-237 of CCN5 where the amino acid in position 195 (proline) is substituted with alanine (SEQ ID No. 38), fused N-terminal of a peptide linker (SEQ ID No. 21) and a chimeric Fc-fragment of IgG subtype IgG2/4 with deletion of the carboxyl-terminal K477- (Eu numbering) (SEQ ID No. 19) resulting in SEQ ID No. 27. The fusion protein was further appended with an N-terminal signal sequence for secretion originating from albumin of SEQ ID No. 32 to generate a fusion protein corresponding to SEQ ID No. 70. A DNA sequence of encoding the fusion protein of SEQ ID No. 70 was codon optimized for protein expression in hamster cells (by the algorithm of the commercial supplier), and a KOZAK sequence for translation was appended at the 5' end and a STOP-codon was introduced at the 3' end resulting in a DNA sequence of SEQ ID No. 71. The DNA sequence was further appended at both ends by Gateway attB sites resulting in a DNA sequence of SEQ ID No. 72.

DNA sequences were synthesized and verified by a commercial supplier before being sub-cloned to generate plasmids as described in example 9 and the protein corresponding to SEQ ID No. 70 expressed by transient transfection of ExpiCHO cells as described in example 9.

The cells were sedimented 6 days after transfection by centrifugation at 4750×g for 20 minutes at 4° C. and the supernatant cell culture medium harvested. 0.1M PMSF in 100% isopropanol was added to a concentration of 0.1 mM. 1M NaCitrate pH 5.5 was added to a final concentration of 30 mM prior to chromatographic purification.

The protein was purified by tandem-chromatography composed of a capture step with a 1 mL HiTrap™ MabSelectSuRe™ column (GE Healthcare) immediately followed by desalting with a BioScale™ Mini Bio-Gel® P-6 10 mL column (BioRad). The columns were mounted on an FPLC chromatography system (BioRad NGC Discover™ 10 Pro system) fitted with a 5 mm UV flow cell. The MabSelect-SuRe™ column was mounted on the first column switching valve and equilibrated with a buffer composed of 30 mM NaCitrate pH 5.5 while the Bio-Gel® column was mounted on the second column switching valve and equilibrated with buffer A2 (100 mM NaH$_2$PO4/Na$_2$HPO4 pH 6.5). With the second column switching valve containing the Bio-Gel® column set to be bypassed 140 mL of the harvested cell culture medium containing the recombinant protein was loaded onto the MabSelectSuRe™ column with a sample pump at a speed of 2.0 ml/min, followed by washing with 5 column volumes of wash buffer A1 (30 mM NaCitrate pH 5.5), followed by 5 column volumes of wash buffer A3 (30 mM NaCitrate, 0.5M NaCl, pH 5.5), followed by 3 column volumes of wash buffer A1. Prior to elution with the elution buffer (30 mM Citric acid pH 3.4) the Bio-Gel® column mounted on the second column switching valve was switched to enter the flow-path. After eluting with 2 mL elution buffer the MabSelectSuRe™ column was switched out of the flow-path and the purified protein was eluted from the Bio-Gel® column with buffer A2. Protein elution was monitored with 280 nm UV absorbance and collection triggered once the absorbance exceeded 100 mAU. The collected fractions were pooled and a 104, sample was subjected to SDS-PAGE utilizing Mini-PROTEAN® TGX Stain-Free™ precast gels in the presence of the reducing agent β-mercaptoethanol and the isolated recombinant proteins were visualized utilizing a ChemiDoc™ imaging system (BioRad).

In FIG. 7 it is shown that the expression and purification of a protein corresponding to SEQ ID No. 27 in which the carboxyl-terminal tail of CCN5 is truncated is substantially more proteolytically resistant than variants in which all the carboxyl-terminal amino acids of CCN5 are included (as in SEQ ID No. 58, 64, 66, 68 and 69), even though the cell culture medium was harvested an additional 2 days after sub-cultivation relative to Example 9 (FIG. 6).

Example 12

A fusion protein was generated comprising amino acids 206-249 of CCN3 where the amino acid in position 207 (isoleucine) is substituted with alanine (SEQ ID No. 44), fused N-terminal of a peptide linker (SEQ ID No. 21) and a chimeric Fc-fragment of IgG subtype IgG2/4 with deletion of the carboxyl-terminal K477- (Eu numbering) (SEQ ID No. 19) resulting in a fusion protein of SEQ ID No. 73. The fusion protein was further appended with an N-terminal signal sequence for secretion originating from albumin of SEQ ID No. 32 to generate a fusion protein corresponding to SEQ ID No. 74. A DNA sequence of encoding the fusion protein of SEQ ID No. 74 was codon optimized for protein expression in hamster cells (by the algorithm of the commercial supplier), and a KOZAK sequence for translation was appended at the 5' end and a STOP-codon was introduced at the 3' end resulting in a DNA sequence of SEQ ID No. 75. The DNA sequence was further appended at both ends by Gateway attB sites resulting in a DNA sequence of SEQ ID No. 76.

DNA sequences were synthesized and verified by a commercial supplier before being sub-cloned to generate plasmids as described in example 9 and the protein corresponding to SEQ ID No. 74 was expressed by transient transfection of ExpiCHO cells as described in example 9.

The cells were sedimented 5 days after transfection by centrifugation at 4750×g for 20 minutes at 4° C. and the supernatant cell culture medium harvested. 0.1M PMSF in 100% isopropanol was added to a concentration of 0.1 mM. 1M NaCitrate pH 5.5 was added to a final concentration of 30 mM prior to chromatographic purification.

The protein was purified by tandem-chromatography composed of a capture step with a 5 mL HiTrap™ MabSelectSuRe™ column (GE Healthcare) immediately followed by desalting with a 53 mL HiPrep™ 26/10 DeSalting column (GE Healthcare). The columns were mounted on an FPLC chromatography system (BioRad NGC Discover™ 10 Pro system) fitted with a 5 mm UV flow cell. The MabSelectSuRe™ column was mounted on the first column switching valve and equilibrated with a buffer composed of 30 mM NaCitrate pH 5.5 while the HiPrep™ column was mounted on the second column switching valve and equilibrated with buffer A2 (100 mM NaH2PO4/Na2HPO4 pH 6.5). With the second column switching valve containing the HiPrep™ column set to be bypassed 260 mL of the harvested cell culture medium containing the recombinant protein was loaded onto the MabSelectSuRe™ column with a sample pump at a speed of 3.5 ml/min, followed by washing with 5 column volumes of wash buffer A1 (30 mM NaCitrate pH 5.5), followed by 5 column volumes of wash buffer A3 (30 mM NaCitrate, 0.5M NaCl, pH 5.5), followed by 2 column volumes of wash buffer A1. Prior to elution with the elution buffer (30 mM Citric acid pH 3.4) the HiPrep™ column mounted on the second column switching valve was set to enter the flow-path. After eluting with 10 mL elution buffer the MabSelectSuRe™ column was switched out of the flow-path and the purified protein was eluted from the HiPrep™ column with buffer A2. Protein elution was monitored by UV absorbance at 280 nm and collection triggered once the absorbance exceeded 100 mAU. The collected fractions were pooled and a 104, sample was subjected to SDS-PAGE utilizing Mini-PRO-TEAN® TGX Stain-Free™ precast gels in the presence or absence of the reducing agent β-mercaptoethanol and the isolated recombinant proteins were visualized utilizing a ChemiDoc™ imaging system (BioRad).

In FIG. 8 it can be seen that the fusion protein containing amino acids derived from CCN3/Nov (domain III/TSP-1 homology domain) as disclosed in SEQ ID No 73, analogous to the fusion protein containing amino acids derived from the homologous CCN5 (domain III/TSP-1 homology domain), as disclosed in SEQ ID No. 27, has similar or better resistance to proteolysis than the fusion protein containing amino acids derived from CCN5, as described in Example 11 and shown in FIG. 7.

Example 13

A fusion protein comprising amino acids 194-246 of CCN5 where the amino acid in position 195 (proline) is substituted with alanine (SEQ ID No. 7), fused C-terminal of a peptide linker (SEQ ID No. 39) and an Fc-fragment of IgG, IgG4 subclass of SEQ ID NO. 15 (S228P, F234A, L235A, K447-, Eu-numbering) resulting in a protein sequence corresponding to SEQ ID No. 41, was appended by an N-terminal signal sequence for secretion originating from albumin of SEQ ID No. 32 resulting in a fusion protein corresponding to SEQ ID No. 77. A DNA sequence of encoding the fusion protein of SEQ ID No. 77 was codon optimized for protein expression in hamster cells (by the algorithm of the commercial supplier), and a KOZAK sequence for translation was appended at the 5' end and a STOP-codon was introduced at the 3' end resulting in a DNA sequence of SEQ ID No. 78. The DNA sequence was further appended at both ends by Gateway attB sites resulting in a DNA sequence of SEQ ID No. 79.

The sequence of SEQ ID No. 79 was synthesized and sequence verified by a commercial supplier. The synthesized sequence was recombined with pDonrZeo by BP Gateway recombinase cloning to generate an Entry vector. Following transfection of competent *E. coli* mutated to allow for efficient propagation of plasmids (One Shot Top 10™ cells), the entry vector was isolated with standard plasmid isolation techniques through use of a QIAprep™ Spin Miniprep kit from Qiagen™. Following plasmid isolation, the entry vector was verified by restriction enzyme digestion followed by DNA gel electrophoresis according to standard techniques well known to the skilled person.

The Entry vector containing sequence SEQ ID No. 78 was further recombined with a destination vector using LR gateway recombinase. The destination vector used was pUCOE-DHFR-DEST, as described by Kaasbøll et al., 2018, J. Biol. Chem, 293:46, pp. 17953-17970.

Following transfection of competent *E. coli*, mutated to allow for efficient propagation of plasmids (One Shot Top 10™ cells), the expression vector was isolated with standard plasmid isolation techniques using a QIAGEN™ Plasmid Plus Maxi Kit. The resulting expression vector was verified by standard restriction enzyme digestion and DNA gel electrophoresis according to standard techniques well known to the skilled person. The resulting expression vector was then transferred into suspension culture adapted DG44 CHO cells by means of electroporation utilizing the Neon transfection system (ThermoFisherScientific).

The cells were maintained in vented Erlenmeyer flasks in cell culture incubators kept at 37° C. with 8% CO2 on a shaker platform (as described in Kaasbøll et al., supra). The transfected cells were kept overnight in CD DG44 cell medium (Gibco, Cat. #12610-010) before being transferred to HyClone™ ActiPro™ medium (without hypoxanthine and thymidine, GE Healthcare) and sub-cultivated until viability approached 80%, at which point the medium was supplemented with 0.1 µM methotrexate. After the addition of 0.1 µM methotrexate the cells were sub-cultured until the viability again approached 80%, at which point the medium was supplemented with 1 µM methotrexate. The cells were again sub-cultured until the viability exceeded 98% and the doubling-time decreased to less than 26 hours, at which point the cell pool was considered stably transfected. Once the stable cell pool was established the cell culture volume was expanded to allow for the seeding of stably transfected cells for production at a density of 1*10^6 cells/mL. The cell cultures were supplemented with 4/0.4% v/v HyClone™ Cell Boost™ 7a/7b every day from day 3 after sub-cultivation. After 10 days the cells were sedimented by centrifugation at 4750×g for 20 minutes at 4° C. and the supernatant cell culture medium harvested. 0.1M PMSF in 100% isopropanol was added to a concentration of 0.1 mM. 1M NaCitrate pH 5.5 was added to a final concentration of 30 mM prior to chromatographic purification.

The protein was purified by tandem-chromatography composed of a capture step with a 5 mL HiTrap™ MabSelectSuRe™ column (GE Healthcare) immediately followed by desalting with a 53 mL HiPrep™ 26/10 DeSalting column (GE Healthcare), as described in example 15. The purified protein preparation (which showed no signs of proteolytic processing) was subsequently tested for its ability to inhibit prosurvival signaling (Serine-473 phosphorylation of AKT) in A549 human lung cancer cells as described in Example 2. As can be seen from FIG. 9, the purified protein corresponding to SEQ ID No. 41 produced from the stably transfected pool of CHO suspension cells surprisingly showed no sign of a capacity to inhibit the phosphorylation of AKT (Serine 473).

Example 14

A fusion protein was generated comprising amino acid amino acid 206-249 of CCN3 (SEQ ID. No. 44), where amino acid in position 207 (isoleucine) is substituted with alanine, fused N-terminal of a peptide linker (SEQ ID No. 22) and a chimeric Fc-fragment of IgG subtype IgG2/4 (SEQ ID No. 19) resulting in a protein sequence corresponding to SEQ ID No. 80, was appended by an N-terminal signal sequence for secretion originating from albumin of SEQ ID No. 32 resulting in a fusion protein corresponding to SEQ ID No. 81. A DNA sequence of encoding the fusion protein of SEQ ID No. 81 was codon optimized for protein expression in hamster cells (by the algorithm of the commercial supplier), and a KOZAK sequence for translation was appended at the 5' end and a STOP-codon was introduced at the 3' end resulting in a DNA sequence of SEQ ID No. 82. The DNA sequence was further appended at both ends by Gateway attB sites resulting in a DNA sequence of SEQ ID No. 83.

The sequence of SEQ ID No. 83 was synthesized and sequence verified by a commercial supplier. The synthesized sequence was recombined with pDonrZeo by BP Gateway recombinase cloning to generate an Entry vector. Following transfection of competent *E. coli* mutated to allow for efficient propagation of plasmids (One Shot Top 10™ cells), the entry vector was isolated with standard plasmid isolation techniques through use of a QIAprep™ Spin Miniprep kit from Qiagen™. Following plasmid isolation, the entry vector was verified by restriction enzyme digestion followed by DNA gel electrophoresis according to standard techniques well known to the skilled person.

The Entry vector containing sequence SEQ ID No. 82 was further recombined with a destination vector using LR gateway recombinase. The destination vector used was pUCOE-DHFR-DEST, as described by Kaasbøll et al., 2018, J. Biol. Chem, 293:46, pp. 17953-17970.

Following transfection of competent *E. coli*, mutated to allow for efficient propagation of plasmids (One Shot Top 10™ cells), the expression vector was isolated with standard plasmid isolation techniques using a QIAGEN™ Plasmid Plus Maxi Kit. The resulting expression vector was verified by standard restriction enzyme digestion and DNA gel electrophoresis according to standard techniques well known to the skilled person. The resulting expression vector was then transferred into ExpiCHO suspension culture adapted CHO cells according to the "Creation and Scale up of a Stable Cell Line Using ExpiCHO™ Products" protocol supplied by the manufacturer of the ExpiCHO™ Stable Production Medium (Gibco Cat. #: A3711001). The cells were maintained in vented Erlenmeyer flasks in cell culture incubators kept at 37° C. with 8% $CO_2$ on a shaker platform (as described in Kaasbøll et al., supra). The transfected cells were kept overnight in ExpiCHO™ Expression medium before being transferred to ExpiCHO™ expression medium supplemented with 0.1 μM methotrexate. The cells were then sub-cultured until the viability again approached 80%, at which point the medium was supplemented with 1 μM methotrexate. The cells were again sub-cultured until the viability exceeded 95% and the doubling-time decreased to less than 20 hours, at which point the cell pool was considered stably transfected. Once the stable cell pool was established the cell culture volume was expanded to allow for the seeding of stably transfected cells for production at a density of $1*10^6$ cells/mL. After 5 days the cells were sedimented by centrifugation at 4750×g for 20 minutes at 4° C. and the supernatant cell culture medium harvested. 0.1M PMSF in 100% isopropanol was added to a concentration of 0.1 mM. 1M NaCitrate pH 5.5 was added to a final concentration of 30 mM and 2M L-Arginine pH 4.0 was added to a final concentration of 100 mM prior to chromatographic purification.

The protein was purified by tandem-chromatography composed of a capture step with a 5 mL HiTrap™ MabSelect PrismA™ column (GE Healthcare) immediately followed by desalting with a 53 mL HiPrep™ 26/10 DeSalting column (GE Healthcare), utilizing the same protocol as described in example 12 except for the addition of 100 mM L-Arginine to buffer A1, A2, A3 and B1. The purified protein preparation (which showed no signs of proteolytic processing) was subsequently tested for its ability to inhibit pro-survival signaling (Serine-473 phosphorylation of AKT) in A549 human lung cancer cells as described in Example 2. As can be seen from FIG. 10, the purified protein corresponding to SEQ ID No. 80 produced from the stably transfected pool of CHO suspension cells surprisingly showed no sign of a capacity to inhibit the phosphorylation of AKT (Serine 473) demonstrating that neither of the intact dimeric Fc-fusion protein preparations containing amino acids derived from CCN5 (SEQ ID No. 41, Example 13, FIG. 9) or amino acids derived from CCN3 (SEQ ID No. 80) are biologically active.

Example 15

The expression plasmid described in example 14 containing SEQ ID No. 82, encoding for a fusion protein comprising amino acid amino acid 206-249 of CCN3 (SEQ ID. No. 44), where amino acid in position 207 (isoleucine) is substituted with alanine, fused N-terminal of a peptide linker (SEQ ID No. 22) and a chimeric Fc-fragment of IgG subtype IgG2/4 (SEQ ID No. 19) resulting in a protein sequence corresponding to SEQ ID No. 80, that is further appended by an N-terminal signal sequence for secretion originating from albumin of SEQ ID No. 32 and corresponding to SEQ ID No. 81, was expressed by transient transfection of ExpiCHO™ cells as described in example 9. The cells were sedimented, as described in example 14, 6 days after transfection and the media supplemented as described in example 14. The protein was purified by tandem-chromatography composed of a capture step with a 5 mL HiTrap™ MabSelect PrismA™ column (GE Healthcare) immediately followed by desalting with a 53 mL HiPrep™ 26/10 DeSalting column (GE Healthcare), as described in example 14.

The purified protein preparation (which was partially proteolytically processed) was subsequently tested for its ability to inhibit prosurvival signaling (Serine-473 phosphorylation of AKT) in A549 human lung cancer cells as described in Example 2. As can be seen from FIG. 11, the purified protein corresponding to SEQ ID No. 80 produced from the transiently transfected ExpiCHO™ cells displayed a concentration dependent capacity to inhibit the phosphorylation of AKT (Serine 473) demonstrating that the expression system used to produce the fusion protein corresponding to SEQ ID No. 80, and consequently the degree of proteolytic processing observed, greatly influences the activity, or lack thereof, of the resulting protein preparation.

Example 16

A fusion protein comprising amino acid amino acid 206-249 of CCN3 (SEQ ID. No. 44), where amino acid in position 207 (isoleucine) is substituted with alanine, fused N-terminal of a peptide linker (SEQ ID No. 21) and an Fc fragment with monomer-inducing and half-life extending mutations (SEQ ID No. 55), resulting in a protein sequence corresponding to SEQ ID No. 84, was appended by an N-terminal signal sequence for secretion originating from albumin of SEQ ID No. 32 resulting in a fusion protein corresponding to SEQ ID No. 85. A DNA sequence encoding the fusion protein of SEQ ID No. 85 was codon optimized for protein expression in hamster cells (by the algorithm of the commercial supplier), and a KOZAK sequence for translation was appended at the 5' end and a STOP-codon was introduced at the 3' end resulting in a DNA sequence of SEQ ID No. 86. The DNA sequence was further appended at both ends by Gateway attB sites resulting in a DNA sequence of SEQ ID No. 86. DNA sequences were synthesized and verified by a commercial supplier before being sub-cloned to generate plasmids as described in example 9 and was expressed by transient transfection of ExpiCHO™ cells as described in example 9. The cells were sedimented, as described in example 14, 5 days after transfection and the media supplemented as described in example 14. The protein was purified by tandem-chromatography composed of a capture step with a 5 mL HiTrap™ Mab Select PrismA™ column (GE Healthcare) immediately followed by desalting with a 53 mL HiPrep™ 26/10 DeSalting column (GE Healthcare), as described in example 14.

The purified protein preparation, which displayed the expected monomeric form, was subsequently tested for its ability to inhibit prosurvival signaling (Serine-473 phosphorylation of AKT) in A549 human lung cancer cells as described in Example 2. As can be seen from FIG. 12, the purified protein corresponding to SEQ ID No. 84 displayed a concentration dependent capacity to inhibit the phosphorylation of AKT (Serine 473) demonstrating that another monomeric fusion protein comprising amino acids from the domain III/TSP-1 homology domain of a CCN protein had the capacity to inhibit phosphorylation of AKT (Serine-473) in A549 human lung cancer cells.

Example 17

A fusion protein comprising amino acid amino acid 206-249 of CCN3 (SEQ ID. No. 44), where amino acid in position 207 (isoleucine) is substituted with alanine, fused N-terminal of a peptide linker (SEQ ID No. 21) and an Fc fragment with monomer-inducing and stability inducing mutations (SEQ ID No. 54), resulting in a protein sequence corresponding to SEQ ID No. 88, was appended by an N-terminal signal sequence for secretion originating from albumin of SEQ ID No. 32 resulting in a fusion protein corresponding to SEQ ID No. 89. A DNA sequence of encoding the fusion protein of SEQ ID No. 89 was codon optimized for protein expression in hamster cells (by the algorithm of the commercial supplier), and a KOZAK sequence for translation was appended at the 5' end and a STOP-codon was introduced at the 3' end resulting in a DNA sequence of SEQ ID No. 90. The DNA sequence was further appended at both ends by Gateway attB sites resulting in a DNA sequence of SEQ ID No. 91. DNA sequences were synthesized and verified by a commercial supplier before being sub-cloned to generate plasmids as described in example 9 and was expressed by transient transfection of ExpiCHO™ cells as described in example 9. The cells were sedimented, as described in example 14, 6 days after transfection and the media supplemented as described in example 14. The protein was purified by tandem-chromatography composed of a capture step with a 5 mL HiTrap™ Mab Select PrismA™ column (GE Healthcare) immediately followed by desalting with a 53 mL HiPrep™ 26/10 DeSalting column (GE Healthcare), as described in example 14.

The purified protein preparation, which predominantly displayed the expected monomeric form, was subsequently tested for its ability to inhibit prosurvival signaling (Serine-473 phosphorylation of AKT) in A549 human lung cancer cells as described in Example 2. As can be seen from FIG. 13, the purified protein corresponding to SEQ ID No. 88 displayed a concentration dependent capacity to inhibit the phosphorylation of AKT (Serine 473) demonstrating that another monomeric fusion protein comprising amino acids from the domain III/TSP-1 homology domain of a CCN protein had the capacity to inhibit phosphorylation of AKT (Serine-473) in A549 human lung cancer cells.

Example 18

A fusion protein comprising amino acid amino acid 206-249 of CCN3 (SEQ ID. No. 44), where amino acid in position 207 (isoleucine) is substituted with alanine, fused N-terminal of a peptide linker (SEQ ID No. 93) and a multifunctional tag comprising 6×His tag, HaloTag and Sumo* elements (SEQ ID No. 92), resulting in a protein sequence corresponding to SEQ ID No. 94, was appended by an N-terminal signal sequence for secretion originating from albumin of SEQ ID No. 32 resulting in a fusion protein corresponding to SEQ ID No. 114. A DNA sequence of encoding the fusion protein of SEQ ID No. 114 was codon optimized for protein expression in hamster cells (by the algorithm of the commercial supplier), and a KOZAK sequence for translation was appended at the 5' end and a STOP-codon was introduced at the 3' end resulting in a DNA sequence of SEQ ID No. 95. The DNA sequence was further appended at both ends by Gateway attB sites resulting in a DNA sequence of SEQ ID No. 96. DNA sequences were synthesized and verified by a commercial supplier before being sub-cloned to generate plasmids as described in example 9 and were expressed by transient transfection of ExpiCHO™ cells as described in example 15. The cells were sedimented, as described in example 14, 5 days after transfection. 0.1M PMSF in 100% isopropanol was added to a concentration of 0.1 mM, 1M NaCitrate pH 5.5 was added to a final concentration of 30 mM and 2M L-Arginine pH 4.0 was added to a final concentration of 0.1M and imidazole was added to a final concentration of 5 mM prior to chromatographic purification.

The protein was purified by tandem-chromatography composed of a capture step with a 5 mL HiTrap™ HisTrap™ excel column (GE Healthcare) immediately followed by desalting with a 53 mL HiPrep™ 26/10 DeSalting column (GE Healthcare). The columns were mounted on an FPLC chromatography system (BioRad NGC Discover™ 10 Pro system) fitted with a 5 mm UV flow cell. The HisTrap™ column was mounted on the first column switching valve and equilibrated with A1 buffer composed of 5 mM Imidazole, 50 mM NaCl, 100 mM L-Arginine while the HiPrep™ column was mounted on the second column switching valve and equilibrated with buffer A2 (100 mM NaH2PO4/Na2HPO4, 100 mM L-Arginine pH 6.5). With the second column switching valve containing the HiPrep™ column set to be bypassed 250 mL of the harvested cell culture medium containing the recombinant protein was loaded onto the HisTrap™ column with a sample pump at a speed of 3.5 ml/min, followed by washing with 5 column volumes of wash buffer A1, followed by 5 column volumes of wash buffer A3 (5 mM Imidazole, 0.5M NaCl, 100 mM L-Arginine), followed by 2 column volumes of wash buffer A1. Prior to elution with the elution buffer (250 mM Imidazole, 50 mM NaCl, 100 mM L-Arginine) the HiPrep™ column mounted on the second column switching valve was set to enter the flow-path. After eluting with 10 mL elution buffer the HisTrap™ column was switched out of the flow-path and the purified protein was eluted from the HiPrep™ column with buffer A2. Protein elution was monitored by UV absorbance at 280 nm and collection triggered once the absorbance exceeded 60 mAU.

The purified protein preparation, which displayed the expected monomeric form, was subsequently tested for its ability to inhibit prosurvival signaling (Serine-473 phosphorylation of AKT) in A549 human lung cancer cells as described in Example 2. As can be seen from FIG. 12, the purified protein corresponding to SEQ ID No. 94 showed a concentration dependent capacity to inhibit the phosphorylation of AKT (Serine 473) demonstrating that another monomeric fusion protein comprising amino acids from the domain III/TSP-1 homology domain of a CCN protein had the capacity to inhibit phosphorylation of AKT (Serine-473) in A549 human lung cancer cells.

Example 19

A fusion protein comprising amino acids 194-237 of CCN5 where the amino acid in position 195 (proline) is substituted with alanine (SEQ ID No. 38), fused N-terminal of a peptide linker (SEQ ID No. 21) and amino acids 25-609 of human serum albumin (SEQ ID No. 52) resulting in SEQ ID No. 97 was appended by an N-terminal signal sequence for secretion originating from albumin of SEQ ID No. 32 resulting in a fusion protein corresponding to SEQ ID No. 98. A DNA sequence of encoding the fusion protein of SEQ ID No. 98 was codon optimized for protein expression in hamster cells (by the algorithm of the commercial supplier), and a KOZAK sequence for translation was appended at the 5' end and a STOP-codon was introduced at the 3' end resulting in a DNA sequence of SEQ ID No. 99. The DNA sequence was further appended at both ends by Gateway attB sites resulting in a DNA sequence of SEQ ID No. 100.

DNA sequences were synthesized and verified by a commercial supplier before being sub-cloned to generate plasmids as described in example 9 and DG44 CHO suspension cells engineered to express a constitutive active form of AKT were used to generate a stable pool of CHO suspension cells expressing the protein of SEQ ID No. 98 as described in Example 13. Once the stable cell pool was established the cell culture volume was expanded to allow for the seeding of stably transfected cells for production at a density of 1*10^6 cells/mL. After 6 days the cells were sedimented by centrifugation at 4750×g for 20 minutes at 4° C. and the supernatant cell culture medium harvested. 0.1M PMSF in 100% isopropanol was added to a concentration of 0.1 mM, 0.5M EDTA was added to a final concentration of 2 mM, 1M NaCitrate pH 5.5 was added to a final concentration of 30 mM and 2M L-Arginine pH 4.0 was added to a final concentration of 0.1M prior to chromatographic purification.

The protein was purified by tandem-chromatography composed of a capture step with a Tricorn column (GE Healthcare) packed with 3 mL of CaptureSelect™ Human Albumin Affinity Matrix (ThermoFisherScientific) immediately followed by desalting with a 53 mL HiPrep™ 26/10 DeSalting column (GE Healthcare). The columns were mounted on an FPLC chromatography system (BioRad NGC Discover™ 10 Pro system) fitted with a 5 mm UV flow cell. The CaptureSelect™-containing column was mounted on the first column switching valve and equilibrated with A1 buffer composed of 100 mM NaH2PO4/Na2HPO4, 100 mM L-Arginine pH 6.5 while the HiPrep™ column was mounted on the second column switching valve and equilibrated with buffer A1 (100 mM NaH2PO4/Na2HPO4, 100 mM L-Arginine pH 6.5). With the second column switching valve containing the HiPrep™ column set to be bypassed 500 mL of the harvested cell culture medium containing the recombinant protein was loaded onto the CaptureSelect™-containing column with a sample pump at a speed of 2.0 ml/min, followed by washing with 5 column volumes of wash buffer A1, followed by 5 column volumes of wash buffer A2 (100 mM NaH2PO4/Na2HPO4, 100 mM L-Arginine, 0.25M NaCl, pH 6.5), followed by 5 column volumes of wash buffer A1. Prior to elution with the elution buffer (30 mM Citric Acid, pH 3.5+0.5M L-arginine) the HiPrep™ column mounted on the second column switching valve was set to enter the flow-path. After eluting with 10 mL elution buffer the CaptureSelect™-containing column was switched out of the flow-path and the purified protein was eluted from the HiPrep™ column with buffer A1. Protein elution was monitored by UV absorbance at 280 nm and collection triggered once the absorbance exceeded 100 mAU.

The purified protein preparation, which displayed the expected monomeric form, was subsequently tested for its ability to inhibit prosurvival signaling (Serine-473 phosphorylation of AKT) in A549 human lung cancer cells as described in Example 2. As can be seen from FIG. 14, the purified protein corresponding to SEQ ID No. 97 displayed a concentration dependent capacity to inhibit the phosphorylation of AKT (Serine 473) demonstrating that another monomeric fusion protein comprising amino acids from the domain III/TSP-1 homology domain of a CCN protein had the capacity to inhibit phosphorylation of AKT (Serine-473) in A549 human lung cancer cells.

Example 20

A fusion protein of human serum albumin (amino acids 25-606, SEQ ID No. 101) was C-terminally fused to a peptide linker (SEQ ID NO. 22) connecting to amino acids 194-246 of human CCN5 where the amino acid in position 195 (proline) is substituted with alanine (SEQ ID No. 7), resulting in SEQ ID No. 103. The fusion protein corresponding to SEQ ID No. 102 was appended by an N-terminal signal sequence for secretion originating from albumin of SEQ ID No. 32 resulting in a fusion protein corresponding to SEQ ID No. 103. A DNA sequence of encoding the fusion protein of SEQ ID No. 103 was codon optimized for protein expression in hamster cells (by the algorithm of the commercial supplier), and a KOZAK sequence for translation was appended at the 5' end and a STOP-codon was introduced at the 3' end resulting in a DNA sequence of SEQ ID No. 104. The DNA sequence was further appended at both ends by Gateway attB sites resulting in a DNA sequence of SEQ ID No. 105.

DNA sequences were synthesized and verified by a commercial supplier before being sub-cloned to generate plasmids as described in example 9 and DG44 CHO suspension cells engineered to express a constitutive active form of AKT were used to generate a stable pool of CHO suspension cells expressing the protein of SEQ ID No. 104 as described in Example 13. Once the stable cell pool was established the cell culture volume was expanded to allow for the seeding of stably transfected cells for production at a density of 1*10^6 cells/mL. After 6 days the cells were sedimented by centrifugation at 4750×g for 20 minutes at 4° C. and the supernatant cell culture medium harvested. 0.1M PMSF in 100% isopropanol was added to a concentration of 0.1 mM, 0.5M EDTA was added to a final concentration of 2 mM, 1M NaCitrate pH 5.5 was added to a final concentration of 30 mM and 2M L-Arginine pH 4.0 was added to a final concentration of 0.1M prior to chromatographic purification.

The protein was purified by tandem-chromatography composed of a capture step with a Tricorn column (GE Healthcare) packed with 3 mL of CaptureSelect™ Human Albumin Affinity Matrix (ThermoFisherScientific) immediately followed by desalting with a 53 mL HiPrep™ 26/10 DeSalting column (GE Healthcare) as described in Example 19 with the exception of the sample loading flow being 0.37 mL/min instead of 2.0 mL/min.

The purified protein preparation, which displayed the expected monomeric form, was subsequently tested for its ability to inhibit prosurvival signaling (Serine-473 phosphorylation of AKT) in A549 human lung cancer cells as described in Example 2. As can be seen from FIG. 14, the purified protein corresponding to SEQ ID No. 102 displayed a concentration dependent capacity to inhibit the phosphorylation of AKT (Serine 473) demonstrating that another monomeric fusion protein comprising amino acids from the domain III/TSP-1 homology domain of a CCN protein had the capacity to inhibit phosphorylation of AKT (Serine-473) in A549 human lung cancer cells.

Example 21

A fusion protein comprising amino acids 206-249 of CCN3 where the amino acid in position 207 (isoleucine) is substituted with alanine (SEQ ID No. 44), fused N-terminal of a peptide linker (SEQ ID No. 21) and amino acids 25-609 of human serum albumin (SEQ ID No. 52) resulting in SEQ ID No. 106 was appended by an N-terminal signal sequence for secretion originating from albumin of SEQ ID No. 32 resulting in a fusion protein corresponding to SEQ ID No. 107. A DNA sequence of encoding the fusion protein of SEQ ID No. 107 was codon optimized for protein expression in hamster cells (by the algorithm of the commercial supplier), and a KOZAK sequence for translation was appended at the 5' end and a STOP-codon was introduced at the 3' end resulting in a DNA sequence of SEQ ID No. 108. The DNA sequence was further appended at both ends by Gateway attB sites resulting in a DNA sequence of SEQ ID No. 109.

DNA sequences were synthesized and verified by a commercial supplier before being sub-cloned to generate plasmids as described in example 9 and were expressed by transient transfection of ExpiCHO™ cells as described in example 9. The cells were sedimented, as described in example 14, 6 days after transfection and the media supplemented as described in example 19. The protein was purified by tandem-chromatography composed of a capture step with a Tricorn column (GE Healthcare) packed with 10 mL of CaptureSelect™ Human Albumin Affinity Matrix (ThermoFisherScientific) immediately followed by desalting with a 53 mL HiPrep™ 26/10 DeSalting column (GE Healthcare). The columns were mounted on an FPLC chromatography system (BioRad NGC Discover™ 10 Pro system) fitted with a 5 mm UV flow cell. The CaptureSelect™-containing column was mounted on the first column switching valve and equilibrated with A1 buffer composed of 100 mM NaH2PO4/Na2HPO4, 100 mM L-Arginine pH 6.5 while the HiPrep™ column was mounted on the second column switching valve and equilibrated with buffer A1 (100 mM NaH2PO4/Na2HPO4, 100 mM L-Arginine pH 6.5). With the second column switching valve containing the HiPrep™ column set to be bypassed 500 mL of the harvested cell culture medium containing the recombinant protein was loaded onto the CaptureSelect™-containing column with a sample pump at a speed of 1.0 ml/min, followed by washing with 3 column volumes of wash buffer A1, followed by 2 column volumes of wash buffer A2 (100 mM NaH2PO4/Na2HPO4, 100 mM L-Arginine, 0.25M NaCl, pH 6.5), followed by 3 column volumes of wash buffer A1. Prior to elution with the elution buffer (30 mM Citric Acid, pH 3.5+0.1M L-arginine) the HiPrep™ column mounted on the second column switching valve was set to enter the flow-path. After eluting with 15 mL elution buffer the CaptureSelect™-containing column was switched out of the flow-path and the purified protein was eluted from the HiPrep™ column with buffer A1. Protein elution was monitored by UV absorbance at 280 nm and collection triggered once the absorbance exceeded 100 mAU.

The purified protein preparation, which contained the expected monomeric form, was subsequently tested for its ability to inhibit prosurvival signaling (Serine-473 phosphorylation of AKT) in A549 human lung cancer cells as described in Example 2. As can be seen from FIG. 12, the purified protein corresponding to SEQ ID No. 106 displayed a concentration dependent capacity to inhibit the phosphorylation of AKT (Serine 473) demonstrating that another monomeric fusion protein comprising amino acids from the domain III/TSP-1 homology domain of a CCN protein had the capacity to inhibit phosphorylation of AKT (Serine-473) in A549 human lung cancer cells.

Example 22

A fusion protein comprising amino acids 206-249 of CCN3 where the amino acid in position 207 (isoleucine) is substituted with alanine (SEQ ID No. 44), fused N-terminal of a peptide linker (SEQ ID No. 22) and amino acids 25-609 of human serum albumin (SEQ ID No. 52) resulting in SEQ ID No. 110 was appended by an N-terminal signal sequence for secretion originating from albumin of SEQ ID No. 32 resulting in a fusion protein corresponding to SEQ ID No. 111. A DNA sequence of encoding the fusion protein of SEQ ID No. 111 was codon optimized for protein expression in hamster cells (by the algorithm of the commercial supplier), and a KOZAK sequence for translation was appended at the 5' end and a STOP-codon was introduced at the 3' end resulting in a DNA sequence of SEQ ID No. 112. The DNA sequence was further appended at both ends by Gateway attB sites resulting in a DNA sequence of SEQ ID No. 113.

DNA sequences were synthesized and verified by a commercial supplier before being sub-cloned to generate plasmids as described in example 9 and was expressed by transient transfection of ExpiCHO™ cells as described in example 9. The cells were sedimented, as described in example 14, 6 days after transfection and the media supplemented as described in example 19. The protein was purified by tandem-chromatography composed of a capture step with a Tricorn column (GE Healthcare) packed with 10 mL of CaptureSelect™ Human Albumin Affinity Matrix (ThermoFisherScientific) immediately followed by desalting with a 53 mL HiPrep™ 26/10 DeSalting column (GE Healthcare). The columns were mounted on an FPLC chromatography system (BioRad NGC Discover™ 10 Pro system) fitted with a 5 mm UV flow cell. The CaptureSelect™-containing column was mounted on the first column switching valve and equilibrated with A1 buffer composed of 100 mM NaH2PO4/Na2HPO4, 100 mM L-Arginine pH 6.5 while the HiPrep™ column was mounted on the second column switching valve and equilibrated with buffer A1 (100 mM NaH2PO4/Na2HPO4, 100 mM L-Arginine pH 6.5). With the second column switching valve containing the HiPrep™ column set to be bypassed 300 mL of the harvested cell culture medium containing the recombinant protein was loaded onto the CaptureSelect™-containing column with a sample pump at a speed of 1.0 ml/min, followed by washing with 3 column volumes of wash buffer A1, followed by 2 column volumes of wash buffer A2 (100 mM NaH2PO4/Na2HPO4, 100 mM L-Arginine, 0.25M NaCl, pH 6.5), followed by 3 column volumes of wash buffer A1. Prior to elution with the elution buffer (30 mM Citric Acid, pH 3.5+0.5M L-arginine) the HiPrep™ column mounted on the second column switching valve was set to enter the flow-path. After eluting with 15 mL elution buffer the CaptureSelect™-containing column was switched out of the flow-path and the purified protein was eluted from the HiPrep™ column with buffer A1. Protein elution was monitored by UV absorbance at 280 nm and collection triggered once the absorbance exceeded 100 mAU.

The purified protein preparation, which contained the expected monomeric form, was subsequently tested for its ability to inhibit prosurvival signaling (Serine-473 phosphorylation of AKT) in A549 human lung cancer cells as described in Example 2. As can be seen from FIG. 15, the purified protein corresponding to SEQ ID No. 110 displayed a concentration dependent capacity to inhibit the phosphorylation of AKT (Serine 473) demonstrating that another monomeric fusion protein comprising amino acids from the domain III/TSP-1 homology domain of a CCN protein had the capacity to inhibit phosphorylation of AKT (Serine-473) in A549 human lung cancer cells.

Example 23

The expression plasmid described in example 21 containing SEQ ID No. 108, encoding for a fusion protein comprising amino acids 206-249 of CCN3 where the amino acid in position 207 (isoleucine) is substituted with alanine (SEQ ID No. 44), fused N-terminal of a peptide linker (SEQ ID No. 21) and amino acids 25-609 of human serum albumin (SEQ ID No. 52) that is further appended by an N-terminal signal sequence for secretion originating from albumin of SEQ ID No. 32 and corresponding to SEQ ID No. 107, was used to generate a pool of stably transfected ExpiCHO™ cells as described in example 14. To produce a batch of conditioned medium containing the secreted protein corresponding to SEQ ID NO. 106 the pool of stably transfected cells was expanded to allow for seeding of a volume of 250 mL of the stably transfected cells at a density of 1*10^6 cells/mL. The cell cultures were supplemented with 5% v/v 2× EfficientFeed™ C+ (Gibco™) every other day starting from day 2 after sub-cultivation, and supplemented with 3% glucose (10% w/v) at day 2 after sub-cultivation and 5% glucose (10% w/v) at day 6 after sub-cultivation. After 9 days the cells were sedimented by centrifugation at 4750×g for 20 minutes at 4° C. and the supernatant cell culture medium harvested. 0.1M PMSF in 100% isopropanol was added to a concentration of 0.1 mM. 1M NaCitrate pH 5.5 was added to a final concentration of 30 mM and 2M L-Arginine pH 4.0 was added to a final concentration of 100 mM prior to chromatographic purification.

The protein was purified by 2D-chromatography composed of a capture step with a Tricorn column (GE Healthcare) packed with 10 mL of CaptureSelect™ Human Albumin Affinity Matrix (ThermoFisherScientific) immediately followed by size exclusion chromatography with two serially connected Superdex 200 Increase 10/300 GL (GE Healthcare) columns. The columns were mounted on an FPLC chromatography system (BioRad NGC Discover™ 10 Pro system) fitted with a 5 mm UV flow cell and an outlet valve connected to a 5 mL sample loop. The CaptureSelect™-containing column was mounted on the first column switching valve and equilibrated with A1 buffer composed of 100 mM NaH2PO4/Na2HPO4, 100 mM L-Arginine pH 6.5 while the Superdex 200 Increase columns were mounted on the second column switching valve and equilibrated with buffer A1 (100 mM NaH2PO4/Na2HPO4, 100 mM L-Arginine pH 6.5). With the second column switching valve containing the Superdex 200 Increase columns set to be bypassed 120 mL of the harvested cell culture medium containing the recombinant protein was loaded onto the CaptureSelect™-containing column with a sample pump at a speed of 3.9 ml/min. After loading the harvested cell culture medium containing the recombinant protein onto the CaptureSelect™-containing column it was washed with 3 column volumes of buffer A1, followed by 2 column volumes of buffer A2 (100 mM NaH2PO4/Na2HPO4, 100 mM L-Arginine, 0.25M NaCl, pH 6.5), followed by 3 column volumes of buffer A1. The CaptureSelect™-containing column was eluted with 15 mL buffer B1 (30 mM citric acid, 0.5M L-Arginine, pH 3.5) during which the system was set to collect eluate with an absorbance exceeding 1200 mAU into the sample loop. Following elution of the CaptureSelect™-containing column, the CaptureSelect™-containing column connected to the first column switching valve was switched out of the flow path and the second column switching valve was set to switch the Superdex 200 Increase containing columns into the flow-path. The eluate from the CaptureSelect™-containing column containing the eluted protein was then loaded onto the Superdex 200 Increase containing columns with buffer A1 at a speed of 0.5 mL/min. Protein elution was monitored by UV absorbance at 280 nm and collection triggered once the absorbance exceeded 200 mAU. The purified protein preparation, which contained the expected monomeric form, was subsequently tested for its ability to inhibit TGFβ-induced and active-CCN2 induced activities of normal human lung fibroblasts (NHLF) (Lonza Bioscience, Catalog #: CC-2512). The NHLFs were subcultured in complete growth medium (Lonza Bioscience bullet kit (Cat #: CC-3132) with all additives (2% fetal bovine serum, insulin, hFGF-B, gentamicin/amphotericin-B)) to maintain a density of maximum 80% confluency according to the commercial supplier's (Lonza Bioscience) instructions. Active-CCN2 was composed of domains 3-4 of CCN2 and produced and purified as described by Kaasbøll et al., 2018, supra.

To test the effect of the protein corresponding to SEQ ID No. 106 on the active-CCN2 and TGFβ-induced cell migration of NHLFs (transwell assay/modified Boyden chamber assay), the cells were first detached with Trypsin/EDTA, neutralized with Trypsin neutralization reagents (Lonza Bioscience, Cat. #CC-5034), and resuspended in basal growth media (Fibroblast basal media (LonzaBioscience Cat. #: CC-3131, without other additives than gensumycin (50 μg/mL))) before seeding 30 000 cells in a volume of 100 μL per well on the upper side of transwell inserts with a 5 μm pore-size (24-well plate, Corning® Transwell®, Cat. #CLS3402-48EA from SigmaAldrich (Merck KGaA)). The lower chamber of the wells contained the test substances or vehicle control dissolved in 500 μL of the basal growth media without other additives than gensumycin. After 20 hours incubation the inserts were removed from the wells, washed twice by dipping in phosphate buffered saline (PBS, Lonza Bioscience, Cat. #: 17-512F) prior to fixation in 4% formaldehyde (Solveco, Swe., Cat. #: 621092) for 15 minutes at 37° C. The cells were permeabilized by treatment with 0.1% Triton X-100 in PBS for 10 minutes prior to washing twice with PBS. The non-migrated cells on the upper side of the inserts were removed by scraping with a cotton swap before the membrane was allowed to dry. The nuclei of the migrated cells on the underside of the insert were stained with Hoechst 33342 20 mM (1:5000 diluted in PBS, ThermoFisherScientific, Cat. #: 62249) for 15 minutes in the dark, prior to washing twice by dipping in PBS. The membrane was cut out from the transwell insert and the mounted on glass slides with the migrated cells towards the glass, covered with one drop of ProLong™ Gold Antifade (ThermoFisherScientific, Cat. #: P36934), mounted with a glass coverslip, and 5-10 images of each well were captured on a Zeiss Axio Observer Z.1 imaging system. Images were semi-automatically analyzed utilizing the ImageJ software v1.51k, Rasband, W. S., ImageJ, U. S. National Institutes of Health, Bethesda, Maryland., USA, https://imagej.nih.gov/ij/, 1997-2018.). As can be seen in FIG. 16A, the protein corresponding to SEQ ID No. 106 inhibits the migration induced by both TGFβ and active-CCN2.

To test the effect of the protein corresponding to SEQ ID No. 106 on the active-CCN2 and TGFβ-induced scratch-wound assay NHLFs were detached with Trypsin/EDTA, neutralized with Trypsin neutralization reagents (Lonza Bioscience, Cat. #CC-5034), before seeding 100 000 cells in a volume of 1 mL in tissue culture treated 12-well plates (Corning Costar®, Cat. #3513). The day after seeding, the cells were washed twice with 0.9% NaCl and the complete growth medium changed to basal growth medium. After having been incubated in the basal growth medium for 16-20 hours, a scratch was made in the cell monolayer with a sterile 12.54, pipette-tip (ThermoFisherScientific, Cat #: 94420053), the cells were washed once with PBS, before the cells were incubated in 1 mL of basal growth media together with test substances or vehicle. The cells were incubated for a further 24 hours before being washed three times in PBS before being fixed for 15 min at 37° C. in 4% formaldehyde. After fixation the cells were again washed for 3×3 minutes in PBS with gentle shaking, permeabilized with 0.1% Triton X-100 in PBS for 10 minutes with gentle shaking. The nuclei of the cells were stained by with Hoechst 33342 20 mM (1:5000 diluted in PBS, ThermoFisherScientific, Cat. #: 62249) for 15 minutes in the dark, prior to washing 3×5 minutes in PBS with gentle shaking. 1 drop of ProLong™ Gold Antifade (ThermoFisherScientific, Cat. #: P36934) was applied before mounting and 5 images centered on the remaining gap were captured from of each well with a Zeiss Axio Observer Z.1 imaging system. Images were analyzed by measuring the remaining gap distance after the scratch at 3 fixed intervals along the length of the scratch wound. The mean of all of the measurements from all of the images from each well was calculated and counted as one biological replicate. As can be seen in FIG. 16B, the protein corresponding to SEQ ID No. 106 inhibits the closure of the scratch wound induced by both TGFβ and active-CCN2.

To test the effect of the protein corresponding to SEQ ID No. 106 on TGFβ-induced gene regulation NHLFs were detached with Trypsin/EDTA, neutralized with Trypsin neutralization reagents (Lonza Bioscience, Cat. #CC-5034), before seeding 100 000 cells in a volume of 1 mL in tissue culture treated 12-well plates (Corning Costar®, Cat. #3513). The day after seeding, the cells were washed twice with 0.9% NaCl and the complete growth medium changed to basal growth medium supplemented with 0.1% heat-inactivated fetal bovine serum (Cat. #16000-044 from Gibco™, heat-inactivation performed as described in Example 2). After incubation in the basal growth medium with 0.1% fetal bovine serum for 6 hours the test substances or vehicle control were added to the wells. After 96 hours the wells were washed twice in PBS and RNA extracted utilizing the Qiagen RNeasy RNA extraction kit (Cat. #74106) according to the manufacturer's protocol. RNA concentrations were quantitated with a NanoDrop® ND-1000 spectrophotometer (NanoDrop Technologies, US), diluted with nuclease-free water to a final RNA concentrations of 50 ng/μL before 200 ng RNA from each replicate was utilized to generate cDNA by utilizing the TaqMan™ Reverse Transcription kit (Cat. #N8080234) according to the manufacturer's protocol. Differential gene expression analysis was analyzed from the resulting cDNA samples by means of respective TaqMan™ assays and the TaqMan Fast Advanced Master Mix (ThermoFisherScientific Cat. #4444557). The TaqMan™ real time PCR reactions were run with technical triplicates for each sample using Applied Biosystems StepOnePlus Real Time PCR System according to the manufacturers' protocols. Relative quantities of the different transcripts were calculated from a standard curve before the technical triplicates were averaged to yield a single value from each sample. All gene expression results were related to GAPDH (ThermoFisherScientific, Cat. #Hs02786624_g1) mRNA levels and normalized to be expressed as folds of the mean of the vehicle control-stimulated wells. As can be seen from FIG. 19C-F, the protein corresponding to SEQ ID No. 107 affords partial inhibition of the TGFβ-induced genes; COL1A1 ("collagen type 1 α-1", ThermoFisherScientific, Cat. #Hs00164004_m1), FN1 ("fibronectin 1", ThermoFisherScientific, Cat. #Hs01549976_m1), ACTA2 ("smooth muscle actin α-2", ThermoFisherScientific, Cat. #Hs00426835_g1) and CCN2 (ThermoFisherScientific, Cat. #Hs00170014 ml), commonly regarded to be pro-fibrotic genes.

Overview of the Sequence Numbers Referred to in the Specification and Sequence Listing

| SEQ ID No. | Sequence information |
| --- | --- |
| 1 | Amino acids 194-246 of human WISP2/CCN5 (domain III/TSP-1 homology domain) (long fragment) |
| 2 | Amino acids 206-249 of human NOV/CCN3 (domain III/TSP-1 homology domain) (44 aa fragment) |

-continued

| SEQ ID No. | Sequence information |
|---|---|
| 3 | Amino acids 199-242 of human CTGF/CCN2 (domain III/TSP-1 homology domain) (44 aa fragment) |
| 4 | Amino acids 229-272 of human Cyr61/CCN1 (domain III/TSP-1 homology domain) (44 aa fragment) |
| 5 | Amino acids 216-259 of human WISP1/CCN4 (domain III/TSP-1 homology domain) (44 aa fragment) |
| 6 | Amino acids 209-252 of human WISP3/CCN6 (domain III/TSP-1 homology domain) (44 aa fragment) |
| 7 | Amino acids 194-246 of human WISP2/CCN5, (long fragment) where amino acid in position 195 (proline) is substituted with alanine |
| 8 | Amino acids 209-263 of human WISP3/CCN6 (domain III/TSP-1 homology domain) (long fragment) |
| 9 | Amino acids 206-258 of human NOV/CCN3 (domain III/TSP-1 homology domain) (long fragment) |
| 10 | Amino acids 199-250 of human CTGF/CCN2 (domain III/TSP-1 homology domain) (long fragment) |
| 11 | Amino acids 229-280 of human Cyr61/CCN1 (domain III/TSP-1 homology domain) (long fragment) |
| 12 | Amino acids 216-267 of human WISP1/CCN4 (domain III/TSP-1 homology domain) (long fragment) |
| 13 | Fc-fragment of IgG4 |
| 14 | Fc-fragment of IgG2 |
| 15 | Mutated Fc-fragment of IgG4 (S228P, F234A, L235A, K447-, cf. Eu-numbering) |
| 16 | Aglycosylated (N297G), disulfide bridge stabilized (R292C, V302C) Fc-fragment of IgG1, Eu numbering |
| 17 | Fc-fragment of IgG1, disulfide bridge stabilized (R292C, V302C), aglycosylated (N297G) and with protease stabilizing mutations in lower hinge region (E233P, L234V, L235A, G236-, Eu numbering) |
| 18 | Fc-fragment of IgG4, and with protease stabilizing mutations in lower hinge region (E233P, F234V, L235A, G236-, Eu-numbering) and with the S228P mutation and K447- deletion. |
| 19 | Fc-fragment being a chimera of the hinge region of IgG2 and the constant heavy domains 2 and 3 of IgG4 with a deletion of the carboxyl-terminal K477- (Eu numbering). |
| 20 | Linker (TEGRMD) |
| 21 | Linker (EAAAK) |
| 22 | Linker (EAAAKEAAAKEAAAKEAAAKEAAAKEAAAKEAAAKEAAAK) n = 8 |
| 23 | Linker (TAEAAAKEAAAKEAAAKEAAAKEAAAKEAAAKEAAAKEAAAK) |
| 24 | Linker (EAAAKEAAAKEAAAKEAAAKEAAAKEAAAKEAAAKEAAAKAAA) |
| 25 | Linker (TAEAAAKEAAAKEAAAKEAAAKEAAAKEAAAKEAAAKEAAAKAAA) |
| 26 | Fusion protein of the invention comprising the domain III of CCN5 (SEQ ID No. 37), coupled N-terminally of a linker of SEQ ID No. 21 that is further coupled N-terminal to the IgG2/4 Fc-fragment of SEQ ID NO. 19. |
| 27 | Fusion protein of the invention comprising the domain III of CCN5 (SEQ ID No. 38), wherein proline position 195 is replaced by alanine, coupled N-terminally of a linker of SEQ ID No. 21 that is further coupled N-terminal to the IgG2/4 Fc-fragment of SEQ ID NO. 19. |

| SEQ ID No. | Sequence information |
|---|---|
| 28 | Fusion protein of the invention comprising amino acid 194-246 of CCN5 (SEQ ID. No. 1), fused N-terminal of a peptide linker (SEQ ID No. 20) and an Fc-fragment of IgG subtype IgG4 of SEQ ID NO. 15 (S228P, F234A, L235A, K447-, Eu-numbering) (CCN5(dIII)-Fcv2) |
| 29 | Fusion protein comprising amino acid 194-246 of CCN5 (SEQ ID. No. 1), fused N-terminal of a peptide linker (SEQ ID No. 20) and an Fc-fragment of IgG subtype IgG4 of SEQ ID No. 18 (S228P, E233P, F234V, L235A, G236-, K447-, Eu-numbering) (CCN5(dIII)-Fcv2.1) |
| 30 | Fusion protein comprising amino acid 194-246 of CCN5 (SEQ ID. No. 1), fused N-terminal of a peptide linker (SEQ ID No. 20) and a chimeric Fc-fragment of IgG subtype IgG2/4 subtype (SEQ ID No. 19) (CCN5(dIII)-Fcv2.3). |
| 31 | Fusion protein comprising amino acid 194-246 of CCN5 (SEQ ID. No. 1), fused N-terminal of a peptide linker (SEQ ID No. 25) and a chimeric Fc-fragment of IgG subtype IgG2/4 subtype (SEQ ID No. 19) (CCN5(dIII)-HLn8-Fcv2.3). |
| 32 | Signal peptide from human serum albumin (MKWVTFISLLFLFSSAYS) |
| 33 | Fusion protein of SEQ ID No. 28 wherein the signal peptide from human serum albumin (SEQ ID No. 32) is appended N-terminally of the fusion protein. |
| 34 | DNA sequence encoding fusion protein of sequence No. 33 |
| 35 | DNA sequence encoding fusion protein of sequence No. 33 and further appended at the 5' end by a KOZAK sequence, GCCACC, and at the 3' end by a translation stop codon. |
| 36 | DNA sequence encoding fusion protein of sequence No. 35 and further including gateway AttB recombinase sites at both ends. |
| 37 | Amino acids 194-237 of human WISP2/CCN5 (domain III/TSP-1 homology domain) (44 aa fragment) |
| 38 | Amino acids 194-237 of human WISP2/CCN5 (domain III/TSP-1 homology domain) (44 aa fragment), where amino acid in position 195 (proline) is substituted with alanine |
| 39 | Linker (AEAAAKEAAAKEAAAKEAAAKEAAAKEAAAKEAAAKEAAAKAAA) |
| 40 | Fusion protein comprising amino acid 194-246 of CCN5 (SEQ ID. No. 1), fused C-terminal of a peptide linker (SEQ ID No. 39) and an Fc-fragment of IgG subtype IgG4 of SEQ ID NO. 15 (S228P, F234A, L235A, K447-, Eu-numbering) (Fc-HLn8-CCN5(dIII)). |
| 41 | Fusion protein comprising amino acid 194-246 of CCN5 (SEQ ID. No. 7), where amino acid in position 195 (proline) is substituted with alanine, fused C-terminal of a peptide linker (SEQ ID No. 39) and an Fc-fragment of IgG subtype IgG4 of SEQ ID NO. 15 (S228P, F234A, L235A, K447-, Eu-numbering) (Fc-HLn8-CCN5(dIII)-P195A). |
| 42 | Amino acids 229-272 of human Cyr61/CCN1 (domain III/TSP-1 homology domain) (44 aa fragment), where amino acid in position 230 (isoleucine) is substituted with alanine |
| 43 | Amino acids 199-242 of human CTGF/CCN2 (domain III/TSP-1 homology domain) (44 aa fragment), where amino acid in position 200 (leucine) is substituted with alanine |
| 44 | Amino acids 206-249 of human NOV/CCN3 (domain III/TSP-1 homology domain) (44 aa fragment), where amino acid in position 207 (isoleucine) is substituted with alanine |
| 45 | Amino acids 216-259 of human WISP1/CCN4 (domain III/TSP-1 homology domain) (44 aa fragment), where amino acid in position 217 (isoleucine) is substituted with alanine |
| 46 | Amino acids 209-252 of human WISP3/CCN6 (domain III/TSP-1 homology domain) (44 aa fragment), where amino acid in position 210 (leucine) is substituted with alanine |

| SEQ ID No. | Sequence information |
|---|---|
| 47 | Amino acids 229-280 of human Cyr61/CCN1 (domain III/TSP-1 homology domain) (long fragment), where amino acid in position 230 (isoleucine) is substituted with alanine |
| 48 | Amino acids 199-250 of human CTGF/CCN2 (domain III/TSP-1 homology domain) (long fragment), where amino acid in position 200 (leucine) is substituted with alanine |
| 49 | Amino acids 206-258 of human NOV/CCN3 (domain III/TSP-1 homology domain) (long fragment), where amino acid in position 207 (isoleucine) is substituted with alanine |
| 50 | Amino acids 216-267 of human WISP1/CCN4 (domain III/TSP-1 homology domain) (long fragment), where amino acid in position 217 (isoleucine) is substituted with alanine |
| 51 | Amino acids 209-263 of human WISP3/CCN6 (domain III/TSP-1 homology domain) (long fragment), where amino acid in position 210 (leucine) is substituted with alanine |
| 52 | Amino acids 25-609 of human serum albumin |
| 53 | Amino acids 20-698 of of human serotransferrin |
| 54 | Fc-fragment of IgG1, disulfide bridge stabilized (R292C, V302C), aglycosylated (N297G) and with monomer-generating mutations (C220Q, C226Q, C229Q, T366R, L368H, P395K, K409T, M428L), Eu numbering) |
| 55 | Fc-fragment being a chimera of the hinge region of IgG2 and the constant heavy domains 2 and 3 of IgG4 with a deletion of the carboxyl-terminal K477- and with monomer-generating mutations (C219Q, C220Q, C226Q, C229Q, L351F, T366R, P395K, F405R, Y407E) and half-life extending mutations (M252Y, S254T, T256E) (Eu numbering). |
| 56 | Amino acids 194-250 of human WISP2/CCN5 (domain III/TSP-1 homology domain) |
| 57 | Linker (IEGRMD) |
| 58 | Fusion protein comprising amino acid 194-250 of CCN5 (SEQ ID. No. 56), fused N-terminal of a peptide linker (SEQ ID No. 57) and an Fc-fragment of IgG subtype IgG4 of SEQ ID NO. 15 (S228P, F234A, L235A, K447-, Eu-numbering) |
| 59 | Fusion protein comprising amino acid 194-250 of CCN5 (SEQ ID. No. 56), fused N-terminal of a peptide linker (SEQ ID No. 57) and an Fc-fragment of IgG subtype IgG4 of SEQ ID NO. 15 (S228P, F234A, L235A, K447-, Eu-numbering) that is appended amino-terminally by the signal peptide from human serum albumin (SEQ ID No. 32) |
| 60 | DNA sequence encoding fusion protein of SEQ ID No. 59 codon-optimized for expression in hamster cells and further appended at the 5' end by a KOZAK sequence, GCCACC, and at the 3' end by a translation stop codon. |
| 61 | DNA sequence of SEQ ID no 60 encoding fusion protein of SEQ ID No. 59 and further including gateway AttB recombinase sites at both ends. |
| 62 | Amino acids 194-249 of human WISP2/CCN5 (domain III/TSP-1 homology domain) (long fragment), where amino acid in position 245 (proline) is substituted with leucine. |
| 63 | Linker (GRMD) |
| 64 | Amino acids 194-249 of human WISP2/CCN5 (domain III/TSP-1 homology domain), where amino acid in position 245 (proline) is substituted with leucine (SEQ ID. No. 62), fused N-terminal of a peptide linker (SEQ ID No. 63) and an Fc-fragment of IgG subtype IgG4 of SEQ ID NO. 15 (S228P, F234A, L235A, K447-, Eu-numbering) that is appended amino-terminally by the signal peptide from human serum albumin (SEQ ID No. 32) |
| 65 | Linker (TEGRMD) |

-continued

| SEQ ID No. | Sequence information |
|---|---|
| 66 | Amino acids 194-246 of human WISP2/CCN5 (domain III/TSP-1 homology domain) (SEQ ID No. 1), fused N-terminal of a peptide linker (SEQ ID No. 65) and an Fc-fragment of IgG subtype IgG4 of SEQ ID NO. 15 (S228P, F234A, L235A, K447-, Eu-numbering) that is appended amino-terminally by the signal peptide from human serum albumin (SEQ ID No. 32) |
| 67 | Linker (TAEAAAKA) |
| 68 | Amino acids 194-246 of human WISP2/CCN5 (domain III/TSP-1 homology domain) (SEQ ID No. 1), fused N-terminal of a peptide linker (SEQ ID No. 67) and an Fc-fragment of IgG subtype IgG4 of SEQ ID NO. 15 (S228P, F234A, L235A, K447-, Eu-numbering) that is appended amino-terminally by the signal peptide from human serum albumin (SEQ ID No. 32) |
| 69 | Amino acids 194-246 of human WISP2/CCN5 (domain III/TSP-1 homology domain) (SEQ ID No. 1), fused N-terminal of a peptide linker (SEQ ID No. 65) and a chimeric Fc fragment composed of the hinge region of IgG2 and the constant heavy domains 2 and 3 of IgG4 with a deletion of the carboxyl-terminal K477- (Eu numbering) of SEQ ID NO. 19 that is appended amino-terminally by the signal peptide from human serum albumin (SEQ ID No. 32) |
| 70 | Fusion protein of the SEQ ID No. 27 (comprising the amino acids 194-237 of domain III of CCN5, wherein proline position 195 is replaced by alanine (SEQ ID No. 38), coupled N-terminally of a linker of SEQ ID No. 21 that is further coupled N-terminal to the IgG2/4 Fc-fragment of SEQ ID NO. 19.) that is appended amino-terminally by the signal peptide from human serum albumin (SEQ ID No. 32) |
| 71 | DNA sequence encoding fusion protein of SEQ ID No. 70 codon-optimized for expression in hamster cells and further appended at the 5' end by a KOZAK sequence, GCCACC, and at the 3' end by a translation stop codon. |
| 72 | DNA sequence of SEQ ID no 71 encoding fusion protein of SEQ ID No. 70 and further including gateway AttB recombinase sites at both ends. |
| 73 | Amino acids 206-249 of human NOV/CCN3 (domain III/TSP-1 homology domain), where amino acid in position 207 (isoleucine) is substituted with alanine (SEQ ID No. 44), fused N-terminal of a peptide linker (SEQ ID No. 21) and a chimeric Fc fragment composed of the hinge region of IgG2 and the constant heavy domains 2 and 3 of IgG4 with a deletion of the carboxyl-terminal K477- (Eu numbering) of SEQ ID NO. 19 |
| 74 | Fusion protein (SEQ ID No. 73) comprising amino acids 206-249 of human NOV/CCN3 (domain III/TSP-1 homology domain), where amino acid in position 207 (isoleucine) is substituted with alanine (SEQ ID No. 44), fused N-terminal of a peptide linker (SEQ ID No. 21) and a chimeric Fc fragment composed of the hinge region of IgG2 and the constant heavy domains 2 and 3 of IgG4 with a deletion of the carboxyl-terminal K477- (Eu numbering) of SEQ ID NO. 19 that is appended amino-terminally by the signal peptide from human serum albumin (SEQ ID No. 32) |
| 75 | DNA sequence encoding fusion protein of SEQ ID No. 74 codon-optimized for expression in hamster cells and further appended at the 5' end by a KOZAK sequence, GCCACC, and at the 3' end by a translation stop codon. |
| 76 | DNA sequence of SEQ ID No 75 encoding fusion protein of SEQ ID No. 74 and further including gateway AttB recombinase sites at both ends. |
| 77 | Fusion protein (SEQ ID No 41) comprising amino acid 194-246 of CCN5 (SEQ ID. No. 7), where amino acid in position 195 (proline) is substituted with alanine, fused C-terminal of a peptide linker (SEQ ID No. 39) and an Fc-fragment of IgG subtype IgG4 of SEQ ID NO. 15 (S228P, F234A, L235A, K447-, Eu-numbering) (Fc-HLn8-CCN5(dIII)-P195A), that is appended amino-terminally by the signal peptide from human serum albumin (SEQ ID No. 32) |
| 78 | DNA sequence encoding fusion protein of SEQ ID No. 77 codon-optimized for expression in hamster cells and further appended at the 5' end by a KOZAK sequence, GCCACC, and at the 3' end by a translation stop codon. |
| 79 | DNA sequence of SEQ ID no 78 encoding fusion protein of SEQ ID No. 77 and further including gateway AttB recombinase sites at both ends. |

| SEQ ID No. | Sequence information |
| --- | --- |
| 80 | Amino acids 206-249 of human NOV/CCN3 (domain III/TSP-1 homology domain), where amino acid in position 207 (isoleucine) is substituted with alanine (SEQ ID No. 44), fused N-terminal of a peptide linker (SEQ ID No. 22) and a chimeric Fc fragment composed of the hinge region of IgG2 and the constant heavy domains 2 and 3 of IgG4 with a deletion of the carboxyl-terminal K477- (Eu numbering) of SEQ ID NO. 19 |
| 81 | Fusion protein (SEQ ID No 81) comprising amino acids 206-249 of human NOV/CCN3 (domain III/TSP-1 homology domain), where amino acid in position 207 (isoleucine) is substituted with alanine (SEQ ID No. 44), fused N-terminal of a peptide linker (SEQ ID No. 22) and a chimeric Fc fragment composed of the hinge region of IgG2 and the constant heavy domains 2 and 3 of IgG4 with a deletion of the carboxyl-terminal K477- (Eu numbering) of SEQ ID NO. 19, that is appended amino-terminally by the signal peptide from human serum albumin (SEQ ID No. 32) |
| 82 | DNA sequence encoding fusion protein of SEQ ID No. 81 codon-optimized for expression in hamster cells and further appended at the 5' end by a KOZAK sequence, GCCACC, and at the 3' end by a translation stop codon. |
| 83 | DNA sequence of SEQ ID no 82 encoding fusion protein of SEQ ID No. 81 and further including gateway AttB recombinase sites at both ends. |
| 84 | Fusion protein comprising amino acids 206-249 of human NOV/CCN3 (domain III/TSP-1 homology domain), where amino acid in position 207 (isoleucine) is substituted with alanine (SEQ ID No. 44), fused N-terminal of a peptide linker (SEQ ID No. 21) and a Fc-fragment being a chimera of the hinge region of IgG2 and the constant heavy domains 2 and 3 of IgG4 with a deletion of the carboxyl-terminal K477- and with monomer-generating mutations (C219Q, C220Q, C226Q, C229Q, L351F, T366R, P395K, F405R, Y407E) and half-life extending mutations (M252Y, S254T, T256E) (Eu numbering) of SEQ ID NO. 55 |
| 85 | Fusion protein (SEQ ID No 84) comprising amino acids 206-249 of human NOV/CCN3 (domain III/TSP-1 homology domain), where amino acid in position 207 (isoleucine) is substituted with alanine (SEQ ID No. 44), fused N-terminal of a peptide linker (SEQ ID No. 21) and a Fc-fragment being a chimera of the hinge region of IgG2 and the constant heavy domains 2 and 3 of IgG4 with a deletion of the carboxyl-terminal K477- and with monomer-generating mutations (C219Q, C220Q, C226Q, C229Q, L351F, T366R, P395K, F405R, Y407E) and half-life extending mutations (M252Y, S254T, T256E) (Eu numbering) of SEQ ID NO. 55, that is appended amino-terminally by the signal peptide from human serum albumin (SEQ ID No. 32) |
| 86 | DNA sequence encoding fusion protein of SEQ ID No. 85 codon-optimized for expression in hamster cells and further appended at the 5' end by a KOZAK sequence, GCCACC, and at the 3' end by a translation stop codon. |
| 87 | DNA sequence of SEQ ID no 86 encoding fusion protein of SEQ ID No. 85 and further including gateway AttB recombinase sites at both ends. |
| 88 | Fusion protein comprising amino acids 206-249 of human NOV/CCN3 (domain III/TSP-1 homology domain), where amino acid in position 207 (isoleucine) is substituted with alanine (SEQ ID No. 44), fused N-terminal of a peptide linker (SEQ ID No. 21) and a Fc-fragment of IgG1, disulfide bridge stabilized (R292C, V302C), aglycosylated (N297G) and with monomer-generating mutations (C220Q, C226Q, C229Q, T366R, L368H, P395K, K409T, M428L), Eu numbering) of SEQ ID NO. 54 |
| 89 | Fusion protein (SEQ ID No. 88) comprising amino acids 206-249 of human NOV/CCN3 (domain III/TSP-1 homology domain), where amino acid in position 207 (isoleucine) is substituted with alanine (SEQ ID No. 44), fused N-terminal of a peptide linker (SEQ ID No. 21) and a Fc-fragment of IgG1, disulfide bridge stabilized (R292C, V302C), aglycosylated (N297G) and with monomer-generating mutations (C220Q, C226Q, C229Q, T366R, L368H, P395K, K409T, M428L), Eu numbering) of SEQ ID NO. 54, that is appended amino-terminally by the signal peptide from human serum albumin (SEQ ID No. 32) |
| 90 | DNA sequence encoding fusion protein of SEQ ID No. 89 codon-optimized for expression in hamster cells and further appended at the 5' end by a KOZAK sequence, GCCACC, and at the 3' end by a translation stop codon. |

| SEQ ID No. | Sequence information |
|---|---|
| 91 | DNA sequence of SEQ ID no 90 encoding fusion protein of SEQ ID No. 89 and further including gateway AttB recombinase sites at both ends. |
| 92 | Multifunctional fusion tag comprised of 6xHis tag, HaloTag and Sumo* elements |
| 93 | GS-linker |
| 94 | Fusion protein comprising amino acids 206-249 of human NOV/CCN3 (domain III/TSP-1 homology domain), where amino acid in position 207 (isoleucine) is substituted with alanine (SEQ ID No. 44), fused C-terminal of a peptide linker (SEQ ID No. 93) and a multifunctional fusion tag comprised of 6xHis tag, HaloTag and Sumo* elements of SEQ ID NO. 92 |
| 95 | DNA sequence encoding fusion protein of SEQ ID No. 114 codon-optimized for expression in hamster cells and further appended at the 5' end by a KOZAK sequence, GCCACC, and at the 3' end by a translation stop codon. |
| 96 | DNA sequence of SEQ ID no 95 encoding fusion protein of SEQ ID No. 114 and further including gateway AttB recombinase sites at both ends. |
| 97 | Fusion protein of the invention comprising the amino acids 194-237 of CCN5, wherein proline position 195 is replaced by alanine (SEQ ID No. 38), coupled N-terminally of a linker of SEQ ID No. 21 that is further coupled N-terminal to amino acids 25-609 of human serum albumin (SEQ ID No. 52) |
| 98 | Fusion protein (SEQ ID No. 97) comprising the amino acids 194-237 of CCN5, wherein proline position 195 is replaced by alanine (SEQ ID No. 38), coupled N-terminally of a linker of SEQ ID No. 21 that is further coupled N-terminal to amino acids 25-609 of human serum albumin (SEQ ID No. 52), that is appended amino-terminally by the signal peptide from human serum albumin (SEQ ID No. 32) |
| 99 | DNA sequence encoding fusion protein of SEQ ID No. 98 codon-optimized for expression in hamster cells and further appended at the 5' end by a KOZAK sequence, GCCACC, and at the 3' end by a translation stop codon. |
| 100 | DNA sequence of SEQ ID no 99 encoding fusion protein of SEQ ID No. 98 and further including gateway AttB recombinase sites at both ends. |
| 101 | Amino acids 25-606 of human serum albumin |
| 102 | Fusion protein of the invention comprising amino acids 194-246 of human WISP2/CCN5, where amino acid in position 195 (proline) is substituted with alanine (SEQ ID No. 7), coupled C-terminally of a linker of SEQ ID No. 22 that is further coupled C-terminal to amino acids 25-606 of human serum albumin (SEQ ID No. 101) |
| 103 | Fusion protein (SEQ ID No. 102) comprising amino acids 194-246 of human WISP2/CCN5, where amino acid in position 195 (proline) is substituted with alanine (SEQ ID No. 7), coupled C-terminally of a linker of SEQ ID No. 22 that is further coupled C-terminal to amino acids 25-606 of human serum albumin (SEQ ID No. 101), that is appended amino-terminally by the signal peptide from human serum albumin (SEQ ID No. 32) |
| 104 | DNA sequence encoding fusion protein of SEQ ID No. 103 codon-optimized for expression in hamster cells and further appended at the 5' end by a KOZAK sequence, GCCACC, and at the 3' end by a translation stop codon. |
| 105 | DNA sequence of SEQ ID no 104 encoding fusion protein of SEQ ID No. 103 and further including gateway AttB recombinase sites at both ends. |
| 106 | Fusion protein of the invention comprising amino acids 206-249 of human NOV/CCN3 (domain III/TSP-1 homology domain), where amino acid in position 207 (isoleucine) is substituted with alanine (SEQ ID No. 44), coupled N-terminally of a linker of SEQ ID No. 21 that is further coupled N-terminal to amino acids 25-609 of human serum albumin (SEQ ID No. 52) |
| 107 | Fusion protein (SEQ ID No. 106) comprising amino acids 206-249 of human NOV/CCN3 (domain III/TSP-1 homology domain), where amino acid in position 207 (isoleucine) is substituted with alanine (SEQ ID No. |

| SEQ ID No. | Sequence information |
|---|---|
| | 44), coupled N-terminally of a linker of SEQ ID No. 21 that is further coupled N-terminal to amino acids 25-609 of human serum albumin (SEQ ID No. 52), that is appended amino-terminally by the signal peptide from human serum albumin (SEQ ID No. 32) |
| 108 | DNA sequence encoding fusion protein of SEQ ID No. 107 codon-optimized for expression in hamster cells and further appended at the 5' end by a KOZAK sequence, GCCACC, and at the 3' end by a translation stop codon. |
| 109 | DNA sequence of SEQ ID no 108 encoding fusion protein of SEQ ID No. 108 and further including gateway AttB recombinase sites at both ends. |
| 110 | Fusion protein of the invention comprising amino acids 206-249 of human NOV/CCN3 (domain III/TSP-1 homology domain), where amino acid in position 207 (isoleucine) is substituted with alanine (SEQ ID No. 44), coupled N-terminally of a linker of SEQ ID No. 22 that is further coupled N-terminal to amino acids 25-609 of human serum albumin (SEQ ID No. 52) |
| 111 | Fusion protein (SEQ ID No. 110) comprising amino acids 206-249 of human NOV/CCN3 (domain III/TSP-1 homology domain), where amino acid in position 207 (isoleucine) is substituted with alanine (SEQ ID No. 44), coupled N-terminally of a linker of SEQ ID No. 22 that is further coupled N-terminal to amino acids 25-609 of human serum albumin (SEQ ID No. 52), that is appended amino-terminally by the signal peptide from human serum albumin (SEQ ID No. 32) |
| 112 | DNA sequence encoding fusion protein of SEQ ID No. 111 codon-optimized for expression in hamster cells and further appended at the 5' end by a KOZAK sequence, GCCACC, and at the 3' end by a translation stop codon. |
| 113 | DNA sequence of SEQ ID no 112 encoding fusion protein of SEQ ID No. 111 and further including gateway AttB recombinase sites at both ends. |
| 114 | Fusion protein (SEQ ID No. 94) comprising amino acids 206-249 of human NOV/CCN3 (domain III/TSP-1 homology domain), where amino acid in position 207 (isoleucine) is substituted with alanine (SEQ ID No. 44), fused C-terminal of a peptide linker (SEQ ID No. 93) and a multifunctional fusion tag comprised of 6xHis tag, HaloTag and Sumo* elements of SEQ ID NO. 92, that is appended amino-terminally by the signal peptide from human serum albumin (SEQ ID No. 32) |
| 115 | Potential section F of formula I |
| 116 | Potential section F of formula I |
| 117 | Potential section F of formula I |
| 118 | Potential section F of formula I |
| 119 | Potential section F of formula I |
| 120 | Potential section F of formula I |
| 121 | GGGGS linker |

Numbering of CCN proteins according to uniprot database, as described in the "Detailed description of the invention", supra. Numbering of the Fc-fragments according to the Eu-numbering system as described in the "Detailed description of the invention", supra.

The invention claimed is:

1. A monomeric fusion protein comprising:
(i) a polypeptide having 40 to 60 amino acids in length and comprising: (a) an amino acid sequence selected from SEQ ID NOs: 37 or 2 to 6; or (b) an amino acid sequence having at least 90% sequence identity to a sequence selected from SEQ ID NOs: 37 or 2 to 6; wherein all of the cysteine residues in said sequence selected from SEQ ID NOs: 37 or 2 to 6 are conserved;
(ii) a monomeric fusion partner N- or C-terminally fused to the amino acid sequence of (i); and
(iii) optionally a peptide linker between the polypeptide of (i) and the monomeric fusion partner of (ii),
wherein the monomeric fusion partner of (ii) and the peptide linker of (iii) are not or do not comprise an IGF binding protein homology domain, a von Willebrand factor type C repeat homology domain, or a cysteine knot domain of a CCN family protein.

2. The fusion protein of claim 1, wherein the polypeptide of (i) is 44 to 57 amino acids in length.

3. The fusion protein of claim 1, wherein the polypeptide of (i) comprises or consists of:

(a) an amino acid sequence selected from SEQ ID NOs: 1 or 8 to 12; or (b) a part of an amino acid sequence of (a), wherein said part comprises at least the 44 amino acid sequence of SEQ ID NOs: 37, 6, 2, 3, 4 or 5, respectively.

4. The fusion protein of claim 1, wherein the polypeptide of (i) consists of an amino acid sequence selected from SEQ ID NOs: 37 or 2 to 6, or a sequence having at least 90% sequence identity to a sequence selected from SEQ ID NOs: 37 or 2 to 6.

5. The fusion protein of claim 1, wherein the peptide linker of (iii) comprises no more than 50 amino acids.

6. The fusion protein of claim 1, wherein the polypeptide of (i) comprises an alanine residue at the position corresponding to position 2 of said sequence selected from SEQ ID NOs: 37 or 2 to 6, or SEQ ID NOs: 1 or 8 to 12.

7. The fusion protein of claim 1, wherein the amino acid sequence of (i) comprises an amino acid sequence selected from SEQ ID NOs: 7, 38, 42 to 46 or 47 to 51, or a sequence with at least 90% sequence identity thereto, wherein the protein comprises an alanine residue at the position corresponding to position 2 of said sequence of SEQ ID NO: 7, 38, 42 to 46 or 47 to 51.

8. The fusion protein of claim 1, wherein said monomeric fusion partner is selected from the group consisting of serum albumin, transferrin, and a part of an immunoglobulin, optionally a monomeric Fc-fragment of human IgG.

9. The fusion protein of claim 8, wherein said monomeric Fc-fragment of human IgG is a monomeric Fc fragment of IgG1, IgG2 or IgG4, wherein optionally the monomeric Fc-fragment is aglycosylated.

10. The fusion protein of claim 8, wherein the monomeric Fc-fragment comprises a stabilizing disulphide bridge and/or a protease stabilizing mutation.

11. The fusion protein of claim 8, wherein the monomeric Fc-fragment does not have immune effector function.

12. The fusion protein of claim 1, wherein the peptide linker between the amino acid sequence of (i) and the monomeric fusion partner has an amino acid sequence selected from the group consisting of SEQ ID NOs: 20 to 25, 39, 57, 63, 65 or 67, or an amino acid sequence having 90% sequence identity thereto.

13. The fusion protein of claim 1, wherein the fusion protein has an amino acid sequence selected from the group consisting of SEQ ID NOs: 84, 85, 88, 89, 97, 98, 102, 103, 106, 107, 110, and 111, or an amino acid sequence having 90% sequence identity thereto.

14. The fusion protein of claim 1, wherein said monomeric fusion partner comprises at least 6 amino acids.

15. An isolated DNA molecule encoding a monomeric fusion protein as defined in claim 1, wherein said molecule optionally further comprises a nucleotide sequence encoding a signal sequence.

16. The isolated DNA molecule of claim 15, wherein said molecule comprises a nucleotide sequence as set forth in SEQ ID NO: 34, 35, 36, 86, 87, 90, 91, 99, 100, 104, 105, 108, 109, 112 or 113 or a nucleotide sequence having at least 90% sequence identity with any aforesaid sequence.

17. An expression vector comprising a DNA molecule as defined in claim 15.

18. A host cell comprising an expression vector as defined in claim 17.

* * * * *

SEQUENCE LISTING

<160> NUMBER OF SEQ ID NOS: 121

<210> SEQ ID NO 1
<211> LENGTH: 53
<212> TYPE: PRT

<213> ORGANISM: Homo sapiens

<400> SEQUENCE: 1

Cys Pro Glu Trp Ser Thr Ala Trp Gly Pro Cys Ser Thr Thr Cys Gly
1               5                   10                  15

Leu Gly Met Ala Thr Arg Val Ser Asn Gln Asn Arg Phe Cys Arg Leu
            20                  25                  30

Glu Thr Gln Arg Arg Leu Cys Leu Ser Arg Pro Cys Pro Pro Ser Arg
        35                  40                  45

Gly Arg Ser Pro Gln
    50

<210> SEQ ID NO 2
<211> LENGTH: 44
<212> TYPE: PRT
<213> ORGANISM: Homo sapiens

<400> SEQUENCE: 2

Cys Ile Glu Gln Thr Thr Glu Trp Thr Ala Cys Ser Lys Ser Cys Gly
1               5                   10                  15

Met Gly Phe Ser Thr Arg Val Thr Asn Arg Asn Arg Gln Cys Glu Met
            20                  25                  30

Leu Lys Gln Thr Arg Leu Cys Met Val Arg Pro Cys
        35                  40

<210> SEQ ID NO 3
<211> LENGTH: 44
<212> TYPE: PRT
<213> ORGANISM: Homo sapiens

<400> SEQUENCE: 3

Cys Leu Val Gln Thr Thr Glu Trp Ser Ala Cys Ser Lys Thr Cys Gly
1               5                   10                  15

Met Gly Ile Ser Thr Arg Val Thr Asn Asp Asn Ala Ser Cys Arg Leu
            20                  25                  30

Glu Lys Gln Ser Arg Leu Cys Met Val Arg Pro Cys
        35                  40

<210> SEQ ID NO 4
<211> LENGTH: 44
<212> TYPE: PRT
<213> ORGANISM: Homo sapiens

<400> SEQUENCE: 4

Cys Ile Val Gln Thr Thr Ser Trp Ser Gln Cys Ser Lys Thr Cys Gly
1               5                   10                  15

Thr Gly Ile Ser Thr Arg Val Thr Asn Asp Asn Pro Glu Cys Arg Leu
            20                  25                  30

Val Lys Glu Thr Arg Ile Cys Glu Val Arg Pro Cys
        35                  40

<210> SEQ ID NO 5
<211> LENGTH: 44
<212> TYPE: PRT
<213> ORGANISM: Homo sapiens

<400> SEQUENCE: 5

Cys Ile Ala Tyr Thr Ser Pro Trp Ser Pro Cys Ser Thr Ser Cys Gly
1               5                   10                  15

Leu Gly Val Ser Thr Arg Ile Ser Asn Val Asn Ala Gln Cys Trp Pro

-continued

```
            20              25              30

Glu Gln Glu Ser Arg Leu Cys Asn Leu Arg Pro Cys
        35              40

<210> SEQ ID NO 6
<211> LENGTH: 44
<212> TYPE: PRT
<213> ORGANISM: Homo sapiens

<400> SEQUENCE: 6

Cys Leu Val Gln Ala Thr Lys Trp Thr Pro Cys Ser Arg Thr Cys Gly
1               5              10              15

Met Gly Ile Ser Asn Arg Val Thr Asn Glu Asn Ser Asn Cys Glu Met
            20              25              30

Arg Lys Glu Lys Arg Leu Cys Tyr Ile Gln Pro Cys
        35              40

<210> SEQ ID NO 7
<211> LENGTH: 53
<212> TYPE: PRT
<213> ORGANISM: Artificial Sequence
<220> FEATURE:
<223> OTHER INFORMATION: Modified CCN5 sequence

<400> SEQUENCE: 7

Cys Ala Glu Trp Ser Thr Ala Trp Gly Pro Cys Ser Thr Thr Cys Gly
1               5              10              15

Leu Gly Met Ala Thr Arg Val Ser Asn Gln Asn Arg Phe Cys Arg Leu
            20              25              30

Glu Thr Gln Arg Arg Leu Cys Leu Ser Arg Pro Cys Pro Pro Ser Arg
        35              40              45

Gly Arg Ser Pro Gln
    50

<210> SEQ ID NO 8
<211> LENGTH: 55
<212> TYPE: PRT
<213> ORGANISM: Homo sapiens

<400> SEQUENCE: 8

Cys Leu Val Gln Ala Thr Lys Trp Thr Pro Cys Ser Arg Thr Cys Gly
1               5              10              15

Met Gly Ile Ser Asn Arg Val Thr Asn Glu Asn Ser Asn Cys Glu Met
            20              25              30

Arg Lys Glu Lys Arg Leu Cys Tyr Ile Gln Pro Cys Asp Ser Asn Ile
        35              40              45

Leu Lys Thr Ile Lys Ile Pro
    50              55

<210> SEQ ID NO 9
<211> LENGTH: 53
<212> TYPE: PRT
<213> ORGANISM: Homo sapiens

<400> SEQUENCE: 9

Cys Ile Glu Gln Thr Thr Glu Trp Thr Ala Cys Ser Lys Ser Cys Gly
1               5              10              15

Met Gly Phe Ser Thr Arg Val Thr Asn Arg Asn Arg Gln Cys Glu Met
            20              25              30

Leu Lys Gln Thr Arg Leu Cys Met Val Arg Pro Cys Glu Gln Glu Pro
```

```
                35                  40                  45

Glu Gln Pro Thr Asp
    50

<210> SEQ ID NO 10
<211> LENGTH: 52
<212> TYPE: PRT
<213> ORGANISM: Homo sapiens

<400> SEQUENCE: 10

Cys Leu Val Gln Thr Thr Glu Trp Ser Ala Cys Ser Lys Thr Cys Gly
1                   5                  10                  15

Met Gly Ile Ser Thr Arg Val Thr Asn Asp Asn Ala Ser Cys Arg Leu
                20                  25                  30

Glu Lys Gln Ser Arg Leu Cys Met Val Arg Pro Cys Glu Ala Asp Leu
        35                  40                  45

Glu Glu Asn Ile
    50

<210> SEQ ID NO 11
<211> LENGTH: 52
<212> TYPE: PRT
<213> ORGANISM: Homo sapiens

<400> SEQUENCE: 11

Cys Ile Val Gln Thr Thr Ser Trp Ser Gln Cys Ser Lys Thr Cys Gly
1                   5                  10                  15

Thr Gly Ile Ser Thr Arg Val Thr Asn Asp Asn Pro Glu Cys Arg Leu
                20                  25                  30

Val Lys Glu Thr Arg Ile Cys Glu Val Arg Pro Cys Gly Gln Pro Val
        35                  40                  45

Tyr Ser Ser Leu
    50

<210> SEQ ID NO 12
<211> LENGTH: 52
<212> TYPE: PRT
<213> ORGANISM: Homo sapiens

<400> SEQUENCE: 12

Cys Ile Ala Tyr Thr Ser Pro Trp Ser Pro Cys Ser Thr Ser Cys Gly
1                   5                  10                  15

Leu Gly Val Ser Thr Arg Ile Ser Asn Val Asn Ala Gln Cys Trp Pro
                20                  25                  30

Glu Gln Glu Ser Arg Leu Cys Asn Leu Arg Pro Cys Asp Val Asp Ile
        35                  40                  45

His Thr Leu Ile
    50

<210> SEQ ID NO 13
<211> LENGTH: 229
<212> TYPE: PRT
<213> ORGANISM: Homo sapiens

<400> SEQUENCE: 13

Glu Ser Lys Tyr Gly Pro Pro Cys Pro Ser Cys Pro Ala Pro Glu Phe
1                   5                  10                  15

Leu Gly Gly Pro Ser Val Phe Leu Phe Pro Pro Lys Pro Lys Asp Thr
                20                  25                  30
```

```
Leu Met Ile Ser Arg Thr Pro Glu Val Thr Cys Val Val Val Asp Val
    35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225

<210> SEQ ID NO 14
<211> LENGTH: 228
<212> TYPE: PRT
<213> ORGANISM: Homo sapiens

<400> SEQUENCE: 14

Glu Arg Lys Cys Cys Val Glu Cys Pro Pro Cys Pro Ala Pro Pro Val
1                   5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
    35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175
```

```
Pro Met Leu Asp Ser Asp Gly Ser Phe Phe Leu Tyr Ser Lys Leu Thr
        180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

```
<210> SEQ ID NO 15
<211> LENGTH: 228
<212> TYPE: PRT
<213> ORGANISM: Artificial Sequence
<220> FEATURE:
<223> OTHER INFORMATION: Modified Fc fragment

<400> SEQUENCE: 15

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225
```

```
<210> SEQ ID NO 16
<211> LENGTH: 232
<212> TYPE: PRT
<213> ORGANISM: Artificial Sequence
<220> FEATURE:
<223> OTHER INFORMATION: Modified Fc fragment

<400> SEQUENCE: 16

Glu Pro Lys Ser Cys Asp Lys Thr His Thr Cys Pro Pro Cys Pro Ala
```

-continued

```
1               5              10             15

Pro Glu Leu Leu Gly Gly Pro Ser Val Phe Leu Phe Pro Pro Lys Pro
            20             25             30

Lys Asp Thr Leu Met Ile Ser Arg Thr Pro Glu Val Thr Cys Val Val
            35             40             45

Val Asp Val Ser His Glu Asp Pro Glu Val Lys Phe Asn Trp Tyr Val
        50             55             60

Asp Gly Val Glu Val His Asn Ala Lys Thr Lys Pro Cys Glu Glu Gln
65                  70             75                  80

Tyr Gly Ser Thr Tyr Arg Cys Val Ser Val Leu Thr Val Leu His Gln
                85             90             95

Asp Trp Leu Asn Gly Lys Glu Tyr Lys Cys Lys Val Ser Asn Lys Ala
            100            105            110

Leu Pro Ala Pro Ile Glu Lys Thr Ile Ser Lys Ala Lys Gly Gln Pro
            115            120            125

Arg Glu Pro Gln Val Tyr Thr Leu Pro Pro Ser Arg Asp Glu Leu Thr
    130            135            140

Lys Asn Gln Val Ser Leu Thr Cys Leu Val Lys Gly Phe Tyr Pro Ser
145            150            155            160

Asp Ile Ala Val Glu Trp Glu Ser Asn Gly Gln Pro Glu Asn Asn Tyr
                165            170            175

Lys Thr Thr Pro Pro Val Leu Asp Ser Asp Gly Ser Phe Phe Leu Tyr
            180            185            190

Ser Lys Leu Thr Val Asp Lys Ser Arg Trp Gln Gln Gly Asn Val Phe
            195            200            205

Ser Cys Ser Val Met His Glu Ala Leu His Asn His Tyr Thr Gln Lys
    210            215            220

Ser Leu Ser Leu Ser Pro Gly Lys
225                 230
```

```
<210> SEQ ID NO 17
<211> LENGTH: 231
<212> TYPE: PRT
<213> ORGANISM: Artificial Sequence
<220> FEATURE:
<223> OTHER INFORMATION: Modified Fc fragment

<400> SEQUENCE: 17
```

```
Glu Pro Lys Ser Cys Asp Lys Thr His Thr Cys Pro Pro Cys Pro Ala
1               5              10             15

Pro Pro Val Ala Gly Pro Ser Val Phe Leu Phe Pro Pro Lys Pro Lys
            20             25             30

Asp Thr Leu Met Ile Ser Arg Thr Pro Glu Val Thr Cys Val Val Val
            35             40             45

Asp Val Ser His Glu Asp Pro Glu Val Lys Phe Asn Trp Tyr Val Asp
        50             55             60

Gly Val Glu Val His Asn Ala Lys Thr Lys Pro Cys Glu Glu Gln Tyr
65                  70             75                  80

Gly Ser Thr Tyr Arg Cys Val Ser Val Leu Thr Val Leu His Gln Asp
                85             90             95

Trp Leu Asn Gly Lys Glu Tyr Lys Cys Lys Val Ser Asn Lys Ala Leu
            100            105            110

Pro Ala Pro Ile Glu Lys Thr Ile Ser Lys Ala Lys Gly Gln Pro Arg
            115            120            125

Glu Pro Gln Val Tyr Thr Leu Pro Pro Ser Arg Asp Glu Leu Thr Lys
```

-continued

```
        130              135              140

Asn Gln Val Ser Leu Thr Cys Leu Val Lys Gly Phe Tyr Pro Ser Asp
145              150              155              160

Ile Ala Val Glu Trp Glu Ser Asn Gly Gln Pro Glu Asn Asn Tyr Lys
                 165              170              175

Thr Thr Pro Pro Val Leu Asp Ser Asp Gly Ser Phe Phe Leu Tyr Ser
                 180              185              190

Lys Leu Thr Val Asp Lys Ser Arg Trp Gln Gln Gly Asn Val Phe Ser
            195              200              205

Cys Ser Val Met His Glu Ala Leu His Asn His Tyr Thr Gln Lys Ser
        210              215              220

Leu Ser Leu Ser Pro Gly Lys
225              230
```

```
<210> SEQ ID NO 18
<211> LENGTH: 227
<212> TYPE: PRT
<213> ORGANISM: Artificial Sequence
<220> FEATURE:
<223> OTHER INFORMATION: Modified Fc fragment

<400> SEQUENCE: 18
```

```
Glu Ser Lys Tyr Gly Pro Pro Cys Pro Pro Cys Pro Ala Pro Pro Val
1              5              10              15

Ala Gly Pro Ser Val Phe Leu Phe Pro Pro Lys Pro Lys Asp Thr Leu
                 20              25              30

Met Ile Ser Arg Thr Pro Glu Val Thr Cys Val Val Val Asp Val Ser
            35              40              45

Gln Glu Asp Pro Glu Val Gln Phe Asn Trp Tyr Val Asp Gly Val Glu
        50              55              60

Val His Asn Ala Lys Thr Lys Pro Arg Glu Glu Gln Phe Asn Ser Thr
65              70              75              80

Tyr Arg Val Val Ser Val Leu Thr Val Leu His Gln Asp Trp Leu Asn
                 85              90              95

Gly Lys Glu Tyr Lys Cys Lys Val Ser Asn Lys Gly Leu Pro Ser Ser
                 100             105             110

Ile Glu Lys Thr Ile Ser Lys Ala Lys Gly Gln Pro Arg Glu Pro Gln
            115             120             125

Val Tyr Thr Leu Pro Pro Ser Gln Glu Glu Met Thr Lys Asn Gln Val
        130             135             140

Ser Leu Thr Cys Leu Val Lys Gly Phe Tyr Pro Ser Asp Ile Ala Val
145             150             155             160

Glu Trp Glu Ser Asn Gly Gln Pro Glu Asn Asn Tyr Lys Thr Thr Pro
                 165             170             175

Pro Val Leu Asp Ser Asp Gly Ser Phe Phe Leu Tyr Ser Arg Leu Thr
                 180             185             190

Val Asp Lys Ser Arg Trp Gln Glu Gly Asn Val Phe Ser Cys Ser Val
            195             200             205

Met His Glu Ala Leu His Asn His Tyr Thr Gln Lys Ser Leu Ser Leu
        210             215             220

Ser Leu Gly
225
```

```
<210> SEQ ID NO 19
<211> LENGTH: 227
<212> TYPE: PRT
```

```
<213> ORGANISM: Artificial Sequence
<220> FEATURE:
<223> OTHER INFORMATION: Modified Fc fragment

<400> SEQUENCE: 19

Glu Arg Lys Cys Cys Val Glu Cys Pro Pro Cys Pro Ala Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

Gln Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Gln Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
            195                 200                 205

Met His Glu Ala Leu His Asn His Tyr Thr Gln Lys Ser Leu Ser Leu
        210                 215                 220

Ser Leu Gly
225

<210> SEQ ID NO 20
<211> LENGTH: 6
<212> TYPE: PRT
<213> ORGANISM: Artificial Sequence
<220> FEATURE:
<223> OTHER INFORMATION: Linker

<400> SEQUENCE: 20

Thr Glu Gly Arg Met Asp
1               5

<210> SEQ ID NO 21
<211> LENGTH: 5
<212> TYPE: PRT
<213> ORGANISM: Artificial Sequence
<220> FEATURE:
<223> OTHER INFORMATION: Linker

<400> SEQUENCE: 21

Glu Ala Ala Ala Lys
1               5

<210> SEQ ID NO 22
```

```
<211> LENGTH: 40
<212> TYPE: PRT
<213> ORGANISM: Artificial Sequence
<220> FEATURE:
<223> OTHER INFORMATION: Linker

<400> SEQUENCE: 22

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys Glu Ala Ala Ala Lys
        35                  40

<210> SEQ ID NO 23
<211> LENGTH: 42
<212> TYPE: PRT
<213> ORGANISM: Artificial Sequence
<220> FEATURE:
<223> OTHER INFORMATION: Linker

<400> SEQUENCE: 23

Thr Ala Glu Ala Ala Ala Lys Glu Ala Ala Ala Lys Glu Ala Ala Ala
1               5                   10                  15

Lys Glu Ala Ala Ala Lys Glu Ala Ala Ala Lys Glu Ala Ala Ala Lys
            20                  25                  30

Glu Ala Ala Ala Lys Glu Ala Ala Ala Lys
        35                  40

<210> SEQ ID NO 24
<211> LENGTH: 43
<212> TYPE: PRT
<213> ORGANISM: Artificial Sequence
<220> FEATURE:
<223> OTHER INFORMATION: Linker

<400> SEQUENCE: 24

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys Glu Ala Ala Ala Lys Ala Ala Ala
        35                  40

<210> SEQ ID NO 25
<211> LENGTH: 45
<212> TYPE: PRT
<213> ORGANISM: Artificial Sequence
<220> FEATURE:
<223> OTHER INFORMATION: Linker

<400> SEQUENCE: 25

Thr Ala Glu Ala Ala Ala Lys Glu Ala Ala Ala Lys Glu Ala Ala Ala
1               5                   10                  15

Lys Glu Ala Ala Ala Lys Glu Ala Ala Ala Lys Glu Ala Ala Ala Lys
            20                  25                  30

Glu Ala Ala Ala Lys Glu Ala Ala Ala Lys Ala Ala Ala
        35                  40                  45

<210> SEQ ID NO 26
<211> LENGTH: 276
<212> TYPE: PRT
<213> ORGANISM: Artificial Sequence
```

<220> FEATURE:
<223> OTHER INFORMATION: Fusion protein

<400> SEQUENCE: 26

```
Cys Pro Glu Trp Ser Thr Ala Trp Gly Pro Cys Ser Thr Thr Cys Gly
1               5                   10                  15

Leu Gly Met Ala Thr Arg Val Ser Asn Gln Asn Arg Phe Cys Arg Leu
            20                  25                  30

Glu Thr Gln Arg Arg Leu Cys Leu Ser Arg Pro Cys Glu Ala Ala Ala
        35                  40                  45

Lys Glu Arg Lys Cys Cys Val Glu Cys Pro Pro Cys Pro Ala Pro Pro
    50                  55                  60

Val Ala Gly Pro Ser Val Phe Leu Phe Pro Pro Lys Pro Lys Asp Thr
65                  70                  75                  80

Leu Met Ile Ser Arg Thr Pro Glu Val Thr Cys Val Val Val Asp Val
                85                  90                  95

Ser Gln Glu Asp Pro Glu Val Gln Phe Asn Trp Tyr Val Asp Gly Val
            100                 105                 110

Glu Val His Asn Ala Lys Thr Lys Pro Arg Glu Glu Gln Phe Asn Ser
        115                 120                 125

Thr Tyr Arg Val Val Ser Val Leu Thr Val Leu His Gln Asp Trp Leu
    130                 135                 140

Asn Gly Lys Glu Tyr Lys Cys Lys Val Ser Asn Lys Gly Leu Pro Ser
145                 150                 155                 160

Ser Ile Glu Lys Thr Ile Ser Lys Ala Lys Gly Gln Pro Arg Glu Pro
                165                 170                 175

Gln Val Tyr Thr Leu Pro Pro Ser Gln Glu Glu Met Thr Lys Asn Gln
            180                 185                 190

Val Ser Leu Thr Cys Leu Val Lys Gly Phe Tyr Pro Ser Asp Ile Ala
        195                 200                 205

Val Glu Trp Glu Ser Asn Gly Gln Pro Glu Asn Asn Tyr Lys Thr Thr
    210                 215                 220

Pro Pro Val Leu Asp Ser Asp Gly Ser Phe Phe Leu Tyr Ser Arg Leu
225                 230                 235                 240

Thr Val Asp Lys Ser Arg Trp Gln Glu Gly Asn Val Phe Ser Cys Ser
                245                 250                 255

Val Met His Glu Ala Leu His Asn His Tyr Thr Gln Lys Ser Leu Ser
            260                 265                 270

Leu Ser Leu Gly
        275
```

<210> SEQ ID NO 27
<211> LENGTH: 276
<212> TYPE: PRT
<213> ORGANISM: Artificial Sequence
<220> FEATURE:
<223> OTHER INFORMATION: Fusion protein

<400> SEQUENCE: 27

```
Cys Ala Glu Trp Ser Thr Ala Trp Gly Pro Cys Ser Thr Thr Cys Gly
1               5                   10                  15

Leu Gly Met Ala Thr Arg Val Ser Asn Gln Asn Arg Phe Cys Arg Leu
            20                  25                  30

Glu Thr Gln Arg Arg Leu Cys Leu Ser Arg Pro Cys Glu Ala Ala Ala
        35                  40                  45

Lys Glu Arg Lys Cys Cys Val Glu Cys Pro Pro Cys Pro Ala Pro Pro
```

-continued

```
        50                55                60

Val Ala Gly Pro Ser Val Phe Leu Phe Pro Pro Lys Pro Lys Asp Thr
65                70                75                80

Leu Met Ile Ser Arg Thr Pro Glu Val Thr Cys Val Val Val Asp Val
                85                90                95

Ser Gln Glu Asp Pro Glu Val Gln Phe Asn Trp Tyr Val Asp Gly Val
                100               105               110

Glu Val His Asn Ala Lys Thr Lys Pro Arg Glu Glu Gln Phe Asn Ser
        115               120               125

Thr Tyr Arg Val Val Ser Val Leu Thr Val Leu His Gln Asp Trp Leu
        130               135               140

Asn Gly Lys Glu Tyr Lys Cys Lys Val Ser Asn Lys Gly Leu Pro Ser
145               150               155               160

Ser Ile Glu Lys Thr Ile Ser Lys Ala Lys Gly Gln Pro Arg Glu Pro
                165               170               175

Gln Val Tyr Thr Leu Pro Pro Ser Gln Glu Glu Met Thr Lys Asn Gln
                180               185               190

Val Ser Leu Thr Cys Leu Val Lys Gly Phe Tyr Pro Ser Asp Ile Ala
        195               200               205

Val Glu Trp Glu Ser Asn Gly Gln Pro Glu Asn Asn Tyr Lys Thr Thr
        210               215               220

Pro Pro Val Leu Asp Ser Asp Gly Ser Phe Phe Leu Tyr Ser Arg Leu
225               230               235               240

Thr Val Asp Lys Ser Arg Trp Gln Glu Gly Asn Val Phe Ser Cys Ser
                245               250               255

Val Met His Glu Ala Leu His Asn His Tyr Thr Gln Lys Ser Leu Ser
                260               265               270

Leu Ser Leu Gly
        275
```

```
<210> SEQ ID NO 28
<211> LENGTH: 287
<212> TYPE: PRT
<213> ORGANISM: Artificial Sequence
<220> FEATURE:
<223> OTHER INFORMATION: Fusion protein

<400> SEQUENCE: 28

Cys Pro Glu Trp Ser Thr Ala Trp Gly Pro Cys Ser Thr Thr Cys Gly
1                5                10                15

Leu Gly Met Ala Thr Arg Val Ser Asn Gln Asn Arg Phe Cys Arg Leu
                20                25                30

Glu Thr Gln Arg Arg Leu Cys Leu Ser Arg Pro Cys Pro Pro Ser Arg
        35                40                45

Gly Arg Ser Pro Gln Thr Glu Gly Arg Met Asp Glu Ser Lys Tyr Gly
        50                55                60

Pro Pro Cys Pro Pro Cys Pro Ala Pro Glu Ala Ala Gly Gly Pro Ser
65                70                75                80

Val Phe Leu Phe Pro Pro Lys Pro Lys Asp Thr Leu Met Ile Ser Arg
                85                90                95

Thr Pro Glu Val Thr Cys Val Val Val Asp Val Ser Gln Glu Asp Pro
                100               105               110

Glu Val Gln Phe Asn Trp Tyr Val Asp Gly Val Glu Val His Asn Ala
        115               120               125

Lys Thr Lys Pro Arg Glu Glu Gln Phe Asn Ser Thr Tyr Arg Val Val
```

-continued

```
                130               135               140
Ser Val Leu Thr Val Leu His Gln Asp Trp Leu Asn Gly Lys Glu Tyr
145               150               155               160

Lys Cys Lys Val Ser Asn Lys Gly Leu Pro Ser Ser Ile Glu Lys Thr
                165               170               175

Ile Ser Lys Ala Lys Gly Gln Pro Arg Glu Pro Gln Val Tyr Thr Leu
                180               185               190

Pro Pro Ser Gln Glu Glu Met Thr Lys Asn Gln Val Ser Leu Thr Cys
                195               200               205

Leu Val Lys Gly Phe Tyr Pro Ser Asp Ile Ala Val Glu Trp Glu Ser
    210               215               220

Asn Gly Gln Pro Glu Asn Asn Tyr Lys Thr Thr Pro Pro Val Leu Asp
225               230               235               240

Ser Asp Gly Ser Phe Phe Leu Tyr Ser Arg Leu Thr Val Asp Lys Ser
                245               250               255

Arg Trp Gln Glu Gly Asn Val Phe Ser Cys Ser Val Met His Glu Ala
                260               265               270

Leu His Asn His Tyr Thr Gln Lys Ser Leu Ser Leu Ser Leu Gly
                275               280               285

<210> SEQ ID NO 29
<211> LENGTH: 286
<212> TYPE: PRT
<213> ORGANISM: Artificial Sequence
<220> FEATURE:
<223> OTHER INFORMATION: Fusion protein

<400> SEQUENCE: 29

Cys Pro Glu Trp Ser Thr Ala Trp Gly Pro Cys Ser Thr Thr Cys Gly
1                 5                 10                15

Leu Gly Met Ala Thr Arg Val Ser Asn Gln Asn Arg Phe Cys Arg Leu
                20                25                30

Glu Thr Gln Arg Arg Leu Cys Leu Ser Arg Pro Cys Pro Pro Ser Arg
                35                40                45

Gly Arg Ser Pro Gln Thr Glu Gly Arg Met Asp Glu Ser Lys Tyr Gly
    50                55                60

Pro Pro Cys Pro Pro Cys Pro Ala Pro Pro Val Ala Gly Pro Ser Val
65                70                75                80

Phe Leu Phe Pro Pro Lys Pro Lys Asp Thr Leu Met Ile Ser Arg Thr
                85                90                95

Pro Glu Val Thr Cys Val Val Val Asp Val Ser Gln Glu Asp Pro Glu
                100               105               110

Val Gln Phe Asn Trp Tyr Val Asp Gly Val Glu Val His Asn Ala Lys
                115               120               125

Thr Lys Pro Arg Glu Glu Gln Phe Asn Ser Thr Tyr Arg Val Val Ser
                130               135               140

Val Leu Thr Val Leu His Gln Asp Trp Leu Asn Gly Lys Glu Tyr Lys
145               150               155               160

Cys Lys Val Ser Asn Lys Gly Leu Pro Ser Ser Ile Glu Lys Thr Ile
                165               170               175

Ser Lys Ala Lys Gly Gln Pro Arg Glu Pro Gln Val Tyr Thr Leu Pro
                180               185               190

Pro Ser Gln Glu Glu Met Thr Lys Asn Gln Val Ser Leu Thr Cys Leu
                195               200               205

Val Lys Gly Phe Tyr Pro Ser Asp Ile Ala Val Glu Trp Glu Ser Asn
```

-continued

```
          210                215                220

Gly Gln Pro Glu Asn Asn Tyr Lys Thr Thr Pro Pro Val Leu Asp Ser
225                230                235                240

Asp Gly Ser Phe Phe Leu Tyr Ser Arg Leu Thr Val Asp Lys Ser Arg
            245                250                255

Trp Gln Glu Gly Asn Val Phe Ser Cys Ser Val Met His Glu Ala Leu
            260                265                270

His Asn His Tyr Thr Gln Lys Ser Leu Ser Leu Ser Leu Gly
        275                280                285

<210> SEQ ID NO 30
<211> LENGTH: 286
<212> TYPE: PRT
<213> ORGANISM: Artificial Sequence
<220> FEATURE:
<223> OTHER INFORMATION: Fusion protein

<400> SEQUENCE: 30

Cys Pro Glu Trp Ser Thr Ala Trp Gly Pro Cys Ser Thr Thr Cys Gly
1                5                10                15

Leu Gly Met Ala Thr Arg Val Ser Asn Gln Asn Arg Phe Cys Arg Leu
            20                25                30

Glu Thr Gln Arg Arg Leu Cys Leu Ser Arg Pro Cys Pro Pro Ser Arg
            35                40                45

Gly Arg Ser Pro Gln Thr Glu Gly Arg Met Asp Glu Arg Lys Cys Cys
        50                55                60

Val Glu Cys Pro Pro Cys Pro Ala Pro Pro Val Ala Gly Pro Ser Val
65                70                75                80

Phe Leu Phe Pro Pro Lys Pro Lys Asp Thr Leu Met Ile Ser Arg Thr
                85                90                95

Pro Glu Val Thr Cys Val Val Val Asp Val Ser Gln Glu Asp Pro Glu
            100                105                110

Val Gln Phe Asn Trp Tyr Val Asp Gly Val Glu Val His Asn Ala Lys
            115                120                125

Thr Lys Pro Arg Glu Glu Gln Phe Asn Ser Thr Tyr Arg Val Val Ser
        130                135                140

Val Leu Thr Val Leu His Gln Asp Trp Leu Asn Gly Lys Glu Tyr Lys
145                150                155                160

Cys Lys Val Ser Asn Lys Gly Leu Pro Ser Ser Ile Glu Lys Thr Ile
                165                170                175

Ser Lys Ala Lys Gly Gln Pro Arg Glu Pro Gln Val Tyr Thr Leu Pro
            180                185                190

Pro Ser Gln Glu Glu Met Thr Lys Asn Gln Val Ser Leu Thr Cys Leu
            195                200                205

Val Lys Gly Phe Tyr Pro Ser Asp Ile Ala Val Glu Trp Glu Ser Asn
        210                215                220

Gly Gln Pro Glu Asn Asn Tyr Lys Thr Thr Pro Pro Val Leu Asp Ser
225                230                235                240

Asp Gly Ser Phe Phe Leu Tyr Ser Arg Leu Thr Val Asp Lys Ser Arg
            245                250                255

Trp Gln Glu Gly Asn Val Phe Ser Cys Ser Val Met His Glu Ala Leu
            260                265                270

His Asn His Tyr Thr Gln Lys Ser Leu Ser Leu Ser Leu Gly
        275                280                285
```

<210> SEQ ID NO 31
<211> LENGTH: 325
<212> TYPE: PRT
<213> ORGANISM: Artificial Sequence
<220> FEATURE:
<223> OTHER INFORMATION: Fusion protein

<400> SEQUENCE: 31

```
Cys Pro Glu Trp Ser Thr Ala Trp Gly Pro Cys Ser Thr Thr Cys Gly
1               5                   10                  15

Leu Gly Met Ala Thr Arg Val Ser Asn Gln Asn Arg Phe Cys Arg Leu
            20                  25                  30

Glu Thr Gln Arg Arg Leu Cys Leu Ser Arg Pro Cys Pro Pro Ser Arg
        35                  40                  45

Gly Arg Ser Pro Gln Thr Ala Glu Ala Ala Ala Lys Glu Ala Ala Ala
    50                  55                  60

Lys Glu Ala Ala Ala Lys Glu Ala Ala Ala Lys Glu Ala Ala Ala Lys
65                  70                  75                  80

Glu Ala Ala Ala Lys Glu Ala Ala Ala Lys Glu Ala Ala Ala Lys Ala
                85                  90                  95

Ala Ala Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly
                325
```

<210> SEQ ID NO 32
<211> LENGTH: 18
<212> TYPE: PRT
<213> ORGANISM: Homo sapiens

<400> SEQUENCE: 32

```
Met Lys Trp Val Thr Phe Ile Ser Leu Leu Phe Leu Phe Ser Ser Ala
1               5                   10                  15

Tyr Ser

<210> SEQ ID NO 33
<211> LENGTH: 305
<212> TYPE: PRT
<213> ORGANISM: Artificial Sequence
<220> FEATURE:
<223> OTHER INFORMATION: Fusion protein

<400> SEQUENCE: 33

Met Lys Trp Val Thr Phe Ile Ser Leu Leu Phe Leu Phe Ser Ser Ala
1               5                   10                  15

Tyr Ser Cys Pro Glu Trp Ser Thr Ala Trp Gly Pro Cys Ser Thr Thr
            20                  25                  30

Cys Gly Leu Gly Met Ala Thr Arg Val Ser Asn Gln Asn Arg Phe Cys
        35                  40                  45

Arg Leu Glu Thr Gln Arg Arg Leu Cys Leu Ser Arg Pro Cys Pro Pro
    50                  55                  60

Ser Arg Gly Arg Ser Pro Gln Thr Glu Gly Arg Met Asp Glu Ser Lys
65                  70                  75                  80

Tyr Gly Pro Pro Cys Pro Pro Cys Pro Ala Pro Glu Ala Ala Gly Gly
                85                  90                  95

Pro Ser Val Phe Leu Phe Pro Pro Lys Pro Lys Asp Thr Leu Met Ile
            100                 105                 110

Ser Arg Thr Pro Glu Val Thr Cys Val Val Val Asp Val Ser Gln Glu
            115                 120                 125

Asp Pro Glu Val Gln Phe Asn Trp Tyr Val Asp Gly Val Glu Val His
    130                 135                 140

Asn Ala Lys Thr Lys Pro Arg Glu Glu Gln Phe Asn Ser Thr Tyr Arg
145                 150                 155                 160

Val Val Ser Val Leu Thr Val Leu His Gln Asp Trp Leu Asn Gly Lys
                165                 170                 175

Glu Tyr Lys Cys Lys Val Ser Asn Lys Gly Leu Pro Ser Ser Ile Glu
            180                 185                 190

Lys Thr Ile Ser Lys Ala Lys Gly Gln Pro Arg Glu Pro Gln Val Tyr
            195                 200                 205

Thr Leu Pro Pro Ser Gln Glu Glu Met Thr Lys Asn Gln Val Ser Leu
    210                 215                 220

Thr Cys Leu Val Lys Gly Phe Tyr Pro Ser Asp Ile Ala Val Glu Trp
225                 230                 235                 240

Glu Ser Asn Gly Gln Pro Glu Asn Asn Tyr Lys Thr Thr Pro Pro Val
                245                 250                 255

Leu Asp Ser Asp Gly Ser Phe Phe Leu Tyr Ser Arg Leu Thr Val Asp
            260                 265                 270

Lys Ser Arg Trp Gln Glu Gly Asn Val Phe Ser Cys Ser Val Met His
            275                 280                 285

Glu Ala Leu His Asn His Tyr Thr Gln Lys Ser Leu Ser Leu Ser Leu
    290                 295                 300

Gly
305

<210> SEQ ID NO 34
<211> LENGTH: 915
```

```
<212> TYPE: DNA
<213> ORGANISM: Artificial Sequence
<220> FEATURE:
<223> OTHER INFORMATION: Fusion protein

<400> SEQUENCE: 34
atgaaatggg tcacctttat ctccctgctg ttcctgttct cctccgccta ctcttgccct     60
gagtggtcta cagcttgggg cccttgctct accacctgtg gactcggcat ggccaccaga    120
gtgtctaacc agaacagatt ctgccggctg gaaacccagc ggagactgtg cctgtctaga    180
ccctgtcctc ctagcagagg cagatcccct cagaccgagg gcagaatgga cgagtctaag    240
tacggccctc cttgtcctcc atgtcctgct ccagaagctg ctggcggccc ttccgtgttt    300
ctgttccctc caaagcctaa ggacaccctg atgatctctc ggacccctga gtgacctgc    360 gtggtggtgg atgtgtccca agaggatccc gaggtgcagt tcaattggta cgtggacggc    420
gtggaagtgc acaacgccaa gaccaagcct agagaggaac agttcaactc cacctacaga    480
gtggtgtccg tgctgaccgt gctgcaccag gattggctga cggcaaaga gtacaagtgc    540 aaggtgtcca caagggcct gccttccagc atcgaaaga ccatctccaa ggccaagggc    600
cagcctaggg aacccaggt ttacaccctg cctccaagcc aagaggaaat gaccaagaac    660
caggtgtccc tgacctgcct ggtcaagggc ttctacccctt ccgatatcgc cgtggaatgg    720
gagagcaatg gccagcctga gaacaactac aagaccacac tcctgtgct ggactccgac    780 ggctccttct ttctgtactc ccgcctgacc gtggacaagt ccagatggca gagggcaac    840 gtgttctcct gctccgtgat gcacgaggcc ctgcacaatc actacaccca gaagtccctg    900
tctctgtccc tgggc                                                      915

<210> SEQ ID NO 35
<211> LENGTH: 924
<212> TYPE: DNA
<213> ORGANISM: Artificial Sequence
<220> FEATURE:
<223> OTHER INFORMATION: Fusion protein

<400> SEQUENCE: 35
gccaccatga atgggtcac ctttatctcc ctgctgttcc tgttctcctc cgcctactct     60
tgccctgagt ggtctacagc ttggggcct tgctctacca cctgtggact cggcatggcc    120
accagagtgt ctaaccagaa cagattctgc cggctggaaa cccagcggag actgtgcctg    180
tctagaccct gtcctcctag cagaggcaga tccctcaga ccgagggcag aatggacgag    240
tctaagtacg ccctccttg tcctccatgt cctgctccag aagctgctgg cggcccttcc    300
gtgtttctgt ccctccaaa gcctaaggac accctgatga tctctcggac ccctgaagtg    360
acctgcgtgt ggtggatgt gtcccaagag gatcccgagg tgcagttcaa ttggtacgtg    420
gacggcgtgg aagtgcacaa cgccaagacc aagcctagag aggaacagtt caactccacc    480
tacagagtgg tgtccgtgct gaccgtgctg caccaggatt ggctgaacgg caaagagtac    540
aagtgcaagg tgtccaacaa gggcctgcct tccagcatcg aaaagaccat ctccaaggcc    600
aagggccagc ctagggaacc ccaggtttac accctgcctc caagccaaga ggaaatgacc    660
aagaaccagg tgtccctgac ctgcctggtc aagggcttct accttccga tatcgccgtg    720 gaatgggaga gcaatggcca gcctgagaac aactacaaga ccacacctcc tgtgctggac    780
tccgacggct ccttctttct gtactcccgc ctgaccgtgg acaagtccag atggcaagag    840
ggcaacgtgt ctcctgctc cgtgatgcac gaggccctgc acaatcacta cacccagaag    900
```
tccctgtctc tgtccctggg ctaa                                                                           924

<210> SEQ ID NO 36
<211> LENGTH: 997
<212> TYPE: DNA
<213> ORGANISM: Artificial Sequence
<220> FEATURE:
<223> OTHER INFORMATION: Fusion protein

<400> SEQUENCE: 36
ggggacaagt ttgtacaaaa aagcaggcta tggtaccgcc accatgaaat gggtcacctt        60
tatctccctg ctgttcctgt tctcctccgc ctactcttgc cctgagtggt ctacagcttg       120
gggcccttgc tctaccacct gtggactcgg catggccacc agagtgtcta accagaacag       180
attctgccgg ctggaaaccc agcggagact gtgcctgtct agaccctgtc ctcctagcag       240
aggcagatcc cctcagaccg agggcagaat ggacgagtct aagtacggcc ctccttgtcc       300
tccatgtcct gctccagaag ctgctggcgg cccttccgtg tttctgttcc ctccaaagcc       360
taaggacacc ctgatgatct ctcggacccc tgaagtgacc tgcgtggtgg tggatgtgtc       420
ccaagaggat cccgaggtgc agttcaattg gtacgtggac ggcgtggaag tgcacaacgc       480
caagaccaag cctagagagg aacagttcaa ctccacctac agagtggtgt ccgtgctgac       540
cgtgctgcac caggattggc tgaacggcaa agagtacaag tgcaaggtgt ccaacaaggg       600
cctgccttcc agcatcgaaa agaccatctc caaggccaag ggccagccta gggaacccca       660
ggtttacacc ctgcctccaa gccaagagga aatgaccaag aaccaggtgt ccctgacctg       720
cctggtcaag ggcttctacc cttccgatat cgccgtggaa tgggagagca atggccagcc       780
tgagaacaac tacaagacca cacctcctgt gctggactcc gacggctcct tctttctgta       840
ctcccgcctg accgtggaca gtccagatg gcaagagggc aacgtgttct cctgctccgt       900
gatgcacgag gccctgcaca tcactacac ccagaagtcc ctgtctctgt ccctgggcta       960
atctagaaac ccagctttct tgtacaaagt ggtcccc                                997

<210> SEQ ID NO 37
<211> LENGTH: 44
<212> TYPE: PRT
<213> ORGANISM: Homo sapiens

<400> SEQUENCE: 37

Cys Pro Glu Trp Ser Thr Ala Trp Gly Pro Cys Ser Thr Thr Cys Gly
1               5                   10                  15

Leu Gly Met Ala Thr Arg Val Ser Asn Gln Asn Arg Phe Cys Arg Leu
            20                  25                  30

Glu Thr Gln Arg Arg Leu Cys Leu Ser Arg Pro Cys
        35                  40

<210> SEQ ID NO 38
<211> LENGTH: 44
<212> TYPE: PRT
<213> ORGANISM: Artificial Sequence
<220> FEATURE:
<223> OTHER INFORMATION: Modified CCN5 sequence

<400> SEQUENCE: 38

Cys Ala Glu Trp Ser Thr Ala Trp Gly Pro Cys Ser Thr Thr Cys Gly
1               5                   10                  15

Leu Gly Met Ala Thr Arg Val Ser Asn Gln Asn Arg Phe Cys Arg Leu
            20                  25                  30

Glu Thr Gln Arg Arg Leu Cys Leu Ser Arg Pro Cys
        35                      40

<210> SEQ ID NO 39
<211> LENGTH: 44
<212> TYPE: PRT
<213> ORGANISM: Artificial Sequence
<220> FEATURE:
<223> OTHER INFORMATION: Linker

<400> SEQUENCE: 39

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Glu Ala Ala Ala Lys Glu
            20                  25                  30

Ala Ala Ala Lys Glu Ala Ala Ala Lys Ala Ala Ala
        35                  40

<210> SEQ ID NO 40
<211> LENGTH: 325
<212> TYPE: PRT
<213> ORGANISM: Artificial Sequence
<220> FEATURE:
<223> OTHER INFORMATION: Fusion protein

<400> SEQUENCE: 40

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
        210                 215                 220

Leu Ser Leu Gly Ala Glu Ala Ala Ala Lys Glu Ala Ala Ala Lys Glu
225                 230                 235                 240

Ala Ala Ala Lys Glu Ala Ala Ala Lys Glu Ala Ala Ala Lys Glu Ala
            245                 250                 255

```
Ala Ala Lys Glu Ala Ala Ala Lys Glu Ala Ala Ala Lys Ala Ala Ala
        260             265             270

Cys Pro Glu Trp Ser Thr Ala Trp Gly Pro Cys Ser Thr Thr Cys Gly
        275             280             285

Leu Gly Met Ala Thr Arg Val Ser Asn Gln Asn Arg Phe Cys Arg Leu
        290             295             300

Glu Thr Gln Arg Arg Leu Cys Leu Ser Arg Pro Cys Pro Pro Ser Arg
305             310             315             320

Gly Arg Ser Pro Gln
        325

<210> SEQ ID NO 41
<211> LENGTH: 325
<212> TYPE: PRT
<213> ORGANISM: Artificial Sequence
<220> FEATURE:
<223> OTHER INFORMATION: Fusion protein

<400> SEQUENCE: 41

Glu Ser Lys Tyr Gly Pro Pro Cys Pro Pro Cys Pro Ala Pro Glu Ala
1               5               10              15

Ala Gly Gly Pro Ser Val Phe Leu Phe Pro Pro Lys Pro Lys Asp Thr
        20              25              30

Leu Met Ile Ser Arg Thr Pro Glu Val Thr Cys Val Val Val Asp Val
        35              40              45

Ser Gln Glu Asp Pro Glu Val Gln Phe Asn Trp Tyr Val Asp Gly Val
        50              55              60

Glu Val His Asn Ala Lys Thr Lys Pro Arg Glu Glu Gln Phe Asn Ser
65              70              75              80

Thr Tyr Arg Val Val Ser Val Leu Thr Val Leu His Gln Asp Trp Leu
                85              90              95

Asn Gly Lys Glu Tyr Lys Cys Lys Val Ser Asn Lys Gly Leu Pro Ser
        100             105             110

Ser Ile Glu Lys Thr Ile Ser Lys Ala Lys Gly Gln Pro Arg Glu Pro
        115             120             125

Gln Val Tyr Thr Leu Pro Pro Ser Gln Glu Glu Met Thr Lys Asn Gln
        130             135             140

Val Ser Leu Thr Cys Leu Val Lys Gly Phe Tyr Pro Ser Asp Ile Ala
145             150             155             160

Val Glu Trp Glu Ser Asn Gly Gln Pro Glu Asn Asn Tyr Lys Thr Thr
                165             170             175

Pro Pro Val Leu Asp Ser Asp Gly Ser Phe Phe Leu Tyr Ser Arg Leu
        180             185             190

Thr Val Asp Lys Ser Arg Trp Gln Glu Gly Asn Val Phe Ser Cys Ser
        195             200             205

Val Met His Glu Ala Leu His Asn His Tyr Thr Gln Lys Ser Leu Ser
        210             215             220

Leu Ser Leu Gly Ala Glu Ala Ala Ala Lys Glu Ala Ala Ala Lys Glu
225             230             235             240

Ala Ala Ala Lys Glu Ala Ala Ala Lys Glu Ala Ala Ala Lys Glu Ala
                245             250             255

Ala Ala Lys Glu Ala Ala Ala Lys Glu Ala Ala Ala Lys Ala Ala Ala
        260             265             270

Cys Ala Glu Trp Ser Thr Ala Trp Gly Pro Cys Ser Thr Thr Cys Gly
        275             280             285
```

-continued

```
Leu Gly Met Ala Thr Arg Val Ser Asn Gln Asn Arg Phe Cys Arg Leu
    290                 295                 300

Glu Thr Gln Arg Arg Leu Cys Leu Ser Arg Pro Cys Pro Pro Ser Arg
305                 310                 315                 320

Gly Arg Ser Pro Gln
                325

<210> SEQ ID NO 42
<211> LENGTH: 44
<212> TYPE: PRT
<213> ORGANISM: Artificial Sequence
<220> FEATURE:
<223> OTHER INFORMATION: Modified CCN1 sequence

<400> SEQUENCE: 42

Cys Ala Val Gln Thr Thr Ser Trp Ser Gln Cys Ser Lys Thr Cys Gly
1               5                   10                  15

Thr Gly Ile Ser Thr Arg Val Thr Asn Asp Asn Pro Glu Cys Arg Leu
                20                  25                  30

Val Lys Glu Thr Arg Ile Cys Glu Val Arg Pro Cys
        35                  40

<210> SEQ ID NO 43
<211> LENGTH: 44
<212> TYPE: PRT
<213> ORGANISM: Artificial Sequence
<220> FEATURE:
<223> OTHER INFORMATION: Modified CCN2 sequence

<400> SEQUENCE: 43

Cys Ala Val Gln Thr Thr Glu Trp Ser Ala Cys Ser Lys Thr Cys Gly
1               5                   10                  15

Met Gly Ile Ser Thr Arg Val Thr Asn Asp Asn Ala Ser Cys Arg Leu
                20                  25                  30

Glu Lys Gln Ser Arg Leu Cys Met Val Arg Pro Cys
        35                  40

<210> SEQ ID NO 44
<211> LENGTH: 44
<212> TYPE: PRT
<213> ORGANISM: Artificial Sequence
<220> FEATURE:
<223> OTHER INFORMATION: Modified CCN3 sequence

<400> SEQUENCE: 44

Cys Ala Glu Gln Thr Thr Glu Trp Thr Ala Cys Ser Lys Ser Cys Gly
1               5                   10                  15

Met Gly Phe Ser Thr Arg Val Thr Asn Arg Asn Arg Gln Cys Glu Met
                20                  25                  30

Leu Lys Gln Thr Arg Leu Cys Met Val Arg Pro Cys
        35                  40

<210> SEQ ID NO 45
<211> LENGTH: 44
<212> TYPE: PRT
<213> ORGANISM: Artificial Sequence
<220> FEATURE:
<223> OTHER INFORMATION: Modified CCN4 sequence

<400> SEQUENCE: 45

Cys Ala Ala Tyr Thr Ser Pro Trp Ser Pro Cys Ser Thr Ser Cys Gly
1               5                   10                  15
```

Leu Gly Val Ser Thr Arg Ile Ser Asn Val Asn Ala Gln Cys Trp Pro
            20                  25                  30

Glu Gln Glu Ser Arg Leu Cys Asn Leu Arg Pro Cys
        35                  40

<210> SEQ ID NO 46
<211> LENGTH: 44
<212> TYPE: PRT
<213> ORGANISM: Artificial Sequence
<220> FEATURE:
<223> OTHER INFORMATION: Modified CCN6 sequence

<400> SEQUENCE: 46

Cys Ala Val Gln Ala Thr Lys Trp Thr Pro Cys Ser Arg Thr Cys Gly
1               5                   10                  15

Met Gly Ile Ser Asn Arg Val Thr Asn Glu Asn Ser Asn Cys Glu Met
            20                  25                  30

Arg Lys Glu Lys Arg Leu Cys Tyr Ile Gln Pro Cys
        35                  40

<210> SEQ ID NO 47
<211> LENGTH: 52
<212> TYPE: PRT
<213> ORGANISM: Artificial Sequence
<220> FEATURE:
<223> OTHER INFORMATION: Modified CCN1 sequence

<400> SEQUENCE: 47

Cys Ala Val Gln Thr Thr Ser Trp Ser Gln Cys Ser Lys Thr Cys Gly
1               5                   10                  15

Thr Gly Ile Ser Thr Arg Val Thr Asn Asp Asn Pro Glu Cys Arg Leu
            20                  25                  30

Val Lys Glu Thr Arg Ile Cys Glu Val Arg Pro Cys Gly Gln Pro Val
        35                  40                  45

Tyr Ser Ser Leu
    50

<210> SEQ ID NO 48
<211> LENGTH: 52
<212> TYPE: PRT
<213> ORGANISM: Artificial Sequence
<220> FEATURE:
<223> OTHER INFORMATION: Modified CCN2 sequence

<400> SEQUENCE: 48

Cys Ala Val Gln Thr Thr Glu Trp Ser Ala Cys Ser Lys Thr Cys Gly
1               5                   10                  15

Met Gly Ile Ser Thr Arg Val Thr Asn Asp Asn Ala Ser Cys Arg Leu
            20                  25                  30

Glu Lys Gln Ser Arg Leu Cys Met Val Arg Pro Cys Glu Ala Asp Leu
        35                  40                  45

Glu Glu Asn Ile
    50

<210> SEQ ID NO 49
<211> LENGTH: 53
<212> TYPE: PRT
<213> ORGANISM: Artificial Sequence
<220> FEATURE:
<223> OTHER INFORMATION: Modified CCN3 sequence

<400> SEQUENCE: 49

```
Cys Ala Glu Gln Thr Thr Glu Trp Thr Ala Cys Ser Lys Ser Cys Gly
1               5                   10                  15

Met Gly Phe Ser Thr Arg Val Thr Asn Arg Asn Arg Gln Cys Glu Met
            20                  25                  30

Leu Lys Gln Thr Arg Leu Cys Met Val Arg Pro Cys Glu Gln Glu Pro
        35                  40                  45

Glu Gln Pro Thr Asp
        50
```

```
<210> SEQ ID NO 50
<211> LENGTH: 52
<212> TYPE: PRT
<213> ORGANISM: Artificial Sequence
<220> FEATURE:
<223> OTHER INFORMATION: Modified CCN4 sequence

<400> SEQUENCE: 50
```

```
Cys Ala Ala Tyr Thr Ser Pro Trp Ser Pro Cys Ser Thr Ser Cys Gly
1               5                   10                  15

Leu Gly Val Ser Thr Arg Ile Ser Asn Val Asn Ala Gln Cys Trp Pro
            20                  25                  30

Glu Gln Glu Ser Arg Leu Cys Asn Leu Arg Pro Cys Asp Val Asp Ile
        35                  40                  45

His Thr Leu Ile
        50
```

```
<210> SEQ ID NO 51
<211> LENGTH: 55
<212> TYPE: PRT
<213> ORGANISM: Artificial Sequence
<220> FEATURE:
<223> OTHER INFORMATION: Modified CCN6 sequence

<400> SEQUENCE: 51
```

```
Cys Ala Val Gln Ala Thr Lys Trp Thr Pro Cys Ser Arg Thr Cys Gly
1               5                   10                  15

Met Gly Ile Ser Asn Arg Val Thr Asn Glu Asn Ser Asn Cys Glu Met
            20                  25                  30

Arg Lys Glu Lys Arg Leu Cys Tyr Ile Gln Pro Cys Asp Ser Asn Ile
        35                  40                  45

Leu Lys Thr Ile Lys Ile Pro
    50                  55
```

```
<210> SEQ ID NO 52
<211> LENGTH: 585
<212> TYPE: PRT
<213> ORGANISM: Homo sapiens

<400> SEQUENCE: 52
```

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80
```

-continued

```
Arg Glu Thr Tyr Gly Glu Met Ala Asp Cys Cys Ala Lys Gln Glu Pro
              85                  90                  95

Glu Arg Asn Glu Cys Phe Leu Gln His Lys Asp Asp Asn Pro Asn Leu
         100                 105                 110

Pro Arg Leu Val Arg Pro Glu Val Asp Val Met Cys Thr Ala Phe His
         115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
              165                 170                 175

Cys Leu Leu Pro Lys Leu Asp Glu Leu Arg Asp Glu Gly Lys Ala Ser
         180                 185                 190

Ser Ala Lys Gln Arg Leu Lys Cys Ala Ser Leu Gln Lys Phe Gly Glu
         195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
              245                 250                 255

Arg Ala Asp Leu Ala Lys Tyr Ile Cys Glu Asn Gln Asp Ser Ile Ser
         260                 265                 270

Ser Lys Leu Lys Glu Cys Cys Glu Lys Pro Leu Leu Glu Lys Ser His
         275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
              325                 330                 335

Arg His Pro Asp Tyr Ser Val Val Leu Leu Leu Arg Leu Ala Lys Thr
         340                 345                 350

Tyr Glu Thr Thr Leu Glu Lys Cys Cys Ala Ala Ala Asp Pro His Glu
         355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
              405                 410                 415

Gln Val Ser Thr Pro Thr Leu Val Glu Val Ser Arg Asn Leu Gly Lys
         420                 425                 430

Val Gly Ser Lys Cys Cys Lys His Pro Glu Ala Lys Arg Met Pro Cys
         435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
              485                 490                 495
```

```
Tyr Val Pro Lys Glu Phe Asn Ala Glu Thr Phe Thr Phe His Ala Asp
            500             505             510

Ile Cys Thr Leu Ser Glu Lys Glu Arg Gln Ile Lys Lys Gln Thr Ala
        515             520             525

Leu Val Glu Leu Val Lys His Lys Pro Lys Ala Thr Lys Glu Gln Leu
        530             535             540

Lys Ala Val Met Asp Asp Phe Ala Ala Phe Val Glu Lys Cys Cys Lys
545             550             555             560

Ala Asp Asp Lys Glu Thr Cys Phe Ala Glu Glu Gly Lys Lys Leu Val
            565             570             575

Ala Ala Ser Gln Ala Ala Leu Gly Leu
            580             585

<210> SEQ ID NO 53
<211> LENGTH: 679
<212> TYPE: PRT
<213> ORGANISM: Homo sapiens

<400> SEQUENCE: 53

Val Pro Asp Lys Thr Val Arg Trp Cys Ala Val Ser Glu His Glu Ala
1               5               10              15

Thr Lys Cys Gln Ser Phe Arg Asp His Met Lys Ser Val Ile Pro Ser
            20              25              30

Asp Gly Pro Ser Val Ala Cys Val Lys Lys Ala Ser Tyr Leu Asp Cys
        35              40              45

Ile Arg Ala Ile Ala Ala Asn Glu Ala Asp Ala Val Thr Leu Asp Ala
        50              55              60

Gly Leu Val Tyr Asp Ala Tyr Leu Ala Pro Asn Asn Leu Lys Pro Val
65              70              75              80

Val Ala Glu Phe Tyr Gly Ser Lys Glu Asp Pro Gln Thr Phe Tyr Tyr
            85              90              95

Ala Val Ala Val Val Lys Lys Asp Ser Gly Phe Gln Met Asn Gln Leu
            100             105             110

Arg Gly Lys Lys Ser Cys His Thr Gly Leu Gly Arg Ser Ala Gly Trp
        115             120             125

Asn Ile Pro Ile Gly Leu Leu Tyr Cys Asp Leu Pro Glu Pro Arg Lys
        130             135             140

Pro Leu Glu Lys Ala Val Ala Asn Phe Phe Ser Gly Ser Cys Ala Pro
145             150             155             160

Cys Ala Asp Gly Thr Asp Phe Pro Gln Leu Cys Gln Leu Cys Pro Gly
            165             170             175

Cys Gly Cys Ser Thr Leu Asn Gln Tyr Phe Gly Tyr Ser Gly Ala Phe
            180             185             190

Lys Cys Leu Lys Asp Gly Ala Gly Asp Val Ala Phe Val Lys His Ser
        195             200             205

Thr Ile Phe Glu Asn Leu Ala Asn Lys Ala Asp Arg Asp Gln Tyr Glu
        210             215             220

Leu Leu Cys Leu Asp Asn Thr Arg Lys Pro Val Asp Glu Tyr Lys Asp
225             230             235             240

Cys His Leu Ala Gln Val Pro Ser His Thr Val Val Ala Arg Ser Met
            245             250             255

Gly Gly Lys Glu Asp Leu Ile Trp Glu Leu Leu Asn Gln Ala Gln Glu
            260             265             270

His Phe Gly Lys Asp Lys Ser Lys Glu Phe Gln Leu Phe Ser Ser Pro
        275             280             285
```

-continued

```
His Gly Lys Asp Leu Leu Phe Lys Asp Ser Ala His Gly Phe Leu Lys
    290                 295                 300

Val Pro Pro Arg Met Asp Ala Lys Met Tyr Leu Gly Tyr Glu Tyr Val
305                 310                 315                 320

Thr Ala Ile Arg Asn Leu Arg Glu Gly Thr Cys Pro Glu Ala Pro Thr
                325                 330                 335

Asp Glu Cys Lys Pro Val Lys Trp Cys Ala Leu Ser His His Glu Arg
                340                 345                 350

Leu Lys Cys Asp Glu Trp Ser Val Asn Ser Val Gly Lys Ile Glu Cys
                355                 360                 365

Val Ser Ala Glu Thr Thr Glu Asp Cys Ile Ala Lys Ile Met Asn Gly
    370                 375                 380

Glu Ala Asp Ala Met Ser Leu Asp Gly Gly Phe Val Tyr Ile Ala Gly
385                 390                 395                 400

Lys Cys Gly Leu Val Pro Val Leu Ala Glu Asn Tyr Asn Lys Ser Asp
                405                 410                 415

Asn Cys Glu Asp Thr Pro Glu Ala Gly Tyr Phe Ala Ile Ala Val Val
                420                 425                 430

Lys Lys Ser Ala Ser Asp Leu Thr Trp Asp Asn Leu Lys Gly Lys Lys
                435                 440                 445

Ser Cys His Thr Ala Val Gly Arg Thr Ala Gly Trp Asn Ile Pro Met
    450                 455                 460

Gly Leu Leu Tyr Asn Lys Ile Asn His Cys Arg Phe Asp Glu Phe Phe
465                 470                 475                 480

Ser Glu Gly Cys Ala Pro Gly Ser Lys Lys Asp Ser Ser Leu Cys Lys
                485                 490                 495

Leu Cys Met Gly Ser Gly Leu Asn Leu Cys Glu Pro Asn Asn Lys Glu
                500                 505                 510

Gly Tyr Tyr Gly Tyr Thr Gly Ala Phe Arg Cys Leu Val Glu Lys Gly
                515                 520                 525

Asp Val Ala Phe Val Lys His Gln Thr Val Pro Gln Asn Thr Gly Gly
    530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Glu Tyr Ala Asn
                565                 570                 575

Cys His Leu Ala Arg Ala Pro Asn His Ala Val Val Thr Arg Lys Asp
                580                 585                 590

Lys Glu Ala Cys Val His Lys Ile Leu Arg Gln Gln His Leu Phe
                595                 600                 605

Gly Ser Asn Val Thr Asp Cys Ser Gly Asn Phe Cys Leu Phe Arg Ser
    610                 615                 620

Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Glu Tyr Val
                645                 650                 655

Lys Ala Val Gly Asn Leu Arg Lys Cys Ser Thr Ser Ser Leu Leu Glu
                660                 665                 670

Ala Cys Thr Phe Arg Arg Pro
    675
```

<210> SEQ ID NO 54
<211> LENGTH: 232

<212> TYPE: PRT
<213> ORGANISM: Artificial Sequence
<220> FEATURE:
<223> OTHER INFORMATION: Modified Fc fragment

<400> SEQUENCE: 54

```
Glu Pro Lys Ser Gln Asp Lys Thr His Thr Gln Pro Pro Gln Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Cys Glu Glu Gln
65                  70                  75                  80

Tyr Gly Ser Thr Tyr Arg Cys Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Arg Cys His Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Lys Pro Val Leu Asp Ser Asp Gly Ser Phe Phe Leu Tyr
            180                 185                 190

Ser Thr Leu Thr Val Asp Lys Ser Arg Trp Gln Gln Gly Asn Val Phe
        195                 200                 205

Ser Cys Ser Val Leu His Glu Ala Leu His Asn His Tyr Thr Gln Lys
    210                 215                 220

Ser Leu Ser Leu Ser Pro Gly Lys
225                 230
```

<210> SEQ ID NO 55
<211> LENGTH: 227
<212> TYPE: PRT
<213> ORGANISM: Artificial Sequence
<220> FEATURE:
<223> OTHER INFORMATION: Modified Fc fragment

<400> SEQUENCE: 55

```
Glu Arg Lys Gln Gln Val Glu Gln Pro Pro Gln Pro Ala Pro Pro Val
1               5                   10                  15

Ala Gly Pro Ser Val Phe Leu Phe Pro Pro Lys Pro Lys Asp Thr Leu
            20                  25                  30

Tyr Ile Thr Arg Glu Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95
```

-continued

```
Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
            115                 120                 125

Val Tyr Thr Phe Pro Pro Ser Gln Glu Glu Met Thr Lys Asn Gln Val
    130                 135                 140

Ser Leu Arg Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Lys
                165                 170                 175

Pro Val Leu Asp Ser Asp Gly Ser Phe Arg Leu Glu Ser Arg Leu Thr
            180                 185                 190

Val Asp Lys Ser Arg Trp Gln Glu Gly Asn Val Phe Ser Cys Ser Val
            195                 200                 205

Met His Glu Ala Leu His Asn His Tyr Thr Gln Lys Ser Leu Ser Leu
    210                 215                 220

Ser Leu Gly
225

<210> SEQ ID NO 56
<211> LENGTH: 57
<212> TYPE: PRT
<213> ORGANISM: Homo sapiens

<400> SEQUENCE: 56

Cys Pro Glu Trp Ser Thr Ala Trp Gly Pro Cys Ser Thr Thr Cys Gly
1               5                   10                  15

Leu Gly Met Ala Thr Arg Val Ser Asn Gln Asn Arg Phe Cys Arg Leu
            20                  25                  30

Glu Thr Gln Arg Arg Leu Cys Leu Ser Arg Pro Cys Pro Pro Ser Arg
        35                  40                  45

Gly Arg Ser Pro Gln Asn Ser Ala Phe
    50                  55

<210> SEQ ID NO 57
<211> LENGTH: 6
<212> TYPE: PRT
<213> ORGANISM: Artificial Sequence
<220> FEATURE:
<223> OTHER INFORMATION: Linker

<400> SEQUENCE: 57

Ile Glu Gly Arg Met Asp
1               5

<210> SEQ ID NO 58
<211> LENGTH: 291
<212> TYPE: PRT
<213> ORGANISM: Artificial Sequence
<220> FEATURE:
<223> OTHER INFORMATION: Fusion protein

<400> SEQUENCE: 58

Cys Pro Glu Trp Ser Thr Ala Trp Gly Pro Cys Ser Thr Thr Cys Gly
1               5                   10                  15

Leu Gly Met Ala Thr Arg Val Ser Asn Gln Asn Arg Phe Cys Arg Leu
            20                  25                  30

Glu Thr Gln Arg Arg Leu Cys Leu Ser Arg Pro Cys Pro Pro Ser Arg
        35                  40                  45
```

-continued

```
Gly Arg Ser Pro Gln Asn Ser Ala Phe Ile Glu Gly Arg Met Asp Glu
    50              55              60

Ser Lys Tyr Gly Pro Pro Cys Pro Pro Cys Pro Ala Pro Glu Ala Ala
65              70              75              80

Gly Gly Pro Ser Val Phe Leu Phe Pro Pro Lys Pro Lys Asp Thr Leu
            85              90              95

Met Ile Ser Arg Thr Pro Glu Val Thr Cys Val Val Val Asp Val Ser
            100             105             110

Gln Glu Asp Pro Glu Val Gln Phe Asn Trp Tyr Val Asp Gly Val Glu
        115             120             125

Val His Asn Ala Lys Thr Lys Pro Arg Glu Glu Gln Phe Asn Ser Thr
    130             135             140

Tyr Arg Val Val Ser Val Leu Thr Val Leu His Gln Asp Trp Leu Asn
145             150             155             160

Gly Lys Glu Tyr Lys Cys Lys Val Ser Asn Lys Gly Leu Pro Ser Ser
            165             170             175

Ile Glu Lys Thr Ile Ser Lys Ala Lys Gly Gln Pro Arg Glu Pro Gln
            180             185             190

Val Tyr Thr Leu Pro Pro Ser Gln Glu Glu Met Thr Lys Asn Gln Val
        195             200             205

Ser Leu Thr Cys Leu Val Lys Gly Phe Tyr Pro Ser Asp Ile Ala Val
    210             215             220

Glu Trp Glu Ser Asn Gly Gln Pro Glu Asn Asn Tyr Lys Thr Thr Pro
225             230             235             240

Pro Val Leu Asp Ser Asp Gly Ser Phe Phe Leu Tyr Ser Arg Leu Thr
            245             250             255

Val Asp Lys Ser Arg Trp Gln Glu Gly Asn Val Phe Ser Cys Ser Val
            260             265             270

Met His Glu Ala Leu His Asn His Tyr Thr Gln Lys Ser Leu Ser Leu
        275             280             285

Ser Leu Gly
    290

<210> SEQ ID NO 59
<211> LENGTH: 309
<212> TYPE: PRT
<213> ORGANISM: Artificial Sequence
<220> FEATURE:
<223> OTHER INFORMATION: Fusion protein

<400> SEQUENCE: 59

Met Lys Trp Val Thr Phe Ile Ser Leu Leu Phe Leu Phe Ser Ser Ala
1               5               10              15

Tyr Ser Cys Pro Glu Trp Ser Thr Ala Trp Gly Pro Cys Ser Thr Thr
            20              25              30

Cys Gly Leu Gly Met Ala Thr Arg Val Ser Asn Gln Asn Arg Phe Cys
        35              40              45

Arg Leu Glu Thr Gln Arg Arg Leu Cys Leu Ser Arg Pro Cys Pro Pro
    50              55              60

Ser Arg Gly Arg Ser Pro Gln Asn Ser Ala Phe Ile Glu Gly Arg Met
65              70              75              80

Asp Glu Ser Lys Tyr Gly Pro Pro Cys Pro Pro Cys Pro Ala Pro Glu
            85              90              95

Ala Ala Gly Gly Pro Ser Val Phe Leu Phe Pro Pro Lys Pro Lys Asp
            100             105             110
```

```
Thr Leu Met Ile Ser Arg Thr Pro Glu Val Thr Cys Val Val Val Asp
        115                 120                 125

Val Ser Gln Glu Asp Pro Glu Val Gln Phe Asn Trp Tyr Val Asp Gly
    130                 135                 140

Val Glu Val His Asn Ala Lys Thr Lys Pro Arg Glu Glu Gln Phe Asn
145                 150                 155                 160

Ser Thr Tyr Arg Val Val Ser Val Leu Thr Val Leu His Gln Asp Trp
            165                 170                 175

Leu Asn Gly Lys Glu Tyr Lys Cys Lys Val Ser Asn Lys Gly Leu Pro
        180                 185                 190

Ser Ser Ile Glu Lys Thr Ile Ser Lys Ala Lys Gly Gln Pro Arg Glu
        195                 200                 205

Pro Gln Val Tyr Thr Leu Pro Pro Ser Gln Glu Glu Met Thr Lys Asn
    210                 215                 220

Gln Val Ser Leu Thr Cys Leu Val Lys Gly Phe Tyr Pro Ser Asp Ile
225                 230                 235                 240

Ala Val Glu Trp Glu Ser Asn Gly Gln Pro Glu Asn Asn Tyr Lys Thr
            245                 250                 255

Thr Pro Pro Val Leu Asp Ser Asp Gly Ser Phe Phe Leu Tyr Ser Arg
        260                 265                 270

Leu Thr Val Asp Lys Ser Arg Trp Gln Glu Gly Asn Val Phe Ser Cys
        275                 280                 285

Ser Val Met His Glu Ala Leu His Asn His Tyr Thr Gln Lys Ser Leu
    290                 295                 300

Ser Leu Ser Leu Gly
305
```

```
<210> SEQ ID NO 60
<211> LENGTH: 936
<212> TYPE: DNA
<213> ORGANISM: Artificial Sequence
<220> FEATURE:
<223> OTHER INFORMATION: Fusion protein

<400> SEQUENCE: 60
gccaccatga atgggtcac ctttatctcc ctgctgttcc tgttctcctc cgcctactct      60
tgccctgagt ggtctacagc ttggggccct tgctctacca cctgtggact cggcatggcc     120
accagagtgt ctaaccagaa cagattctgc cggctggaaa cccagcggag actgtgtctg     180
tccagacctt gtcctcctag ccggggcaga tcccctcaga actctgcctt atcgagggc      240 agaatggacg agtctaagta cggccctcct tgtccaccat gtcctgctcc agaagctgct     300
ggcggccctt ccgtgtttct gttcctcca aagcctaagg acaccctgat gatctctcgg     360 accctgaag tgacctgcgt ggtggtggat gtgtcccaag aggatcccga ggtgcagttc     420
aattggtacg tggacggcgt ggaagtgcac aacgccaaga ccaagcctag agaggaacag     480
ttcaactcca cctacagagt ggtgtccgtg ctgaccgtgc tgcaccagga ttggctgaac     540
ggcaaagagt acaagtgcaa ggtgtccaac aagggcctgc cttccagcat cgaaaagacc     600
atctccaagg ccaagggcca gcctagggaa ccccaggttt acaccctgcc tccaagccaa     660
gaggaaatga ccaagaacca ggtgtccctg acctgcctgg tcaagggctt ctacccttcc     720
gatatcgccg tggaatggga gagcaatggc cagcctgaga caactacaa gaccacacct      780 cctgtgctgg actccgacgg ctccttcttt ctgtactccc gcctgaccgt ggacaagtcc     840
agatggcaag agggcaacgt gttctcctgc tccgtgatgc acgaggccct gcacaatcac     900
```

```
tacacccaga agtccctgtc tctgtccctg ggctaa                                    936

<210> SEQ ID NO 61
<211> LENGTH: 1009
<212> TYPE: DNA
<213> ORGANISM: Artificial Sequence
<220> FEATURE:
<223> OTHER INFORMATION: Fusion protein

<400> SEQUENCE: 61
ggggacaagt ttgtacaaaa aagcaggcta tggtaccgcc accatgaaat gggtcacctt     60
tatctccctg ctgttcctgt tctcctccgc ctactcttgc cctgagtggt ctacagcttg    120
gggcccttgc tctaccacct gtggactcgg catggccacc agagtgtcta accagaacag    180
attctgccgg ctggaaaccc agcggagact gtgtctgtcc agaccttgtc ctcctagccg    240
gggcagatcc cctcagaact ctgcctttat cgagggcaga atggacgagt ctaagtacgg    300
ccctccttgt ccaccatgtc ctgctccaga agctgctggc ggcccttccg tgtttctgtt    360
ccctccaaag cctaaggaca ccctgatgat ctctcggacc cctgaagtga cctgcgtggt    420
ggtggatgtg tcccaagagg atcccgaggt gcagttcaat tggtacgtgg acggcgtgga    480
agtgcacaac gccaagacca gcctagaga ggaacagttc aactccacct acagagtggt    540
gtccgtgctg accgtgctgc accaggattg gctgaacggc aaagagtaca agtgcaaggt    600
gtccaacaag ggcctgcctt ccagcatcga aaagaccatc tccaaggcca agggccagcc    660
tagggaaccc caggtttaca ccctgcctcc aagccaagag aaatgaccca gaaccaggt    720 gtccctgacc tgcctggtca agggcttcta cccttccgat atcgccgtgg aatgggagag    780
caatggccag cctgagaaca actacaagac cacacctcct gtgctggact ccgacggctc    840
cttctttctg tactcccgcc tgaccgtgga caagtccaga tggcaagagg caacgtgtt    900 ctcctgctcc gtgatgcacg aggccctgca caatcactac acccagaagt ccctgtctct    960
gtccctgggc taatctagaa acccagcttt cttgtacaaa gtggtcccc               1009

<210> SEQ ID NO 62
<211> LENGTH: 56
<212> TYPE: PRT
<213> ORGANISM: Artificial Sequence
<220> FEATURE:
<223> OTHER INFORMATION: Modified CCN5 sequence

<400> SEQUENCE: 62

Cys Pro Glu Trp Ser Thr Ala Trp Gly Pro Cys Ser Thr Thr Cys Gly
1               5                   10                  15

Leu Gly Met Ala Thr Arg Val Ser Asn Gln Asn Arg Phe Cys Arg Leu
            20                  25                  30

Glu Thr Gln Arg Arg Leu Cys Leu Ser Arg Pro Cys Pro Pro Ser Arg
        35                  40                  45

Gly Arg Ser Leu Gln Asn Ser Ala
    50                  55

<210> SEQ ID NO 63
<211> LENGTH: 4
<212> TYPE: PRT
<213> ORGANISM: Artificial Sequence
<220> FEATURE:
<223> OTHER INFORMATION: Linker

<400> SEQUENCE: 63
```

-continued

Gly Arg Met Asp
1

<210> SEQ ID NO 64
<211> LENGTH: 306
<212> TYPE: PRT
<213> ORGANISM: Artificial Sequence
<220> FEATURE:
<223> OTHER INFORMATION: Fusion protein

<400> SEQUENCE: 64

Met Lys Trp Val Thr Phe Ile Ser Leu Leu Phe Leu Phe Ser Ser Ala
1               5                   10                  15

Tyr Ser Cys Pro Glu Trp Ser Thr Ala Trp Gly Pro Cys Ser Thr Thr
            20                  25                  30

Cys Gly Leu Gly Met Ala Thr Arg Val Ser Asn Gln Asn Arg Phe Cys
        35                  40                  45

Arg Leu Glu Thr Gln Arg Arg Leu Cys Leu Ser Arg Pro Cys Pro Pro
    50                  55                  60

Ser Arg Gly Arg Ser Leu Gln Asn Ser Ala Gly Arg Met Asp Glu Ser
65                  70                  75                  80

Lys Tyr Gly Pro Pro Cys Pro Pro Cys Pro Ala Pro Glu Ala Ala Gly
                85                  90                  95

Gly Pro Ser Val Phe Leu Phe Pro Pro Lys Pro Lys Asp Thr Leu Met
            100                 105                 110

Ile Ser Arg Thr Pro Glu Val Thr Cys Val Val Val Asp Val Ser Gln
            115                 120                 125

Glu Asp Pro Glu Val Gln Phe Asn Trp Tyr Val Asp Gly Val Glu Val
        130                 135                 140

His Asn Ala Lys Thr Lys Pro Arg Glu Glu Gln Phe Asn Ser Thr Tyr
145                 150                 155                 160

Arg Val Val Ser Val Leu Thr Val Leu His Gln Asp Trp Leu Asn Gly
                165                 170                 175

Lys Glu Tyr Lys Cys Lys Val Ser Asn Lys Gly Leu Pro Ser Ser Ile
            180                 185                 190

Glu Lys Thr Ile Ser Lys Ala Lys Gly Gln Pro Arg Glu Pro Gln Val
            195                 200                 205

Tyr Thr Leu Pro Pro Ser Gln Glu Glu Met Thr Lys Asn Gln Val Ser
    210                 215                 220

Leu Thr Cys Leu Val Lys Gly Phe Tyr Pro Ser Asp Ile Ala Val Glu
225                 230                 235                 240

Trp Glu Ser Asn Gly Gln Pro Glu Asn Asn Tyr Lys Thr Thr Pro Pro
                245                 250                 255

Val Leu Asp Ser Asp Gly Ser Phe Phe Leu Tyr Ser Arg Leu Thr Val
            260                 265                 270

Asp Lys Ser Arg Trp Gln Glu Gly Asn Val Phe Ser Cys Ser Val Met
        275                 280                 285

His Glu Ala Leu His Asn His Tyr Thr Gln Lys Ser Leu Ser Leu Ser
        290                 295                 300

Leu Gly
305

<210> SEQ ID NO 65
<211> LENGTH: 6
<212> TYPE: PRT
<213> ORGANISM: Artificial Sequence
<220> FEATURE:

<223> OTHER INFORMATION: Linker

<400> SEQUENCE: 65

Thr Glu Gly Arg Met Asp
1               5

<210> SEQ ID NO 66
<211> LENGTH: 305
<212> TYPE: PRT
<213> ORGANISM: Artificial Sequence
<220> FEATURE:
<223> OTHER INFORMATION: Fusion protein

<400> SEQUENCE: 66

Met Lys Trp Val Thr Phe Ile Ser Leu Leu Phe Leu Phe Ser Ser Ala
1               5                   10                  15

Tyr Ser Cys Pro Glu Trp Ser Thr Ala Trp Gly Pro Cys Ser Thr Thr
                20                  25                  30

Cys Gly Leu Gly Met Ala Thr Arg Val Ser Asn Gln Asn Arg Phe Cys
            35                  40                  45

Arg Leu Glu Thr Gln Arg Arg Leu Cys Leu Ser Arg Pro Cys Pro Pro
        50                  55                  60

Ser Arg Gly Arg Ser Pro Gln Thr Glu Gly Arg Met Asp Glu Ser Lys
65                  70                  75                  80

Tyr Gly Pro Pro Cys Pro Pro Cys Pro Ala Pro Glu Ala Ala Gly Gly
                85                  90                  95

Pro Ser Val Phe Leu Phe Pro Pro Lys Pro Lys Asp Thr Leu Met Ile
                100                 105                 110

Ser Arg Thr Pro Glu Val Thr Cys Val Val Val Asp Val Ser Gln Glu
            115                 120                 125

Asp Pro Glu Val Gln Phe Asn Trp Tyr Val Asp Gly Val Glu Val His
        130                 135                 140

Asn Ala Lys Thr Lys Pro Arg Glu Glu Gln Phe Asn Ser Thr Tyr Arg
145                 150                 155                 160

Val Val Ser Val Leu Thr Val Leu His Gln Asp Trp Leu Asn Gly Lys
                165                 170                 175

Glu Tyr Lys Cys Lys Val Ser Asn Lys Gly Leu Pro Ser Ser Ile Glu
            180                 185                 190

Lys Thr Ile Ser Lys Ala Lys Gly Gln Pro Arg Glu Pro Gln Val Tyr
            195                 200                 205

Thr Leu Pro Pro Ser Gln Glu Glu Met Thr Lys Asn Gln Val Ser Leu
        210                 215                 220

Thr Cys Leu Val Lys Gly Phe Tyr Pro Ser Asp Ile Ala Val Glu Trp
225                 230                 235                 240

Glu Ser Asn Gly Gln Pro Glu Asn Asn Tyr Lys Thr Thr Pro Pro Val
                245                 250                 255

Leu Asp Ser Asp Gly Ser Phe Phe Leu Tyr Ser Arg Leu Thr Val Asp
                260                 265                 270

Lys Ser Arg Trp Gln Glu Gly Asn Val Phe Ser Cys Ser Val Met His
            275                 280                 285

Glu Ala Leu His Asn His Tyr Thr Gln Lys Ser Leu Ser Leu Ser Leu
        290                 295                 300

Gly
305

<210> SEQ ID NO 67

-continued

```
<211> LENGTH: 8
<212> TYPE: PRT
<213> ORGANISM: Artificial Sequence
<220> FEATURE:
<223> OTHER INFORMATION: Linker

<400> SEQUENCE: 67

Thr Ala Glu Ala Ala Ala Lys Ala
1               5

<210> SEQ ID NO 68
<211> LENGTH: 307
<212> TYPE: PRT
<213> ORGANISM: Artificial Sequence
<220> FEATURE:
<223> OTHER INFORMATION: Fusion protein

<400> SEQUENCE: 68

Met Lys Trp Val Thr Phe Ile Ser Leu Leu Phe Leu Phe Ser Ser Ala
1               5                   10                  15

Tyr Ser Cys Pro Glu Trp Ser Thr Ala Trp Gly Pro Cys Ser Thr Thr
            20                  25                  30

Cys Gly Leu Gly Met Ala Thr Arg Val Ser Asn Gln Asn Arg Phe Cys
        35                  40                  45

Arg Leu Glu Thr Gln Arg Arg Leu Cys Leu Ser Arg Pro Cys Pro Pro
    50                  55                  60

Ser Arg Gly Arg Ser Pro Gln Thr Ala Glu Ala Ala Lys Ala Glu
65                  70                  75                  80

Ser Lys Tyr Gly Pro Pro Cys Pro Pro Cys Pro Ala Pro Glu Ala Ala
                85                  90                  95

Gly Gly Pro Ser Val Phe Leu Phe Pro Pro Lys Pro Lys Asp Thr Leu
                100                 105                 110

Met Ile Ser Arg Thr Pro Glu Val Thr Cys Val Val Val Asp Val Ser
            115                 120                 125

Gln Glu Asp Pro Glu Val Gln Phe Asn Trp Tyr Val Asp Gly Val Glu
            130                 135                 140

Val His Asn Ala Lys Thr Lys Pro Arg Glu Glu Gln Phe Asn Ser Thr
145                 150                 155                 160

Tyr Arg Val Val Ser Val Leu Thr Val Leu His Gln Asp Trp Leu Asn
                165                 170                 175

Gly Lys Glu Tyr Lys Cys Lys Val Ser Asn Lys Gly Leu Pro Ser Ser
                180                 185                 190

Ile Glu Lys Thr Ile Ser Lys Ala Lys Gly Gln Pro Arg Glu Pro Gln
            195                 200                 205

Val Tyr Thr Leu Pro Pro Ser Gln Glu Glu Met Thr Lys Asn Gln Val
    210                 215                 220

Ser Leu Thr Cys Leu Val Lys Gly Phe Tyr Pro Ser Asp Ile Ala Val
225                 230                 235                 240

Glu Trp Glu Ser Asn Gly Gln Pro Glu Asn Asn Tyr Lys Thr Thr Pro
                245                 250                 255

Pro Val Leu Asp Ser Asp Gly Ser Phe Phe Leu Tyr Ser Arg Leu Thr
                260                 265                 270

Val Asp Lys Ser Arg Trp Gln Glu Gly Asn Val Phe Ser Cys Ser Val
                275                 280                 285

Met His Glu Ala Leu His Asn His Tyr Thr Gln Lys Ser Leu Ser Leu
    290                 295                 300

Ser Leu Gly
```

305

<210> SEQ ID NO 69
<211> LENGTH: 304
<212> TYPE: PRT
<213> ORGANISM: Artificial Sequence
<220> FEATURE:
<223> OTHER INFORMATION: Fusion protein

<400> SEQUENCE: 69

Met Lys Trp Val Thr Phe Ile Ser Leu Leu Phe Leu Phe Ser Ser Ala
1               5                   10                  15

Tyr Ser Cys Pro Glu Trp Ser Thr Ala Trp Gly Pro Cys Ser Thr Thr
            20                  25                  30

Cys Gly Leu Gly Met Ala Thr Arg Val Ser Asn Gln Asn Arg Phe Cys
        35                  40                  45

Arg Leu Glu Thr Gln Arg Arg Leu Cys Leu Ser Arg Pro Cys Pro Pro
    50                  55                  60

Ser Arg Gly Arg Ser Pro Gln Thr Glu Gly Arg Met Asp Glu Arg Lys
65                  70                  75                  80

Cys Cys Val Glu Cys Pro Pro Cys Pro Ala Pro Pro Val Ala Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser Gln Glu Asp
            115                 120                 125

Pro Glu Val Gln Phe Asn Trp Tyr Val Asp Gly Val Glu Val His Asn
            130                 135                 140

Ala Lys Thr Lys Pro Arg Glu Glu Gln Phe Asn Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Gly Leu Pro Ser Ser Ile Glu Lys
            180                 185                 190

Thr Ile Ser Lys Ala Lys Gly Gln Pro Arg Glu Pro Gln Val Tyr Thr
            195                 200                 205

Leu Pro Pro Ser Gln Glu Glu Met Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Arg Leu Thr Val Asp Lys
            260                 265                 270

Ser Arg Trp Gln Glu Gly Asn Val Phe Ser Cys Ser Val Met His Glu
            275                 280                 285

Ala Leu His Asn His Tyr Thr Gln Lys Ser Leu Ser Leu Ser Leu Gly
    290                 295                 300

<210> SEQ ID NO 70
<211> LENGTH: 294
<212> TYPE: PRT
<213> ORGANISM: Artificial Sequence
<220> FEATURE:
<223> OTHER INFORMATION: Fusion protein

<400> SEQUENCE: 70

```
Met Lys Trp Val Thr Phe Ile Ser Leu Leu Phe Leu Phe Ser Ser Ala
1               5                   10                  15

Tyr Ser Cys Ala Glu Trp Ser Thr Ala Trp Gly Pro Cys Ser Thr Thr
            20                  25                  30

Cys Gly Leu Gly Met Ala Thr Arg Val Ser Asn Gln Asn Arg Phe Cys
        35                  40                  45

Arg Leu Glu Thr Gln Arg Arg Leu Cys Leu Ser Arg Pro Cys Glu Ala
    50                  55                  60

Ala Ala Lys Glu Arg Lys Cys Cys Val Glu Cys Pro Pro Cys Pro Ala
65                  70                  75                  80

Pro Pro Val Ala Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser Gln Glu Asp Pro Glu Val Gln Phe Asn Trp Tyr Val Asp
        115                 120                 125

Gly Val Glu Val His Asn Ala Lys Thr Lys Pro Arg Glu Glu Gln Phe
    130                 135                 140

Asn Ser Thr Tyr Arg Val Val Ser Val Leu Thr Val Leu His Gln Asp
145                 150                 155                 160

Trp Leu Asn Gly Lys Glu Tyr Lys Cys Lys Val Ser Asn Lys Gly Leu
                165                 170                 175

Pro Ser Ser Ile Glu Lys Thr Ile Ser Lys Ala Lys Gly Gln Pro Arg
            180                 185                 190

Glu Pro Gln Val Tyr Thr Leu Pro Pro Ser Gln Glu Glu Met Thr Lys
        195                 200                 205

Asn Gln Val Ser Leu Thr Cys Leu Val Lys Gly Phe Tyr Pro Ser Asp
    210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Arg Leu Thr Val Asp Lys Ser Arg Trp Gln Glu Gly Asn Val Phe Ser
            260                 265                 270

Cys Ser Val Met His Glu Ala Leu His Asn His Tyr Thr Gln Lys Ser
        275                 280                 285

Leu Ser Leu Ser Leu Gly
    290
```

```
<210> SEQ ID NO 71
<211> LENGTH: 891
<212> TYPE: DNA
<213> ORGANISM: Artificial Sequence
<220> FEATURE:
<223> OTHER INFORMATION: Fusion protein

<400> SEQUENCE: 71
gccaccatga aatgggtcac ctttatctcc ctgctgttcc tgttctcctc cgcctactct        60
tgcgccgagt ggtctacagc ttggggccct tgttctacca cctgtggcct cggcatggcc       120
accagagtgt ccaaccagaa cagattctgc cggctggaaa cccagcggag actgtgtttg       180
tccagacctt gcgaggccgc tgccaaagaa agaaagtgct gcgtggaatg ccctccttgt       240
cctgctcctc ctgtggctgg cccttccgtg tttctgttcc ctccaaagcc taaggacacc       300
ctgatgatct ctcggacccc tgaagtgacc tgcgtggtgg tggatgtgtc ccaagaggat       360
```

-continued

```
cccgaggtgc agttcaattg gtacgtggac ggcgtggaag tgcacaacgc caagaccaag      420
cctagagagg aacagttcaa ctccacctac agagtggtgt ccgtgctgac cgtgctgcac      480
caggattggc tgaacggcaa agagtacaag tgcaaggtgt ccaacaaggg actgccctcc      540
agcatcgaaa agaccatctc caaggccaag ggacagccca gagaacccca ggtgtacaca      600
ctgcctccaa gccaagagga aatgaccaag aaccaggtgt ccctgacctg cctggtcaag      660
ggcttctacc cttccgatat cgccgtggaa tgggagtcca atggccagcc tgagaacaac      720
tacaagacca cacctccagt gctggactcc gacggctcct tctttctgta ctcccgcctg      780
accgtggaca gtccagatg gcaagagggc aacgtgttct cctgctccgt gatgcacgag      840
gccctgcaca atcactacac ccagaagtcc ctgtctctgt ccctgggcta a             891
```

```
<210> SEQ ID NO 72
<211> LENGTH: 964
<212> TYPE: DNA
<213> ORGANISM: Artificial Sequence
<220> FEATURE:
<223> OTHER INFORMATION: Fusion protein

<400> SEQUENCE: 72
ggggacaagt ttgtacaaaa aagcaggcta tggtaccgcc accatgaaat gggtcacctt       60
tatctccctg ctgttcctgt tctcctccgc ctactcttgc gccgagtggt ctacagcttg      120
gggcccttgt tctaccacct gtggcctcgg catggccacc agagtgtcca accagaacag      180
attctgccgg ctggaaaccc agcggagact gtgtttgtcc agaccttgcg aggccgctgc      240
caaagaaaga aagtgctgcg tggaatgccc tccttgtcct gctcctcctg tggctggccc      300
ttccgtgttt ctgttccctc caaagcctaa ggacaccctg atgatctctc ggacccctga      360
agtgacctgc gtggtggtgg atgtgtccca gaggatccc gaggtgcagt tcaattggta      420
cgtggacggc gtggaagtgc acaacgccaa gaccaagcct agagaggaac agttcaactc      480
cacctacaga gtggtgtccg tgctgaccgt gctgcaccag gattggctga acggcaaaga      540
gtacaagtgc aaggtgtcca acaagggact gccctccagc atcgaaaaga ccatctccaa      600
ggccaaggga cagcccagag aaccccaggt gtacacactg cctccaagcc aagaggaaat      660
gaccaagaac caggtgtccc tgacctgcct ggtcaagggc ttctacccctt ccgatatcgc      720 cgtggaatgg gagtccaatg ccagcctga gaacaactac aagaccacac tccagtgct      780 ggactccgac ggctccttct ttctgtactc ccgcctgacc gtggacaagt ccagatggca      840
agagggcaac gtgttctcct gctccgtgat gcacgaggcc ctgcacaatc actacaccca      900
gaagtccctg tctctgtccc tgggctaatc tagaaaccca gctttcttgt acaaagtggt      960
cccc                                                                   964
```

```
<210> SEQ ID NO 73
<211> LENGTH: 276
<212> TYPE: PRT
<213> ORGANISM: Artificial Sequence
<220> FEATURE:
<223> OTHER INFORMATION: Fusion protein

<400> SEQUENCE: 73

Cys Ala Glu Gln Thr Thr Glu Trp Thr Ala Cys Ser Lys Ser Cys Gly
1               5                   10                  15

Met Gly Phe Ser Thr Arg Val Thr Asn Arg Asn Arg Gln Cys Glu Met
            20                  25                  30

Leu Lys Gln Thr Arg Leu Cys Met Val Arg Pro Cys Glu Ala Ala Ala
```

-continued

```
            35                  40                  45

Lys Glu Arg Lys Cys Cys Val Glu Cys Pro Pro Cys Pro Ala Pro Pro
        50                  55                  60

Val Ala Gly Pro Ser Val Phe Leu Phe Pro Pro Lys Pro Lys Asp Thr
65                  70                  75                  80

Leu Met Ile Ser Arg Thr Pro Glu Val Thr Cys Val Val Val Asp Val
                85                  90                  95

Ser Gln Glu Asp Pro Glu Val Gln Phe Asn Trp Tyr Val Asp Gly Val
            100                 105                 110

Glu Val His Asn Ala Lys Thr Lys Pro Arg Glu Glu Gln Phe Asn Ser
            115                 120                 125

Thr Tyr Arg Val Val Ser Val Leu Thr Val Leu His Gln Asp Trp Leu
        130                 135                 140

Asn Gly Lys Glu Tyr Lys Cys Lys Val Ser Asn Lys Gly Leu Pro Ser
145                 150                 155                 160

Ser Ile Glu Lys Thr Ile Ser Lys Ala Lys Gly Gln Pro Arg Glu Pro
                165                 170                 175

Gln Val Tyr Thr Leu Pro Pro Ser Gln Glu Glu Met Thr Lys Asn Gln
            180                 185                 190

Val Ser Leu Thr Cys Leu Val Lys Gly Phe Tyr Pro Ser Asp Ile Ala
        195                 200                 205

Val Glu Trp Glu Ser Asn Gly Gln Pro Glu Asn Asn Tyr Lys Thr Thr
        210                 215                 220

Pro Pro Val Leu Asp Ser Asp Gly Ser Phe Phe Leu Tyr Ser Arg Leu
225                 230                 235                 240

Thr Val Asp Lys Ser Arg Trp Gln Glu Gly Asn Val Phe Ser Cys Ser
                245                 250                 255

Val Met His Glu Ala Leu His Asn His Tyr Thr Gln Lys Ser Leu Ser
            260                 265                 270

Leu Ser Leu Gly
        275

<210> SEQ ID NO 74
<211> LENGTH: 294
<212> TYPE: PRT
<213> ORGANISM: Artificial Sequence
<220> FEATURE:
<223> OTHER INFORMATION: Fusion protein

<400> SEQUENCE: 74

Met Lys Trp Val Thr Phe Ile Ser Leu Leu Phe Leu Phe Ser Ser Ala
1               5                   10                  15

Tyr Ser Cys Ala Glu Gln Thr Thr Glu Trp Thr Ala Cys Ser Lys Ser
            20                  25                  30

Cys Gly Met Gly Phe Ser Thr Arg Val Thr Asn Arg Asn Arg Gln Cys
        35                  40                  45

Glu Met Leu Lys Gln Thr Arg Leu Cys Met Val Arg Pro Cys Glu Ala
        50                  55                  60

Ala Ala Lys Glu Arg Lys Cys Cys Val Glu Cys Pro Pro Cys Pro Ala
65                  70                  75                  80

Pro Pro Val Ala Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser Gln Glu Asp Pro Glu Val Gln Phe Asn Trp Tyr Val Asp
```

```
        115              120              125

Gly Val Glu Val His Asn Ala Lys Thr Lys Pro Arg Glu Glu Gln Phe
    130              135              140

Asn Ser Thr Tyr Arg Val Val Ser Val Leu Thr Val Leu His Gln Asp
145              150              155              160

Trp Leu Asn Gly Lys Glu Tyr Lys Cys Lys Val Ser Asn Lys Gly Leu
                165              170              175

Pro Ser Ser Ile Glu Lys Thr Ile Ser Lys Ala Lys Gly Gln Pro Arg
            180              185              190

Glu Pro Gln Val Tyr Thr Leu Pro Pro Ser Gln Glu Glu Met Thr Lys
            195              200              205

Asn Gln Val Ser Leu Thr Cys Leu Val Lys Gly Phe Tyr Pro Ser Asp
    210              215              220

Ile Ala Val Glu Trp Glu Ser Asn Gly Gln Pro Glu Asn Asn Tyr Lys
225              230              235              240

Thr Thr Pro Pro Val Leu Asp Ser Asp Gly Ser Phe Phe Leu Tyr Ser
            245              250              255

Arg Leu Thr Val Asp Lys Ser Arg Trp Gln Glu Gly Asn Val Phe Ser
            260              265              270

Cys Ser Val Met His Glu Ala Leu His Asn His Tyr Thr Gln Lys Ser
    275              280              285

Leu Ser Leu Ser Leu Gly
    290
```

```
<210> SEQ ID NO 75
<211> LENGTH: 891
<212> TYPE: DNA
<213> ORGANISM: Artificial Sequence
<220> FEATURE:
<223> OTHER INFORMATION: Fusion protein

<400> SEQUENCE: 75
gccaccatga aatgggtcac ctttatctcc ctgctgttcc tgttctcctc cgcctactct      60
tgtgccgagc agaccacaga gtggaccgcc tgctctaagt cttgcggcat gggcttctcc     120
accagagtga ccaaccggaa cagacagtgc gagatgctga agcagacccg gctgtgtatg     180
gttcgacctt gcgaggccgc tgccaaagaa agaaagtgct gcgtggaatg ccctccttgt     240
cctgctcctc ctgtggctgg cccttccgtg tttctgttcc ctccaaagcc taaggacacc     300
ctgatgatct ctcggacccc tgaagtgacc tgcgtggtgg tggatgtgtc caagaggat     360 cccgaggtgc agttcaattg gtacgtggac ggcgtggaag tgcacaacgc caagaccaag     420
cctagagagg aacagttcaa ctccacctac agagtggtgt ccgtgctgac cgtgctgcac     480
caggattggc tgaacggcaa agagtacaag tgcaaggtgt ccaacaaggg cctgccttcc     540
agcatcgaaa agaccatctc caaggccaag ggacagccca gagaacccca ggtgtacaca     600
ctgcctccaa gccaagagga aatgaccaag aaccaggtgt ccctgacctg cctggtcaag     660
ggcttctacc cttccgatat cgccgtggaa tgggagtcca atggccagcc tgagaacaac     720
tacaagacca cacctccagt gctggactcc gacggctcct tctttctgta ctcccgcctg     780
accgtggaca agtccagatg caagagggc aacgtgttct cctgctccgt gatgcacgag     840
gccctgcaca tcactacac ccagaagtcc ctgtctctgt ccctgggcta a             891
```

```
<210> SEQ ID NO 76
<211> LENGTH: 964
<212> TYPE: DNA
```

```
<213> ORGANISM: Artificial Sequence
<220> FEATURE:
<223> OTHER INFORMATION: Fusion protein

<400> SEQUENCE: 76
ggggacaagt tgtacaaaa aagcaggcta tggtaccgcc accatgaaat gggtcacctt      60
tatctccctg ctgttcctgt tctcctccgc ctactcttgt gccgagcaga ccacagagtg     120
gaccgcctgc tctaagtctt gcggcatggg cttctccacc agagtgacca accggaacag     180
acagtgcgag atgctgaagc agacccggct gtgtatggtt cgaccttgcg aggccgctgc     240
caaagaaaga aagtgctgcg tggaatgccc tccttgtcct gctcctcctg tggctggccc     300
ttccgtgttt ctgttccctc caaagcctaa ggacaccctg atgatctctc ggacccctga     360
agtgacctgc gtggtggtgg atgtgtccca gaggatcccc gaggtgcagt tcaattggta     420
cgtggacggc gtggaagtgc acaacgccaa gaccaagcct agagaggaac agttcaactc     480
cacctacaga gtggtgtccg tgctgaccgt gctgcaccag gattggctga acggcaaaga     540
gtacaagtgc aaggtgtcca acaagggcct gccttccagc atcgaaaaga ccatctccaa     600
ggccaaggga cagcccagag aaccccaggt gtacacactg cctccaagcc aagaggaaat     660
gaccaagaac caggtgtccc tgacctgcct ggtcaagggc ttctacccctt ccgatatcgc     720 cgtggaatgg gagtccaatg gccagcctga gaacaactac aagaccacac tccagtgct     780 ggactccgac ggctccttct ttctgtactc ccgcctgacc gtggacaagt ccagatggca     840
agagggcaac gtgttctcct gctccgtgat gcacgaggcc ctgcacaatc actacaccca     900
gaagtccctg tctctgtccc tgggctaatc tagaaaccca gctttcttgt acaaagtggt     960
cccc                                                                  964

<210> SEQ ID NO 77
<211> LENGTH: 343
<212> TYPE: PRT
<213> ORGANISM: Artificial Sequence
<220> FEATURE:
<223> OTHER INFORMATION: Fusion protein

<400> SEQUENCE: 77

Met Lys Trp Val Thr Phe Ile Ser Leu Leu Phe Leu Phe Ser Ser Ala
1               5                   10                  15

Tyr Ser Glu Ser Lys Tyr Gly Pro Pro Cys Pro Pro Cys Pro Ala Pro
            20                  25                  30

Glu Ala Ala Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser Gln Glu Asp Pro Glu Val Gln Phe Asn Trp Tyr Val Asp
65                  70                  75                  80

Gly Val Glu Val His Asn Ala Lys Thr Lys Pro Arg Glu Glu Gln Phe
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Gly Leu
        115                 120                 125

Pro Ser Ser Ile Glu Lys Thr Ile Ser Lys Ala Lys Gly Gln Pro Arg
    130                 135                 140

Glu Pro Gln Val Tyr Thr Leu Pro Pro Ser Gln Glu Glu Met Thr Lys
145                 150                 155                 160
```

-continued

```
Asn Gln Val Ser Leu Thr Cys Leu Val Lys Gly Phe Tyr Pro Ser Asp
            165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Arg Leu Thr Val Asp Lys Ser Arg Trp Gln Glu Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Leu Gly Ala Glu Ala Ala Ala Lys Glu Ala Ala Ala
            245                 250                 255

Lys Glu Ala Ala Ala Lys Glu Ala Ala Ala Lys Glu Ala Ala Ala Lys
            260                 265                 270

Glu Ala Ala Ala Lys Glu Ala Ala Ala Lys Glu Ala Ala Ala Lys Ala
        275                 280                 285

Ala Ala Cys Ala Glu Trp Ser Thr Ala Trp Gly Pro Cys Ser Thr Thr
    290                 295                 300

Cys Gly Leu Gly Met Ala Thr Arg Val Ser Asn Gln Asn Arg Phe Cys
305                 310                 315                 320

Arg Leu Glu Thr Gln Arg Arg Leu Cys Leu Ser Arg Pro Cys Pro Pro
            325                 330                 335

Ser Arg Gly Arg Ser Pro Gln
            340
```

```
<210> SEQ ID NO 78
<211> LENGTH: 1038
<212> TYPE: DNA
<213> ORGANISM: Artificial Sequence
<220> FEATURE:
<223> OTHER INFORMATION: Fusion protein

<400> SEQUENCE: 78
gccaccatga aatgggtcac ctttatctcc ctgctgttcc tgttctccag cgcctactcc      60
gagtctaagt acggccctcc ttgtcctcca tgtcctgctc agaagctgc tggcggccct      120 tccgtgtttc tgttccctcc aaagcctaag gacaccctga tgatctctcg gaccccctgaa    180 gtgacctgcg tggtggtgga tgtgtcccaa gaggatcccg aggtgcagtt caattggtac      240
gtggacggcg tggaagtgca caacgccaag accagcccta gagaggaaca gttcaactcc      300
acctacagag tggtgtccgt gctgaccgtg ctgcaccagg attggctgaa cggcaaagag      360
tacaagtgca aggtgtccaa caagggcctg ccttccagca tcgaaaagac catctccaag      420
gccaagggcc agcctaggga accccaggtt tacaccctgc ctccaagcca agaggaaatg      480
accaagaacc aggtgtccct gacctgcctg gtcaagggct ctacccttc cgatatcgcc      540 gtggaatggg agagcaatgg ccagcctgag aacaactaca agaccacacc tcctgtgctg      600
gactccgacg gctccttctt tctgtactcc cgcctgaccg tggacaagtc cagatggcaa      660
gagggcaacg tgttctcctg ctccgtgatg cacgaggccc tgcacaatca ctacacccag      720
aagtccctgt ctctgtccct gggagctgag gccgctgcta agaagctgc cgctaaagag      780 gccgcagcca agaggcagc cgccaaagaa gccgctgcaa agaggctgc tgcaaaagaa       840 gcagcagcta agaagctgc tgccaaggcc gctgcttgtg ccgaatggtc tacagcttgg      900
ggcccttgct ctaccacctg ggactcggc atggccacca gagtgtctaa ccagaacaga      960
```

-continued

```
ttctgccggc tggaaaccca gcggagactg tgcctgtcta gaccctgtcc tcctagcaga      1020
ggcagatccc ctcagtga                                                     1038

<210> SEQ ID NO 79
<211> LENGTH: 1111
<212> TYPE: DNA
<213> ORGANISM: Artificial Sequence
<220> FEATURE:
<223> OTHER INFORMATION: Fusion protein

<400> SEQUENCE: 79
ggggacaagt ttgtacaaaa aagcaggcta tggtaccgcc accatgaaat gggtcacctt        60
tatctccctg ctgttcctgt ctccagcgc ctactccgag tctaagtacg ccctccttg       120 tcctccatgt cctgctccag aagctgctgg cggcccttcc gtgtttctgt tccctccaaa      180
gcctaaggac accctgatga tctctcggac ccctgaagtg acctgcgtgg tggtggatgt      240
gtcccaagag gatcccgagg tgcagttcaa ttggtacgtg gacggcgtgg aagtgcacaa      300
cgccaagacc aagcctagag aggaacagtt caactccacc tacagagtgg tgtccgtgct      360
gaccgtgctg caccaggatt ggctgaacgg caaagagtac aagtgcaagg tgtccaacaa      420
gggcctgcct tccagcatcg aaaagaccat ctccaaggcc aagggccagc ctagggaacc      480
ccaggtttac accctgcctc caagccaaga ggaaatgacc aagaaccagg tgtccctgac      540
ctgcctggtc aagggcttct acccttccga tatcgccgtg gaatgggaga gcaatggcca      600
gcctgagaac aactacaaga ccacacctcc tgtgctggac tccgacggct ccttctttct      660
gtactcccgc ctgaccgtgg acaagtccag atggcaagag ggcaacgtgt tctcctgctc      720
cgtgatgcac gaggccctgc acaatcacta cacccagaag tccctgtctc tgtccctggg      780
agctgaggcc gctgctaaag aagctgccgc taaagaggcc gcagccaaag aggcagccgc      840
caaagaagcc gctgcaaaag aggctgctgc aaaagaagca gcagctaaag aagctgctgc      900
caaggccgct gcttgtgccg aatggtctac agcttggggc ccttgctcta ccacctgtgg      960
actcggcatg gccaccagag tgtctaacca gaacagattc tgccggctgg aaacccagcg     1020
gagactgtgc ctgtctagac cctgtcctcc tagcagaggc agatcccctc agtgatctag     1080
aaacccagct ttcttgtaca aagtggtccc c                                    1111

<210> SEQ ID NO 80
<211> LENGTH: 311
<212> TYPE: PRT
<213> ORGANISM: Artificial Sequence
<220> FEATURE:
<223> OTHER INFORMATION: Fusion protein

<400> SEQUENCE: 80

Cys Ala Glu Gln Thr Thr Glu Trp Thr Ala Cys Ser Lys Ser Cys Gly
1               5                   10                  15

Met Gly Phe Ser Thr Arg Val Thr Asn Arg Asn Arg Gln Cys Glu Met
            20                  25                  30

Leu Lys Gln Thr Arg Leu Cys Met Val Arg Pro Cys Glu Ala Ala Ala
        35                  40                  45

Lys Glu Ala Ala Ala Lys Glu Ala Ala Ala Lys Glu Ala Ala Ala Lys
    50                  55                  60

Glu Ala Ala Ala Lys Glu Ala Ala Ala Lys Glu Ala Ala Ala Lys Glu
65                  70                  75                  80

Ala Ala Ala Lys Glu Arg Lys Cys Cys Val Glu Cys Pro Pro Cys Pro
                85                  90                  95
```

-continued

```
Ala Pro Pro Val Ala Gly Pro Ser Val Phe Leu Phe Pro Pro Lys Pro
            100                 105                 110

Lys Asp Thr Leu Met Ile Ser Arg Thr Pro Glu Val Thr Cys Val Val
            115                 120                 125

Val Asp Val Ser Gln Glu Asp Pro Glu Val Gln Phe Asn Trp Tyr Val
            130                 135                 140

Asp Gly Val Glu Val His Asn Ala Lys Thr Lys Pro Arg Glu Glu Gln
145                 150                 155                 160

Phe Asn Ser Thr Tyr Arg Val Val Ser Val Leu Thr Val Leu His Gln
                165                 170                 175

Asp Trp Leu Asn Gly Lys Glu Tyr Lys Cys Lys Val Ser Asn Lys Gly
            180                 185                 190

Leu Pro Ser Ser Ile Glu Lys Thr Ile Ser Lys Ala Lys Gly Gln Pro
            195                 200                 205

Arg Glu Pro Gln Val Tyr Thr Leu Pro Pro Ser Gln Glu Glu Met Thr
            210                 215                 220

Lys Asn Gln Val Ser Leu Thr Cys Leu Val Lys Gly Phe Tyr Pro Ser
225                 230                 235                 240

Asp Ile Ala Val Glu Trp Glu Ser Asn Gly Gln Pro Glu Asn Asn Tyr
                245                 250                 255

Lys Thr Thr Pro Pro Val Leu Asp Ser Asp Gly Ser Phe Phe Leu Tyr
                260                 265                 270

Ser Arg Leu Thr Val Asp Lys Ser Arg Trp Gln Glu Gly Asn Val Phe
            275                 280                 285

Ser Cys Ser Val Met His Glu Ala Leu His Asn His Tyr Thr Gln Lys
            290                 295                 300

Ser Leu Ser Leu Ser Leu Gly
305                 310
```

<210> SEQ ID NO 81
<211> LENGTH: 329
<212> TYPE: PRT
<213> ORGANISM: Artificial Sequence
<220> FEATURE:
<223> OTHER INFORMATION: Fusion protein

<400> SEQUENCE: 81

```
Met Lys Trp Val Thr Phe Ile Ser Leu Leu Phe Leu Phe Ser Ser Ala
1               5                   10                  15

Tyr Ser Cys Ala Glu Gln Thr Thr Glu Trp Thr Ala Cys Ser Lys Ser
            20                  25                  30

Cys Gly Met Gly Phe Ser Thr Arg Val Thr Asn Arg Asn Arg Gln Cys
            35                  40                  45

Glu Met Leu Lys Gln Thr Arg Leu Cys Met Val Arg Pro Cys Glu Ala
            50                  55                  60

Ala Ala Lys Glu Ala Ala Ala Lys Glu Ala Ala Ala Lys Glu Ala Ala
65                  70                  75                  80

Ala Lys Glu Ala Ala Ala Lys Glu Ala Ala Ala Lys Glu Ala Ala Ala
                85                  90                  95

Lys Glu Ala Ala Ala Lys Glu Arg Lys Cys Cys Val Glu Cys Pro Pro
            100                 105                 110

Cys Pro Ala Pro Pro Val Ala Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140
```

-continued

```
Val Val Val Asp Val Ser Gln Glu Asp Pro Glu Val Gln Phe Asn Trp
145             150             155             160

Tyr Val Asp Gly Val Glu Val His Asn Ala Lys Thr Lys Pro Arg Glu
                165             170             175

Glu Gln Phe Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Gly Leu Pro Ser Ser Ile Glu Lys Thr Ile Ser Lys Ala Lys Gly
    210             215             220

Gln Pro Arg Glu Pro Gln Val Tyr Thr Leu Pro Pro Ser Gln Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
        275             280             285

Leu Tyr Ser Arg Leu Thr Val Asp Lys Ser Arg Trp Gln Glu Gly Asn
    290             295             300

Val Phe Ser Cys Ser Val Met His Glu Ala Leu His Asn His Tyr Thr
305             310             315             320

Gln Lys Ser Leu Ser Leu Ser Leu Gly
            325
```

```
<210> SEQ ID NO 82
<211> LENGTH: 996
<212> TYPE: DNA
<213> ORGANISM: Artificial Sequence
<220> FEATURE:
<223> OTHER INFORMATION: Fusion protein

<400> SEQUENCE: 82
gccaccatga atgggtcac ctttatctcc ctgctgttcc tgttctcctc cgcctactct      60
tgtgccgagc agaccacaga gtggaccgcc tgctctaagt cttgcggcat gggcttctcc     120
accagagtga ccaaccggaa cagacagtgc gagatgctga agcagacccg gctgtgtatg     180
gttcgacctt gcgaggccgc tgccaaagag gctgctgcta agaagccgc cgcaaaagag      240 gcagcagcaa agaggctgc cgccaaagag gccgcagcca agaagcagc agctaaagag       300 gccgctgcaa agaacggaa gtgctgcgtg aatgccctc cttgtcctgc tcctcctgtg       360
gctggccctt ccgtgtttct gttccctcca aagcctaagg acaccctgat gatctctcgg     420 accctgaag tgacctgcgt ggtggtggat gtgtcccaag aggatcccga ggtgcagttc      480
aattggtacg tggacggcgt ggaagtgcac aacgccaaga ccaagcctag agaggaacag     540
ttcaactcca cctacagagt ggtgtccgtg ctgaccgtgc tgcaccagga ttggctgaac     600
ggcaaagagt acaagtgcaa ggtgtccaac aagggcctgc cttccagcat cgaaaagacc     660
atctccaagg ccaagggaca gcccagagaa ccccaggtgt acacactgcc tccaagccaa     720
gaggaaatga ccaagaacca ggtgtccctg acctgcctgg tcaagggctt ctacccttcc     780
gatatcgccg tggaatggga gtccaatggc cagcctgaga caactacaa gaccacacct      840 ccagtgctgg actccgacgg ctccttcttt ctgtactccc gcctgaccgt ggacaagtcc     900
agatggcaag agggcaacgt gttctcctgc tccgtgatgc acgaggccct gcacaatcac     960
```

-continued

```
tacacccaga agtccctgtc tctgtccctg ggctaa                                    996

<210> SEQ ID NO 83
<211> LENGTH: 1069
<212> TYPE: DNA
<213> ORGANISM: Artificial Sequence
<220> FEATURE:
<223> OTHER INFORMATION: Fusion protein

<400> SEQUENCE: 83
ggggacaagt ttgtacaaaa aagcaggcta tggtaccgcc accatgaaat gggtcacctt        60
tatctccctg ctgttcctgt tctcctccgc ctactcttgt gccgagcaga ccacagagtg       120
gaccgcctgc tctaagtctt gcggcatggg cttctccacc agagtgacca accggaacag       180
acagtgcgag atgctgaagc agacccggct gtgtatggtt cgaccttgcg aggccgctgc       240
caaagaggct gctgctaaag aagccgccgc aaaagaggca gcagcaaaag aggctgccgc       300
caaagaggcc gcagccaaag aagcagcagc taaagaggcc gctgcaaaag aacggaagtg       360
ctgcgtggaa tgccctcctt gtcctgctcc tcctgtggct ggcccttccg tgtttctgtt       420
ccctccaaag cctaaggaca ccctgatgat ctctcggacc cctgaagtga cctgcgtggt       480
ggtggatgtg tcccaagagg atcccgaggt gcagttcaat tggtacgtgg acggcgtgga       540
agtgcacaac gccaagacca gcctagaga ggaacagttc aactccacct acagagtggt       600
gtccgtgctg accgtgctgc accaggattg gctgaacggc aaagagtaca gtgcaaggt       660 gtccaacaag ggcctgcctt ccagcatcga aaagaccatc tccaaggcca agggacagcc       720
cagagaaccc caggtgtaca cactgcctcc aagccaagag gaaatgacca gaaccaggt       780 gtccctgacc tgcctggtca agggcttcta cccttccgat atcgccgtgg aatgggagtc       840
caatggccag cctgagaaca actacaagac cacacctcca gtgctggact ccgacggctc       900
cttctttctg tactcccgcc tgaccgtgga caagtccaga tggcaagagg caacgtgtt       960 ctcctgctcc gtgatgcacg aggccctgca caatcactac acccagaagt ccctgtctct      1020
gtccctgggc taatctagaa acccagcttt cttgtacaaa gtggtcccc                  1069

<210> SEQ ID NO 84
<211> LENGTH: 276
<212> TYPE: PRT
<213> ORGANISM: Artificial Sequence
<220> FEATURE:
<223> OTHER INFORMATION: Fusion protein

<400> SEQUENCE: 84

Cys Ala Glu Gln Thr Thr Glu Trp Thr Ala Cys Ser Lys Ser Cys Gly
1               5                   10                  15

Met Gly Phe Ser Thr Arg Val Thr Asn Arg Asn Arg Gln Cys Glu Met
            20                  25                  30

Leu Lys Gln Thr Arg Leu Cys Met Val Arg Pro Cys Glu Ala Ala Ala
        35                  40                  45

Lys Glu Arg Lys Gln Gln Val Glu Gln Pro Pro Gln Pro Ala Pro Pro
    50                  55                  60

Val Ala Gly Pro Ser Val Phe Leu Phe Pro Pro Lys Pro Lys Asp Thr
65                  70                  75                  80

Leu Tyr Ile Thr Arg Glu Pro Glu Val Thr Cys Val Val Val Asp Val
                85                  90                  95

Ser Gln Glu Asp Pro Glu Val Gln Phe Asn Trp Tyr Val Asp Gly Val
            100                 105                 110
```

```
Glu Val His Asn Ala Lys Thr Lys Pro Arg Glu Glu Gln Phe Asn Ser
    115                 120                 125

Thr Tyr Arg Val Val Ser Val Leu Thr Val Leu His Gln Asp Trp Leu
    130                 135                 140

Asn Gly Lys Glu Tyr Lys Cys Lys Val Ser Asn Lys Gly Leu Pro Ser
145                 150                 155                 160

Ser Ile Glu Lys Thr Ile Ser Lys Ala Lys Gly Gln Pro Arg Glu Pro
                165                 170                 175

Gln Val Tyr Thr Phe Pro Pro Ser Gln Glu Glu Met Thr Lys Asn Gln
                180                 185                 190

Val Ser Leu Arg Cys Leu Val Lys Gly Phe Tyr Pro Ser Asp Ile Ala
                195                 200                 205

Val Glu Trp Glu Ser Asn Gly Gln Pro Glu Asn Asn Tyr Lys Thr Thr
    210                 215                 220

Lys Pro Val Leu Asp Ser Asp Gly Ser Phe Arg Leu Glu Ser Arg Leu
225                 230                 235                 240

Thr Val Asp Lys Ser Arg Trp Gln Glu Gly Asn Val Phe Ser Cys Ser
                245                 250                 255

Val Met His Glu Ala Leu His Asn His Tyr Thr Gln Lys Ser Leu Ser
                260                 265                 270

Leu Ser Leu Gly
            275

<210> SEQ ID NO 85
<211> LENGTH: 294
<212> TYPE: PRT
<213> ORGANISM: Artificial Sequence
<220> FEATURE:
<223> OTHER INFORMATION: Fusion protein

<400> SEQUENCE: 85

Met Lys Trp Val Thr Phe Ile Ser Leu Leu Phe Leu Phe Ser Ser Ala
1               5                   10                  15

Tyr Ser Cys Ala Glu Gln Thr Thr Glu Trp Thr Ala Cys Ser Lys Ser
                20                  25                  30

Cys Gly Met Gly Phe Ser Thr Arg Val Thr Asn Arg Asn Arg Gln Cys
            35                  40                  45

Glu Met Leu Lys Gln Thr Arg Leu Cys Met Val Arg Pro Cys Glu Ala
    50                  55                  60

Ala Ala Lys Glu Arg Lys Gln Gln Val Glu Gln Pro Pro Gln Pro Ala
65                  70                  75                  80

Pro Pro Val Ala Gly Pro Ser Val Phe Leu Phe Pro Pro Lys Pro Lys
                85                  90                  95

Asp Thr Leu Tyr Ile Thr Arg Glu Pro Glu Val Thr Cys Val Val Val
                100                 105                 110

Asp Val Ser Gln Glu Asp Pro Glu Val Gln Phe Asn Trp Tyr Val Asp
                115                 120                 125

Gly Val Glu Val His Asn Ala Lys Thr Lys Pro Arg Glu Glu Gln Phe
    130                 135                 140

Asn Ser Thr Tyr Arg Val Val Ser Val Leu Thr Val Leu His Gln Asp
145                 150                 155                 160

Trp Leu Asn Gly Lys Glu Tyr Lys Cys Lys Val Ser Asn Lys Gly Leu
                165                 170                 175

Pro Ser Ser Ile Glu Lys Thr Ile Ser Lys Ala Lys Gly Gln Pro Arg
                180                 185                 190
```

```
Glu Pro Gln Val Tyr Thr Phe Pro Pro Ser Gln Glu Glu Met Thr Lys
        195                 200                 205
```

```
Asn Gln Val Ser Leu Arg Cys Leu Val Lys Gly Phe Tyr Pro Ser Asp
        210                 215                 220
```

```
Ile Ala Val Glu Trp Glu Ser Asn Gly Gln Pro Glu Asn Asn Tyr Lys
225                 230                 235                 240
```

```
Thr Thr Lys Pro Val Leu Asp Ser Asp Gly Ser Phe Arg Leu Glu Ser
                245                 250                 255
```

```
Arg Leu Thr Val Asp Lys Ser Arg Trp Gln Glu Gly Asn Val Phe Ser
                260                 265                 270
```

```
Cys Ser Val Met His Glu Ala Leu His Asn His Tyr Thr Gln Lys Ser
        275                 280                 285
```

```
Leu Ser Leu Ser Leu Gly
        290
```

<210> SEQ ID NO 86
<211> LENGTH: 891
<212> TYPE: DNA
<213> ORGANISM: Artificial Sequence
<220> FEATURE:
<223> OTHER INFORMATION: Fusion protein

<400> SEQUENCE: 86

```
gccaccatga aatgggtcac ctttatctcc ctgctgttcc tgttctcctc cgcctactct     60
tgtgccgagc agaccacaga gtggaccgcc tgctctaagt cttgcggcat gggcttctcc    120
accagagtga ccaaccggaa cagacagtgc gagatgctga agcagacccg gctgtgtatg    180
gttcgacctt gcgaggccgc tgccaaagaa agaaagcagc aggtcgagca gcctcctcag    240
cctgctcctc ctgttgctgg cccttccgtg tttctgttcc ctccaaagcc taaggacacc    300
ctgtacatca cccgcgagcc tgaagtgacc tgcgtggtgg tggatgtgtc ccaagaggat    360
cccgaggtgc agttcaattg gtacgtggac ggcgtggaag tgcacaacgc caagaccaag    420
cctagagagg aacagttcaa ctccacctac agagtggtgt ccgtgctgac cgtgctgcac    480
caggattggc tgaacggcaa agagtacaag tgcaaggtgt ccaacaaggg cctgccttcc    540
agcatcgaaa agaccatctc caaggccaag ggacagccca gagaacccca ggtgtacaca    600
ttccctccat ctcaagagga aatgaccaag aaccaggtgt ccctgcggtg cctggtcaag    660
ggcttctacc cttctgatat cgccgtggaa tgggagtcca acggccagcc tgagaacaac    720
tacaagacca ccaagcctgt gctggactcc gacggctcct tccggcttga atctagactg    780
accgtggaca gtcccggtg caagagggc aacgtgttct cctgctctgt gatgcacgag    840
gccctgcaca accactacac ccagaagtcc ctgtctctgt ccctgggcta a             891
```

<210> SEQ ID NO 87
<211> LENGTH: 964
<212> TYPE: DNA
<213> ORGANISM: Artificial Sequence
<220> FEATURE:
<223> OTHER INFORMATION: Fusion protein

<400> SEQUENCE: 87

```
ggggacaagt ttgtacaaaa aagcaggcta tggtaccgcc accatgaaat gggtcacctt     60
tatctccctg ctgttcctgt tctcctccgc ctactcttgt gccgagcaga ccacagagtg    120
gaccgcctgc tctaagtctt gcggcatggg cttctccacc agagtgacca accgaacag    180 acagtgcgag atgctgaagc agacccggct gtgtatggtt cgaccttgcg aggccgctgc    240
```

```
caaagaaaga aagcagcagg tcgagcagcc tcctcagcct gctcctcctg ttgctggccc    300
ttccgtgttt ctgttccctc caaagcctaa ggacaccctg tacatcaccc gcgagcctga    360
agtgacctgc gtggtggtgg atgtgtccca agaggatccc gaggtgcagt tcaattggta    420
cgtggacggc gtggaagtgc acaacgccaa gaccaagcct agagaggaac agttcaactc    480
cacctacaga gtggtgtccg tgctgaccgt gctgcaccag gattggctga acggcaaaga    540
gtacaagtgc aaggtgtcca acaagggcct gccttccagc atcgaaaaga ccatctccaa    600
ggccaaggga cagcccagag aaccccaggt gtacacattc cctccatctc aagaggaaat    660
gaccaagaac caggtgtccc tgcggtgcct ggtcaagggc ttctacccctt ctgtatcgc     720 cgtggaatgg gagtccaacg gccagcctga gaacaactac aagaccacca gcctgtgct     780 ggactccgac ggctccttcc ggcttgaatc tagactgacc gtggacaagt cccggtggca    840
agagggcaac gtgttctcct gctctgtgat gcacgaggcc ctgcacaacc actacaccca    900
gaagtccctg tctctgtccc tgggctaatc tagaaaccca gctttcttgt acaaagtggt    960
cccc    964
```

```
<210> SEQ ID NO 88
<211> LENGTH: 281
<212> TYPE: PRT
<213> ORGANISM: Artificial Sequence
<220> FEATURE:
<223> OTHER INFORMATION: Fusion protein

<400> SEQUENCE: 88

Cys Ala Glu Gln Thr Thr Glu Trp Thr Ala Cys Ser Lys Ser Cys Gly
1               5                   10                  15

Met Gly Phe Ser Thr Arg Val Thr Asn Arg Asn Arg Gln Cys Glu Met
                20                  25                  30

Leu Lys Gln Thr Arg Leu Cys Met Val Arg Pro Cys Glu Ala Ala Ala
            35                  40                  45

Lys Glu Pro Lys Ser Gln Asp Lys Thr His Thr Gln Pro Pro Gln Pro
        50                  55                  60

Ala Pro Glu Leu Leu Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser His Glu Asp Pro Glu Val Lys Phe Asn Trp Tyr
                100                 105                 110

Val Asp Gly Val Glu Val His Asn Ala Lys Thr Lys Pro Cys Glu Glu
            115                 120                 125

Gln Tyr Gly Ser Thr Tyr Arg Cys Val Ser Val Leu Thr Val Leu His
        130                 135                 140

Gln Asp Trp Leu Asn Gly Lys Glu Tyr Lys Cys Lys Val Ser Asn Lys
145                 150                 155                 160

Ala Leu Pro Ala Pro Ile Glu Lys Thr Ile Ser Lys Ala Lys Gly Gln
                165                 170                 175

Pro Arg Glu Pro Gln Val Tyr Thr Leu Pro Pro Ser Arg Asp Glu Leu
                180                 185                 190

Thr Lys Asn Gln Val Ser Leu Arg Cys His Val Lys Gly Phe Tyr Pro
            195                 200                 205

Ser Asp Ile Ala Val Glu Trp Glu Ser Asn Gly Gln Pro Glu Asn Asn
        210                 215                 220

Tyr Lys Thr Thr Lys Pro Val Leu Asp Ser Asp Gly Ser Phe Phe Leu
```

225               230               235               240

Tyr Ser Thr Leu Thr Val Asp Lys Ser Arg Trp Gln Gln Gly Asn Val
            245               250               255

Phe Ser Cys Ser Val Leu His Glu Ala Leu His Asn His Tyr Thr Gln
        260               265               270

Lys Ser Leu Ser Leu Ser Pro Gly Lys
    275               280

<210> SEQ ID NO 89
<211> LENGTH: 299
<212> TYPE: PRT
<213> ORGANISM: Artificial Sequence
<220> FEATURE:
<223> OTHER INFORMATION: Fusion protein

<400> SEQUENCE: 89

Met Lys Trp Val Thr Phe Ile Ser Leu Leu Phe Leu Phe Ser Ser Ala
1               5               10               15

Tyr Ser Cys Ala Glu Gln Thr Thr Glu Trp Thr Ala Cys Ser Lys Ser
            20               25               30

Cys Gly Met Gly Phe Ser Thr Arg Val Thr Asn Arg Asn Arg Gln Cys
        35               40               45

Glu Met Leu Lys Gln Thr Arg Leu Cys Met Val Arg Pro Cys Glu Ala
    50               55               60

Ala Ala Lys Glu Pro Lys Ser Gln Asp Lys Thr His Thr Gln Pro Pro
65               70               75               80

Gln Pro Ala Pro Glu Leu Leu Gly Gly Pro Ser Val Phe Leu Phe Pro
            85               90               95

Pro Lys Pro Lys Asp Thr Leu Met Ile Ser Arg Thr Pro Glu Val Thr
        100               105               110

Cys Val Val Val Asp Val Ser His Glu Asp Pro Glu Val Lys Phe Asn
        115               120               125

Trp Tyr Val Asp Gly Val Glu Val His Asn Ala Lys Thr Lys Pro Cys
    130               135               140

Glu Glu Gln Tyr Gly Ser Thr Tyr Arg Cys Val Ser Val Leu Thr Val
145               150               155               160

Leu His Gln Asp Trp Leu Asn Gly Lys Glu Tyr Lys Cys Lys Val Ser
            165               170               175

Asn Lys Ala Leu Pro Ala Pro Ile Glu Lys Thr Ile Ser Lys Ala Lys
            180               185               190

Gly Gln Pro Arg Glu Pro Gln Val Tyr Thr Leu Pro Pro Ser Arg Asp
        195               200               205

Glu Leu Thr Lys Asn Gln Val Ser Leu Arg Cys His Val Lys Gly Phe
    210               215               220

Tyr Pro Ser Asp Ile Ala Val Glu Trp Glu Ser Asn Gly Gln Pro Glu
225               230               235               240

Asn Asn Tyr Lys Thr Thr Lys Pro Val Leu Asp Ser Asp Gly Ser Phe
            245               250               255

Phe Leu Tyr Ser Thr Leu Thr Val Asp Lys Ser Arg Trp Gln Gln Gly
        260               265               270

Asn Val Phe Ser Cys Ser Val Leu His Glu Ala Leu His Asn His Tyr
        275               280               285

Thr Gln Lys Ser Leu Ser Leu Ser Pro Gly Lys
    290               295

```
<210> SEQ ID NO 90
<211> LENGTH: 906
<212> TYPE: DNA
<213> ORGANISM: Artificial Sequence
<220> FEATURE:
<223> OTHER INFORMATION: Fusion protein

<400> SEQUENCE: 90
gccaccatga aatgggtcac ctttatctcc ctgctgttcc tgttctcctc cgcctactct      60
tgtgccgagc agaccacaga gtggaccgcc tgctctaagt cttgcggcat gggcttctcc     120
accagagtga ccaaccggaa cagacagtgc gagatgctga agcagacccg gctgtgtatg     180
gttcgacctt gcgaggccgc tgccaaagag cctaagagcc aggacaagac ccacacacag     240
cctccacagc ctgctccaga attgctcgga ggcccttccg tgtttctgtt ccctccaaag     300
cctaaggaca ccctgatgat ctctcggacc cctgaagtga cctgcgtggt ggtggatgtg     360
tctcacgagg atcccgaagt gaagttcaat tggtacgtgg acggcgtgga agtgcacaac     420
gccaagacaa agccctgcga ggaacagtac ggctccacct acagatgcgt gtccgtgctg     480
acagtgctgc accaggattg gctgaacggc aaagagtaca agtgcaaggt gtccaacaag     540
gccctgcctg ctcctatcga aaagaccatc tccaaggcca agggccagcc tagagaaccc     600
caggtgtaca cactgccacc ttctagggac gagctgacca gaaccaggt gtccctgaga      660 tgccacgtga agggcttcta cccctccgat atcgccgtgg aatgggagtc taatggacag     720
cccgagaaca actacaagac caccaagcct gtgctggact ccgacggctc cttcttcctg     780
tactctaccc tgaccgtgga caagtccaga tggcagcagg gcaacgtgtt ctcctgctct     840
gtgctgcacg aggccctgca caatcactac acccagaagt ccctgtctct gtcccctggc     900
aagtga                                                                 906

<210> SEQ ID NO 91
<211> LENGTH: 979
<212> TYPE: DNA
<213> ORGANISM: Artificial Sequence
<220> FEATURE:
<223> OTHER INFORMATION: Fusion protein

<400> SEQUENCE: 91
ggggacaagt ttgtacaaaa aagcaggcta tggtaccgcc accatgaaat gggtcacctt      60
tatctccctg ctgttcctgt tctcctccgc ctactcttgt gccgagcaga ccacagagtg     120
gaccgcctgc tctaagtctt gcggcatggg cttctccacc agagtgacca accggaacag     180
acagtgcgag atgctgaagc agacccggct gtgtatggtt cgaccttgcg aggccgctgc     240
caaagagcct aagagccagg acaagaccca cacagcct ccacagcctg ctccagaatt      300
gctcggaggc ccttccgtgt ttctgttccc tccaaagcct aaggacaccc tgatgatctc     360
tcggacccct gaagtgacct gcgtggtggt ggatgtgtct cacgaggatc cgaagtgaa      420 gttcaattgg tacgtggacg gcgtggaagt gcacaacgcc aagacaaagc ctgcgagga      480 acagtacggc tccacctaca gatgcgtgtc cgtgctgaca gtgctgcacc aggattggct     540
gaacggcaaa gagtacaagt gcaaggtgtc caacaaggcc ctgcctgctc ctatcgaaaa     600
gaccatctcc aaggccaagg ccagcctag agaaccccag gtgtacacac tgccaccttc      660
tagggacgag ctgaccaaga accaggtgtc cctgagatgc cacgtgaagg gcttctaccc     720
ctccgatatc gccgtggaat gggagtctaa tggacagccc gagaacaact acaagaccac     780
caagcctgtg ctgactccg acggctcctt cttcctgtac tctaccctga ccgtggacaa     840
```

```
gtccagatgg cagcagggca acgtgttctc ctgctctgtg ctgcacgagg ccctgcacaa    900
tcactacacc cagaagtccc tgtctctgtc ccctggcaag tgatctagaa acccagcttt    960
cttgtacaaa gtggtcccc                                                  979
```

<210> SEQ ID NO 92
<211> LENGTH: 402
<212> TYPE: PRT
<213> ORGANISM: Artificial Sequence
<220> FEATURE:
<223> OTHER INFORMATION: Fusion tag

<400> SEQUENCE: 92

```
Gly His His His His His His Gly Ser Glu Ile Gly Thr Gly Phe Pro
1               5                   10                  15

Phe Asp Pro His Tyr Val Glu Val Leu Gly Glu Arg Met His Tyr Val
            20                  25                  30

Asp Val Gly Pro Arg Asp Gly Thr Pro Val Leu Phe Leu His Gly Asn
        35                  40                  45

Pro Thr Ser Ser Tyr Val Trp Arg Asn Ile Ile Pro His Val Ala Pro
    50                  55                  60

Thr His Arg Cys Ile Ala Pro Asp Leu Ile Gly Met Gly Lys Ser Asp
65                  70                  75                  80

Lys Pro Asp Leu Gly Tyr Phe Phe Asp Asp His Val Arg Phe Met Asp
            85                  90                  95

Ala Phe Ile Glu Ala Leu Gly Leu Glu Glu Val Val Leu Val Ile His
            100                 105                 110

Asp Trp Gly Ser Ala Leu Gly Phe His Trp Ala Lys Arg Asn Pro Glu
            115                 120                 125

Arg Val Lys Gly Ile Ala Phe Met Glu Phe Ile Arg Pro Ile Pro Thr
        130                 135                 140

Trp Asp Glu Trp Pro Glu Phe Ala Arg Glu Thr Phe Gln Ala Phe Arg
145                 150                 155                 160

Thr Thr Asp Val Gly Arg Lys Leu Ile Ile Asp Gln Asn Val Phe Ile
                165                 170                 175

Glu Gly Thr Leu Pro Met Gly Val Val Arg Pro Leu Thr Glu Val Glu
            180                 185                 190

Met Asp His Tyr Arg Glu Pro Phe Leu Asn Pro Val Asp Arg Glu Pro
            195                 200                 205

Leu Trp Arg Phe Pro Asn Glu Leu Pro Ile Ala Gly Glu Pro Ala Asn
        210                 215                 220

Ile Val Ala Leu Val Glu Glu Tyr Met Asp Trp Leu His Gln Ser Pro
225                 230                 235                 240

Val Pro Lys Leu Leu Phe Trp Gly Thr Pro Gly Val Leu Ile Pro Pro
            245                 250                 255

Ala Glu Ala Ala Arg Leu Ala Lys Ser Leu Pro Asn Cys Lys Ala Val
            260                 265                 270

Asp Ile Gly Pro Gly Leu Asn Leu Leu Gln Glu Asp Asn Pro Asp Leu
            275                 280                 285

Ile Gly Ser Glu Ile Ala Arg Trp Leu Ser Thr Leu Glu Ile Ser Gly
    290                 295                 300

Leu Gln Asp Ser Glu Val Asn Gln Glu Ala Lys Pro Glu Val Lys Pro
305                 310                 315                 320

Glu Val Lys Pro Glu Thr His Ile Asn Leu Lys Val Ser Asp Gly Ser
                325                 330                 335
```

-continued

```
Ser Glu Ile Phe Phe Lys Ile Lys Lys Thr Thr Pro Leu Arg Arg Leu
        340                 345                 350

Met Glu Ala Phe Ala Lys Arg Gln Gly Lys Glu Met Asp Ser Leu Thr
        355                 360                 365

Phe Leu Tyr Asp Gly Ile Glu Ile Gln Ala Asp Gln Thr Pro Glu Asp
        370                 375                 380

Leu Asp Met Glu Asp Asn Asp Ile Ile Glu Ala His Arg Glu Gln Ile
385                 390                 395                 400

Gly Gly

<210> SEQ ID NO 93
<211> LENGTH: 20
<212> TYPE: PRT
<213> ORGANISM: Artificial Sequence
<220> FEATURE:
<223> OTHER INFORMATION: Linker

<400> SEQUENCE: 93

Ser Gly Gly Ser Gly Gly Ser Gly Gly Ser Gly Gly Ser Ser Gly Gly
1               5                   10                  15

Gly Ser Ser Gly
            20

<210> SEQ ID NO 94
<211> LENGTH: 466
<212> TYPE: PRT
<213> ORGANISM: Artificial Sequence
<220> FEATURE:
<223> OTHER INFORMATION: Fusion protein

<400> SEQUENCE: 94

Gly His His His His His His Gly Ser Glu Ile Gly Thr Gly Phe Pro
1               5                   10                  15

Phe Asp Pro His Tyr Val Glu Val Leu Gly Glu Arg Met His Tyr Val
            20                  25                  30

Asp Val Gly Pro Arg Asp Gly Thr Pro Val Leu Phe Leu His Gly Asn
        35                  40                  45

Pro Thr Ser Ser Tyr Val Trp Arg Asn Ile Ile Pro His Val Ala Pro
    50                  55                  60

Thr His Arg Cys Ile Ala Pro Asp Leu Ile Gly Met Gly Lys Ser Asp
65                  70                  75                  80

Lys Pro Asp Leu Gly Tyr Phe Phe Asp Asp His Val Arg Phe Met Asp
            85                  90                  95

Ala Phe Ile Glu Ala Leu Gly Leu Glu Glu Val Val Leu Val Ile His
            100                 105                 110

Asp Trp Gly Ser Ala Leu Gly Phe His Trp Ala Lys Arg Asn Pro Glu
            115                 120                 125

Arg Val Lys Gly Ile Ala Phe Met Glu Phe Ile Arg Pro Ile Pro Thr
        130                 135                 140

Trp Asp Glu Trp Pro Glu Phe Ala Arg Glu Thr Phe Gln Ala Phe Arg
145                 150                 155                 160

Thr Thr Asp Val Gly Arg Lys Leu Ile Ile Asp Gln Asn Val Phe Ile
            165                 170                 175

Glu Gly Thr Leu Pro Met Gly Val Val Arg Pro Leu Thr Glu Val Glu
            180                 185                 190

Met Asp His Tyr Arg Glu Pro Phe Leu Asn Pro Val Asp Arg Glu Pro
        195                 200                 205
```

```
Leu Trp Arg Phe Pro Asn Glu Leu Pro Ile Ala Gly Glu Pro Ala Asn
    210                 215                 220

Ile Val Ala Leu Val Glu Glu Tyr Met Asp Trp Leu His Gln Ser Pro
225                 230                 235                 240

Val Pro Lys Leu Leu Phe Trp Gly Thr Pro Gly Val Leu Ile Pro Pro
                245                 250                 255

Ala Glu Ala Ala Arg Leu Ala Lys Ser Leu Pro Asn Cys Lys Ala Val
                260                 265                 270

Asp Ile Gly Pro Gly Leu Asn Leu Leu Gln Glu Asp Asn Pro Asp Leu
                275                 280                 285

Ile Gly Ser Glu Ile Ala Arg Trp Leu Ser Thr Leu Glu Ile Ser Gly
    290                 295                 300

Leu Gln Asp Ser Glu Val Asn Gln Glu Ala Lys Pro Glu Val Lys Pro
305                 310                 315                 320

Glu Val Lys Pro Glu Thr His Ile Asn Leu Lys Val Ser Asp Gly Ser
                325                 330                 335

Ser Glu Ile Phe Phe Lys Ile Lys Lys Thr Thr Pro Leu Arg Arg Leu
                340                 345                 350

Met Glu Ala Phe Ala Lys Arg Gln Gly Lys Glu Met Asp Ser Leu Thr
                355                 360                 365

Phe Leu Tyr Asp Gly Ile Glu Ile Gln Ala Asp Gln Thr Pro Glu Asp
    370                 375                 380

Leu Asp Met Glu Asp Asn Asp Ile Ile Glu Ala His Arg Glu Gln Ile
385                 390                 395                 400

Gly Gly Ser Gly Gly Ser Gly Gly Ser Gly Gly Ser Gly Gly Ser Ser
                405                 410                 415

Gly Gly Gly Ser Ser Gly Cys Ala Glu Gln Thr Thr Glu Trp Thr Ala
                420                 425                 430

Cys Ser Lys Ser Cys Gly Met Gly Phe Ser Thr Arg Val Thr Asn Arg
                435                 440                 445

Asn Arg Gln Cys Glu Met Leu Lys Gln Thr Arg Leu Cys Met Val Arg
    450                 455                 460

Pro Cys
465
```

<210> SEQ ID NO 95
<211> LENGTH: 1461
<212> TYPE: DNA
<213> ORGANISM: Artificial Sequence
<220> FEATURE:
<223> OTHER INFORMATION: Fusion protein

<400> SEQUENCE: 95

```
gccaccatga atgggtcac ctttatctcc ctgctgttcc tgttctcctc cgcctactct      60
ggccaccacc atcaccatca cggctccgag atcggaaccg ctttcctttt cgaccctcac     120
tacgtggaag tgctgggcga gagaatgcac tatgtggacg tgggccccag agatggaacc     180
cctgtgctgt ttctgcacgg caaccctacc tccagctacg tgtggcggaa catcatccct     240
cacgtggccc ctacacacag atgtatcgcc cctgacctga tcggcatggg caagtctgac     300
aagcctgacc tgggctactt cttcgacgac cacgtgcggt tcatggacgc ctttatcgag     360
gctctgggcc tcgaagaggt ggtgctggtc atccatgatt ggggctctgc cctgggcttt     420
cactgggcca agagaaaccc cgagagagtg aagggaatcg ccttcatgga attcatccgg     480
cctattccta cctgggacga gtggcctgag ttcgccagag agacattcca ggccttcaga     540
```

-continued

```
accaccgacg tgggcagaaa gctgatcatc gaccagaacg tgttcatcga gggcaccctg        600
cctatgggag tcgtcagacc tctgaccgag gtggaaatgg accactacag agagcccttt        660
ctgaaccccg tggaccggga acctctttgg agattcccta acgagctgcc tatcgctggc        720
gagcctgcca atattgtggc cctggtggaa gagtacatgg actggctgca tcagagcccc        780
gtgcctaagc tgctgttttg gggaacaccc ggcgtgctga ttcctcctgc tgaagctgct        840
agactggcca agagcctgcc taactgcaag gccgtggata tcggccctgg cctgaatctg        900
ctgcaagagg acaaccccga tctgatcgga tctgagatcg cccggtggct gagcaccctg        960
gaaatcagtg gactgcagga ctccgaagtg aatcaagagg ccaagcctga agtgaagccc       1020
gaagtcaagc ctgagacaca catcaacctg aaggtgtccg acggctccag cgagatcttc       1080
ttcaagatca agaaaaccac acctctgcgg cggctgatgg aagcctttgc caagagacag       1140
ggcaaagaga tggactccct gaccttcctg tacgacggca tcgagatcca ggccgatcag       1200
acccctgagg acctggacat ggaagataac gacatcattg aggcccacag agagcagatc       1260
ggcggctctg gtggtagcgg aggttctggt ggatctggtg gttcttctgg cggcggatct       1320
tctggctgtg ctgagcagac aaccgagtgg accgcctgct ctaagtcttg tggcatgggc       1380
ttctccacca gagtgaccaa ccggaacaga cagtgcgaga tgctgaagca gacccggctg       1440
tgtatggtcc gaccttgcta a                                                  1461
```

```
<210> SEQ ID NO 96
<211> LENGTH: 1552
<212> TYPE: DNA
<213> ORGANISM: Artificial Sequence
<220> FEATURE:
<223> OTHER INFORMATION: Fusion protein

<400> SEQUENCE: 96
ggggacaagt ttgtacaaaa aagcaggcta taagcttgct gccaccatga aatgggtcac         60
ctttatctcc ctgctgttcc tgttctcctc cgcctactct ggccaccacc atcaccatca        120
cggctccgag atcggaaccg gctttccttt cgaccctcac tacgtggaag tgctgggcga        180
gagaatgcac tatgtggacg tgggccccag agatggaacc cctgtgctgt ttctgcacgg        240
caaccctacc tccagctacg tgtggcggaa catcatccct cacgtggccc tacacacag        300 atgtatcgcc cctgacctga tcggcatggg caagtctgac aagcctgacc tgggctactt        360
cttcgacgac cacgtgcggt tcatggacgc ctttatcgag gctctgggcc tcgaagaggt        420
ggtgctggtc atcatgatt ggggctctgc cctgggcttt cactgggcca agagaaaccc        480
cgagagagtg aagggaatcg ccttcatgga attcatccgg cctattccta cctgggacga        540
gtggcctgag ttcgccagag agacattcca ggccttcaga accaccgacg tgggcagaaa        600
gctgatcatc gaccagaacg tgttcatcga gggcaccctg cctatgggag tcgtcagacc        660
tctgaccgag gtggaaatgg accactacag agagcccttt ctgaaccccg tggaccggga        720
acctctttgg agattcccta acgagctgcc tatcgctggc gagcctgcca atattgtggc        780
cctggtggaa gagtacatgg actggctgca tcagagcccc gtgcctaagc tgctgttttg        840
gggaacaccc ggcgtgctga ttcctcctgc tgaagctgct agactggcca agagcctgcc        900
taactgcaag gccgtggata tcggccctgg cctgaatctg ctgcaagagg acaaccccga        960
tctgatcgga tctgagatcg cccggtggct gagcaccctg gaaatcagtg gactgcagga       1020
ctccgaagtg aatcaagagg ccaagcctga agtgaagccc gaagtcaagc ctgagacaca       1080
catcaacctg aaggtgtccg acggctccag cgagatcttc ttcaagatca agaaaaccac       1140
```

-continued

```
acctctgcgg cggctgatgg aagcctttgc caagagacag ggcaaagaga tggactccct    1200
gaccttcctg tacgacggca tcgagatcca ggccgatcag accctgagg acctggacat     1260 ggaagataac gacatcattg aggcccacag agagcagatc ggcggctctg tggtagcgg     1320 aggttctggt ggatctggtg gttcttctgg cggcggatct tctggctgtg ctgagcagac    1380
aaccgagtgg accgcctgct ctaagtcttg tggcatgggc ttctccacca gagtgaccaa    1440
ccggaacaga cagtgcgaga tgctgaagca gaccccggctg tgtatggtcc gaccttgcta   1500
aatctagagc ggccgcggta ccaacccagc tttcttgtac aaagtggtcc cc            1552
```

<210> SEQ ID NO 97
<211> LENGTH: 634
<212> TYPE: PRT
<213> ORGANISM: Artificial Sequence
<220> FEATURE:
<223> OTHER INFORMATION: Fusion protein

<400> SEQUENCE: 97

```
Cys Ala Glu Trp Ser Thr Ala Trp Gly Pro Cys Ser Thr Thr Cys Gly
1               5                   10                  15

Leu Gly Met Ala Thr Arg Val Ser Asn Gln Asn Arg Phe Cys Arg Leu
            20                  25                  30

Glu Thr Gln Arg Arg Leu Cys Leu Ser Arg Pro Cys Glu Ala Ala Ala
        35                  40                  45

Lys Asp Ala His Lys Ser Glu Val Ala His Arg Phe Lys Asp Leu Gly
    50                  55                  60

Glu Glu Asn Phe Lys Ala Leu Val Leu Ile Ala Phe Ala Gln Tyr Leu
65                  70                  75                  80

Gln Gln Cys Pro Phe Glu Asp His Val Lys Leu Val Asn Glu Val Thr
                85                  90                  95

Glu Phe Ala Lys Thr Cys Val Ala Asp Glu Ser Ala Glu Asn Cys Asp
            100                 105                 110

Lys Ser Leu His Thr Leu Phe Gly Asp Lys Leu Cys Thr Val Ala Thr
        115                 120                 125

Leu Arg Glu Thr Tyr Gly Glu Met Ala Asp Cys Cys Ala Lys Gln Glu
    130                 135                 140

Pro Glu Arg Asn Glu Cys Phe Leu Gln His Lys Asp Asp Asn Pro Asn
145                 150                 155                 160

Leu Pro Arg Leu Val Arg Pro Glu Val Asp Val Met Cys Thr Ala Phe
                165                 170                 175

His Asp Asn Glu Glu Thr Phe Leu Lys Lys Tyr Leu Tyr Glu Ile Ala
            180                 185                 190

Arg Arg His Pro Tyr Phe Tyr Ala Pro Glu Leu Leu Phe Phe Ala Lys
        195                 200                 205

Arg Tyr Lys Ala Ala Phe Thr Glu Cys Cys Gln Ala Ala Asp Lys Ala
    210                 215                 220

Ala Cys Leu Leu Pro Lys Leu Asp Glu Leu Arg Asp Glu Gly Lys Ala
225                 230                 235                 240

Ser Ser Ala Lys Gln Arg Leu Lys Cys Ala Ser Leu Gln Lys Phe Gly
                245                 250                 255

Glu Arg Ala Phe Lys Ala Trp Ala Val Ala Arg Leu Ser Gln Arg Phe
            260                 265                 270

Pro Lys Ala Glu Phe Ala Glu Val Ser Lys Leu Val Thr Asp Leu Thr
        275                 280                 285
```

-continued

```
Lys Val His Thr Glu Cys Cys His Gly Asp Leu Leu Glu Cys Ala Asp
    290             295             300

Asp Arg Ala Asp Leu Ala Lys Tyr Ile Cys Glu Asn Gln Asp Ser Ile
305             310             315             320

Ser Ser Lys Leu Lys Glu Cys Cys Glu Lys Pro Leu Leu Glu Lys Ser
            325             330             335

His Cys Ile Ala Glu Val Glu Asn Asp Glu Met Pro Ala Asp Leu Pro
            340             345             350

Ser Leu Ala Ala Asp Phe Val Glu Ser Lys Asp Val Cys Lys Asn Tyr
            355             360             365

Ala Glu Ala Lys Asp Val Phe Leu Gly Met Phe Leu Tyr Glu Tyr Ala
    370             375             380

Arg Arg His Pro Asp Tyr Ser Val Val Leu Leu Leu Arg Leu Ala Lys
385             390             395             400

Thr Tyr Glu Thr Thr Leu Glu Lys Cys Cys Ala Ala Ala Asp Pro His
            405             410             415

Glu Cys Tyr Ala Lys Val Phe Asp Glu Phe Lys Pro Leu Val Glu Glu
            420             425             430

Pro Gln Asn Leu Ile Lys Gln Asn Cys Glu Leu Phe Glu Gln Leu Gly
            435             440             445

Glu Tyr Lys Phe Gln Asn Ala Leu Leu Val Arg Tyr Thr Lys Lys Val
    450             455             460

Pro Gln Val Ser Thr Pro Thr Leu Val Glu Val Ser Arg Asn Leu Gly
465             470             475             480

Lys Val Gly Ser Lys Cys Cys Lys His Pro Glu Ala Lys Arg Met Pro
            485             490             495

Cys Ala Glu Asp Tyr Leu Ser Val Val Leu Asn Gln Leu Cys Val Leu
            500             505             510

His Glu Lys Thr Pro Val Ser Asp Arg Val Thr Lys Cys Cys Thr Glu
            515             520             525

Ser Leu Val Asn Arg Arg Pro Cys Phe Ser Ala Leu Glu Val Asp Glu
    530             535             540

Thr Tyr Val Pro Lys Glu Phe Asn Ala Glu Thr Phe Thr Phe His Ala
545             550             555             560

Asp Ile Cys Thr Leu Ser Glu Lys Glu Arg Gln Ile Lys Lys Gln Thr
            565             570             575

Ala Leu Val Glu Leu Val Lys His Lys Pro Lys Ala Thr Lys Glu Gln
            580             585             590

Leu Lys Ala Val Met Asp Asp Phe Ala Ala Phe Val Glu Lys Cys Cys
            595             600             605

Lys Ala Asp Asp Lys Glu Thr Cys Phe Ala Glu Glu Gly Lys Lys Leu
    610             615             620

Val Ala Ala Ser Gln Ala Ala Leu Gly Leu
625             630
```

<210> SEQ ID NO 98
<211> LENGTH: 652
<212> TYPE: PRT
<213> ORGANISM: Artificial Sequence
<220> FEATURE:
<223> OTHER INFORMATION: Fusion protein

<400> SEQUENCE: 98

```
Met Lys Trp Val Thr Phe Ile Ser Leu Leu Phe Leu Phe Ser Ser Ala
1               5               10              15
```

-continued

```
Tyr Ser Cys Ala Glu Trp Ser Thr Ala Trp Gly Pro Cys Ser Thr Thr
            20              25                  30

Cys Gly Leu Gly Met Ala Thr Arg Val Ser Asn Gln Asn Arg Phe Cys
            35              40              45

Arg Leu Glu Thr Gln Arg Arg Leu Cys Leu Ser Arg Pro Cys Glu Ala
        50              55              60

Ala Ala Lys Asp Ala His Lys Ser Glu Val Ala His Arg Phe Lys Asp
65              70              75                  80

Leu Gly Glu Glu Asn Phe Lys Ala Leu Val Leu Ile Ala Phe Ala Gln
                85              90                  95

Tyr Leu Gln Gln Cys Pro Phe Glu Asp His Val Lys Leu Val Asn Glu
            100             105             110

Val Thr Glu Phe Ala Lys Thr Cys Val Ala Asp Glu Ser Ala Glu Asn
            115             120             125

Cys Asp Lys Ser Leu His Thr Leu Phe Gly Asp Lys Leu Cys Thr Val
        130             135             140

Ala Thr Leu Arg Glu Thr Tyr Gly Glu Met Ala Asp Cys Cys Ala Lys
145             150             155             160

Gln Glu Pro Glu Arg Asn Glu Cys Phe Leu Gln His Lys Asp Asp Asn
            165             170             175

Pro Asn Leu Pro Arg Leu Val Arg Pro Glu Val Asp Val Met Cys Thr
            180             185             190

Ala Phe His Asp Asn Glu Glu Thr Phe Leu Lys Lys Tyr Leu Tyr Glu
            195             200             205

Ile Ala Arg Arg His Pro Tyr Phe Tyr Ala Pro Glu Leu Leu Phe Phe
        210             215             220

Ala Lys Arg Tyr Lys Ala Ala Phe Thr Glu Cys Cys Gln Ala Ala Asp
225             230             235             240

Lys Ala Ala Cys Leu Leu Pro Lys Leu Asp Glu Leu Arg Asp Glu Gly
            245             250             255

Lys Ala Ser Ser Ala Lys Gln Arg Leu Lys Cys Ala Ser Leu Gln Lys
            260             265             270

Phe Gly Glu Arg Ala Phe Lys Ala Trp Ala Val Ala Arg Leu Ser Gln
            275             280             285

Arg Phe Pro Lys Ala Glu Phe Ala Glu Val Ser Lys Leu Val Thr Asp
        290             295             300

Leu Thr Lys Val His Thr Glu Cys Cys His Gly Asp Leu Leu Glu Cys
305             310             315             320

Ala Asp Asp Arg Ala Asp Leu Ala Lys Tyr Ile Cys Glu Asn Gln Asp
            325             330             335

Ser Ile Ser Ser Lys Leu Lys Glu Cys Cys Glu Lys Pro Leu Leu Glu
            340             345             350

Lys Ser His Cys Ile Ala Glu Val Glu Asn Asp Glu Met Pro Ala Asp
            355             360             365

Leu Pro Ser Leu Ala Ala Asp Phe Val Glu Ser Lys Asp Val Cys Lys
        370             375             380

Asn Tyr Ala Glu Ala Lys Asp Val Phe Leu Gly Met Phe Leu Tyr Glu
385             390             395             400

Tyr Ala Arg Arg His Pro Asp Tyr Ser Val Val Leu Leu Leu Arg Leu
            405             410             415

Ala Lys Thr Tyr Glu Thr Thr Leu Glu Lys Cys Cys Ala Ala Ala Asp
            420             425             430

Pro His Glu Cys Tyr Ala Lys Val Phe Asp Glu Phe Lys Pro Leu Val
```

```
              435                 440                 445
Glu Glu Pro Gln Asn Leu Ile Lys Gln Asn Cys Glu Leu Phe Glu Gln
        450                 455                 460
Leu Gly Glu Tyr Lys Phe Gln Asn Ala Leu Leu Val Arg Tyr Thr Lys
465                 470                 475                 480
Lys Val Pro Gln Val Ser Thr Pro Thr Leu Val Glu Val Ser Arg Asn
                485                 490                 495
Leu Gly Lys Val Gly Ser Lys Cys Cys Lys His Pro Glu Ala Lys Arg
            500                 505                 510
Met Pro Cys Ala Glu Asp Tyr Leu Ser Val Val Leu Asn Gln Leu Cys
            515                 520                 525
Val Leu His Glu Lys Thr Pro Val Ser Asp Arg Val Thr Lys Cys Cys
        530                 535                 540
Thr Glu Ser Leu Val Asn Arg Arg Pro Cys Phe Ser Ala Leu Glu Val
545                 550                 555                 560
Asp Glu Thr Tyr Val Pro Lys Glu Phe Asn Ala Glu Thr Phe Thr Phe
                565                 570                 575
His Ala Asp Ile Cys Thr Leu Ser Glu Lys Glu Arg Gln Ile Lys Lys
            580                 585                 590
Gln Thr Ala Leu Val Glu Leu Val Lys His Lys Pro Lys Ala Thr Lys
            595                 600                 605
Glu Gln Leu Lys Ala Val Met Asp Asp Phe Ala Ala Phe Val Glu Lys
        610                 615                 620
Cys Cys Lys Ala Asp Asp Lys Glu Thr Cys Phe Ala Glu Glu Gly Lys
625                 630                 635                 640
Lys Leu Val Ala Ala Ser Gln Ala Ala Leu Gly Leu
                645                 650
```

<210> SEQ ID NO 99
<211> LENGTH: 1965
<212> TYPE: DNA
<213> ORGANISM: Artificial Sequence
<220> FEATURE:
<223> OTHER INFORMATION: Fusion protein

<400> SEQUENCE: 99

```
gccaccatga aatgggtcac ctttatctcc ctgctgttcc tgttctcctc cgcctactct      60
tgcgccgagt ggtctacagc ttggggccct tgttctacca cctgtggcct cggcatggcc     120
accagagtgt ccaaccagaa cagattctgc cggctggaaa cccagcggag actgtgcttg     180
tctagacctt gcgaggccgc tgccaaggac gctcataagt ctgaggtggc caccggttc      240 aaggacctgg gcgaagagaa cttcaaggcc ctggtgctga tcgccttcgc tcagtacttg     300
cagcagtgcc ccttcgagga ccacgtgaag ctggtcaacg aagtgaccga gttcgccaag     360
acctgcgtgg ccgatgagtc tgccgagaac tgcgacaagt ctctgcacac cctgttcggc     420
gacaagctgt gtaccgtggc taccctgaga gaaacctacg gcgagatggc cgactgctgc     480
gctaagcaag agcccgagag aaacgagtgc ttcctgcagc acaaggacga caaccctaac     540
ctgcctagac tcgtgcggcc tgaggtggac gtgatgtgta ccgccttcca cgacaacgag     600
gaaaccttcc tgaagaagta cctgtacgag atcgccagac ggcaccccta cttttacgcc     660
cctgagctgc tgttcttcgc caagcggtac aaggccgcct tcaccgagtg ttgtcaggcc     720
gctgataagg ccgcttgcct gctgcctaaa ctggacgagc tgagagatga aggcaaggcc     780
tccagcgcca agcagagact gaagtgtgcc agcctgcaga agttcggcga gagagccttt     840
```

-continued

```
aaggcctggg ccgtcgctag actgtcccag agatttccca aggccgagtt tgccgaggtg      900
tccaagctgg ttaccgacct gaccaaggtg cacaccgaat gctgtcacgg cgacctgctg      960
gaatgcgccg atgatagagc cgatctggcc aagtacatct gcgagaacca ggactccatc     1020
tcctccaagc tgaaagagtg ctgcgagaag cctctgctgg aaaagtccca ctgtatcgcc     1080
gaggtggaaa cgacgagat gcctgccgat ctgccttctc tggccgccga cttcgtggaa      1140
tctaaggacg tgtgcaagaa ctacgccgag gctaaggatg tgttcctggg catgtttctg     1200
tacgagtacg ctcggcggca ccccgactat tctgttgtgc tgctgctgag actggctaag     1260
acctacgaga caaccctcga gaagtgctgt gccgccgctg atcctcacga gttgttacgcc    1320 aaggtgttcg acgagttcaa gccactggtg gaagaacccc agaacctgat caagcagaat     1380
tgcgagctgt tcgagcagct gggcgagtac aagttccaga cgccctgct cgtgcggtac      1440 accaagaaag tgccccaggt gtccacacct acactggttg aggtgtcccg gaacctgggc     1500
aaagtgggct ctaagtgctg caagcacccc gaggccaaga gaatgccttg tgccgaggac     1560
tacctgtccg tggtgctgaa ccagctgtgc gtgctgcacg aaaagacccc tgtgtccgac     1620
agagtgacca agtgctgtac cgagagcctg gtcaacagac ggccttgctt ctctgccctg     1680
gaagtggacg agacatacgt gcccaaagag ttcaacgccg agacattcac cttccacgcc     1740
gacatctgca ccctgtccga aaagagcgg cagatcaaga aacagaccgc tctggtggaa      1800
ctggtcaagc acaagcccaa ggccaccaaa gaacagctga aggccgtgat ggacgacttc     1860 gccgccttg tggaaaagtg ttgcaaggcc gacgacaaag agacatgctt cgccgaagag      1920
ggcaagaaac tggtggccgc ttctcaggct gctctgggac tttaa                     1965
```

```
<210> SEQ ID NO 100
<211> LENGTH: 2038
<212> TYPE: DNA
<213> ORGANISM: Artificial Sequence
<220> FEATURE:
<223> OTHER INFORMATION: Fusion protein

<400> SEQUENCE: 100
```

```
ggggacaagt ttgtacaaaa aagcaggcta tggtaccgcc accatgaaat gggtcacctt       60
tatctccctg ctgttcctgt tctcctccgc ctactcttgc gccgagtggt ctacagcttg      120
gggcccttgt tctaccacct gtggcctcgg catggccacc agagtgtcca accagaacag      180
attctgccgg ctggaaaccc agcggagact gtgcttgtct agaccttgcg aggccgctgc      240
caaggacgct cataagtctg aggtggccca ccggttcaag gacctgggcg aagagaactt      300
caaggccctg gtgctgatcg ccttcgctca gtacttgcag cagtgcccct tcgaggacca      360
cgtgaagctg gtcaacgaag tgaccgagtt cgccaagacc tgcgtggccg atgagtctgc      420
cgagaactgc gacaagtctc tgcacaccct gttcggcgac aagctgtgta ccgtggctac      480
cctgagagaa accttacggcg agatggccga ctgctgcgct aagcaagagc ccgagagaaa      540
cgagtgcttc ctgcagcaca ggacgacaa ccctaacctg cctagactcg tgcggcctga      600
ggtggacgtg atgtgtaccg ccttccacga caacgaggaa accttcctga agaagtacct      660
gtacgagatc gccagacggc accctactt ttacgcccct gagctgctgt tcttcgccaa       720
gcggtacaag gccgccttca ccgagtgttg tcaggccgct gataaggccg cttgcctgct      780
gcctaaactg gacgagctga gagatgaagg caaggcctcc agcgccaagc agagactgaa      840
gtgtgccagc ctgcagaagt tcggcgagag agcctttaag gctgggccg tcgctagact       900 gtcccagaga tttcccaagg ccgagtttgc cgaggtgtcc aagctggtta ccgacctgac      960
```

-continued

```
caaggtgcac accgaatgct gtcacggcga cctgctggaa tgcgccgatg atagagccga    1020
tctggccaag tacatctgcg agaaccagga ctccatctcc tccaagctga aagagtgctg    1080
cgagaagcct ctgctggaaa agtcccactg tatcgccgag gtggaaaacg acgagatgcc    1140
tgccgatctg ccttctctgg ccgccgactt cgtggaatct aaggacgtgt gcaagaacta    1200
cgccgaggct aaggatgtgt tcctgggcat gtttctgtac gagtacgctc ggcggcaccc    1260
cgactattct gttgtgctgc tgctgagact ggctaagacc tacgagacaa ccctcgagaa    1320
gtgctgtgcc gccgctgatc ctcacgagtg ttacgccaag gtgttcgacg agttcaagcc    1380
actggtggaa gaaccccaga acctgatcaa gcagaattgc gagctgttcg agcagctggg    1440
cgagtacaag ttccagaacg ccctgctcgt gcggtacacc aagaaagtgc cccaggtgtc    1500
cacacctaca ctggttgagg tgtcccggaa cctgggcaaa gtgggctcta agtgctgcaa    1560
gcaccccgag gccaagagaa tgccttgtgc cgaggactac ctgtccgtgg tgctgaacca    1620
gctgtgcgtg ctgcacgaaa agacccctgt gtccgacaga gtgaccaagt gctgtaccga    1680
gagcctggtc aacagacggc cttgcttctc tgccctggaa gtggacgaga catacgtgcc    1740
caaagagttc aacgccgaga cattcacctt ccacgccgac atctgcaccc tgtccgagaa    1800
agagcggcag atcaagaaac agaccgctct ggtggaactg gtcaagcaca gcccaaggc    1860 caccaaagaa cagctgaagg ccgtgatgga cgacttcgcc gcctttgtgg aaaagtgttg    1920
caaggccgac gacaaagaga catgcttcgc cgaagagggc aagaaactgg tggccgcttc    1980
tcaggctgct ctgggacttt aatctagaaa cccagctttc ttgtacaaag tggtcccc     2038
```

<210> SEQ ID NO 101
<211> LENGTH: 582
<212> TYPE: PRT
<213> ORGANISM: Homo sapiens

<400> SEQUENCE: 101

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
```

```
                    180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala
            580

<210> SEQ ID NO 102
```

<211> LENGTH: 675
<212> TYPE: PRT
<213> ORGANISM: Artificial Sequence
<220> FEATURE:
<223> OTHER INFORMATION: Fusion protein

<400> SEQUENCE: 102

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380
```

-continued

```
Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Glu Ala Ala Ala Lys Glu Ala Ala Ala Lys
                580                 585                 590

Glu Ala Ala Ala Lys Glu Ala Ala Ala Lys Glu Ala Ala Ala Lys Glu
                595                 600                 605

Ala Ala Ala Lys Glu Ala Ala Ala Lys Glu Ala Ala Ala Lys Cys Ala
            610                 615                 620

Glu Trp Ser Thr Ala Trp Gly Pro Cys Ser Thr Thr Cys Gly Leu Gly
625                 630                 635                 640

Met Ala Thr Arg Val Ser Asn Gln Asn Arg Phe Cys Arg Leu Glu Thr
                645                 650                 655

Gln Arg Arg Leu Cys Leu Ser Arg Pro Cys Pro Pro Ser Arg Gly Arg
                660                 665                 670

Ser Pro Gln
        675
```

```
<210> SEQ ID NO 103
<211> LENGTH: 693
<212> TYPE: PRT
<213> ORGANISM: Artificial Sequence
<220> FEATURE:
<223> OTHER INFORMATION: Fusion protein

<400> SEQUENCE: 103
```

```
Met Lys Trp Val Thr Phe Ile Ser Leu Leu Phe Leu Phe Ser Ser Ala
1               5                   10                  15

Tyr Ser Asp Ala His Lys Ser Glu Val Ala His Arg Phe Lys Asp Leu
                20                  25                  30

Gly Glu Glu Asn Phe Lys Ala Leu Val Leu Ile Ala Phe Ala Gln Tyr
            35                  40                  45

Leu Gln Gln Cys Pro Phe Glu Asp His Val Lys Leu Val Asn Glu Val
        50                  55                  60
```

```
Thr Glu Phe Ala Lys Thr Cys Val Ala Asp Glu Ser Ala Glu Asn Cys
65              70                  75                  80

Asp Lys Ser Leu His Thr Leu Phe Gly Asp Lys Leu Cys Thr Val Ala
                85                  90                  95

Thr Leu Arg Glu Thr Tyr Gly Glu Met Ala Asp Cys Cys Ala Lys Gln
            100                 105                 110

Glu Pro Glu Arg Asn Glu Cys Phe Leu Gln His Lys Asp Asp Asn Pro
            115                 120                 125

Asn Leu Pro Arg Leu Val Arg Pro Glu Val Asp Val Met Cys Thr Ala
    130                 135                 140

Phe His Asp Asn Glu Glu Thr Phe Leu Lys Lys Tyr Leu Tyr Glu Ile
145                 150                 155                 160

Ala Arg Arg His Pro Tyr Phe Tyr Ala Pro Glu Leu Leu Phe Phe Ala
            165                 170                 175

Lys Arg Tyr Lys Ala Ala Phe Thr Glu Cys Cys Gln Ala Ala Asp Lys
            180                 185                 190

Ala Ala Cys Leu Leu Pro Lys Leu Asp Glu Leu Arg Asp Glu Gly Lys
        195                 200                 205

Ala Ser Ser Ala Lys Gln Arg Leu Lys Cys Ala Ser Leu Gln Lys Phe
    210                 215                 220

Gly Glu Arg Ala Phe Lys Ala Trp Ala Val Ala Arg Leu Ser Gln Arg
225                 230                 235                 240

Phe Pro Lys Ala Glu Phe Ala Glu Val Ser Lys Leu Val Thr Asp Leu
            245                 250                 255

Thr Lys Val His Thr Glu Cys Cys His Gly Asp Leu Leu Glu Cys Ala
            260                 265                 270

Asp Asp Arg Ala Asp Leu Ala Lys Tyr Ile Cys Glu Asn Gln Asp Ser
            275                 280                 285

Ile Ser Ser Lys Leu Lys Glu Cys Cys Glu Lys Pro Leu Leu Glu Lys
    290                 295                 300

Ser His Cys Ile Ala Glu Val Glu Asn Asp Glu Met Pro Ala Asp Leu
305                 310                 315                 320

Pro Ser Leu Ala Ala Asp Phe Val Glu Ser Lys Asp Val Cys Lys Asn
            325                 330                 335

Tyr Ala Glu Ala Lys Asp Val Phe Leu Gly Met Phe Leu Tyr Glu Tyr
            340                 345                 350

Ala Arg Arg His Pro Asp Tyr Ser Val Val Leu Leu Leu Arg Leu Ala
            355                 360                 365

Lys Thr Tyr Glu Thr Thr Leu Glu Lys Cys Cys Ala Ala Ala Asp Pro
    370                 375                 380

His Glu Cys Tyr Ala Lys Val Phe Asp Glu Phe Lys Pro Leu Val Glu
385                 390                 395                 400

Glu Pro Gln Asn Leu Ile Lys Gln Asn Cys Glu Leu Phe Glu Gln Leu
            405                 410                 415

Gly Glu Tyr Lys Phe Gln Asn Ala Leu Leu Val Arg Tyr Thr Lys Lys
            420                 425                 430

Val Pro Gln Val Ser Thr Pro Thr Leu Val Glu Val Ser Arg Asn Leu
            435                 440                 445

Gly Lys Val Gly Ser Lys Cys Cys Lys His Pro Glu Ala Lys Arg Met
    450                 455                 460

Pro Cys Ala Glu Asp Tyr Leu Ser Val Val Leu Asn Gln Leu Cys Val
465                 470                 475                 480
```

```
Leu His Glu Lys Thr Pro Val Ser Asp Arg Val Thr Lys Cys Cys Thr
            485             490             495

Glu Ser Leu Val Asn Arg Arg Pro Cys Phe Ser Ala Leu Glu Val Asp
            500             505             510

Glu Thr Tyr Val Pro Lys Glu Phe Asn Ala Glu Thr Phe Thr Phe His
            515             520             525

Ala Asp Ile Cys Thr Leu Ser Glu Lys Glu Arg Gln Ile Lys Lys Gln
    530             535             540

Thr Ala Leu Val Glu Leu Val Lys His Lys Pro Lys Ala Thr Lys Glu
545             550             555             560

Gln Leu Lys Ala Val Met Asp Asp Phe Ala Ala Phe Val Glu Lys Cys
            565             570             575

Cys Lys Ala Asp Asp Lys Glu Thr Cys Phe Ala Glu Glu Gly Lys Lys
            580             585             590

Leu Val Ala Ala Ser Gln Ala Ala Glu Ala Ala Ala Lys Glu Ala Ala
            595             600             605

Ala Lys Glu Ala Ala Ala Lys Glu Ala Ala Ala Lys Glu Ala Ala Ala
    610             615             620

Lys Glu Ala Ala Ala Lys Glu Ala Ala Ala Lys Glu Ala Ala Ala Lys
625             630             635             640

Cys Ala Glu Trp Ser Thr Ala Trp Gly Pro Cys Ser Thr Thr Cys Gly
            645             650             655

Leu Gly Met Ala Thr Arg Val Ser Asn Gln Asn Arg Phe Cys Arg Leu
            660             665             670

Glu Thr Gln Arg Arg Leu Cys Leu Ser Arg Pro Cys Pro Pro Ser Arg
            675             680             685

Gly Arg Ser Pro Gln
    690
```

```
<210> SEQ ID NO 104
<211> LENGTH: 2088
<212> TYPE: DNA
<213> ORGANISM: Artificial Sequence
<220> FEATURE:
<223> OTHER INFORMATION: Fusion protein

<400> SEQUENCE: 104
gccaccatga aatgggtcac ctttatctcc ctgctgttcc tgttctcctc cgcctactct      60
gacgcccaca agtctgaggt ggcccacaga ttcaaggacc tgggcgaaga gaacttcaag     120
gccctggtgc tgatcgcctt cgctcagtac ttgcagcagt gccccttcga ggaccacgtg     180
aagctggtca acgaagtgac cgagttcgcc aagacctgcg tggccgatga gtctgccgag     240
aactgcgaca gtctctgca caccctgttc ggcgacaagc tgtgtaccgt ggctaccctg     300
agagaaacct acggcgagat ggccgactgc tgcgctaagc aagagcccga gagaaacgag     360
tgcttcctgc agcacaagga cgacaaccct aacctgccta gactcgtgcg gcctgaggtg     420
gacgtgatgt gtaccgcctt ccacgacaac gaggaaacct tcctgaagaa gtacctgtac     480
gagatcgcca gacggcaccc ctactttac gcccctgagc tgctgttctt cgccaagcgg     540
tacaaggccg ccttcaccga gtgttgtcag gccgctgata aggccgcttg cctgctgcct     600
aaactggacg agctgagaga tgaaggcaag gcctccagcg ccaagcagag actgaagtgt     660
gccagcctgc agaagttcgg cgagagagcc tttaaggcct gggccgtcgc tagactgtcc     720
cagagatttc ccaaggccga gtttgccgag gtgtccaagc tggttaccga cctgaccaag     780
gtgcacaccg aatgctgtca cggcgacctg ctggaatgcg ccgatgatag agccgatctg     840
```

```
gccaagtaca tctgcgagaa ccaggactcc atctcctcca agctgaaaga gtgctgcgag      900
aagcctctgc tggaaaagtc ccactgtatc gccgaggtgg aaaacgacga gatgcctgcc      960
gatctgcctt ctctggccgc cgacttcgtg gaatctaagg acgtgtgcaa gaactacgcc     1020
gaggccaagg atgtgttcct gggcatgttt ctgtacgagt acgctcggcg gcaccccgac     1080
tattctgttg tgctgctgct gagactggct aagacctacg agacaaccct cgagaagtgc     1140
tgtgccgccg ctgatcctca cgagtgttac gccaaggtgt cgacgagtt caagccactg      1200 gtggaagaac cccagaacct gatcaagcag aattgcgagc tgttcgagca gctgggcgag     1260
tacaagttcc agaacgccct gctcgtgcgg tacaccaaga aagtgcccca ggtgtccaca     1320
cctacactgg ttgaggtgtc ccggaacctg ggcaaagtgg gctctaagtg ctgcaagcac     1380
cctgaggcca agagaatgcc ttgcgccgag gactacctgt ccgtggtgct gaatcagctg     1440
tgcgtgctgc acgaaaagac ccctgtgtcc gacagagtga ccaagtgctg taccgagagc     1500
ctggtcaaca gacggccttg cttctctgcc ctggaagtgg acgagacata cgtgcccaaa     1560
gagttcaacg ccgagacatt caccttccac gccgacatct gcaccctgtc cgagaaagag     1620
cggcagatca gaaacagac cgctctggtg gaactggtca gcacaagcc caaggccacc       1680 aaagaacagc tgaaggccgt gatggacgac ttcgccgcct ttgtggaaaa gtgttgcaag     1740
gccgacgaca agagacatg cttcgccgaa gagggcaaga aactggtggc cgcttctcag      1800
gctgctgagg ccgctgctaa agaggctgcc gctaaagaag ccgcagccaa agaggcagct     1860
gcaaaagaag ctgctgcaaa agaggcagcc gccaaagagg ccgctgctaa agaagcagcc     1920
gccaagtgtg ctgagtggtc tacagcttgg ggccctgct ctacaacctg tggactcggc      1980
atggccacca gagtgtctaa ccagaacaga ttctgccggc tggaaaccca gcggagactg     2040
tgcctgtcta gaccctgtcc tcctagcaga ggcagatccc ctcagtga                  2088
```

```
<210> SEQ ID NO 105
<211> LENGTH: 2161
<212> TYPE: DNA
<213> ORGANISM: Artificial Sequence
<220> FEATURE:
<223> OTHER INFORMATION: Fusion protein

<400> SEQUENCE: 105
```

```
ggggacaagt ttgtacaaaa aagcaggcta tggtaccgcc accatgaaat gggtcacctt       60
tatctccctg ctgttcctgt tctcctccgc ctactctgac gcccacaagt ctgaggtggc      120
ccacagattc aaggacctgg gcgaagagaa cttcaaggcc ctggtgctga tcgccttcgc      180
tcagtacttg cagcagtgcc ccttcgagga ccacgtgaag ctggtcaacg aagtgaccga      240
gttcgccaag acctgcgtgg ccgatgagtc tgccgagaac tgcgacaagt ctctgcacac      300
cctgttcggc gacaagctgt gtaccgtggc taccctgaga gaaacctacg gcgagatggc      360
cgactgctgc gctaagcaag agcccgagag aaacgagtgc ttcctgcagc acaaggacga     420
caaccctaac ctgcctagac tcgtgcggcc tgaggtggac gtgatgtgta ccgccttcca      480
cgacaacgag gaaaccttcc tgaagaagta cctgtacgag atcgccagac ggcacccta       540 cttttacgcc cctgagctgc tgttcttcgc caagcggtac aaggccgcct tcaccgagtg      600
ttgtcaggcc gctgataagg ccgcttgcct gctgcctaaa ctggacgagc tgagagatga      660
aggcaaggcc tccagcgcca agcagagact gaagtgtgcc agcctgcaga gttcggcga      720 gagagccttt aaggcctggg ccgtcgctag actgtcccag agatttccca aggccgagtt      780
```

-continued

```
tgccgaggtg tccaagctgg ttaccgacct gaccaaggtg cacaccgaat gctgtcacgg      840
cgacctgctg gaatgcgccg atgatagagc cgatctggcc aagtacatct gcgagaacca      900
ggactccatc tcctccaagc tgaaagagtg ctgcgagaag cctctgctgg aaaagtccca      960
ctgtatcgcc gaggtggaaa cgacgagat gcctgccgat ctgccttctc tggccgccga     1020
cttcgtggaa tctaaggacg tgtgcaagaa ctacgccgag gccaaggatg tgttcctggg     1080
catgtttctg tacgagtacg ctcggcggca ccccgactat tctgttgtgc tgctgctgag     1140
actggctaag acctacgaga caaccctcga gaagtgctgt gccgccgctg atcctcacga     1200
gtgttacgcc aaggtgttcg acgagttcaa gccactggtg gaagaacccc agaacctgat     1260
caagcagaat tgcgagctgt tcgagcagct gggcgagtac aagttccaga acgccctgct     1320
cgtgcggtac accaagaaag tgccccaggt gtccacacct acactggttg aggtgtcccg     1380
gaacctgggc aaagtgggct ctaagtgctg caagcaccct gaggccaaga gaatgccttg     1440
cgccgaggac tacctgtccg tggtgctgaa tcagctgtgc gtgctgcacg aaaagacccc     1500
tgtgtccgac agagtgacca agtgctgtac cgagagcctg gtcaacagac ggccttgctt     1560
ctctgccctg gaagtggacg agacatacgt gcccaaagag ttcaacgccg agacattcac     1620
cttccacgcc gacatctgca ccctgtccga gaaagagcgg cagatcaaga acagaccgc      1680 tctggtggaa ctggtcaagc acaagcccaa ggccaccaaa gaacagctga aggccgtgat     1740
ggacgacttc gccgcctttg tggaaaagtg ttgcaaggcc gacgacaaag agacatgctt     1800
cgccgaagag ggcaagaaac tggtggccgc ttctcaggct gctgaggccg ctgctaaaga     1860
ggctgccgct aaagaagccg cagccaaaga ggcagctgca aaagaagctg ctgcaaaaga     1920
ggcagccgcc aaagaggccg ctgctaaaga agcagccgcc aagtgtgctg agtggtctac     1980
agcttggggc ccctgctcta caacctgtgg actcggcatg gccaccagag tgtctaacca     2040
gaacagattc tgccggctgg aaacccagcg gagactgtgc ctgtctagac cctgtcctcc     2100
tagcagaggc agatcccctc agtgatctag aaacccagct ttcttgtaca aagtggtccc     2160
c                                                                     2161
```

<210> SEQ ID NO 106
<211> LENGTH: 634
<212> TYPE: PRT
<213> ORGANISM: Artificial Sequence
<220> FEATURE:
<223> OTHER INFORMATION: Fusion protein

<400> SEQUENCE: 106

```
Cys Ala Glu Gln Thr Thr Glu Trp Thr Ala Cys Ser Lys Ser Cys Gly
1               5                   10                  15

Met Gly Phe Ser Thr Arg Val Thr Asn Arg Asn Arg Gln Cys Glu Met
            20                  25                  30

Leu Lys Gln Thr Arg Leu Cys Met Val Arg Pro Cys Glu Ala Ala Ala
        35                  40                  45

Lys Asp Ala His Lys Ser Glu Val Ala His Arg Phe Lys Asp Leu Gly
    50                  55                  60

Glu Glu Asn Phe Lys Ala Leu Val Leu Ile Ala Phe Ala Gln Tyr Leu
65                  70                  75                  80

Gln Gln Cys Pro Phe Glu Asp His Val Lys Leu Val Asn Glu Val Thr
                85                  90                  95

Glu Phe Ala Lys Thr Cys Val Ala Asp Glu Ser Ala Glu Asn Cys Asp
            100                 105                 110
```

```
Lys Ser Leu His Thr Leu Phe Gly Asp Lys Leu Cys Thr Val Ala Thr
        115                 120                 125

Leu Arg Glu Thr Tyr Gly Glu Met Ala Asp Cys Cys Ala Lys Gln Glu
        130                 135                 140

Pro Glu Arg Asn Glu Cys Phe Leu Gln His Lys Asp Asp Asn Pro Asn
145                     150                 155                 160

Leu Pro Arg Leu Val Arg Pro Glu Val Asp Val Met Cys Thr Ala Phe
                165                 170                 175

His Asp Asn Glu Glu Thr Phe Leu Lys Lys Tyr Leu Tyr Glu Ile Ala
            180                 185                 190

Arg Arg His Pro Tyr Phe Tyr Ala Pro Glu Leu Leu Phe Phe Ala Lys
            195                 200                 205

Arg Tyr Lys Ala Ala Phe Thr Glu Cys Cys Gln Ala Ala Asp Lys Ala
        210                 215                 220

Ala Cys Leu Leu Pro Lys Leu Asp Glu Leu Arg Asp Glu Gly Lys Ala
225                 230                 235                 240

Ser Ser Ala Lys Gln Arg Leu Lys Cys Ala Ser Leu Gln Lys Phe Gly
                245                 250                 255

Glu Arg Ala Phe Lys Ala Trp Ala Val Ala Arg Leu Ser Gln Arg Phe
            260                 265                 270

Pro Lys Ala Glu Phe Ala Glu Val Ser Lys Leu Val Thr Asp Leu Thr
        275                 280                 285

Lys Val His Thr Glu Cys Cys His Gly Asp Leu Leu Glu Cys Ala Asp
        290                 295                 300

Asp Arg Ala Asp Leu Ala Lys Tyr Ile Cys Glu Asn Gln Asp Ser Ile
305                 310                 315                 320

Ser Ser Lys Leu Lys Glu Cys Cys Glu Lys Pro Leu Leu Glu Lys Ser
                325                 330                 335

His Cys Ile Ala Glu Val Glu Asn Asp Glu Met Pro Ala Asp Leu Pro
            340                 345                 350

Ser Leu Ala Ala Asp Phe Val Glu Ser Lys Asp Val Cys Lys Asn Tyr
            355                 360                 365

Ala Glu Ala Lys Asp Val Phe Leu Gly Met Phe Leu Tyr Glu Tyr Ala
        370                 375                 380

Arg Arg His Pro Asp Tyr Ser Val Val Leu Leu Leu Arg Leu Ala Lys
385                 390                 395                 400

Thr Tyr Glu Thr Thr Leu Glu Lys Cys Cys Ala Ala Ala Asp Pro His
                405                 410                 415

Glu Cys Tyr Ala Lys Val Phe Asp Glu Phe Lys Pro Leu Val Glu Glu
            420                 425                 430

Pro Gln Asn Leu Ile Lys Gln Asn Cys Glu Leu Phe Glu Gln Leu Gly
            435                 440                 445

Glu Tyr Lys Phe Gln Asn Ala Leu Leu Val Arg Tyr Thr Lys Lys Val
        450                 455                 460

Pro Gln Val Ser Thr Pro Thr Leu Val Glu Val Ser Arg Asn Leu Gly
465                 470                 475                 480

Lys Val Gly Ser Lys Cys Cys Lys His Pro Glu Ala Lys Arg Met Pro
                485                 490                 495

Cys Ala Glu Asp Tyr Leu Ser Val Val Leu Asn Gln Leu Cys Val Leu
            500                 505                 510

His Glu Lys Thr Pro Val Ser Asp Arg Val Thr Lys Cys Cys Thr Glu
        515                 520                 525

Ser Leu Val Asn Arg Arg Pro Cys Phe Ser Ala Leu Glu Val Asp Glu
```

-continued

```
        530                 535                 540

Thr Tyr Val Pro Lys Glu Phe Asn Ala Glu Thr Phe Thr Phe His Ala
545                 550                 555                 560

Asp Ile Cys Thr Leu Ser Glu Lys Glu Arg Gln Ile Lys Lys Gln Thr
                565                 570                 575

Ala Leu Val Glu Leu Val Lys His Lys Pro Lys Ala Thr Lys Glu Gln
                580                 585                 590

Leu Lys Ala Val Met Asp Asp Phe Ala Ala Phe Val Glu Lys Cys Cys
        595                 600                 605

Lys Ala Asp Asp Lys Glu Thr Cys Phe Ala Glu Glu Gly Lys Lys Leu
        610                 615                 620

Val Ala Ala Ser Gln Ala Ala Leu Gly Leu
625                 630

<210> SEQ ID NO 107
<211> LENGTH: 652
<212> TYPE: PRT
<213> ORGANISM: Artificial Sequence
<220> FEATURE:
<223> OTHER INFORMATION: Fusion protein

<400> SEQUENCE: 107

Met Lys Trp Val Thr Phe Ile Ser Leu Leu Phe Leu Phe Ser Ser Ala
1               5                   10                  15

Tyr Ser Cys Ala Glu Gln Thr Thr Glu Trp Thr Ala Cys Ser Lys Ser
                20                  25                  30

Cys Gly Met Gly Phe Ser Thr Arg Val Thr Asn Arg Asn Arg Gln Cys
                35                  40                  45

Glu Met Leu Lys Gln Thr Arg Leu Cys Met Val Arg Pro Cys Glu Ala
        50                  55                  60

Ala Ala Lys Asp Ala His Lys Ser Glu Val Ala His Arg Phe Lys Asp
65                  70                  75                  80

Leu Gly Glu Glu Asn Phe Lys Ala Leu Val Leu Ile Ala Phe Ala Gln
                85                  90                  95

Tyr Leu Gln Gln Cys Pro Phe Glu Asp His Val Lys Leu Val Asn Glu
                100                 105                 110

Val Thr Glu Phe Ala Lys Thr Cys Val Ala Asp Glu Ser Ala Glu Asn
        115                 120                 125

Cys Asp Lys Ser Leu His Thr Leu Phe Gly Asp Lys Leu Cys Thr Val
        130                 135                 140

Ala Thr Leu Arg Glu Thr Tyr Gly Glu Met Ala Asp Cys Cys Ala Lys
145                 150                 155                 160

Gln Glu Pro Glu Arg Asn Glu Cys Phe Leu Gln His Lys Asp Asp Asn
                165                 170                 175

Pro Asn Leu Pro Arg Leu Val Arg Pro Glu Val Asp Val Met Cys Thr
                180                 185                 190

Ala Phe His Asp Asn Glu Glu Thr Phe Leu Lys Lys Tyr Leu Tyr Glu
        195                 200                 205

Ile Ala Arg Arg His Pro Tyr Phe Tyr Ala Pro Glu Leu Leu Phe Phe
        210                 215                 220

Ala Lys Arg Tyr Lys Ala Ala Phe Thr Glu Cys Cys Gln Ala Ala Asp
225                 230                 235                 240

Lys Ala Ala Cys Leu Leu Pro Lys Leu Asp Glu Leu Arg Asp Glu Gly
                245                 250                 255

Lys Ala Ser Ser Ala Lys Gln Arg Leu Lys Cys Ala Ser Leu Gln Lys
```

-continued

```
                260             265              270
Phe Gly Glu Arg Ala Phe Lys Ala Trp Ala Val Ala Arg Leu Ser Gln
        275             280              285

Arg Phe Pro Lys Ala Glu Phe Ala Glu Val Ser Lys Leu Val Thr Asp
    290             295             300

Leu Thr Lys Val His Thr Glu Cys Cys His Gly Asp Leu Leu Glu Cys
305             310             315             320

Ala Asp Asp Arg Ala Asp Leu Ala Lys Tyr Ile Cys Glu Asn Gln Asp
            325             330             335

Ser Ile Ser Ser Lys Leu Lys Glu Cys Cys Glu Lys Pro Leu Leu Glu
            340             345             350

Lys Ser His Cys Ile Ala Glu Val Glu Asn Asp Glu Met Pro Ala Asp
            355             360             365

Leu Pro Ser Leu Ala Ala Asp Phe Val Glu Ser Lys Asp Val Cys Lys
    370             375             380

Asn Tyr Ala Glu Ala Lys Asp Val Phe Leu Gly Met Phe Leu Tyr Glu
385             390             395             400

Tyr Ala Arg Arg His Pro Asp Tyr Ser Val Val Leu Leu Leu Arg Leu
            405             410             415

Ala Lys Thr Tyr Glu Thr Thr Leu Glu Lys Cys Cys Ala Ala Ala Asp
            420             425             430

Pro His Glu Cys Tyr Ala Lys Val Phe Asp Glu Phe Lys Pro Leu Val
            435             440             445

Glu Glu Pro Gln Asn Leu Ile Lys Gln Asn Cys Glu Leu Phe Glu Gln
    450             455             460

Leu Gly Glu Tyr Lys Phe Gln Asn Ala Leu Leu Val Arg Tyr Thr Lys
465             470             475             480

Lys Val Pro Gln Val Ser Thr Pro Thr Leu Val Glu Val Ser Arg Asn
            485             490             495

Leu Gly Lys Val Gly Ser Lys Cys Cys Lys His Pro Glu Ala Lys Arg
            500             505             510

Met Pro Cys Ala Glu Asp Tyr Leu Ser Val Val Leu Asn Gln Leu Cys
            515             520             525

Val Leu His Glu Lys Thr Pro Val Ser Asp Arg Val Thr Lys Cys Cys
    530             535             540

Thr Glu Ser Leu Val Asn Arg Arg Pro Cys Phe Ser Ala Leu Glu Val
545             550             555             560

Asp Glu Thr Tyr Val Pro Lys Glu Phe Asn Ala Glu Thr Phe Thr Phe
            565             570             575

His Ala Asp Ile Cys Thr Leu Ser Glu Lys Glu Arg Gln Ile Lys Lys
            580             585             590

Gln Thr Ala Leu Val Glu Leu Val Lys His Lys Pro Lys Ala Thr Lys
            595             600             605

Glu Gln Leu Lys Ala Val Met Asp Asp Phe Ala Ala Phe Val Glu Lys
    610             615             620

Cys Cys Lys Ala Asp Asp Lys Glu Thr Cys Phe Ala Glu Glu Gly Lys
625             630             635             640

Lys Leu Val Ala Ala Ser Gln Ala Ala Leu Gly Leu
            645             650
```

<210> SEQ ID NO 108
<211> LENGTH: 1965
<212> TYPE: DNA
<213> ORGANISM: Artificial Sequence -continued
<220> FEATURE:
<223> OTHER INFORMATION: Fusion protein

<400> SEQUENCE: 108

```
gccaccatga aatgggtcac ctttatctcc ctgctgttcc tgttctcctc cgcctactct      60
tgtgccgagc agaccacaga gtggaccgcc tgctctaagt cttgcggcat gggcttctcc     120
accagagtga ccaaccggaa cagacagtgc gagatgctga agcagacccg gctgtgtatg     180
gttcgacctt gcgaggccgc tgccaaggat gctcataagt ctgaggtggc ccaccggttc     240
aaggacctgg gcgaagagaa cttcaaggcc ctggtgctga tcgccttcgc tcagtacttg     300
cagcagtgcc ccttcgagga ccacgtgaag ctggtcaacg aagtgaccga gttcgccaag     360
acctgcgtgg ccgatgagtc tgccgagaac tgcgacaagt ctctgcacac cctgttcggc     420
gacaagctgt gtaccgtggc taccctgaga gaaacctacg gcgagatggc cgactgctgc     480
gctaagcaag agcccgagag aaacgagtgc ttcctgcagc acaaggacga caaccctaac     540
ctgcctagac tcgtgcggcc tgaggtggac gtgatgtgta ccgccttcca cgacaacgag     600
gaaaccttcc tgaagaagta cctgtacgag atcgccagac ggcacccta cttttacgcc     660 cctgagctgc tgttcttcgc caagcggtac aaggccgcct tcaccgagtg ttgtcaggcc     720
gctgataagg ccgcttgcct gctgcctaaa ctggacgagc tgagagatga aggcaaggcc     780
tccagcgcca agcagagact gaagtgtgcc agcctgcaga agttcggcga gagagccttt     840
aaggcctggg ccgtcgctag actgtcccag agatttccca aggccgagtt tgccgaggtg     900
tccaagctgg ttaccgacct gaccaaggtg cacaccgaat gctgtcacgg cgacctgctg     960
gaatgcgccg atgatagagc cgatctggcc aagtacatct gcgagaacca ggactccatc    1020
tcctccaagc tgaaagagtg ctgcgagaag cctctgctgg aaaagtccca ctgtatcgcc    1080
gaggtggaaa cgacgagat gcctgccgat ctgccttctc tggccgccga cttcgtggaa     1140
tctaaggacg tgtgcaagaa ctacgccgag gctaaggatg tgttcctggg catgtttctg    1200
tacgagtacg ctcggcggca ccccgattat agtgtggtgc tgctgctgag actggctaag    1260
acctacgaga caacctcga gaagtgctgt gccgccgctg atcctcacga gtgttacgcc     1320
aaggtgttcg acgagttcaa gcccactggtg gaagaacccc agaacctgat caagcagaat    1380
tgcgagctgt tcgagcagct gggcgagtac aagttccaga acgccctgct cgtgcggtac    1440
accaagaaag tgccccaggt gtccacacct acactggttg aggtgtcccg gaacctgggc    1500
aaagtgggct ctaagtgctg caagcacccc gaggccaaga gaatgccttg cgccgaggat    1560
tacctgtccg tggtgctgaa ccagctgtgc gtgctgcacg aaaagacccc tgtgtccgac    1620
cgcgtgacca agtgctgtac agagtccctg gtcaacagac ggccctgctt ctctgccctg    1680
gaagtggacg agacatacgt gcccaaagag ttcaacgccg agacattcac cttccacgcc    1740
gacatctgca ccctgtccga gaaagagcgg cagatcaaga acagaccgc tctggtcgaa     1800 ctggtcaagc acaagcccaa ggccaccaaa gaacagctga aggccgtgat ggacgacttc    1860
gccgcctttg tggaaaagtg ttgcaaggcc gacgacaaag agacatgctt cgccgaagag    1920
ggcaagaaac tggtggccgc ttctcaggct gctctgggac tttaa                    1965
```

<210> SEQ ID NO 109
<211> LENGTH: 2038
<212> TYPE: DNA
<213> ORGANISM: Artificial Sequence
<220> FEATURE:
<223> OTHER INFORMATION: Fusion protein

```
<400> SEQUENCE: 109
ggggacaagt tgtacaaaa aagcaggcta tggtaccgcc accatgaaat gggtcacctt      60
tatctccctg ctgttcctgt tctcctccgc ctactcttgt gccgagcaga ccacagagtg     120
gaccgcctgc tctaagtctt gcggcatggg cttctccacc agagtgacca accggaacag     180
acagtgcgag atgctgaagc agacccggct gtgtatggtt cgaccttgcg aggccgctgc     240
caaggatgct cataagtctg aggtggccca ccggttcaag gacctgggcg aagagaactt     300
caaggccctg gtgctgatcg ccttcgctca gtacttgcag cagtgcccct tcgaggacca     360
cgtgaagctg gtcaacgaag tgaccgagtt cgccaagacc tgcgtggccg atgagtctgc     420
cgagaactgc gacaagtctc tgcacaccct gttcggcgac aagctgtgta ccgtggctac     480
cctgagagaa acctacggcg agatggccga ctgctgcgct aagcaagagc cgagagaaa     540 cgagtgcttc ctgcagcaca aggacgacaa ccctaacctg cctagactcg tgcggcctga     600
ggtggacgtg atgtgtaccg ccttccacga caacgaggaa accttcctga agaagtacct     660
gtacgagatc gccagacggc accctactt ttacgcccct gagctgctgt cttcgccaa      720 gcggtacaag gccgccttca ccgagtgttg tcaggccgct gataaggccg cttgcctgct     780
gcctaaactg gacgagctga gagatgaagg caaggcctcc agcgccaagc agagactgaa     840
gtgtgccagc ctgcagaagt tcggcgagag agcctttaag gcctgggccg tcgctagact     900
gtcccagaga tttcccaagg ccgagtttgc cgaggtgtcc aagctggtta ccgacctgac     960
caaggtgcac accgaatgct gtcacggcga cctgctggaa tgcgccgatg atagagccga    1020
tctggccaag tacatctgcg agaaccagga ctccatctcc tccaagctga agagtgctg     1080 cgagaagcct ctgctggaaa agtcccactg tatcgccgag gtggaaaacg acgagatgcc    1140
tgccgatctg ccttctctgg ccgccgactt cgtggaatct aaggacgtgt gcaagaacta    1200
cgccgaggct aaggatgtgt tcctgggcat gtttctgtac gagtacgctc ggcggcaccc    1260
cgattatagt gtggtgctgc tgctgagact ggctaagacc tacgagacaa ccctcgagaa    1320
gtgctgtgcc gccgctgatc ctcacgagtg ttacgccaag gtgttcgacg agttcaagcc    1380
actggtggaa gaaccccaga acctgatcaa gcagaattgc gagctgttcg agcagctggg    1440
cgagtacaag ttccagaacg ccctgctcgt gcggtacacc aagaaagtgc cccaggtgtc    1500
cacacctaca ctggttgagg tgtcccggaa cctgggcaaa gtgggctcta agtgctgcaa    1560
gcaccccgag gccaagagaa tgccttgcgc cgaggattac ctgtccgtgg tgctgaacca    1620
gctgtgcgtg ctgcacgaaa agacccctgt gtccgaccgc gtgaccaagt gctgtacaga    1680
gtccctggtc aacagacggc cctgcttctc tgccctggaa gtggacgaga catacgtgcc    1740
caaagagttc aacgccgaga cattcacctt ccacgccgac atctgcaccc tgtccgagaa    1800
agagcggcag atcaagaaac agaccgctct ggtcgaactg gtcaagcaca gcccaaggc     1860 caccaaagaa cagctgaagg ccgtgatgga cgacttcgcc gcctttgtgg aaaagtgttg    1920
caaggccgac gacaaagaga catgcttcgc cgaagagggc aagaaactgg tggccgcttc    1980
tcaggctgct ctgggacttt aatctagaaa cccagctttc ttgtacaaag tggtcccc      2038

<210> SEQ ID NO 110
<211> LENGTH: 669
<212> TYPE: PRT
<213> ORGANISM: Artificial Sequence
<220> FEATURE:
<223> OTHER INFORMATION: Fusion protein

<400> SEQUENCE: 110
```

```
Cys Ala Glu Gln Thr Thr Glu Trp Thr Ala Cys Ser Lys Ser Cys Gly
1               5                   10                  15

Met Gly Phe Ser Thr Arg Val Thr Asn Arg Asn Arg Gln Cys Glu Met
            20                  25                  30

Leu Lys Gln Thr Arg Leu Cys Met Val Arg Pro Cys Glu Ala Ala Ala
        35                  40                  45

Lys Glu Ala Ala Ala Lys Glu Ala Ala Ala Lys Glu Ala Ala Ala Lys
    50                  55                  60

Glu Ala Ala Ala Lys Glu Ala Ala Ala Lys Glu Ala Ala Ala Lys Glu
65                  70                  75                  80

Ala Ala Ala Lys Asp Ala His Lys Ser Glu Val Ala His Arg Phe Lys
                85                  90                  95

Asp Leu Gly Glu Glu Asn Phe Lys Ala Leu Val Leu Ile Ala Phe Ala
            100                 105                 110

Gln Tyr Leu Gln Gln Cys Pro Phe Glu Asp His Val Lys Leu Val Asn
        115                 120                 125

Glu Val Thr Glu Phe Ala Lys Thr Cys Val Ala Asp Glu Ser Ala Glu
    130                 135                 140

Asn Cys Asp Lys Ser Leu His Thr Leu Phe Gly Asp Lys Leu Cys Thr
145                 150                 155                 160

Val Ala Thr Leu Arg Glu Thr Tyr Gly Glu Met Ala Asp Cys Cys Ala
            165                 170                 175

Lys Gln Glu Pro Glu Arg Asn Glu Cys Phe Leu Gln His Lys Asp Asp
            180                 185                 190

Asn Pro Asn Leu Pro Arg Leu Val Arg Pro Glu Val Asp Val Met Cys
            195                 200                 205

Thr Ala Phe His Asp Asn Glu Glu Thr Phe Leu Lys Lys Tyr Leu Tyr
            210                 215                 220

Glu Ile Ala Arg Arg His Pro Tyr Phe Tyr Ala Pro Glu Leu Leu Phe
225                 230                 235                 240

Phe Ala Lys Arg Tyr Lys Ala Ala Phe Thr Glu Cys Cys Gln Ala Ala
            245                 250                 255

Asp Lys Ala Ala Cys Leu Leu Pro Lys Leu Asp Glu Leu Arg Asp Glu
            260                 265                 270

Gly Lys Ala Ser Ser Ala Lys Gln Arg Leu Lys Cys Ala Ser Leu Gln
            275                 280                 285

Lys Phe Gly Glu Arg Ala Phe Lys Ala Trp Ala Val Ala Arg Leu Ser
    290                 295                 300

Gln Arg Phe Pro Lys Ala Glu Phe Ala Glu Val Ser Lys Leu Val Thr
305                 310                 315                 320

Asp Leu Thr Lys Val His Thr Glu Cys Cys His Gly Asp Leu Leu Glu
            325                 330                 335

Cys Ala Asp Asp Arg Ala Asp Leu Ala Lys Tyr Ile Cys Glu Asn Gln
            340                 345                 350

Asp Ser Ile Ser Ser Lys Leu Lys Glu Cys Cys Glu Lys Pro Leu Leu
        355                 360                 365

Glu Lys Ser His Cys Ile Ala Glu Val Glu Asn Asp Glu Met Pro Ala
    370                 375                 380

Asp Leu Pro Ser Leu Ala Ala Asp Phe Val Glu Ser Lys Asp Val Cys
385                 390                 395                 400

Lys Asn Tyr Ala Glu Ala Lys Asp Val Phe Leu Gly Met Phe Leu Tyr
            405                 410                 415
```

```
Glu Tyr Ala Arg Arg His Pro Asp Tyr Ser Val Val Leu Leu Leu Arg
            420                 425                 430

Leu Ala Lys Thr Tyr Glu Thr Thr Leu Glu Lys Cys Cys Ala Ala Ala
            435                 440                 445

Asp Pro His Glu Cys Tyr Ala Lys Val Phe Asp Glu Phe Lys Pro Leu
            450                 455                 460

Val Glu Glu Pro Gln Asn Leu Ile Lys Gln Asn Cys Glu Leu Phe Glu
465                 470                 475                 480

Gln Leu Gly Glu Tyr Lys Phe Gln Asn Ala Leu Leu Val Arg Tyr Thr
                485                 490                 495

Lys Lys Val Pro Gln Val Ser Thr Pro Thr Leu Val Glu Val Ser Arg
            500                 505                 510

Asn Leu Gly Lys Val Gly Ser Lys Cys Cys Lys His Pro Glu Ala Lys
            515                 520                 525

Arg Met Pro Cys Ala Glu Asp Tyr Leu Ser Val Val Leu Asn Gln Leu
            530                 535                 540

Cys Val Leu His Glu Lys Thr Pro Val Ser Asp Arg Val Thr Lys Cys
545                 550                 555                 560

Cys Thr Glu Ser Leu Val Asn Arg Arg Pro Cys Phe Ser Ala Leu Glu
                565                 570                 575

Val Asp Glu Thr Tyr Val Pro Lys Glu Phe Asn Ala Glu Thr Phe Thr
                580                 585                 590

Phe His Ala Asp Ile Cys Thr Leu Ser Glu Lys Glu Arg Gln Ile Lys
            595                 600                 605

Lys Gln Thr Ala Leu Val Glu Leu Val Lys His Lys Pro Lys Ala Thr
            610                 615                 620

Lys Glu Gln Leu Lys Ala Val Met Asp Asp Phe Ala Ala Phe Val Glu
625                 630                 635                 640

Lys Cys Cys Lys Ala Asp Asp Lys Glu Thr Cys Phe Ala Glu Glu Gly
                645                 650                 655

Lys Lys Leu Val Ala Ala Ser Gln Ala Ala Leu Gly Leu
            660                 665
```

```
<210> SEQ ID NO 111
<211> LENGTH: 687
<212> TYPE: PRT
<213> ORGANISM: Artificial Sequence
<220> FEATURE:
<223> OTHER INFORMATION: Fusion protein

<400> SEQUENCE: 111
```

```
Met Lys Trp Val Thr Phe Ile Ser Leu Leu Phe Leu Phe Ser Ser Ala
1               5                   10                  15

Tyr Ser Cys Ala Glu Gln Thr Thr Glu Trp Thr Ala Cys Ser Lys Ser
            20                  25                  30

Cys Gly Met Gly Phe Ser Thr Arg Val Thr Asn Arg Asn Arg Gln Cys
            35                  40                  45

Glu Met Leu Lys Gln Thr Arg Leu Cys Met Val Arg Pro Cys Glu Ala
            50                  55                  60

Ala Ala Lys Glu Ala Ala Ala Lys Glu Ala Ala Ala Lys Glu Ala Ala
65                  70                  75                  80

Ala Lys Glu Ala Ala Ala Lys Glu Ala Ala Ala Lys Glu Ala Ala Ala
                85                  90                  95

Lys Glu Ala Ala Ala Lys Asp Ala His Lys Ser Glu Val Ala His Arg
            100                 105                 110
```

-continued

```
Phe Lys Asp Leu Gly Glu Glu Asn Phe Lys Ala Leu Val Leu Ile Ala
        115                 120                 125

Phe Ala Gln Tyr Leu Gln Gln Cys Pro Phe Glu Asp His Val Lys Leu
        130                 135                 140

Val Asn Glu Val Thr Glu Phe Ala Lys Thr Cys Val Ala Asp Glu Ser
145                 150                 155                 160

Ala Glu Asn Cys Asp Lys Ser Leu His Thr Leu Phe Gly Asp Lys Leu
                165                 170                 175

Cys Thr Val Ala Thr Leu Arg Glu Thr Tyr Gly Glu Met Ala Asp Cys
                180                 185                 190

Cys Ala Lys Gln Glu Pro Glu Arg Asn Glu Cys Phe Leu Gln His Lys
        195                 200                 205

Asp Asp Asn Pro Asn Leu Pro Arg Leu Val Arg Pro Glu Val Asp Val
        210                 215                 220

Met Cys Thr Ala Phe His Asp Asn Glu Glu Thr Phe Leu Lys Lys Tyr
225                 230                 235                 240

Leu Tyr Glu Ile Ala Arg Arg His Pro Tyr Phe Tyr Ala Pro Glu Leu
                245                 250                 255

Leu Phe Phe Ala Lys Arg Tyr Lys Ala Ala Phe Thr Glu Cys Cys Gln
                260                 265                 270

Ala Ala Asp Lys Ala Ala Cys Leu Leu Pro Lys Leu Asp Glu Leu Arg
        275                 280                 285

Asp Glu Gly Lys Ala Ser Ser Ala Lys Gln Arg Leu Lys Cys Ala Ser
        290                 295                 300

Leu Gln Lys Phe Gly Glu Arg Ala Phe Lys Ala Trp Ala Val Ala Arg
305                 310                 315                 320

Leu Ser Gln Arg Phe Pro Lys Ala Glu Phe Ala Glu Val Ser Lys Leu
                325                 330                 335

Val Thr Asp Leu Thr Lys Val His Thr Glu Cys Cys His Gly Asp Leu
                340                 345                 350

Leu Glu Cys Ala Asp Asp Arg Ala Asp Leu Ala Lys Tyr Ile Cys Glu
        355                 360                 365

Asn Gln Asp Ser Ile Ser Ser Lys Leu Lys Glu Cys Cys Glu Lys Pro
        370                 375                 380

Leu Leu Glu Lys Ser His Cys Ile Ala Glu Val Glu Asn Asp Glu Met
385                 390                 395                 400

Pro Ala Asp Leu Pro Ser Leu Ala Ala Asp Phe Val Glu Ser Lys Asp
                405                 410                 415

Val Cys Lys Asn Tyr Ala Glu Ala Lys Asp Val Phe Leu Gly Met Phe
                420                 425                 430

Leu Tyr Glu Tyr Ala Arg Arg His Pro Asp Tyr Ser Val Val Leu Leu
        435                 440                 445

Leu Arg Leu Ala Lys Thr Tyr Glu Thr Thr Leu Glu Lys Cys Cys Ala
        450                 455                 460

Ala Ala Asp Pro His Glu Cys Tyr Ala Lys Val Phe Asp Glu Phe Lys
465                 470                 475                 480

Pro Leu Val Glu Glu Pro Gln Asn Leu Ile Lys Gln Asn Cys Glu Leu
                485                 490                 495

Phe Glu Gln Leu Gly Glu Tyr Lys Phe Gln Asn Ala Leu Leu Val Arg
                500                 505                 510

Tyr Thr Lys Lys Val Pro Gln Val Ser Thr Pro Thr Leu Val Glu Val
        515                 520                 525

Ser Arg Asn Leu Gly Lys Val Gly Ser Lys Cys Cys Lys His Pro Glu
```

-continued

```
             530                  535                   540
Ala Lys Arg Met Pro Cys Ala Glu Asp Tyr Leu Ser Val Val Leu Asn
545                  550                   555                   560

Gln Leu Cys Val Leu His Glu Lys Thr Pro Val Ser Asp Arg Val Thr
                 565                   570                   575

Lys Cys Cys Thr Glu Ser Leu Val Asn Arg Arg Pro Cys Phe Ser Ala
                 580                   585                   590

Leu Glu Val Asp Glu Thr Tyr Val Pro Lys Glu Phe Asn Ala Glu Thr
                 595                   600                   605

Phe Thr Phe His Ala Asp Ile Cys Thr Leu Ser Glu Lys Glu Arg Gln
         610                   615                   620

Ile Lys Lys Gln Thr Ala Leu Val Glu Leu Val Lys His Lys Pro Lys
625                  630                   635                   640

Ala Thr Lys Glu Gln Leu Lys Ala Val Met Asp Asp Phe Ala Ala Phe
                 645                   650                   655

Val Glu Lys Cys Cys Lys Ala Asp Asp Lys Glu Thr Cys Phe Ala Glu
                 660                   665                   670

Glu Gly Lys Lys Leu Val Ala Ala Ser Gln Ala Ala Leu Gly Leu
         675                   680                   685
```

<210> SEQ ID NO 112
<211> LENGTH: 2070
<212> TYPE: DNA
<213> ORGANISM: Artificial Sequence
<220> FEATURE:
<223> OTHER INFORMATION: Fusion protein

<400> SEQUENCE: 112

```
gccaccatga aatgggtcac ctttatctcc ctgctgttcc tgttctcctc cgcctactct      60
tgtgccgagc agaccacaga gtggaccgcc tgctctaagt cttgcggcat gggcttctcc     120
accagagtga ccaaccggaa cagacagtgc gagatgctga agcagacccg gctgtgtatg     180
gttcgacctt gcgaggccgc tgccaaagag gctgctgcta agaagccgc cgcaaaagag      240 gcagcagcaa aagaggctgc cgccaaagag gccgcagcca agaagcagc agctaaagag      300 gccgctgcta aggacgccca caagtctgaa gtggcccacc ggtttaagga cctgggcgaa     360
gagaacttca aggccctggt gctgatcgcc ttcgctcagt acttgcagca gtgccccttc     420
gaggaccacg tgaagctggt caacgaagtg accgagttcg ccaagacctg cgtggccgat     480
gagtctgccg agaactgcga caagtctctg cacaccctgt tcggcgacaa gctgtgtacc     540
gtggctaccc tgagagaaac ctacggcgag atggccgact gctgcgctaa gcaagagccc     600
gagagaaacg agtgcttcct gcagcacaag gacgacaacc ctaacctgcc tagactcgtg     660
cggcctgagg tggacgtgat gtgtaccgcc ttccacgaca cgaggaaac cttcctgaag      720 aagtacctgt acgagatcgc cagacggcac ccctactttt acgccctga gctgctgttt      780 ttcgccaagc ggtacaaggc cgccttcacc gagtgttgtc aggccgccga taaggccgct     840
tgtctgctgc ctaaactgga cgagctgcgc gacgaaggca aggcctcttc tgctaagcag     900
cggctgaagt gcgccagcct gcagaagttt ggcgagagag ccttcaaggc ttgggccgtc     960
gctagactgt cccagagatt tcccaaggcc gagtttgccg aggtgtccaa gctggttacc    1020
gacctgacca aggtgcacac cgaatgctgt cacggcgacc tgctggaatg cgccgatgat    1080
agagccgatc tggccaagta catctgcgag aaccaggact ccatctcctc caagctgaaa    1140
gagtgctgcg agaagcctct gctggaaaag tcccactgta tcgccgaggt ggaaaacgac    1200
```

```
gagatgcctg ccgatctgcc ttctctggcc gccgacttcg tggaatctaa ggacgtgtgc    1260
aagaactacg ccgaggccaa ggatgtgttc ctgggcatgt ttctgtacga gtacgctcgg    1320
cggcaccccg attatagtgt ggtgctgctg ctgagactgg ctaagaccta cgagacaacc    1380
ctcgagaagt gctgtgccgc cgctgatcct cacgagtgtt acgccaaggt gttcgacgag    1440
ttcaagccac tggtggaaga accccagaac ctgatcaagc agaattgcga gctgttcgag    1500
cagctgggcg agtacaagtt ccagaacgcc ctgctcgtgc ggtacaccaa gaaagtgccc    1560
caggtgtcca cacctacact ggttgaggtg tcccggaacc tgggcaaagt gggctctaag    1620
tgctgcaagc accctgaggc caagagaatg ccttgcgccg aggactacct gtccgtggtg    1680
ctgaatcagc tgtgcgtgct gcacgaaaag accctgtgt ccgaccgcgt gaccaagtgc    1740
tgtacagagt ccctggtcaa cagacggccc tgcttctctg ccctggaagt ggacgagaca    1800
tacgtgccca aagagttcaa cgccgagaca ttcaccttcc acgccgacat ctgcaccctg    1860
tccgagaaag agcggcagat caagaaacag accgctctgg tcgagctggt taagcacaag    1920
cccaaggcca ccaaagaaca gctgaaggcc gtgatggacg acttcgccgc ctttgtggaa    1980
aagtgttgca aggccgacga caaagagaca tgcttcgccg aagagggcaa gaaactggtg    2040
gccgcttctc aggctgctct gggactttaa                                     2070
```

<210> SEQ ID NO 113
<211> LENGTH: 2143
<212> TYPE: DNA
<213> ORGANISM: Artificial Sequence
<220> FEATURE:
<223> OTHER INFORMATION: Fusion protein

<400> SEQUENCE: 113

```
ggggacaagt ttgtacaaaa aagcaggcta tggtaccgcc accatgaaat gggtcacctt     60
tatctccctg ctgttcctgt tctcctccgc ctactcttgt gccgagcaga ccacagagtg    120
gaccgcctgc tctaagtctt gcggcatggg cttctccacc agagtgacca accggaacag    180
acagtgcgag atgctgaagc agacccggct gtgtatggtt cgaccttgcg aggccgctgc    240
caaagaggct gctgctaaag aagccgccgc aaaagaggca gcagcaaaag aggctgccgc    300
caaagaggcc gcagccaaag aagcagcagc taaagaggcc gctgctaagg acgcccacaa    360
gtctgaagtg gcccaccggt ttaaggacct gggcgaagag aacttcaagg ccctggtgct    420
gatcgccttc gctcagtact tgcagcagtg cccccttcgag gaccacgtga agctggtcaa    480
cgaagtgacc gagttcgcca agaccctgcgt ggccgatgag tctgccgaga ctgcgacaa    540 gtctctgcac accctgttcg gcgacaagct gtgtaccgtg gctaccctga gagaaaccta    600
cggcgagatg gccgactgct gcgctaagca agagcccgag agaaacgagt gcttcctgca    660
gcacaaggac gacaacccta acctgcctag actcgtgcgg cctgaggtgg acgtgatgtg    720
taccgccttc cacgacaacg aggaaacctt cctgaagaag tacctgtacg agatcgccag    780
acggcacccc tacttttacg ccccttgagct gctgttttc gccaagcggt acaaggccgc    840
cttcaccgag tgttgtcagg ccgccgataa ggccgcttgt ctgctgccta aactggacga    900
gctgcgcgac gaaggcaagg cctcttctgc taagcagcgg ctgaagtgcg ccagcctgca    960
gaagtttggc gagagagcct tcaaggcttg ggccgtcgct agactgtccc agagatttcc   1020
caaggccgag tttgccgagg tgtccaagct ggttaccgac ctgaccaagg tgcacaccga   1080 atgcgtcac ggcgacctgc tggaatgcgc cgatgataga gccgatctgg ccaagtacat   1140
ctgcgagaac caggactcca tctcctccaa gctgaaagag tgctgcgaga agcctctgct   1200
```

```
ggaaaagtcc cactgtatcg ccgaggtgga aaacgacgag atgcctgccg atctgccttc      1260
tctggccgcc gacttcgtgg aatctaagga cgtgtgcaag aactacgccg aggccaagga      1320
tgtgttcctg ggcatgtttc tgtacgagta cgctcggcgg cacccgatt ataagtgtggt      1380 gctgctgctg agactggcta agacctacga gacaaccctc gagaagtgct gtgccgccgc      1440
tgatcctcac gagtgttacg ccaaggtgtt cgacgagttc aagccactgg tggaagaacc      1500
ccagaacctg atcaagcaga attgcgagct gttcgagcag ctgggcgagt acaagttcca      1560
gaacgccctg ctcgtgcggt acaccaagaa agtgcccag gtgtccacac ctacactggt       1620
tgaggtgtcc cggaacctgg gcaaagtggg ctctaagtgc tgcaagcacc ctgaggccaa      1680
gagaatgcct tgcgccgagg actacctgtc cgtggtgctg aatcagctgt gcgtgctgca      1740
cgaaaagacc cctgtgtccg accgcgtgac caagtgctgt acagagtccc tggtcaacag      1800
acggccctgc ttctctgccc tggaagtgga cgagacatac gtgcccaaag agttcaacgc      1860
cgagacattc accttccacg ccgacatctg caccctgtcc gagaaagagc ggcagatcaa      1920
gaaacagacc gctctggtcg agctggttaa gcacaagccc aaggccacca agaacagct       1980 gaaggccgtg atggacgact cgccgcctt tgtggaaaag tgttgcaagg ccgacgacaa       2040
agagacatgc ttcgccgaag agggcaagaa actggtggcc gcttctcagg ctgctctggg      2100
actttaatct agaaacccag ctttcttgta caaagtggtc ccc                        2143
```

<210> SEQ ID NO 114
<211> LENGTH: 484
<212> TYPE: PRT
<213> ORGANISM: Artificial Sequence
<220> FEATURE:
<223> OTHER INFORMATION: Fusion protein

<400> SEQUENCE: 114

```
Met Lys Trp Val Thr Phe Ile Ser Leu Leu Phe Leu Phe Ser Ser Ala
1               5                   10                  15

Tyr Ser Gly His His His His His His Gly Ser Glu Ile Gly Thr Gly
            20                  25                  30

Phe Pro Phe Asp Pro His Tyr Val Glu Val Leu Gly Glu Arg Met His
        35                  40                  45

Tyr Val Asp Val Gly Pro Arg Asp Gly Thr Pro Val Leu Phe Leu His
    50                  55                  60

Gly Asn Pro Thr Ser Ser Tyr Val Trp Arg Asn Ile Ile Pro His Val
65                  70                  75                  80

Ala Pro Thr His Arg Cys Ile Ala Pro Asp Leu Ile Gly Met Gly Lys
                85                  90                  95

Ser Asp Lys Pro Asp Leu Gly Tyr Phe Phe Asp Asp His Val Arg Phe
            100                 105                 110

Met Asp Ala Phe Ile Glu Ala Leu Gly Leu Glu Glu Val Val Leu Val
        115                 120                 125

Ile His Asp Trp Gly Ser Ala Leu Gly Phe His Trp Ala Lys Arg Asn
    130                 135                 140

Pro Glu Arg Val Lys Gly Ile Ala Phe Met Glu Phe Ile Arg Pro Ile
145                 150                 155                 160

Pro Thr Trp Asp Glu Trp Pro Glu Phe Ala Arg Glu Thr Phe Gln Ala
                165                 170                 175

Phe Arg Thr Thr Asp Val Gly Arg Lys Leu Ile Ile Asp Gln Asn Val
            180                 185                 190
```

-continued

```
Phe Ile Glu Gly Thr Leu Pro Met Gly Val Val Arg Pro Leu Thr Glu
        195                 200                 205

Val Glu Met Asp His Tyr Arg Glu Pro Phe Leu Asn Pro Val Asp Arg
    210                 215                 220

Glu Pro Leu Trp Arg Phe Pro Asn Glu Leu Pro Ile Ala Gly Glu Pro
225                 230                 235                 240

Ala Asn Ile Val Ala Leu Val Glu Glu Tyr Met Asp Trp Leu His Gln
            245                 250                 255

Ser Pro Val Pro Lys Leu Leu Phe Trp Gly Thr Pro Gly Val Leu Ile
            260                 265                 270

Pro Pro Ala Glu Ala Ala Arg Leu Ala Lys Ser Leu Pro Asn Cys Lys
            275                 280                 285

Ala Val Asp Ile Gly Pro Gly Leu Asn Leu Leu Gln Glu Asp Asn Pro
    290                 295                 300

Asp Leu Ile Gly Ser Glu Ile Ala Arg Trp Leu Ser Thr Leu Glu Ile
305                 310                 315                 320

Ser Gly Leu Gln Asp Ser Glu Val Asn Gln Glu Ala Lys Pro Glu Val
            325                 330                 335

Lys Pro Glu Val Lys Pro Glu Thr His Ile Asn Leu Lys Val Ser Asp
            340                 345                 350

Gly Ser Ser Glu Ile Phe Phe Lys Ile Lys Lys Thr Thr Pro Leu Arg
            355                 360                 365

Arg Leu Met Glu Ala Phe Ala Lys Arg Gln Gly Lys Glu Met Asp Ser
    370                 375                 380

Leu Thr Phe Leu Tyr Asp Gly Ile Glu Ile Gln Ala Asp Gln Thr Pro
385                 390                 395                 400

Glu Asp Leu Asp Met Glu Asp Asn Asp Ile Ile Glu Ala His Arg Glu
            405                 410                 415

Gln Ile Gly Gly Ser Gly Gly Ser Gly Gly Ser Gly Gly Ser Gly Gly
            420                 425                 430

Ser Ser Gly Gly Gly Ser Ser Gly Cys Ala Glu Gln Thr Thr Glu Trp
            435                 440                 445

Thr Ala Cys Ser Lys Ser Cys Gly Met Gly Phe Ser Thr Arg Val Thr
    450                 455                 460

Asn Arg Asn Arg Gln Cys Glu Met Leu Lys Gln Thr Arg Leu Cys Met
465                 470                 475                 480

Val Arg Pro Cys
```

<210> SEQ ID NO 115
<211> LENGTH: 13
<212> TYPE: PRT
<213> ORGANISM: Artificial Sequence
<220> FEATURE:
<223> OTHER INFORMATION: part of recombinant protein

<400> SEQUENCE: 115

```
Pro Pro Ser Arg Gly Arg Ser Pro Gln Asn Ser Ala Phe
1               5                   10
```

<210> SEQ ID NO 116
<211> LENGTH: 8
<212> TYPE: PRT
<213> ORGANISM: Artificial Sequence
<220> FEATURE:
<223> OTHER INFORMATION: part of recombinant protein

<400> SEQUENCE: 116

-continued

```
Gly Gln Pro Val Tyr Ser Ser Leu
1               5

<210> SEQ ID NO 117
<211> LENGTH: 7
<212> TYPE: PRT
<213> ORGANISM: Artificial Sequence
<220> FEATURE:
<223> OTHER INFORMATION: part of recombinant protein

<400> SEQUENCE: 117

Glu Ala Asp Leu Glu Glu Asn
1               5

<210> SEQ ID NO 118
<211> LENGTH: 9
<212> TYPE: PRT
<213> ORGANISM: Artificial Sequence
<220> FEATURE:
<223> OTHER INFORMATION: part of recombinant protein

<400> SEQUENCE: 118

Glu Gln Gln Pro Glu Gln Pro Thr Asp
1               5

<210> SEQ ID NO 119
<211> LENGTH: 8
<212> TYPE: PRT
<213> ORGANISM: Artificial Sequence
<220> FEATURE:
<223> OTHER INFORMATION: part of recombinant protein

<400> SEQUENCE: 119

Asp Val Asp Ile His Thr Leu Ile
1               5

<210> SEQ ID NO 120
<211> LENGTH: 11
<212> TYPE: PRT
<213> ORGANISM: Artificial Sequence
<220> FEATURE:
<223> OTHER INFORMATION: part of recombinant protein

<400> SEQUENCE: 120

Asp Ser Asn Ile Leu Lys Thr Ile Lys Ile Pro
1               5                   10

<210> SEQ ID NO 121
<211> LENGTH: 5
<212> TYPE: PRT
<213> ORGANISM: Artificial Sequence
<220> FEATURE:
<223> OTHER INFORMATION: Linker

<400> SEQUENCE: 121

Gly Gly Gly Gly Ser
1               5
```